United States Patent
Beetham et al.

(10) Patent No.: US 9,957,515 B2
(45) Date of Patent: May 1, 2018

(54) METHODS AND COMPOSITIONS FOR TARGETED GENE MODIFICATION

(71) Applicants: CIBUS US LLC, San Diego, CA (US); CIBUS EUROPE B.V., AD Kapelle (NL)

(72) Inventors: Peter R. Beetham, Carlsbad, CA (US); Gregory F. W. Gocal, San Diego, CA (US); Christian Schopke, Carlsbad, CA (US); Noel Sauer, Oceanside, CA (US); James Pearce, La Jolla, CA (US); Rosa E. Segami, Escondio, CA (US); Jerry Mozoruk, Encinitas, CA (US)

(73) Assignees: CIBUS US LLC, San Diego, CA (US); CIBUS EUROPE, B.V., Ad Kapelle (NL)

( * ) Notice: Subject to any disclaimer, the term of this patent is extended or adjusted under 35 U.S.C. 154(b) by 0 days. days.

(21) Appl. No.: 15/069,885

(22) Filed: Mar. 14, 2016

(65) Prior Publication Data
US 2017/0051296 A1    Feb. 23, 2017

Related U.S. Application Data

(63) Continuation-in-part of application No. 14/777,357, filed on Sep. 15, 2015, which is a continuation-in-part of application No. PCT/US2015/020622, filed as application No. PCT/US2014/029566 on Mar. 14, 2014.

(60) Provisional application No. 61/953,333, filed on Mar. 14, 2014, provisional application No. 62/051,579, filed on Sep. 17, 2014, provisional application No. 62/075,811, filed on Nov. 5, 2014, provisional application No. 62/075,816, filed on Nov. 5, 2014, provisional application No. 62/133,129, filed on Mar. 13, 2015, provisional application No. 61/801,333, filed on Mar. 15, 2013.

(51) Int. Cl.
*C12N 15/82* (2006.01)
*C12N 9/22* (2006.01)

(52) U.S. Cl.
CPC .......... *C12N 15/8213* (2013.01); *C12N 9/22* (2013.01); *C12N 2800/80* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,873,191 A | 10/1989 | Wagner et al. |
| 4,945,050 A | 7/1990 | Sanford et al. |
| 5,008,200 A | 4/1991 | Ranch et al. |
| 5,024,944 A | 6/1991 | Collins et al. |
| 5,100,792 A | 3/1992 | Sanford et al. |
| 5,204,253 A | 4/1993 | Sanford et al. |
| 5,219,746 A | 6/1993 | Brinegar et al. |
| 5,268,463 A | 12/1993 | Jefferson |
| 5,302,523 A | 4/1994 | Coffee et al. |
| 5,334,711 A | 8/1994 | Sproat et al. |
| 5,380,831 A | 1/1995 | Adang et al. |
| 5,399,680 A | 3/1995 | Zhu et al. |
| 5,424,412 A | 6/1995 | Brown et al. |
| 5,436,391 A | 7/1995 | Fujimoto et al. |
| 5,466,785 A | 11/1995 | De Framond |
| 5,569,597 A | 10/1996 | Grimsley et al. |
| 5,593,874 A | 1/1997 | Brown et al. |
| 5,604,121 A | 2/1997 | Hilder et al. |
| 5,608,142 A | 3/1997 | Barton et al. |
| 5,608,144 A | 3/1997 | Baden et al. |
| 5,608,149 A | 3/1997 | Barry et al. |
| 5,659,026 A | 8/1997 | Baszczynski et al. |
| 5,756,325 A | 5/1998 | Kmiec |
| 5,760,012 A | 6/1998 | Kmiec et al. |
| 5,780,296 A | 7/1998 | Holloman et al. |
| 5,795,972 A | 8/1998 | Kmiec |
| 5,871,984 A | 2/1999 | Kmiec |
| 5,888,983 A | 3/1999 | Kmiec et al. |
| 5,945,339 A | 8/1999 | Holloman et al. |
| 5,962,426 A | 10/1999 | Glazer |
| 5,986,053 A | 11/1999 | Ecker et al. |
| 6,004,804 A | 12/1999 | Kumar et al. |

(Continued)

FOREIGN PATENT DOCUMENTS

| | | |
|---|---|---|
| EP | 0629387 A1 | 12/1994 |
| EP | 0679657 A2 | 11/1995 |

(Continued)

OTHER PUBLICATIONS

Majlessi et al 1998 Nucleic Acids Research 26:2224-2229.*
Gallois et al., Electroporation of Tobacco Leaf Protoplasts Using Plasmid DNA or Total Genomic DNA. Methods Mol Biol. 1995;55:89-107.
Gamborg et al. Nutrient requirements of suspension cultures of soybean root cells. Exp Cell Res. Apr. 1968;50(1):151-158.
Golovkin et al., Production of transgenic maize plants by direct DNA uptake into embryogenic protoplasts . Plant Sci. 1993;90:41-52.

(Continued)

*Primary Examiner* — Brent T Page
(74) *Attorney, Agent, or Firm* — Acuity Law Group, PC; Michael A. Whittaker

(57) ABSTRACT

Provided herein include methods and compositions for effecting a targeted genetic change in DNA in a cell. Certain aspects and embodiments relate to improving the efficiency of the targeting of modifications to specific locations in genomic or other nucleotide sequences. As described herein, nucleic acids which direct specific changes to the genome may be combined with various approaches to enhance the availability of components of the natural repair systems present in the cells being targeted for modification.

17 Claims, 43 Drawing Sheets

(56) References Cited

U.S. PATENT DOCUMENTS

| | | | |
|---|---|---|---|
| 6,010,907 | A | 1/2000 | Kmiec et al. |
| 6,072,050 | A | 6/2000 | Bowen et al. |
| 6,177,611 | B1 | 1/2001 | Rice |
| 6,271,360 | B1 | 8/2001 | Metz et al. |
| 6,479,292 | B1 | 11/2002 | Metz et al. |
| 6,753,458 | B1 | 6/2004 | Filho et al. |
| 7,060,500 | B2 | 6/2006 | Metz et al. |
| 7,070,934 | B2 | 7/2006 | Cox et al. |
| 7,220,719 | B2 | 5/2007 | Case et al. |
| 7,262,054 | B2 | 8/2007 | Jamieson et al. |
| 7,273,923 | B2 | 9/2007 | Jamieson et al. |
| 7,285,416 | B2 | 10/2007 | Choo et al. |
| 7,361,635 | B2 | 4/2008 | Miller et al. |
| 7,521,241 | B2 | 4/2009 | Choo et al. |
| 8,268,622 | B2 | 9/2012 | Gocal et al. |
| 8,278,036 | B2 | 10/2012 | Kariko et al. |
| 8,338,157 | B2 | 12/2012 | Jantz et al. |
| 8,470,973 | B2 | 6/2013 | Bonas |
| 8,771,945 | B1 | 7/2014 | Zhang |
| 2003/0115641 | A1 | 6/2003 | Dobres et al. |
| 2009/0205064 | A1* | 8/2009 | Schopke ............ C12N 15/8274 800/260 |
| 2011/0124072 | A1 | 5/2011 | Walker et al. |
| 2011/0201118 | A1 | 8/2011 | Yang et al. |
| 2012/0122223 | A1 | 5/2012 | Gocal et al. |
| 2012/0178628 | A1 | 7/2012 | Schopke et al. |
| 2014/0298547 | A1* | 10/2014 | Sastry-Dent ......... C12Q 1/6858 800/306 |

FOREIGN PATENT DOCUMENTS

| | | | |
|---|---|---|---|
| WO | 9849350 | A1 | 11/1998 |
| WO | 9907865 | A1 | 2/1999 |
| WO | 9940789 | A1 | 8/1999 |
| WO | 9943838 | A1 | 9/1999 |
| WO | 9958702 | A1 | 11/1999 |
| WO | 9958723 | A1 | 11/1999 |
| WO | 0125460 | A2 | 4/2001 |
| WO | 2007073149 | A1 | 6/2007 |
| WO | 2008148223 | A1 | 12/2008 |
| WO | 2009046334 | A1 | 4/2009 |
| WO | 2013028188 | A1 | 2/2013 |
| WO | 2013176772 | A1 | 11/2013 |
| WO | 2014093661 | A2 | 6/2014 |

OTHER PUBLICATIONS

Guerineau et al., Effect of deletions in the cauliflower mosaic virus polyadenylation sequence on the choice of the polyadenylation sites in tobacco protoplasts. Mol Gen Genet. Apr. 1991;226(1-2):141-144.
Guevara-Garcia et al., Tissue-specific and wound-inducible pattern of expression of the mannopine synthase promoter is determined by the interaction between positive and negative cis-regulatory elements. Plant J. Sep. 1993;4 (3):495-505.
Guo, Transgenic Plants Obtained From Wheat Protoplasts Transformed by PEG-mediated Direct Gene Transfer. Chin Sci. Bull. Dec. 1993;38(24):2072-2078.
Gustafsson et al., Codon bias and heterologous protein expression. Trends Biotechnol. Jul. 2004;22(7):346-353.
Hansen et al., Wound-inducible and organ-specific expression of ORF13 from Agrobacterium rhizogenes 8196 T-DNA in transgenic tobacco plants. Mol Gen Genet. Apr. 16, 1997;254(3):337-343.
Hartman et al., Herbicide Resistant Turf grass (*Agrostis palustris* Huds.) by Biolistic Transformation. Nature BioTechnol. 1994;12:919-923.
Havre and Glazer, Targeted Mutagenesis of Simian Virus 40 DNA Mediated by a Triple Helix-Forming Oligonucleotide. J Virol. Dec. 1993;67(12):7324-7331.
Havre et al., Targeted mutagenesis of DNA using triple helix-forming oligonucleotides linked to psoralen. Proc Natl Acad Sci U S A. Aug. 15, 1993;90(16):7879-7883.
He et al., A simplified system for generating recombinant adenoviruses. Proc Natl Acad Sci U S A. Mar. 3, 1998;95(5):2509-2514.
Jinek et al., A Programmable Dual-RNA—Guided DNA Endonuclease in Adaptive Bacterial Immunity. Science. Aug. 17, 2012;337(6096):816-821.
Joshi et al., Putative polyadenylation signals in nuclear genes of higher plants: a compilation and analysis. Nucleic Acids Res. Dec. 10, 1987;15(23):9627-9640.
Kagale and Rozwadowski, EAR motif-mediated transcriptional repression in plants: an underlying mechanism for epigenetic regulation of gene expression. Epigenetics. Feb. 2011;6(2):141-146.
Kane et al., Specific Cleavage of a DNA Triple Helix by FenII-Bleomycin. Biochemistry. Dec. 26, 1995;34(51):16715-24.
Kartha et al., In vitro Plant Formation from Stem Explants of Rape (*Brassica napus* cv. Zephyr). Physiol. Plant, 1974;31:217-220.
Kawamata et al., Temporal and Spatial Pattern of Expression of the Pea Phenylalanine Ammonia-Lyase Gene1 Promoter in Transgenic Tobacco. Plant Cell Physiol. Jul. 1997;38(7):792-803.
Kim et al., DNA. RNA heteroduplex containing 8-oxo-7,8-dihydroguanosine: base pairing, structures, and thermodynamic stability. J Biochem Mol Biol. Nov. 30, 2004;37(6):657-662.
Kim et al., Hybrid restriction enzymes: zinc finger fusions to Fok I cleavage domain. Proc Natl Acad Sci U S A. Feb. 6, 1996;93(3):1156-1160.
Kipp et al., Gene Targeting in Plants via Site-Directed Mutagenesis. Methods Mol Biol. 2000;133:213-221.
Komatsuda et al., Genotype X Sucrose Interactions for Somatic Embryogenesis in Soybeans. Crop Sci. 1991;31(2):333-337.
Komatsuda et al., Maturation and germination of somatic embryos as affected by sucrose and plant growth regulators in soybeans Glycine gracilis Skvortz and *Glycine max* (L.) Merr Plant Cell, Tissue and Organ Culture, 1992;28(1):103-113.
Kunzelmann et al., Gene targeting of CFTR DNA in CF epithelial cells. Gene Ther. Oct. 1996;3(10):859-867.
Lam, Analysis of Tissue-Specific Elements in the Camv 35S Promoter. Results Probl Cell Differ. 1994;20:181-196.
Lamppa et al., The Chlorophyll a/b-binding Protein Inserts into the Thylakoids Independent of Its Cognate Transit Peptide. J Biol Chem. Oct. 15, 1988;263(29):14996-14999.
Lanza et al., A condition-specific codon optimization approach for improved heterologous gene expression in Saccharomyces cerevisiae. BMC Syst Biol. Mar. 17, 2014;8:33 (10 pages).
Last et al., pEmu: an improved promoter for gene expression in cereal cells. Theor Appl Genet. May 1991;81(5):581-588.
Lawrence and Kindle, Alterations in the Chlamydomonas plastocyanin transit peptide have distinct effects on in vitro import and in vivo protein accumulation. J Biol Chem. Aug. 15, 1997;272(33):20357-20363.
Lukhtanov et al., Minor Groove DNA Alkylation Directed by Major Groove Triplex Forming Oligodeoxyribonucleotides. Nucleic Acids Res. Dec. 15, 1997;25(24):5077-5084.
Maeder et al., CRISPR RNA-guided activation of endogenous human genes. Nat Methods. Oct. 2013;10(10):977-979.
Mali et al., CAS9 transcriptional activators for target specificity screening and paired nickases for cooperative genome engineering. Nat Biotechnol. Sep. 2013;31(9):833-838.
Maniatis et al., Regulation of Inducible and Tissue-Specific Gene Expression. Science. Jun. 5, 1987;236(4806):1237-1245.
Mathur et al., A simple method for isolation, fiquid culture, transformation and regeneration of Arabidopsis thaliana protoplasts. Plant Cell Rep. Jan. 1995;14(4):221-226.
Matsuoka et al., Tissue-specific light-regulated expression directed by the promoter of a C4 gene, maize pyruvate, orthophosphate dikinase, in a C3 plant, rice. Proc Natl Acad Sci U S A. Oct. 15, 1993;90(20):9586-9590.
McBride et al., Controlled expression of plastid transgenes in plants based on a nuclear DNA-encoded and plastid-targeted T7 RNA polymerase. Proc Natl Acad Sci U S A. Jul. 19, 1994;91(15):7301-7305.
McElroy et al., Isolation of an Efficient Actin Promoter for Use in Rice Transformation. Plant Cell. Feb. 1990;2(2):163-171.

(56) References Cited

OTHER PUBLICATIONS

Mogen et al., Upstream Sequences Other than AAUAAA Are Required for Efficient Messenger RNA 3'-End Formation in Plants. Plant Cell. Dec. 1990;2(12):1261-1272.
Morlan et al., Mutation Detection by Real-Time PCR: A Simple, Robust and Highly Selective Method. PLoS One. 2009;4(2):e4584 (11 pages).
Munroe and Jacobson, Tales of poly(A): a review. Gene. Jul. 16, 1990;91(2):151-158.
Murray et al., Codon usage in plant genes. Nucleic Acids Res. Jan. 25, 1989;17(2):477-498.
Narasimhulu and Chopra, Species specific shoot regeneration response of cotyledonary explants of Brassicas. Plant Cell Rep. Mar. 1988;7(2):104-106.
Nunez et al., Long-Range Guanine Oxidation in DNA Restriction Fragments by a Triplex-Directed Naphthalene Diimide Intercalator. Biochemistry. May 23, 2000;39(20):6190-6199.
Odell et al., Identification of DNA sequences required for activity of the cauliflower mosaic virus 35S promoter. Nature Feb. 28, 1985;313:810-812.
Oh and Hanawalt, Triple helix-forming oligonucleotides target psoralen adducts to specific chromosomal sequences in human cells. Nucleic Acids Res. Dec. 15, 1999;27(24):4734-4742.
Orozco and Ogren, Localization of light-inducible and tissue-specific regions of the spinach ribulose bisphosphate carboxylase/oxygenase (rubisco) activase promoter in transgenic tobacco plants. Plant Mol Biol. Dec. 1993;23 (6):1129-1138.
Pandey et al., Plant Regeneration from Leaf and Hypocotyl Explants of Glycine wightii (W. and A.) VERDC. var. longicauda Japan J. Breed. 1992;42:1-5.
Pasupathy et al., Direct plant gene delivery with a poly(amidoamine) dendrimer. Biotechnol J. Aug. 2008;3(8):1078-1082.
Perez-Pinera et al., RNA-guided gene activation by CRISPR-Cas9-based transcription factors. Nat Methods. Oct. 2013;10(10):973-976.
Pilch et al., The Thermodynamics of Polyamide—DNA Recognition: Hairpin Polyamide Binding in the Minor Groove of Duplex DNA. Biochemistry. Feb. 16, 1999;38(7):2143-2151.
Proudfoot, Poly(A) Signals. Cell. Feb. 22, 1991;64(4):671-674.
Rinehart et al., Tissue-Specific and Developmental Regulation of Cotton Gene FbL2A. Demonstration of Promoter Activity in Transgenic Plants. Plant Physiol. Nov. 1996;112(3):1331-1341.
Ritala et al., Fertile transgenic barley to particle bombardment of immature embryos. Plant Mol Biol. Jan. 1994;24(2):317-325.
Romer et al., Expression of the genes encoding the early carotenoid biosynthetic enzymes in Capsicum annuum. Biochem Biophys Res Commun. Nov. 15, 1993;196(3):1414-1421.
Rouet et al., Expression of a site-specific endonuclease stimulates homologous recombination in mammalian cells. Proc Natl Acad Sci U S A. Jun. 21, 1994;91(13):6064-6068.
Rubnitz and Subramani, The Minimum Amount of Homology Required for Homologous Recombination in Mammalian Cells. Mol Cell Biol. Nov. 1984;4(11):2253-2258.
Russell and Fromm, Tissue-specific expression in transgenic maize of four endosperm promoters from maize and rice. Transgenic Res. Mar. 1997;6(2):157-168.
Sanfacon et al., A dissection of the cauliflower mosaic virus polyadenylation signal. Genes Dev. Jan. 1991;5(1):141-149.
Schmidt et al., A Novel Operon Organization Involving the Genes for Chorismate Synthase (Aromatic Biosynthesis Pathway) and Ribosomal GTPase Center Proteins (LII, LI, LIO, L12: rpIKAJL) in Cyanobacterium Synechocystis PCC 6803. J Biol Chem. Dec. 25, 1993;268(36):27447-27457.
Schnell et al., Signal Peptide Analogs Derived from Two Chloroplast Precursors Interact with the Signal Recognition System of the Chloroplast Envelope. J Biol Chem. Feb. 15, 1991;266(5):3335-3342.
Segal and Carroll, Endonuclease-induced, targeted homologous extrachromosomal recombination in Xenopus oocytes. Proc Natl Acad Sci U S A. Jan. 31, 1995;92(3):806-810.
Senaratna et al., Desiccation of microspore derived embryos of oilseed rape (Brassica napus L.). Plant Cell Rep. Sep. 1991;10(6-7):342-344.
Sergeyev et al., Catalytic site-specific cleavage of a DNA-target by an oligonucleotide carrying bleomycin A5. Nucleic Acids Res. Nov. 11, 1995;23(21):4400-4406.
Shah et al., Engineering Herbicide Tolerance in Transgenic Plants. Science. Jul. 25, 1986;233(4762):478-481.
Shetty et al., Stimulation of in vitro shoot organogenesis in Glycine max(Merrill.) by allantoin and amides. Plant Science 1992;81:245-251.
Skuzeski et al., Analysis of leaky viral translation termination codons in vivo by transient expression of improved beta-glucuronidase vectors. Plant Mol Biol. Jul. 1990;15(1):65-79.
Sommer et al., Reporter System for the Detection of In Vivo Gene Conversion: Changing Colors From Blue to Green Using GFP Variants. Mol Biotechnol. Jun. 2006;33(2):115-122.
Staub and Maliga, Accumulation of D1 polypeptide in tobacco plastids is regulated via the untranslated region of the psbA mRNA. Embo J. Feb. 1993;12(2):601-606.
Stephens et al., Agronomic evaluation of tissue-culture-derived soybean plants. Theor Appl Genet. Oct. 1991;82(5):633-635.
Svab and Maliga, High-frequency plastid transformation in tobacco by selection for a chimeric aadA gene. Proc Natl Acad Sci U S A. Feb. 1, 1993;90(3):913-917.
Svab et al., Stable transformation of plastids in higher plants. Proc Natl Acad Sci U S A. Nov. 1990;87(21):8526-8530.
Swanson, Microspore Culture in Brassica. Methods Mol Biol. 1990;6:159-169.
Takasugi et al., Sequence-specific photo-induced cross-linking of the two strands of double-helical DNA by a psoralen covalently linked to a triple helix-forming oligonucleotide. Proc Natl Acad Sci U S A. Jul. 1, 1991;88(13):5602-5606.
Takeshita et al., Oligodeoxynucleotides Containing Synthetic Abasic Sites. Model Substrates for DNA Polymerases and Apurinic/Apyrimidinic Endonucleases. J Biol Chem. Jul. 25, 1987;262(21):10171-10179.
Topfer et al., Uptake and Transient Expression of Chimeric Genes in Seed-Derived Embryos. Plant Cell. Jan. 1989;1(1):133-139.
Torney et al., Mesoporous Silica Nanoparticles Deliver DNA and Chemicals into Plants, Nature Nanotechnol. May 2007:2:295-300.
Van Camp et al., Tissue-Specific Activity of Two Manganese Superoxide Dismutase Promoters in Transgenic Tobacco. Plant Physiol. Oct. 1996;112(2):525-535.
Velten et al., Isolation of a dual plant promoter fragment from the Ti plasmid of Agrobacterium tumefaciens. EMBO J. Dec. 1, 1984;3(12):2723-2730.
von Heijne et al., CHLPEP—A Database of Chloroplast Transit Peptides. Plant Mol Biol Rep. 1991;9(2):104-126.
Wan and Lemaux, Generation of Large Numbers of Independently Transformed Fertile Barley Plants. Plant Physiol. Jan. 1994;104(1):37-48.
Wang et al., Carcinogens Can Induce Homologous Recombination between Duplicated Chromosomal Sequences in Mouse L Cells. Mol Cell Biol. Jan. 1988;8(1):196-202.
Wang et al., Hairpin RNAs derived from RNA polymerase II and polymerase III promoter-directed transgenes are processed differently in plants. RNA. May 2008;14(5):903-913.
Wang et al., Mutagenesis in Mammalian Cells Induced by Triple Helix Formation and Transcription-Coupled Repair. Science. Feb. 9, 1996;271(5250):802-805.
Wang et al., Targeted Mutagenesis in Mammalian Cells Mediated by Intracellular Triple Helix Formation. Mol Cell Biol. Mar. 1995;15(3):1759-1768.
Wong and Capecchi, Homologous Recombination between Coinjected DNA Sequences Peaks in Early to Mid-S Phase. Mol Cell Biol. Jun. 1987;7(6):2294-2295.
Yamamoto et al., Light-responsive elements of the tobacco PSI-D gene are located both upstream and within the transcribed region. Plant J. Aug. 1997;12(2):255-265.

(56) References Cited

OTHER PUBLICATIONS

Yamamoto et al., The Promoter of a Pine Photosynthetic Gene Allows Expression of a β-Glucuronidase Reporter Gene in Transgenic Rice Plants in a Light-Independent but Tissue-Specific Manner. Plant Cell Physiol. Jul. 1994;35(5):773-778.
Zhang et al., Transcription Activator-Like Effector Nucleases Enable Efficient Plant Genome Engineering 1[W][OA]. Plant Physiol. Jan. 2013;161(1):20-27.
Zhao and Last, Immunological Characterization and Chloroplast Localization of the Tryptophan Biosynthetic Enzymes of the Flowering Plant Arabidopsis Thaliana. J Biol Chem. Mar. 17, 1995;270(11):6081-6087.
The International Search Report issued in PCT/US2015/020622 dated Jun. 25, 2015.
The International Preliminary Report on Patentability issued in PCT/US2015/020622 dated Jun. 22, 2016.
Office Action issued by SIPO in PRC patent application No. 201480024688.5, dated Nov. 2, 2016—incl Eng lang transl.
An et al., Transformation of Tobacco, Tomato, Potato, and Arabidopsis thaliana Using a Binary Ti Vector System. Plant Physiol. May, 1986;81(1):301-305.
Archer and Keegstra, Current Views on Chloroplast Protein Import and Hypotheses on the Origin of the Transport Mechanism. J Bioenerg Biomembr. Dec. 1990;22(6):789-810.
Arimondo et al., Recognition and Cleavage of DNA by Rebeccamycin- or Benzopyridoquinoxaline Conjugated of Triple Helix-Forming Oligonucleotides. Bioorg Med Chem. Apr. 2000;8(4):777-784.
Asano and Ugaki, Transgenic plants of Agrostis alba obtained by electroporation-mediated direct gene transfer into protoplasts. Plant Cell Rep. Feb. 1994;13(5):243-246.
Ayres and Park, Genetic Transformation of Rice. Crit Rev Plant Sci 13:219-239.
Ballas et al., Efficient functioning of plant promoters and poly(A) sites in Xenopus oocytes. Nucleic Acids Res. Oct. 11, 1989;17(19):7891-7903.
Barcelo et al., Transgenic cereal (tritordeum) plants obtained at high efficiency by microprojectile bombardment of inflorescence tissue. Plant J. Apr. 1994;5(4):583-592.
Barsby et al., A rapid and efficient alternative procedure for the regeneration of plants from hypocotyl protoplasts of Brassica napus. Plant Cell Rep. Apr. 1986;5(2):101-103.
Becker, et al., Fertile transgenic wheat from microprojectile bombardment of scutellar tissue. Plant J. Feb. 1994;5(2):299-307.
Belousov et al., Sequence-specific targeting and covalent modification of human genomic DNA. Nucleic Acids Res. Sep. 1, 1997;25(17):3440-3444.
Bendinskas et al., Sequence-Specific Photomodification of DNA by an Oligonucleotide-Phenanthrodihydrodioxin Conjugate. Bioconjug Chem. Sep.-Oct. 1998;9(5):555-563.
Borkowska et al., Transformation of diploid potato with an Agrobacterium tumefaciens binary vector system: I. Methodological approach. Acta Physiol Plant. 1994;16(3):225-230.
Burgess-Brown et al., Codon optimization can improve expression of human genes in *Escherichia coli*: A multi-gene study. Protein Expr Purif. May 2008;59(1):94-102.
Callis et al., Introns increase gene expression in cultured maize cells. Genes Dev. Dec. 1987;1(10):1183-1200.
Campbell and Gowri, Codon Usage in Higher Plants, Green Algae, and Cyanobacteria. Plant Physiol. Jan. 1990;92(1):1-11.
Canevascini et al., Tissue-Specific Expression and Promoter Analysis of the Tobacco ltp1 Gene. Plant Physiol. Oct. 1996;112(2):513-524.
Capecchi et al., Altering the Genome by Homologous Recombination. Science. Jun. 16, 1989;244(4910):1288-1292.
Casas et al., Transgenic sorghum plants via microprojectile bombardment. Proc Natl Acad Sci U S A. Dec. 1, 1993;90(23):11212-11216.

Cermak et al., Efficient design and assembly of custom TALEN and other TAL effector-based constructs for DNA targeting. Nucleic Acids Res. Jul. 2011;39(12):e82 (11 pages).
Chan et al., Targeted Correction of an Episomal Gene in Mammalian Cells by a Short DNA Fragment Tethered to a Triplex-forming Oligonucleotide. J Biol Chem. Apr. 23, 1999;274(17):11541-11548.
Chee and Slightom, Transformation of cucumber tissues by microprojectile bombardment: identification of plants containing functional and non-functional transferred genes. Gene. Sep. 10, 1992;118(2):255-260.
Cheng et al., Multiplexed activation of endogenous genes by CRISPR-on, an RNA-guided transcriptional activator system. Cell Res. 2013:1-9.
Christensen and Quail, Sequence analysis and transcriptional regulation by heat shock of polyubiquitin transcripts from maize. Plant Mol Biol. Jun. 1989;12(6):619-632.
Christensen et al., Maize polyubiquitin genes: structure, thermal perturbation of expression and transcript splicing, and promoter activity following transfer to protoplasts by electroporation. Plant Mol Biol. Feb. 1992;18(4):675-689.
Christou et al., The development of a variety-independent gene-transfer method for rice. Trends Biotechnol. 1992;10:239-246.
Christou, Genetic engineering of crop legumes and cereals: current status and recent advances. Agro Food Ind Hi Tech. Mar.-Apr. 1994:5:17-27.
Christou, Philosophy and Practice of Variety-Independent Gene Transfer into Recalcitrant Crops. In Vitro Cell Dev Biol—Plant 1993;29:119-124.
Chuong et al., A Simple Culture Method for *Brassica hypocotyls* Protoplasts. Plant Cell Rep. Feb. 1985;4(1):4-6.
Clark et al., Mutations at the Transit Peptide-Mature Protein Junction Separate Two Cleavage Events During Chloroplast Import of the Chlorophyll a/b-Binding Protein. J Biol Chem. Oct. 15, 1989;264(29):17544-17550.
Clough and Bent, Floral dip: a simplified method for Agrobacterium-mediated transformation of *Arabidopsis thaliana*. Plant J. Dec. 1998;16(6):735-43.
Columbier et al., Interstrand cross-linking reaction in triplexes containing a monofunctional transplatin-adduct. Nucleic Acids Res. Nov. 15, 1996;24(22):4519-4524.
Cong et al., Multiplex Genome Engineering Using CRISPR/Cas Systems. Science. Feb. 15, 2013;339(6121):819-823.
Davies et al., Transformation of peas. Plant Cell Rep. Jan. 1993;12(3):180-183.
De Block, Genotype-independent leaf disc transformation of potato (*Solanum tuberosum*) using Agrobacterium tumefaciens. Theor Appl Genet. Nov. 1988;76(5):767-774.
de Castro Silva Filho et al., Mitochondrial and chloroplast targeting sequences in tandem modify protein import specificity in plant organelles. Plant Mol Biol. Feb. 1996;30(4):769-780.
Della-Cioppa et al. Protein Trafficking in Plant Cells. Plant Physiol. Aug. 1987;84(4):965-968.
Dervan and Bürli, Sequence-specific DNA recognition by polyamides. Curr Opin Chem Biol. Dec. 1999;3(6):688-693.
D'Halluin et al., Transformation of Sugarbeet (*Beta vulgaris* L.) and Evaluation of Herbicide Resistance in Transgenic Plants. Bio/Technol. Mar. 1992;10:309-314.
Dhir et al., Regeneration of fertile plants from protoplasts of soybean (*Glycine max* L. Merr.): genotypic differences in culture response. Plant Cell Rep. Jun. 1992;11(5-6):285-289.
Dhir et al., Regeneration of Transgenic Soybean (*Glycine max*) Plants from Electroporated Protoplasts. Plant Physiol. May 1992;99(1):81-88.
Dicarlo et al., Genome engineering in *Saccharomyces cerevisiae* using CRISPR-Cas systems. Nucleic Acids Res. Apr. 2013;41(7):4336-4343.
Dong and McHughen, Transgenic flax plants from Agrobacterium mediated transformation: incidence of chimeric regenerants and inheritance of transgenic plants. Plant Sci. 1993;91:139-148.
Eapen and George, Agrobacterium tumefaciens mediated gene transfer in peanut (*Arachis hypogaea* L). Plant Cell Rep. Jul. 1994;13(10):582-586.

(56) References Cited

OTHER PUBLICATIONS

Eudes and Chugh, Cell-penetrating peptides: From mammalian to plant cells. Plant Signal Behav. Aug. 2008;3(8):549-550.

Faruqi et al., Recombination Induced by Triple-Helix-Targeted DNA Damage in Mammalian Cells. Mol Cell Biol. Dec. 1996;16(12):6820-6828.

Folger et al., Patterns of Integration of DNA Microinjected into Cultured Mammalian Cells: Evidence for Homologous Recombination Between Injected Plasmid DNA Molecules. Mol Cell Biol. Nov. 1982;2(11):1372-1387.

Fry et al., Transformation of *Brassica napus* with Agrobacterium tumefaciens based vectors. Plant Cell Rep. Oct. 1987;6(5):321-325.

Fujiwara and Kato, Split luciferase complementation assay to study protein-protein interactions in *Arabidopsis* protoplasts. Plant J. Oct. 2007;52(1):185-195.

Gallie and Young, The Regulation of Gene Expression in Transformed Maize Aleurone and Endosperm Protoplasts. Analysis of Promoter Activity, Intron Enhancement, and Mrna Untranslated Regions on Expression. Plant Physiol. Nov. 1994;106(3):929-939.

Gallie et al., A comparison of eukaryotic viral 5'-leader sequences as enhancers of mRNA expression in vivo. Nucleic Acids Res. Nov. 11, 1987;15(21):8693-8711.

Extended European Search Report and Written Opinion issued in EP 15761154 dated Sep. 25, 2017.

Feng et al., Efficient genome editing in plants using a CRISPR/Cas system. Cell Res. Oct. 2013;23(10):1229-1232.

Sander and Joung, CRISPR-Cas systems for editing, regulating and targeting genomes. Nat Biotechnol. Apr. 2014;32(4):347-355.

Voytas, Plant Genome Engineering with Sequence-Specific Nucleases. Annu Rev Plant Biol. 2013;64:327-350.

Wei et al., TALEN or Cas9—Rapid, Efficient and Specific Choices for Genome Modifications. J Genet Genomics. Jun. 20, 2013;40(6):281-289.

Restriction Requirement issued in related U.S. Appl. No. 15/126,279 dated Nov. 17, 2017.

\* cited by examiner

FIG. 2A

Okazaki Fragment GRONs (BFP4 or 0/C or NC/71/5' 2' -O-Me (1))

BFP4/NC: U UCA UGU GG U CGG GGT AGC G GC TGA AGC ACT GCA CGC CGT AGG TGA AGG TGG TCA CGA GGG TGG GCC AGG G (71 -mer)

BFP0/NC: U UCA UGU GG U CGG GGT AGC G GC TGA AGC ACT GCA CGC CGT GGG TGA AGG TGG TCA CGA GGG TGG GCC AGG G (71 -mer)

BFP4/C: G CUG CCC GUG CCC TGG CCC A CC CTC GTG ACC ACC TTC ACC TAC GGC GTG CAG TGC TTC AGC CGC TAC CCC G (71 -mer)

BFP0/C: G CUG CCC GUG CC C TGG CCC A CC CTC GTG ACC ACC TTC ACC CAC GGC GTG CAG TGC TTC AGC CGC TAC CCC G (71 -mer)

RNA bases

2' - O- Me group on first 5' RNA base (RNA bases without the 2'- O -Me groups are in boxes)

FIG. 2B

Okazaki Fragment GRONs ( BFP4 or 0 /C or NC/71/5' 2' -O-Me (9))

BFP4/NC: U UCA UGU GG U CGG GGT AGC G GC TGA AGC ACT GCA CGC CGT AGG TGA AGG TGG TCA CGA GGG TGG GCC AGG G (7 1- mer)

BFP0/NC: U UCA UGU GG U CGG GGT AGC G GC TGA AGC ACT GCA CGC CGT GGG TGA AGG TGG TCA CGA GGG TGG GCC AGG G (7 1 -mer)

BFP4/C: G CUG CCC GUG CC C TGG CCC A CC CTC GTG ACC ACC TTC ACC TAC GGC GTG CAG TGC TTC AGC CGC TAC CCC G (7 1 -mer)

BFP0/C: G CUG CCC GUG CCC TGG CCC A CC CTC GTG ACC ACC TTC ACC CAC GGC GTG CAG TGC TTC AGC CGC TAC CCC G (7 1 -mer)

RNA bases

2' - O- Me group on all of the RNA bases except for the base closest to the first DNA base of the GRON (RNA base without the 2' - O -Me groups are in boxes)

BFP gene

5' CCTTCACCCACGGCGTGCAGTGCTTCAGCCGCTACCccgaccacatgAAGCAGCACGAC 3'
3' GGAAGTGGGTGCCGCACGTCACGAAGTCGGCGATGGGGCTGGTGTACTTCGTCGTGCTG 5'

BFP CRISPR spacer sequence
BFP CRISPR PAM Sequence
Conversion site: BFP C>T
*Wobble bases (wt sequence)*

FIG.3

| Treatment | Time * | GRON | TALEN | % Conversion | % Indels |
|---|---|---|---|---|---|
| Protoplats** | 24 h | Yes | Yes | 0.067 | 2.60 |
| Microcalli** | 3 W | Yes | Yes | 0.051 | 1.84 |

\* denotes time after PEG delivery of TALEN plasmids and GRONS.
\*\* denotes protoplasts and micromalli are not from the same experiment.

FIG.14

| Treatment** | Time * | CRISPR | % Indels |
|---|---|---|---|
| Microcalli | 3W | Yes | 46.5 |
| Microcalli | 6W | Yes | 54.7 |

\* Time after PEG delivery of CRISPR plasmids
\*\* Treatments are not from the same experiment.

FIG.15

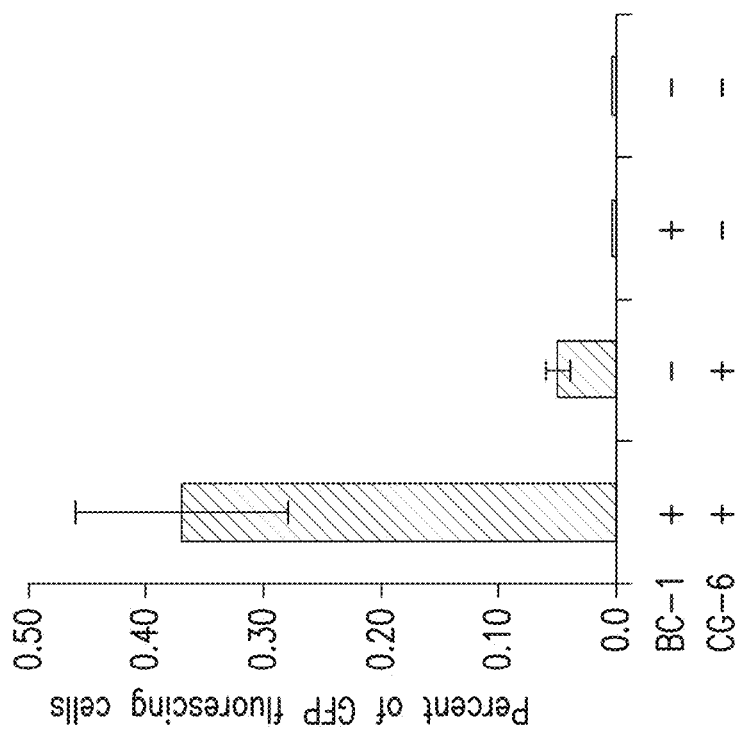
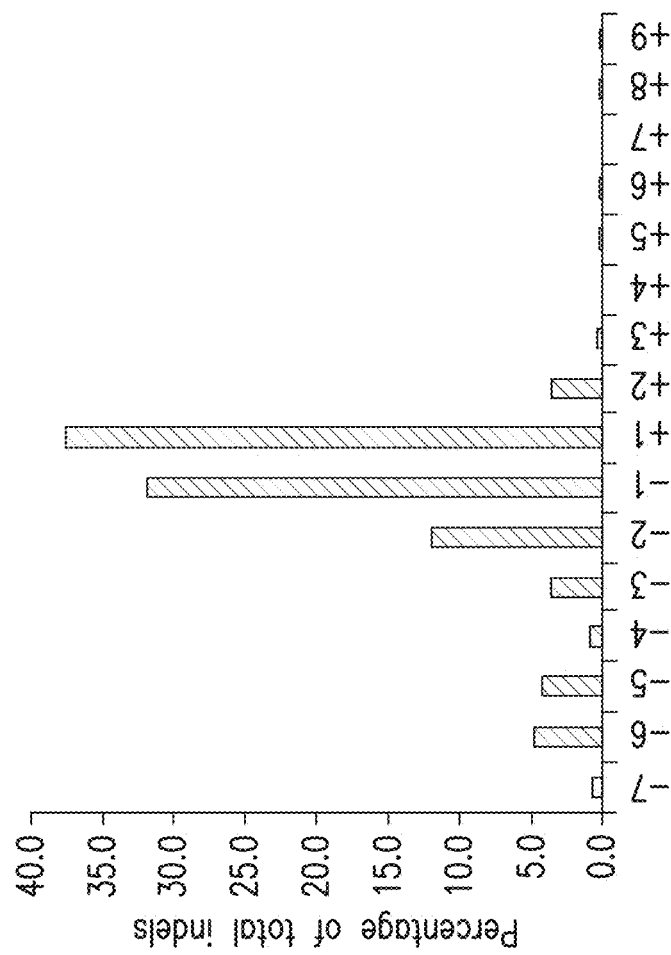
FIG. 16A
FIG. 16B

AMY310767 - *Alopecurus myosuroides* plastidal ACCase translated protein
(SEQ ID NO:1)

```
   1   MGSTHLPIVG FNASTTPSLS TLRQINSAAA AFQSSSPSRS SKKKSRRVKS
  51   IRDDGDGSVP DPAGHGQSIR QGLAGIIDLP KEGASAPDVD ISHGSEDHKA
 101   SYQMNGILNE SHNGRHASLS KVYEFCTELG GKTPIHSVLV ANNGMAAAKF
 151   MRSVRTWAND TFGSEKAIQL IAMATPEDMR INAEHIRIAD QFVEVPGGTN
 201   NNNYANVQLI VEIAERTGVS AVWPGWGHAS ENPELPDALT AKGIVFLGPP
 251   ASSMNALGDK VGSALIAQAA GVPTLAWSGS HVEIPLELCL DSIPEEMYRK
 301   ACVTTADEAV ASCQMIGYPA MIKASWGGGG KGIRKVNNDD EVKALFKQVQ
 351   GEVPGSPIFI MRLASQSRHL EVQLLCDEYG NVAALHSRDC SVQRRHQKII
 401   EEGPVTVAPR ETVKELEQAA RRLAKAVGYV GAATVEYLYS METGEYYFLE
 451   LNPRLQVEHP VTESIAEVNL PAAQVAVGMG IPLWQIPEIR RFYGMDNGGG
 501   YDIWRKTAAL ATPFNFDEVD SQWPKGHCVA VRITSENPDD GFKPTGGKVK
 551   EISFKSKPNV WGYFSVKSGG GIHEFADSQF GHVFAYGETR SAAITSMSLA
 601   LKEIQIRGEI HTNVDYTVDL LNAPDFRENT IHTGWLDTRI AMRVQAERPP
 651   WYISVVGGAL YKTITTNAET VSEYVSYLIK GQIPPKHISL VHSTISLNIE
 701   ESKYTIEIVR SGQGSYRLRL NGSLIEANVQ TLCDGGLLMQ LDGNSHVIYA
 751   EEEAGGTRLL IDGKTCLLQN DHDPSRLLAE TPCKLLRFLI ADGAHVDADV
 801   PYAEVEVMKM CMPLLSPAAG VINVLLSEGQ AMQAGDLIAR LDLDDPSAVK
 851   RAEPFEGSFP EMSLPIAASG QVHKRCAASL NAARMVLAGY DHAANKVVQD
 901   LVWCLDTPAL PFLQWEELMS VLATRLPRRL KSELEGKYNE YKLNVDHVKI
 951   KDFPTEMLRE TIEENLACVS EKEMVTIERL VDPLMSLLKS YEGGRESHAH
1001   FIVKSLFEEY LSVEELFSDG IQSDVIERLR LQYSKDLQKV VDIVLSHQGV
1051   RNKTKLILAL MEKLVYPNPA AYRDQLIRFS SLNHKRYYKL ALKASELLEQ
1101   TKLSELRTSI ARNLSALDMF TEEKADFSLQ DRKLAINESM GDLVTAPLPV
1151   EDALVSLFDC TDQTLQQRVI QTYISRLYQP QLVKDSIQLK YQDSGVIALW
1201   EFTEGNHEKR LGAMVILKSL ESVSTAIGAA LKDASHYASS AGNTVHIALL
1251   DADTQLNTTE DSGDNDQAQD KMDKLSFVLK QDVVMADLRA ADVKVVSCIV
1301   QRDGAIMPMR RTFLLSEEKL CYEEEPILRH VEPPLSALLE LDKLKVKGYN
1351   EMKYTPSRDR QWHIYTLRNT ENPKMLHRVF FRTLVRQPSA GNRFTSDHIT
1401   DVEVGHAEEP LSFTSSSILK SLKIAKEELE LHAIRTGHSH MYLCILKEQK
1451   LLDLVPVSGN TVVDVGQDEA TACSLLKEMA LKIHELVGAR MHHLSVCQWE
1501   VKLKLVSDGP ASGSWRVVTT NVTGHTCTVD IYREVEDTES QKLVYHSTAL
1551   SSGPLHGVAL NTSYQPLSVI DLKRCSARNN KTTYCYDFPL TFEAAVQKSW
1601   SNISSENNQC YVKATELVFA EKNGSWGTPI IPMQRAAGLN DIGMVAWILD
1651   MSTPEFPSGR QIIVIANDIT FRAGSFGPRE DAFFEAVTNL ACEKKLPLIY
1701   LAANSGARIG IADEVKSCFR VGWTDDSSPE RGFRYIYMTD EDHDRIGSSV
1751   IAHKMQLDSG EIRWVIDSVV GKEDGLGVEN IHGSAAIASA YSRAYEETFT
1801   LTFVTGRTVG IGAYLARLGI RCIQRIDQPI ILTGFSALNK LLGREVYSSH
1851   MQLGGPKIMA TNGVVHLTVP DDLEGVSNIL RWLSYVPANI GGPLPITKSL
1901   DPIDRPVAYI PENTCDPRAA ISGIDDSQGK WLGGMFDKDS FVETFEGWAK
1951   TVVTGRAKLG GIPVGVIAVE TQTMMQLVPA DPGQPDSHER SVPRAGQVWF
2001   PDSATKTAQA MLDFNREGLP LFILANWRGF SGGQRDLFEG ILQAGSTIVE
2051   NLRTYNQPAF VYIPKAAELR GGAWVVIDSK INPDRIECYA ERTAKGNVLE
2101   PQGLIEIKFR SEELKECMGR LDPELIDLKA RLQGANGSLS DGESLQKSIE
2151   ARKKQLLPLY TQIAVRFAEL HDTSLRMAAK GVIRKVVDWE DSRSFFYKRL
2201   RRRLSEDVLA KEIRGVIGEK FPHKSAIELI KKWYLASEAA AAGSTDWDDD
2251   DAFVAWRENP ENYKEYIKEL RAQRVSRLLS DVAGSSSDLQ ALPQGLSMLL
2301   DKMDPSKRAQ FIEEVMKVLK
```

FIG.23

The *E. coli* EPSPS gene product has the following sequence (UniProt Accession # P0A6D3, SEQ ID NO:2):

MESLTLQPIARVDGTINLPGSKSVSNRALLLAALAHGKTVLTNLLDSDDVRHMLNALTAL

GVSYTLSADRTRCEIIGNGGPLHAEGALELFLGNAGTAMRPLAAALCLGSNDIVLTGEPR

MKERPIGHLVDALRLGGAKITYLEQENYPPLRLQGGFTGGNVDVDGSVSSQFLTALLMTA

PLAPEDTVIRIKGDLVSKPYIDITLNLMKTFGVEIENQHYQQFVVKGGQSYQSPGTYLVE

GDASSASYFLAAAAIKGGTVKVTGIGRNSMQGDIRFADVLEKMGATICWGDDYISCTRGE

LNAIDMDMNHIPDAAMTIATAALFAKGTTTLRNIYNWRVKETDRLFAMATELRKVGAEVE

EGHDYIRITPPEKLNFAEIATYNDHRMAMCFSLVALSDTPVTILDPKCTAKTFPDYFEQL

ARISQAA

FIG.24

| Protein | Genbank Accession # | L82 | T97 | P101 | N111 |
|---|---|---|---|---|---|
| E. coli | X00557 | 82 | 97 | 101 | 111* |
| Arabidopsis thaliana | AF360224 | 160 | 179 | 183 | 194 |
| Petunia hybrida | M21084.1 | 155 | 174 | 178 | 189 |
| Brassica napus | X51475.1 | 155 | 174 | 178 | 189 |
| Zea mays | X63374 | 84 | 102 | 106 | 117 |
| Oryza sativa | AF413082 | 150 | 169 | 173 | 184 |
| Arabidopsis thaliana | NM 130093 | 159 | 178 | 182 | 193 |

* No true E. coli homologous acid

FIG. 25

AMY310767 - Alopecurus myosuroides plastidal ACCase cDNA

```
   1 TCGATAAACT TCCTGTTGCA TGTCTCTATC TCTATGGACT AACGGTTCCT ATGTGCATGC
  61 ATCTGTCAGG TTTCCAGACC TGGGGTTTAC AATCAGTTTA TGGCAGTCTG TGTTTGAAGA
 121 ACACTGCAAC TCTGCTGTCT GTCCAAAGGG AGGACGATGG GATCCACACA TCTGCCCATT
 181 GTCGGGTTTA ATGCATCCAC AACACCATCG CTATCCACTC TTCGCCAGAT AAACTCAGCT
 241 GCTGCTGCAT TCCAATCTTC GTCCCCTTCA AGGTCATCCA AGAAGAAAAG CCGACGTGTT
 301 AAGTCAATAA GGGATGATGG CGATGGAAGC GTGCCAGACC CTGCAGGCCA TGGCCAGTCT
 361 ATTCGCCAAG GTCTCGCTGG CATCATCGAC CTCCCAAAGG AGGGCGCATC AGCTCCAGAT
 421 GTGGACATTT CACATGGGTC TGAAGACCAC AAGGCCTCCT ACCAAATGAA TGGGATACTG
 481 AATGAATCAC ATAACGGGAG GCACGCCTCT CTGTCTAAAG TTTATGAATT TTGCACGGAA
 541 TTGGGTGGAA AAACACCAAT TCACAGTGTA TTAGTCGCCA ACAATGGAAT GGCAGCAGCT
 601 AAGTTCATGC GGAGTGTCCG GACATGGGCT AATGATACAT TTGGGTCAGA GAAGGCGATT
 661 CAGTTGATAG CTATGGCAAC TCCGGAAGAC ATGAGAATAA ATGCAGAGCA CATTAGAATT
 721 GCTGATCAGT TTGTTGAAGT ACCTGGTGGA ACAAACAATA ACAACTATGC AAATGTCCAA
 781 CTCATAGTGG AGATAGCAGA GAGAACTGGT GTCTCCGCCG TTTGGCCTGG TTGGGGCCAT
 841 GCATCTGAGA ATCCTGAACT TCCAGATGCA CTAACTGCAA AAGGAATTGT TTTTCTTGGG
 901 CCACCAGCAT CATCAATGAA CGCACTAGGC GACAAGGTTG GTTCAGCTCT CATTGCTCAA
 961 GCAGCAGGGG TTCCCACTCT TGCTTGGAGT GGATCACATG TGGAAATTCC ATTAGAACTT
1021 TGTTTGGACT CGATACCTGA GGAGATGTAT AGGAAAGCCT GTGTTACAAC CGCTGATGAA
1081 GCAGTTGCAA GTTGTCAGAT GATTGGTTAC CCTGCCATGA TCAAGGCATC CTGGGGTGGT
1141 GGTGGTAAAG GGATTAGAAA GGTTAATAAT GATGACGAGG TGAAAGCACT GTTTAAGCAA
1201 GTACAGGGTG AAGTTCCTGG CTCCCCGATA TTTATCATGA GACTTGCATC TCAGAGTCGT
1261 CATCTTGAAG TCCAGCTGCT TTGTGATGAA TATGGCAATG TAGCAGCACT TCACAGTCGT
1321 GATTGCAGTG TGCAACGACG ACACCAAAAG ATTATCGAGG AAGGACCAGT TACTGTTGCT
1381 CCTCGTGAAA CAGTGAAAGA GCTAGAGCAA GCAGCAAGGA GGCTTGCTAA GGCCGTGGGT
1441 TACGTCGGTG CTGCTACTGT TGAATATCTC TACAGCATGG AGACTGGTGA ATACTATTTT
1501 CTGGAGCTTA ATCCACGGTT GCAGGTTGAG CACCCAGTCA CCGAGTCGAT AGCTGAAGTA
1561 AATTTGCCTG CAGCCCAAGT TGCAGTTGGG ATGGGTATAC CCCTTTGGCA GATTCCAGAG
1621 ATCAGACGTT TCTACGGAAT GGACAATGGA GGAGGCTATG ATATTTGGAG GAAAACAGCA
1681 GCTCTCGCTA CTCCATTCAA CTTTGATGAA GTAGATTCTC AATGGCCGAA GGGTCATTGT
1741 GTGGCAGTTA GGATAACCAG TGAGAATCCA GATGATGGAT TCAAGCCTAC TGGTGGAAAA
1801 GTAAAGGAGA TAAGTTTTAA AAGTAAGCCA AATGTCTGGG GATATTTCTC AGTTAAGTCT
1861 GGTGGAGGCA TTCATGAATT TGCGGATTCT CAGTTTGGAC ACGTTTTTGC CTATGGAGAG
1921 ACTAGATCAG CAGCAATAAC CAGCATGTCT CTTGCACTAA AAGAGATTCA AATTCGTGGA
1981 GAAATTCATA CAAACGTTGA TTACACGGTT GATCTCTTGA ATGCCCCAGA CTTCAGAGAA
2041 AACACGATCC ATACCGGTTG GCTGGATACC AGAATAGCTA TGCGTGTTCA AGCTGAGAGG
2101 CCTCCCTGGT ATATTTCAGT GGTTGGAGGA GCTCTATATA AAACAATAAC CACCAATGCG
2161 GAGACCGTTT CTGAATATGT TAGCTATCTC ATCAAGGGTC AGATTCCACC AAAGCACATA
2221 TCCCTTGTCC ATTCAACTAT TTCTTTGAAT ATAGAGGAAA GCAAATATAC AATTGAGATT
2281 GTGAGGAGTG GACAGGGTAG CTACAGATTG AGACTGAATG GATCACTTAT TGAAGCCAAT
2341 GTACAAACAT TATGTGATGG AGGCCTTTTA ATGCAGCTGG ATGGAAATAG CCATGTTATT
2401 TATGCTGAAG AAGAAGCGGG TGGTACACGG CTTCTTATTG ATGGAAAAAC ATGCTTGCTA
```

FIG. 26A

```
2461 CAGAATGACC ATGATCCGTC AAGGTTATTA GCTGAGACAC CCTGCAAACT TCTTCGTTTC
2521 TTGATTGCCG ATGGTGCTCA TGTTGATGCT GATGTACCAT ACGCGGAAGT TGAGGTTATG
2581 AAGATGTGCA TGCCCCTCTT GTCGCCTGCT GCTGGTGTCA TTAATGTTTT GTTGTCTGAG
2641 GGCCAGGCGA TGCAGGCTGG TGATCTTATA GCGAGACTTG ATCTCGATGA CCCTTCTGCT
2701 GTGAAGAGAG CCGAGCCATT TGAAGGATCT TTTCCAGAAA TGAGCCTTCC TATTGCTGCT
2761 TCTGGCCAAG TTCACAAAAG ATGTGCTGCA AGTTTGAACG CTGCTCGAAT GGTCCTTGCA
2821 GGATATGACC ATGCGGCCAA CAAAGTTGTG CAAGATTTGG TATGGTGCCT TGATACACCT
2881 GCTCTTCCTT TCCTACAATG GGAAGAGCTT ATGTCTGTTT TAGCAACTAG ACTTCCAAGA
2941 CGTCTTAAGA GCGAGTTGGA GGGCAAATAC AATGAATACA AGTTAAATGT TGACCATGTG
3001 AAGATCAAGG ATTTCCCTAC CGAGATGCTT AGAGAGACAA TCGAGGAAAA TCTTGCATGT
3061 GTTTCCGAGA AGGAAATGGT GACAATTGAG AGGCTTGTTG ACCCTCTGAT GAGCCTGCTG
3121 AAGTCATACG AGGGTGGGAG AGAAAGCCAT GCCCACTTTA TTGTCAAGTC CCTTTTTGAG
3181 GAGTATCTCT CGGTTGAGGA ACTATTCAGT GATGGCATTC AGTCTGACGT GATTGAACGC
3241 CTGCGCCTAC AATATAGTAA AGACCTCCAG AAGGTTGTAG ACATTGTTTT GTCTCACCAG
3301 GGTGTGAGAA ACAAAACAAA GCTGATACTC GCGCTCATGG AGAAACTGGT CTATCCAAAC
3361 CCTGCTGCCT ACAGAGATCA GTTGATTCGC TTTTCTTCCC TCAACCATAA AAGATATTAT
3421 AAGTTGGCTC TTAAAGCTAG TGAACTTCTT GAACAAACCA AGCTCAGCGA ACTCCGCACA
3481 AGCATTGCAA GGAACCTTTC AGCGCTGGAT ATGTTCACCG AGGAAAAGGC AGATTTCTCC
3541 TTGCAAGACA GAAAATTGGC CATTAATGAG AGCATGGGAG ATTTAGTCAC TGCCCCACTG
3601 CCAGTTGAAG ATGCACTTGT TTCTTTGTTT GATTGTACTG ATCAAACTCT TCAGCAGAGA
3661 GTGATTCAGA CATACATATC TCGATTATAC CAGCCTCAAC TTGTGAAGGA TAGCATCCAG
3721 CTGAAATATC AGGATTCTGG TGTTATTGCT TTATGGGAAT TCACTGAAGG AAATCATGAG
3781 AAGAGATTGG GTGCTATGGT TATCCTGAAG TCACTAGAAT CTGTGTCAAC AGCCATTGGA
3841 GCTGCTCTAA AGGATGCATC ACATTATGCA AGCTCTGCGG GCAACACGGT GCATATTGCT
3901 TTGTTGGATG CTGATACCCA ACTGAATACA ACTGAAGATA GTGGTGATAA TGACCAAGCT
3961 CAAGACAAGA TGGATAAACT TTCTTTTGTA CTGAAACAAG ATGTTGTCAT GGCTGATCTA
4021 CGTGCTGCTG ATGTCAAGGT TGTTAGTTGC ATTGTTCAAA GAGATGGAGC AATCATGCCT
4081 ATGCGCCGTA CCTTCCTCTT GTCAGAGGAA AAACTTTGTT ACGAGGAAGA GCCGATTCTT
4141 CGGCATGTGG AGCCTCCACT TTCTGCACTT CTTGAGTTGG ATAAATTGAA AGTGAAAGGA
4201 TACAATGAGA TGAAGTATAC ACCGTCACGT GATCGTCAGT GGCATATATA CACACTTAGA
4261 AATACTGAAA ATCCAAAAAT GCTGCACAGG GTATTTTTCC GAACACTTGT CAGACAACCC
4321 AGTGCAGGCA ACAGGTTTAC ATCAGACCAT ATCACTGATG TTGAAGTAGG ACACGCAGAG
4381 GAACCTCTTT CATTTACTTC AAGCAGCATA TTAAAATCGT TGAAGATTGC TAAAGAAGAA
4441 TTGGAGCTTC ACGCGATCAG GACTGGCCAT TCTCATATGT ACTTGTGCAT ATTGAAAGAG
4501 CAAAAGCTTC TTGACCTTGT TCCTGTTTCA GGGAACACTG TTGTGGATGT TGGTCAAGAT
4561 GAAGCTACTG CATGCTCTCT TTTGAAAGAA ATGGCTTTAA AGATACATGA ACTTGTTGGT
4621 GCAAGAATGC ATCATCTTTC TGTATGCCAG TGGGAAGTGA AACTTAAGTT GGTGAGCGAT
4681 GGGCCTGCCA GTGGTAGCTG GAGAGTTGTA ACAACCAATG TTACTGGTCA CACCTGCACT
4741 GTGGATATCT ACCGGGAGGT CGAAGATACA GAATCACAGA AACTAGTATA CCACTCCACC
4801 GCATTGTCAT CTGGTCCTTT GCATGGTGTT GCACTGAATA CTTCGTATCA GCCTTTGAGT
4861 GTTATTGATT TAAAACGTTG CTCTGCCAGG AACAACAAAA CTACATACTG CTATGATTTT
4921 CCATTGACAT TTGAAGCTGC AGTGCAGAAG TCGTGGTCTA ACATTTCCAG TGAAAACAAC
```

FIG.26A
(continued)

```
4981 CAATGTTATG TTAAAGCGAC AGAGCTTGTG TTTGCTGAAA AGAATGGGTC GTGGGGCACT
5041 CCTATAATTC CTATGCAGCG TGCTGCTGGG CTGAATGACA TTGGTATGGT AGCCTGGATC
5101 TTGGACATGT CCACTCCTGA ATTTCCCAGC GGCAGACAGA TCATTGTTAT CGCAAATGAT
5161 ATTACATTTA GAGCTGGATC ATTTGGCCCA AGGGAAGATG CATTTTTCGA AGCTGTAACC
5221 AACCTGGCTT GTGAGAAGAA GCTTCCACTT ATCTACTTGG CTGCAAACTC TGGTGCTCGG
5281 ATTGGCATTG CTGATGAAGT AAAATCTTGC TTCCGTGTTG GATGGACTGA TGATAGCAGC
5341 CCTGAACGTG GATTTAGGTA CATTTATATG ACTGACGAAG ACCATGATCG TATTGGCTCT
5401 TCAGTTATAG CACACAAGAT GCAGCTAGAT AGTGGCGAGA TCAGGTGGGT TATTGATTCT
5461 GTTGTGGGAA AAGAGGATGG ACTAGGTGTG GAGAACATAC ATGGAAGTGC TGCTATTGCC
5521 AGTGCCTATT CTAGGGCGTA CGAGGAGACA TTTACACTTA CATTCGTTAC TGGACGAACT
5581 GTTGGAATCG GAGCCTATCT TGCTCGACTT GGCATACGGT GCATACAGCG TATTGACCAG
5641 CCCATTATTT TGACCGGGTT TTCTGCCCTG AACAAGCTTC TTGGGCGGGA GGTGTACAGC
5701 TCCCACATGC AGTTGGGTGG TCCCAAAATC ATGGCGACGA ATGGTGTTGT CCATCTGACT
5761 GTTCCAGATG ACCTTGAAGG TGTTTCTAAT ATATTGAGGT GGCTCAGCTA TGTTCCTGCA
5821 AACATTGGTG GACCTCTTCC TATTACAAAA TCTTTGGACC CAATAGACAG ACCCGTTGCA
5881 TACATCCCTG AGAATACATG TGATCCTCGT GCAGCCATCA GTGGCATTGA TGACAGCCAA
5941 GGGAAATGGT TGGGTGGCAT GTTTGACAAA GACAGTTTTG TGGAGACATT TGAAGGATGG
6001 GCGAAGACAG TAGTTACTGG CAGAGCAAAA CTTGGAGGGA TTCCTGTTGG TGTTATAGCT
6061 GTGGAGACAC AGACCATGAT GCAGCTCGTC CCCGCTGATC CAGGCCAGCC TGATTCCCAC
6121 GAGCGGTCTG TTCCTCGTGC TGGGCAAGTT TGGTTTCCAG ATTCTGCTAC CAAGACAGCG
6181 CAGGCGATGT TGGACTTCAA CCGTGAAGGA TTACCTCTGT TCATACTTGC TAACTGGAGA
6241 GGCTTCTCTG GAGGGCAAAG AGATCTTTTT GAAGGAATTC TGCAGGCTGG GTCAACAATT
6301 GTTGAGAACC TTAGGACATA CAATCAGCCT GCCTTTGTAT ATATCCCCAA GGCTGCAGAG
6361 CTACGTGGAG GAGCCTGGGT CGTGATTGAT AGCAAGATAA ACCCAGATCG CATCGAGTGC
6421 TATGCTGAGA GGACTGCAAA GGGTAATGTT CTCGAACCTC AAGGGTTGAT TGAGATCAAG
6481 TTCAGGTCAG AGGAACTCAA AGAATGCATG GGTAGGCTTG ATCCAGAATT GATAGATCTG
6541 AAAGCAAGAC TCCAGGGAGC AAATGGAAGC CTATCTGATG GAGAATCCCT TCAGAAGAGC
6601 ATAGAAGCTC GGAAGAAACA GTTGCTGCCT CTGTACACCC AAATCGCGGT ACGTTTTGCG
6661 GAATTGCACG ACACTTCCCT TAGAATGGCT GCTAAAGGTG TGATCAGGAA AGTTGTAGAC
6721 TGGGAAGACT CTCGGTCTTT CTTCTACAAG AGATTACGGA GGAGGCTATC CGAGGACGTT
6781 CTGGCAAAGG AGATTAGAGG TGTAATTGGT GAGAAGTTTC CTCACAAATC AGCGATCGAG
6841 CTGATCAAGA AATGGTACTT GGCTTCTGAG GCAGCTGCAG CAGGAAGCAC CGACTGGGAT
6901 GACGACGATG CTTTTGTCGC CTGGAGGGAG AACCCTGAAA ACTATAAGGA GTATATCAAA
6961 GAGCTTAGGG CTCAAAGGGT ATCTCGGTTG CTCTCAGATG TTGCAGGCTC CAGTTCGGAT
7021 TTACAAGCCT TGCCGCAGGG TCTTTCCATG CTACTAGATA AGATGGATCC CTCTAAGAGA
7081 GCACAGTTTA TCGAGGAGGT CATGAAGGTC CTGAAATGAT CAAATGATAC CAACACATCC
7141 AATACAGTAT GTGCATGATA TCTGTTTCTC TTGAAGTACA TATATAGATG GATACAAGGC
7201 GGCTGTAACT GATGGTAGCT AATCTGGGCC AACCATTACT TTTGTGAACT TGCTGGTGGC
7261 CTTTATTATT CAAGGCACAG CTCGCCTTCG GACCCCCTCC GGCTGGTTGA TGATGAGTGT
7321 AACTGGATGT GTTAGTTCTG CTGCCACAGA ATTCGAGAAG GATAGGGGCA TGCGGGTTTT
7381 GCCTCCTGTT GGCAAGAACA CTGGTGATTT TGAGTTCTTG TTATGTGGAC TGTGGTAGTC
7441 TTGTTTCGCT GTAGTTCTGT GATGTTCTAT CTCCTGTAAT TCTAGTCTTG GGAGAGTGAT
7501 TCAGATGTCC ATTCAATTTT GAACTTGAAT AATAATATGC TTTGTAGGCC TATGCGTACC
7561 AGTATGTGGA ATAAATGTTC GTTGAGTTA
```

FIG.26A (continued)

AMY310767 - Alopecurus myosuroides plastidal ACCase translated protein

```
   1    MGSTHLPIVG FNASTTPSLS TLRQINSAAA AFQSSSPSRS SKKKSRRVKS
  51    IRDDGDGSVP DPAGHGQSIR QGLAGIIDLP KEGASAPDVD ISHGSEDHKA
 101    SYQMNGILNE SHNGRHASLS KVYEFCTELG GKTPIHSVLV ANNGMAAAKF
 151    MRSVRTWAND TFGSEKAIQL IAMATPEDMR INAEHIRIAD QFVEVPGGTN
 201    NNNYANVQLI VEIAERTGVS AVWPGWGHAS ENPELPDALT AKGIVFLGPP
 251    ASSMNALGDK VGSALIAQAA GVPTLAWSGS HVEIPLELCL DSIPEEMYRK
 301    ACVTTADEAV ASCQMIGYPA MIKASWGGGG KGIRKVNNDD EVKALFKQVQ
 351    GEVPGSPIFI MRLASQSRHL EVQLLCDEYG NVAALHSRDC SVQRRHQKII
 401    EEGPVTVAPR ETVKELEQAA RRLAKAVGYV GAATVEYLYS METGEYYFLE
 451    LNPRLQVEHP VTESIAEVNL PAAQVAVGMG IPLWQIPEIR RFYGMDNGGG
 501    YDIWRKTAAL ATPFNFDEVD SQWPKGHCVA VRITSENPDD GFKPTGGKVK
 551    EISFKSKPNV WGYFSVKSGG GIHEFADSQF GHVFAYGETR SAAITSMSLA
 601    LKEIQIRGEI HTNVDYTVDL LNAPDFRENT IHTGWLDTRI AMRVQAERPP
 651    WYISVVGGAL YKTITTNAET VSEYVSYLIK GQIPPKHISL VHSTISLNIE
 701    ESKYTIEIVR SGQGSYRLRL NGSLIEANVQ TLCDGGLLMQ LDGNSHVIYA
 751    EEEAGGTRLL IDGKTCLLQN DHDPSRLLAE TPCKLLRFLI ADGAHVDADV
 801    PYAEVEVMKM CMPLLSPAAG VINVLLSEGQ AMQAGDLIAR LDLDDPSAVK
 851    RAEPFEGSFP EMSLPIAASG QVHKRCAASL NAARMVLAGY DHAANKVVQD
 901    LVWCLDTPAL PFLQWEELMS VLATRLPRRL KSELEGKYNE YKLNVDHVKI
 951    KDFPTEMLRE TIEENLACVS EKEMVTIERL VDPLMSLLKS YEGGRESHAH
1001    FIVKSLFEEY LSVEELFSDG IQSDVIERLR LQYSKDLQKV VDIVLSHQGV
1051    RNKTKLILAL MEKLVYPNPA AYRDQLIRFS SLNHKRYYKL ALKASELLEQ
1101    TKLSELRTSI ARNLSALDMF TEEKADFSLQ DRKLAINESM GDLVTAPLPV
1151    EDALVSLFDC TDQTLQQRVI QTYISRLYQP QLVKDSIQLK YQDSGVIALW
1201    EFTEGNHEKR LGAMVILKSL ESVSTAIGAA LKDASHYASS AGNTVHIALL
1251    DADTQLNTTE DSGDNDQAQD KMDKLSFVLK QDVVMADLRA ADVKVVSCIV
1301    QRDGAIMPMR RTFLLSEEKL CYEEEPILRH VEPPLSALLE LDKLKVKGYN
1351    EMKYTPSRDR QWHIYTLRNT ENPKMLHRVF FRTLVRQPSA GNRFTSDHIT
1401    DVEVGHAEEP LSFTSSSILK SLKIAKEELE LHAIRTGHSH MYLCILKEQK
1451    LLDLVPVSGN TVVDVGQDEA TACSLLKEMA LKIHELVGAR MHHLSVCQWE
1501    VKLKLVSDGP ASGSWRVVTT NVTGHTCTVD IYREVEDTES QKLVYHSTAL
1551    SSGPLHGVAL NTSYQPLSVI DLKRCSARNN KTTYCYDFPL TFEAAVQKSW
1601    SNISSENNQC YVKATELVFA EKNGSWGTPI IPMQRAAGLN DIGMVAWILD
1651    MSTPEFPSGR QIIVIANDIT FRAGSFGPRE DAFFEAVTNL ACEKKLPLIY
1701    LAANSGARIG IADEVKSCFR VGWTDDSSPE RGFRYIYMTD EDHDRIGSSV
1751    IAHKMQLDSG EIRWVIDSVV GKEDGLGVEN IHGSAAIASA YSRAYEETFT
1801    LTFVTGRTVG IGAYLARLGI RCIQRIDQPI ILTGFSALNK LLGREVYSSH
1851    MQLGGPKIMA TNGVVHLTVP DDLEGVSNIL RWLSYVPANI GGPLPITKSL
1901    DPIDRPVAYI PENTCDPRAA ISGIDDSQGK WLGGMFDKDS FVETFEGWAK
1951    TVVTGRAKLG GIPVGVIAVE TQTMMQLVPA DPGQPDSHER SVPRAGQVWF
2001    PDSATKTAQA MLDFNREGLP LFILANWRGF SGGQRDLFEG ILQAGSTIVE
2051    NLRTYNQPAF VYIPKAAELR GGAWVVIDSK INPDRIECYA ERTAKGNVLE
2101    PQGLIEIKFR SEELKECMGR LDPELIDLKA RLQGANGSLS DGESLQKSIE
2151    ARKKQLLPLY TQIAVRFAEL HDTSLRMAAK GVIRKVVDWE DSRSFFYKRL
2201    RRRLSEDVLA KEIRGVIGEK FPHKSAIELI KKWYLASEAA AAGSTDWDDD
2251    DAFVAWRENP ENYKEYIKEL RAQRVSRLLS DVAGSSSDLQ ALPQGLSMLL
2301    DKMDPSKRAQ FIEEVMKVLK
```

FIG.26B

Oryza sativa plastidal ACCase Os05g22940 rice cDNA(Cypress)

```
   1 ATGACATCCA CACATGTGGC GACATTGGGA GTTGGTGCCC AGGCACCTCC TCGTCACCAG
  61 AAAAAGTCAG CTGGCACTGC ATTTGTATCA TCTGGGTCAT CAAGACCCTC ATACCGAAAG
 121 AATGGTCAGC GTACTCGGTC ACTTAGGGAA GAAAGCAATG GAGGAGTGTC TGATTCCAAA
 181 AAGCTTAACC ACTCTATTCG CCAAGGTCTT GCTGGCATCA TTGACCTCCC AAATGACGCA
 241 GCTTCAGAAG TTGATATTTC ACATGGTTCC GAAGATCCCA GGGGGCCTAC GGTCCCAGGT
 301 TCCTACCAAA TGAATGGGAT TATCAATGAA ACACATAATG GGAGGCATGC TTCAGTCTCC
 361 AAGGTTGTTG AGTTTTGTAC GGCACTTGGT GGCAAAACAC CAATTCACAG TGTATTAGTG
 421 GCCAACAATG GAATGGCAGC AGCTAAGTTC ATGCGGAGTG TCCGAACATG GCTAATGAT
 481 ACTTTTGGAT CAGAGAAGGC AATTCAGCTG ATAGCTATGG CAACTCCGGA GGATCTGAGG
 541 ATAAATGCAG AGCACATCAG AATTGCCGAT CAATTTGTAG AGGTACCTGG TGGAACAAAC
 601 AACAACAACT ATGCAAATGT CCAACTCATA GTGGAGATAG CAGAGAGAAC AGGTGTTTCT
 661 GCTGTTTGGC CTGGTTGGGG TCATGCATCT GAGAATCCTG AACTTCCAGA TGCGCTGACT
 721 GCAAAAGGAA TTGTTTTTCT TGGGCCACCA GCATCATCAA TGCATGCATT AGGAGACAAG
 781 GTTGGCTCAG CTCTCATTGC TCAAGCAGCT GGAGTTCCAA CACTTGCTTG GAGTGGATCA
 841 CATGTGGAAG TTCCTCTGGA GTGTTGCTTG GACTCAATAC CTGATGAGAT GTATAGAAAA
 901 GCTTGTGTTA CTACCACAGA GGAAGCAGTT GCAAGTTGTC AGGTGGTTGG TTATCCTGCC
 961 ATGATTAAGG CATCTTGGGG TGGTGGTGGT AAAGGAATAA GGAAGGTTCA TAATGATGAT
1021 GAGGTTAGGA CATTATTTAA GCAAGTTCAA GGCGAAGTAC CTGGTTCCCC AATATTTATC
1081 ATGAGGCTAG CTGCTCAGAG TCGACATCTT GAAGTTCAGT TGCTTTGTGA TCAATATGGC
1141 AACGTAGCAG CACTTCACAG TCGAGATTGC AGTGTACAAC GGCGACACCA AAAGATAATC
1201 GAGGAAGGAC CAGTTACTGT TGCTCCTCGT GAGACTGTGA AAGAGCTTGA GCAGGCAGCA
1261 CGGAGGCTTG CTAAAGCTGT GGGTTATGTT GGTGCTGCTA CTGTTGAATA CCTTTACAGC
1321 ATGGAAACTG GTGAATATTA TTTTCTGGAA CTTAATCCAC GGCTACAGGT TGAGCATCCT
1381 GTCACTGAGT GGATAGCTGA AGTAAATTTG CCTGCGGCTC AAGTTGCTGT TGGAATGGGT
1441 ATACCCCTTT GGCAGATTCC AGAGATCAGG CGCTTCTACG GAATGAACCA TGGAGGAGGC
1501 TATGACCTTT GGAGGAAAAC AGCAGCTCTA GCGACTCCAT TTAACTTTGA TGAAGTAGAT
1561 TCTAAATGGC CAAAAGGCCA CTGCGTAGCT GTTAGAATAA CTAGCGAGGA TCCAGATGAT
1621 GGGTTTAAGC CTACTGGTGG AAAAGTAAAG GAGATAAGTT TCAAGAGTAA ACCAAATGTT
1681 TGGGCCTATT TCTCAGTAAA GTCTGGTGGA GGCATCCATG AATTCGCTGA TTCTCAGTTC
1741 GGACATGTTT TTGCGTATGG AACTACTAGA TCGGCAGCAA TAACTACCAT GGCTCTTGCA
1801 CTAAAAGAGG TTCAAATTCG TGGAGAAATT CATTCAAACG TAGACTACAC AGTTGACCTA
1861 TTAAATGCCT CAGATTTTAG AGAAAATAAG ATTCATACTG GTTGGCTGGA TACCAGGATA
1921 GCCATGCGTG TTCAAGCTGA GAGGCCTCCA TGGTATATTT CAGTCGTTGG AGGGGCTTTA
1981 TATAAAACAG TAACTGCCAA CACGGCCACT GTTTCTGATT ATGTTGGTTA TCTTACCAAG
2041 GGCCAGATTC CACCAAAGCA TATATCCCTT GTCTATACGA CTGTTGCTTT GAATATAGAT
2101 GGGAAAAAAT ATACAATCGA TACTGTGAGG AGTGGACATG GTAGCTACAG ATTGCGAATG
2161 AATGGATCAA CGGTTGACGC AAATGTACAA ATATTATGTG ATGGTGGGCT TTTAATGCAG
2221 CTGGATGGAA ACAGCCATGT AATTTATGCT GAAGAAGAGG CCAGTGGTAC ACGACTTCTT
2281 ATTGATGGAA AGACATGCAT GTTACAGAAT GACCATGACC CATCAAAGTT ATTAGCTGAG
2341 ACACCATGCA AACTTCTTCG TTTCTTGGTT GCTGATGGTG CTCATGTTGA TGCTGATGTA
```

FIG.26C

```
2401 CCATATGCGG AAGTTGAGGT TATGAAGATG TGCATGCCCC TCTTATCACC CGCTTCTGGT
2461 GTCATACATG TTGTAATGTC TGAGGGCCAA GCAATGCAGG CTGGTGATCT TATAGCTAGG
2521 CTGGATCTTG ATGACCCTTC TGCTGTTAAG AGAGCTGAGC CGTTCGAAGA TACTTTTCCA
2581 CAAATGGGTC TCCCTATTGC TGCTTCTGGC CAAGTTCACA AATTATGTGC TGCAAGTCTG
2641 AATGCTTGTC GAATGATCCT TGCGGGGTAT GAGCATGATA TTGACAAGGT TGTGCCAGAG
2701 TTGGTATACT GCCTAGACAC TCCGGAGCTT CCTTTCCTGC AGTGGGAGGA GCTTATGTCT
2761 GTTTTAGCAA CTAGACTTCC AAGAAATCTT AAAAGTGAGT TGGAGGGCAA ATATGAGGAA
2821 TACAAAGTAA AATTTGACTC TGGGATAATC AATGATTTCC CTGCCAATAT GCTACGAGTG
2881 ATAATTGAGG AAAATCTTGC ATGTGGTTCT GAGAAGGAGA AGGCTACAAA TGAGAGGCTT
2941 GTTGAGCCTC TTATGAGCCT ACTGAAGTCA TATGAGGGTG GGAGAGAAAG TCATGCTCAC
3001 TTTGTTGTCA AGTCCCTTTT TGAGGAGTAT CTCTATGTTG AAGAATTGTT CAGTGATGGA
3061 ATTCAGTCTG ATGTGATTGA GCGTCTGCGC CTTCAACATA GTAAAGACCT ACAGAAGGTC
3121 GTAGACATTG TGTTGTCCCA CCAGAGTGTT AGAAATAAAA CTAAGCTGAT ACTAAAACTC
3181 ATGGAGAGTC TGGTCTATCC AAATCCTGCT GCCTACAGGG ATCAATTGAT TCGCTTTTCT
3241 TCCCTTAATC ACAAAGCGTA TTACAAGTTG GCACTTAAAG CTAGTGAACT TCTTGAACAA
3301 ACAAAACTTA GTGAGCTCCG TGCAAGAATA GCAAGGAGCC TTTCAGAGCT GGAGATGTTT
3361 ACTGAGGAAA GCAAGGGTCT CTCCATGCAT AAGCGAGAAA TTGCCATTAA GGAGAGCATG
3421 GAAGATTTAG TCACTGCTCC ACTGCCAGTT GAAGATGCGC TCATTTCTTT ATTTGATTGT
3481 AGTGATACAA CTGTTCAACA GAGAGTGATT GAGACTTATA TAGCTCGATT ATACCAGCCT
3541 CATCTTGTAA AGGACAGTAT CAAAATGAAA TGGATAGAAT CGGGTGTTAT TGCTTTATGG
3601 GAATTTCCTG AAGGGCATTT TGATGCAAGA AATGGAGGAG CGGTTCTTGG TGACAAAAGA
3661 TGGGGTGCCA TGGTCATTGT CAAGTCTCTT GAATCACTTT CAATGGCCAT TAGATTTGCA
3721 CTAAAGGAGA CATCACACTA CACTAGCTCT GAGGGCAATA TGATGCATAT TGCTTTGTTG
3781 GGTGCTGATA ATAAGATGCA TATAATTCAA GAAAGTGGTG ATGATGCTGA CAGAATAGCC
3841 AAACTTCCCT TGATACTAAA GGATAATGTA ACCGATCTGC ATGCCTCTGG TGTGAAAACA
3901 ATAAGTTTCA TTGTTCAAAG AGATGAAGCA CGGATGACAA TGCGTCGTAC CTTCCTTTGG
3961 TCTGATGAAA AGCTTTCTTA TGAGGAAGAG CCAATTCTCC GGCATGTGGA ACCTCCTCTT
4021 TCTGCACTTC TTGAGTTGGA CAAGTTGAAA GTGAAAGGAT ACAATGAAAT GAAGTATACC
4081 CCATCACGGG ATCGTCAATG GCATATCTAC ACACTTAGAA ATACTGAAAA CCCCAAAATG
4141 TTGCACCGGG TATTTTTCCG AACCCTTGTC AGGCAACCCA GTGTATCCAA CAAGTTTTCT
4201 TCGGGCCAGA TTGGTGACAT GGAAGTTGGG AGTGCTGAAG AACCTCTGTC ATTTACATCA
4261 ACCAGCATAT TAAGATCTTT GATGACTGCT ATAGAGGAAT TGGAGCTTCA CGCAATTAGA
4321 ACTGGCCATT CACACATGTA TTTGCATGTA TTGAAAGAAC AAAAGCTTCT TGATCTTGTT
4381 CCAGTTTCAG GGAATACAGT TTTGGATGTT GGTCAAGATG AAGCTACTGC ATATTCACTT
4441 TTAAAAGAAA TGGCTATGAA GATACATGAA CTTGTTGGTG CAAGAATGCA CCATCTTTCT
4501 GTATGCCAAT GGGAAGTGAA ACTTAAGTTG GACTGCGATG GTCCTGCCAG TGGTACCTGG
4561 AGGATTGTAA CAACCAATGT TACTAGTCAC ACTTGCACTG TGGATATCTA CCGTGAGATG
4621 GAAGATAAAG AATCACGGAA GTTAGTATAC CATCCCGCCA CTCCGGCGGC TGGTCCTCTG
4681 CATGGTGTGG CACTGAATAA TCCATATCAG CCTTTGAGTG TCATTGATCT CAAACGCTGT
4741 TCTGCTAGGA ATAATAGAAC TACATACTGC TATGATTTTC CACTGGCATT TGAAACTGCA
4801 GTGAGGAAGT CATGGTCCTC TAGTACCTCT GGTGCTTCTA AAGGTGTTGA AAATGCCCAA
4861 TGTTATGTTA AAGCTACAGA GTTGGTATTT GCGGACAAAC ATGGGTCATG GGGCACTCCT
```

FIG.26C
(continued)

```
4921 TTAGTTCAAA TGGACCGGCC TGCTGGGCTC AATGACATTG GTATGGTAGC TTGGACCTTG
4981 AAGATGTCCA CTCCTGAATT TCCTAGTGGT AGGGAGATTA TTGTTGTTGC AAATGATATT
5041 ACGTTCAGAG CTGGATCATT TGGCCCAAGG GAAGATGCAT TTTTTGAAGC TGTTACCAAC
5101 CTAGCCTGTG AGAAGAAACT TCCTCTTATT TATTTGGCAG CAAATTCTGG TGCTCGAATT
5161 GGCATAGCAG ATGAAGTGAA ATCTTGCTTC CGTGTTGGGT GGTCTGATGA TGGCAGCCCT
5221 GAACGTGGGT TTCAGTACAT TTATCTAAGC GAAGAAGACT ATGCTCGTAT TGGCACTTCT
5281 GTCATAGCAC ATAAGATGCA GCTAGACAGT GGTGAAATTA GGTGGGTTAT TGATTCTGTT
5341 GTGGGCAAGG AAGATGGACT TGGTGTGGAG AATATACATG GAAGTGCTGC TATTGCCAGT
5401 GCTTATTCTA GGGCATATAA GGAGACATTT ACACTTACAT TTGTGACTGG AAGAACTGTT
5461 GGAATAGGAG CTTATCTTGC TCGACTTGGC ATCCGGTGCA TACAGCGTCT TGACCAGCCT
5521 ATTATTCTTA CAGGCTATTC TGCACTGAAC AAGCTTCTTG GGCGGGAAGT GTACAGCTCC
5581 CACATGCAGT TGGGTGGTCC CAAAATCATG GCAACTAATG GTGTTGTCCA TCTTACTGTT
5641 TCAGATGACC TTGAAGGCGT TTCTAATATA TTGAGGTGGC TCAGTTATGT TCCTGCCTAC
5701 ATTGGTGGAC CACTTCCAGT AACAACACCG TTGGACCCAC CGGACAGACC TGTTGCATAC
5761 ATTCCTGAGA ACTCGTGTGA TCCTCGAGCG GCTATCCGTG GTGTTGATGA CAGCCAAGGG
5821 AAATGGTTAG GTGGTATGTT TGATAAAGAC AGCTTTGTGG AAACATTTGA AGGTTGGGCT
5881 AAGACAGTGG TTACTGGCAG AGCAAAGCTT GGTGGAATTC CAGTGGGTGT GATAGCTGTG
5941 GAGACTCAGA CCATGATGCA AACTATCCCT GCTGACCCTG GTCAGCTTGA TTCCCGTGAG
6001 CAATCTGTTC CTCGTGCTGG ACAAGTGTGG TTTCCAGATT CTGCAACCAA GACTGCGCAG
6061 GCATTGCTGG ACTTCAACCG TGAAGGATTA CCTCTGTTCA TCCTCGCTAA CTGGAGAGGC
6121 TTCTCTGGTG GACAAAGAGA TCTTTTTGAA GGAATTCTTC AGGCTGGCTC GACTATTGTT
6181 GAGAACCTTA GGACATACAA TCAGCCTGCC TTTGTCTACA TTCCCATGGC TGCAGAGCTA
6241 CGAGGAGGGG CTTGGGTTGT GGTTGATAGC AAGATAAACC CAGACCGCAT TGAGTGCTAT
6301 GCTGAGAGGA CTGCAAAAGG CAATGTTCTG GAACCGCAAG GGTTAATTGA GATCAAGTTC
6361 AGGTCAGAGG AACTCCAGGA TTGCATGAGT CGGCTTGACC CAACATTAAT TGATCTGAAA
6421 GCAAAACTCG AAGTAGCAAA TAAAAATGGA AGTGCTGACA CAAAATCGCT TCAAGAAAAT
6481 ATAGAAGCTC GAACAAAACA GTTGATGCCT CTATATACTC AGATTGCGAT ACGGTTTGCT
6541 GAATTGCATG ATACATCCCT CAGAATGGCT GCGAAAGGTG TGATTAAGAA AGTTGTGGAC
6601 TGGGAAGAAT CACGATCTTT CTTCTATAAG AGATTACGGA GGAGGATCTC TGAGGATGTT
6661 CTTGCAAAAG AAATTAGAGC TGTAGCAGGT GAGCAGTTTT CCCACCAACC AGCAATCGAG
6721 CTGATCAAGA AATGGTATTC AGCTTCACAT GCAGCTGAAT GGGATGATGA CGATGCTTTT
6781 GTTGCTTGGA TGGATAACCC TGAAAACTAC AAGGATTATA TTCAATATCT TAAGGCTCAA
6841 AGAGTATCCC AATCCCTCTC AAGTCTTTCA GATTCCAGCT CAGATTTGCA AGCCCTGCCA
6901 CAGGGTCTTT CCATGTTACT AGATAAGATG GATCCCTCTA GAAGAGCTCA ACTTGTTGAA
6961 GAAATCAGGA AGGTCCTTGG TTGAATCATA TGATGCCAAA ACTATTATTG GAGGCACAAA
7021 TAGCTTGTGG ACCCTGTCGG ATTGTTGGTG AGTGTATATT GGATTTGTTA GTTCTGCCAG
7081 ATGAAAGTGC AAGTCTGATG ATTCATGATA CCGTCAGTTG GCAAGAACAC CGGTTAACCT
7141 GAGTGCTTGT TTACAAATGG TCCTTTATGA CAATCGTTGT TTCGCGCTAG TTCCGTGATC
7201 TACTATCATC TGTTAGACGC TGTAATTAGT GAGTCTCCGC GGATCCACAG TATACGGTTG
7261 AGCTGTTGAT TCAATTTTGG ACACGAATAA TATGATTTTG TAGGCATAAA TGCGTCTGTA
7321 TGTGAAATAA ATTGTCTGTT GAGTTAACAC ACAAGATGAC AATATGTTTG TGCTCTACTG
7381 CTATTGTCCA TGAATACTGA TTGCGGAATC AACCACATGC ATTAT
```

FIG.26C (continued)

Oryza sativa plastidal ACCase Os05g22940 rice protein (Cypress)

```
   1  MTSTHVATLG VGAQAPPRHQ KKSAGTAFVS SGSSRPSYRK NGQRTRSLRE
  51  ESNGGVSDSK KLNHSIRQGL AGIIDLPNDA ASEVDISHGS EDPRGPTVPG
 101  SYQMNGIINE THNGRHASVS KVVEFCTALG GKTPIHSVLV ANNGMAAAKF
 151  MRSVRTWAND TFGSEKAIQL IAMATPEDLR INAEHIRIAD QFVEVPGGTN
 201  NNNYANVQLI VEIAERTGVS AVWPGWGHAS ENPELPDALT AKGIVFLGPP
 251  ASSMHALGDK VGSALIAQAA GVPTLAWSGS HVEVPLECCL DSIPDEMYRK
 301  ACVTTTEEAV ASCQVVGYPA MIKASWGGGG KGIRKVHNDD EVRTLFKQVQ
 351  GEVPGSPIFI MRLAAQSRHL EVQLLCDQYG NVAALHSRDC SVQRRHQKII
 401  EEGPVTVAPR ETVKELEQAA RRLAKAVGYV GAATVEYLYS METGEYYFLE
 451  LNPRLQVEHP VTEWIAEVNL PAAQVAVGMG IPLWQIPEIR RFYGMNHGGG
 501  YDLWRKTAAL ATPFNFDEVD SKWPKGHCVA VRITSEDPDD GFKPTGGKVK
 551  EISFKSKPNV WAYFSVKSGG GIHEFADSQF GHVFAYGTTR SAAITTMALA
 601  LKEVQIRGEI HSNVDYTVDL LNASDFRENK IHTGWLDTRI AMRVQAERPP
 651  WYISVVGGAL YKTVTANTAT VSDYVGYLTK GQIPPKHISL VYTTVALNID
 701  GKKYTIDTVR SGHGSYRLRM NGSTVDANVQ ILCDGGLLMQ LDGNSHVIYA
 751  EEEASGTRLL IDGKTCMLQN DHDPSKLLAE TPCKLLRFLV ADGAHVDADV
 801  PYAEVEVMKM CMPLLSPASG VIHVVMSEGQ AMQAGDLIAR LDLDDPSAVK
 851  RAEPFEDTFP QMGLPIAASG QVHKLCAASL NACRMILAGY EHDIDKVVPE
 901  LVYCLDTPEL PFLQWEELMS VLATRLPRNL KSELEGKYEE YKVKFDSGII
 951  NDFPANMLRV IIEENLACGS EKEKATNERL VEPLMSLLKS YEGGRESHAH
1001  FVVKSLFEEY LYVEELFSDG IQSDVIERLR LQHSKDLQKV VDIVLSHQSV
1051  RNKTKLILKL MESLVYPNPA AYRDQLIRFS SLNHKAYYKL ALKASELLEQ
1101  TKLSELRARI ARSLSELEMF TEESKGLSMH KREIAIKESM EDLVTAPLPV
1151  EDALISLFDC SDTTVQQRVI ETYIARLYQP HLVKDSIKMK WIESGVIALW
1201  EFPEGHFDAR NGGAVLGDKR WGAMVIVKSL ESLSMAIRFA LKETSHYTSS
1251  EGNMMHIALL GADNKMHIIQ ESGDDADRIA KLPLILKDNV TDLHASGVKT
1301  ISFIVQRDEA RMTMRRTFLW SDEKLSYEEE PILRHVEPPL SALLELDKLK
1351  VKGYNEMKYT PSRDRQWHIY TLRNTENPKM LHRVFFRTLV RQPSVSNKFS
1401  SGQIGDMEVG SAEEPLSFTS TSILRSLMTA IEELELHAIR TGHSHMYLHV
1451  LKEQKLLDLV PVSGNTVLDV GQDEATAYSL LKEMAMKIHE LVGARMHHLS
1501  VCQWEVKLKL DCDGPASGTW RIVTTNVTSH TCTVDIYREM EDKESRKLVY
1551  HPATPAAGPL HGVALNNPYQ PLSVIDLKRC SARNNRTTYC YDFPLAFETA
1601  VRKSWSSSTS GASKGVENAQ CYVKATELVF ADKHGSWGTP LVQMDRPAGL
1651  NDIGMVAWTL KMSTPEFPSG REIIVVANDI TFRAGSFGPR EDAFFEAVTN
1701  LACEKKLPLI YLAANSGARI GIADEVKSCF RVGWSDDGSP ERGFQYIYLS
1751  EEDYARIGTS VIAHKMQLDS GEIRWVIDSV VGKEDGLGVE NIHGSAAIAS
1801  AYSRAYKETF TLTFVTGRTV GIGAYLARLG IRCIQRLDQP IILTGYSALN
1851  KLLGREVYSS HMQLGGPKIM ATNGVVHLTV SDDLEGVSNI LRWLSYVPAY
1901  IGGPLPVTTP LDPPDRPVAY IPENSCDPRA AIRGVDDSQG KWLGGMFDKD
1951  SFVETFEGWA KTVVTGRAKL GGIPVGVIAV ETQTMMQTIP ADPGQLDSRE
2001  QSVPRAGQVW FPDSATKTAQ ALLDFNREGL PLFILANWRG FSGGQRDLFE
2051  GILQAGSTIV ENLRTYNQPA FVYIPMAAEL RGGAWVVVDS KINPDRIECY
2101  AERTAKGNVL EPQGLIEIKF RSEELQDCMS RLDPTLIDLK AKLEVANKNG
2151  SADTKSLQEN IEARTKQLMP LYTQIAIRFA ELHDTSLRMA AKGVIKKVVD
2201  WEESRSFFYK RLRRRISEDV LAKEIRAVAG EQFSHQPAIE LIKKWYSASH
2251  AAEWDDDDAF VAWMDNPENY KDYIQYLKAQ RVSQSLSSLS DSSSDLQALP
2301  QGLSMLLDKM DPSRRAQLVE EIRKVLG
```

FIG. 26D

*Oryza sativa* plastidal ACCase Os05g22940 rice genomic DNA - AP008211 reverse complemented fragment

```
   1 TCATTCTTAT ATATTTTCAT CTGTCAGATT TCACACATCT GGGGATTTAT CTTCTCTTTG
  61 TATGGCACTA CACATTTGAG AAACCGTGCA ATTCTACTGT TTGGTCAGCA GGACAACAAT
 121 GACATCCACA CATGTGGCGA CATTGGGAGT TGGTGCCCAG GCACCTCCTC GTCACCAGAA
 181 AAAGTCAGCT GGCACTGCAT TTGTATCATC TGGGTCATCA AGACCCTCAT ACCGAAAGAA
 241 TGGTCAGCGT ACTCGGTCAC TTAGGGAAGA AAGCAATGGA GGAGTGTCTG ATTCCAAAAA
 301 GCTTAACCAC TCTATTCGCC AAGGTGACCA CTAGCTACTT TACATATGCT ATAATTTGTG
 361 CCAAACATAA ACATGCAATG GCTGCTATTA TTTAAACGTT AATGTTGAAA TAGCTGCTAT
 421 AGGATACAGC AAAAATATAT AATTGACTGG GCAAGATGCA ACAATTGTTT TTCACTAAAG
 481 TTAGTTATCT TTTGCTGTAA AAGACAACTG TTTTTTACAT AAAATGGTAT TAATAACCTT
 541 GTAATATTCA ATGCAACATG TTCTCAAGTA AAAAAAAACA TTGCCTGGTT GTATAAGCAA
 601 ATGTGTCGTT GTAGACATCT TATTAAACCT TTTTGTGATA TCTATTACCG TAGGGAACAG
 661 GGGAGCTGTT TAAATCTGTT ATCATAGAGT AATATGAGAA AAGTGGATTG TGCGACTTTG
 721 GCATGTATAC CTGCTCAATT TCAAATATAT GTCTATGTGC AGGTCTTGCT GGCATCATTG
 781 ACCTCCCAAA TGACGCAGCT TCAGAAGTTG ATATTTCACA GTAAGGACTT TATATTTTAT
 841 AATAATTATT ATATAATTTT CTGACATGTT TTGAGAACCT CAAAACATGT GATTGCACCT
 901 TCCTTTTTTA TGTCTGGTTC AGAAACTGAT AAGTTTTGAC AGTGTTTAGG ATGGATCTTT
 961 GATGCGCACA GTGCTTTCTA ATGTTTTCAT TTTTGAAAGT AATGTTTTAG GAAGAAATAT
1021 CTGATTAAAT TTATACTTTA TCTTTACAAA AGTCAAATGC GTTCTGTATC AATTGCGGTT
1081 TGTAATATGG CAAGAACATG CTTTCAGAAT TTGTTCATAC AATGCTTTCT TTCTATTATT
1141 ATGTAGAACA AATACCTAAT ACTTTGTTCA CCTTTTATAG TGGACACCTC TCACAGCTTT
1201 TTCAGTAAGT GATGCAATTT TGTACATTTG TAAGATGTGT TCCAGAAACC TTTTCTCCTG
1261 CAATTCTAAT GTACCCACTC AAACTGGTAT CACCAAAGAT CTCCATCTGA TTGAAAAAAA
1321 GCTGCGTGAA GTATGCTTAT TTATGCTAAC CATACATGAT TTATACTGTT TTATAGTACA
1381 ATGCTTATTT ATGCTAACCA TACATAATTT TATTCTGTTT TCTAGTACAT TATTTGTGCC
1441 CCTGACCATA AATGATCCTT TCTTTTACAG TGGTTCCGAA GATCCCAGGG GGCCTACGGT
1501 CCCAGGTTCC TACCAAATGA ATGGGATTAT CAATGAAACA CATAATGGGA GGCATGCTTC
1561 AGTCTCCAAG GTTGTTGAGT TTTGTACGGC ACTTGGTGGC AAAACACCAA TTCACAGTGT
1621 ATTAGTGGCC AACAATGGAA TGGCAGCAGC TAAGTTCATG CGGAGTGTCC GAACATGGGC
1681 TAATGATACT TTTGGATCAG AGAAGGCAAT TCAGCTGATA GCTATGGCAA CTCCGGAGGA
1741 TCTGAGGATA AATGCAGAGC ACATCAGAAT TGCCGATCAA TTTGTAGAGG TACCTGGTGG
1801 AACAAACAAC AACAACTATG CAAATGTCCA ACTCATAGTG GAGGTTAGTT CAGCTCATCC
1861 CTCAACACAA CATTTTCGTT TCTATTTAAG TTAGGGAAAA ATCTCTACGA CCCTCCAATT
1921 TCTGAACATC CAATTTTCAC CATCAACTGC AATCACAGAT AGCAGAGAGA ACAGGTGTTT
1981 CTGCTGTTTG GCCTGGTTGG GGTCATGCAT CTGAGAATCC TGAACTTCCA GATGCGCTGA
2041 CTGCAAAAGG AATTGTTTTT CTTGGGCCAC CAGCATCATC AATGCATGCA TTAGGAGACA
2101 AGGTTGGCTC AGCTCTCATT GCTCAAGCAG CTGGAGTTCC AACACTTGCT TGGAGTGGAT
2161 CACATGTGAG CCTTGTCTTC TCTTTTTTAG CTTATCATCT TATCTTTTCG GTGATGCATT
2221 ATCCCAATGA CACTAAACCA TAGGTGGAAG TTCCTCTGGA GTGTTGCTTG GACTCAATAC
2281 CTGATGAGAT GTATAGAAAA GCTTGTGTTA CTACCACAGA GGAAGCAGTT GCAAGTTGTC
2341 AGGTGGTTGG TTATCCTGCC ATGATTAAGG CATCTTGGGG TGGTGGTGGT AAAGGAATAA
```

FIG.26E

```
2401 GGAAGGTTTG TTCTTCTTGT AGTTATCAAG AGATTGTTTG GATTGCAAGT GTTTAGTGCC
2461 CATAGTTAAC TCTGGTCTTT CTAACATGAG TAACTCAACT TTCTTGCAGG TTCATAATGA
2521 TGATGAGGTT AGGACATTAT TTAAGCAAGT TCAAGGCGAA GTACCTGGTT CCCCAATATT
2581 TATCATGAGG CTAGCTGCTC AGGTGGGGCC TTTTATGGAA GTTACACCTT TTCCCTTAAT
2641 GTTGAGTTAT TCCGGAGTTA TTATGGTTAT GTTCTGTATG TTTGATCTGT AAATTATTGA
2701 AATTCACCTC CATTGGTTCT CCAGATTAGC AGACCTACAA TTCTACATAT GGTTTATACT
2761 TTATAAATAC TAGGATTTAG GGATCTTCAT ATAGTTTATA CATGGTATTT AGATTTCATT
2821 TGTAACCCTA TTGAAGACAT CCTGATTGTT GTCTTATGTA GAGTCGACAT CTTGAAGTTC
2881 AGTTGCTTTG TGATCAATAT GGCAACGTAG CAGCACTTCA CAGTCGAGAT TGCAGTGTAC
2941 AACGGCGACA CCAAAAGGTC TGCTGTCTCA GTTAAATCAC CCCTCTGAAT GATCTACTTC
3001 TTGCCTGCTG CGTTGGTCAG AGGAATAATG GTTGTATTCT ACTGAACAGA TAATCGAGGA
3061 AGGACCAGTT ACTGTTGCTC CTCGTGAGAC TGTGAAAGAG CTTGAGCAGG CAGCACGGAG
3121 GCTTGCTAAA GCTGTGGGTT ATGTTGGTGC TGCTACTGTT GAATACCTTT ACAGCATGGA
3181 AACTGGTGAA TATTATTTTC TGGAACTTAA TCCACGGCTA CAGGTCGGCT CCTTTGACAT
3241 TCTTCAGGAA TTAATTTCTG TTGACCACAT GATTTACATT GTCAAATGGT CTCACAGGTT
3301 GAGCATCCTG TCACTGAGTG GATAGCTGAA GTAAATTTGC CTGCGGCTCA AGTTGCTGTT
3361 GGAATGGGTA TACCCCTTTG GCAGATTCCA GGTAATGCTT CTTCATTTAG TTCCTGCTCT
3421 TTGTTAATTG AATGAGCTCT TATACAGACC ATGAGACACA TTCTACTGTT AATTCATAGT
3481 ATCCCCTGAC TTGTTAGTGT TAGAGATACA GAGATGTATC ACAAATTCAT TGTATCTCCT
3541 CAAGGACTGT AAAAATCCTA TAATTAAATT TCTGAAAATT TGTTCTTTTA AGCAGAAAAA
3601 AAATCTCTAA ATTATCTCCC TGTATACAGA GATCAGGCGC TTCTACGGAA TGAACCATGG
3661 AGGAGGCTAT GACCTTTGGA GGAAAACAGC AGCTCTAGCG ACTCCATTTA ACTTTGATGA
3721 AGTAGATTCT AAATGGCCAA AAGGCCACTG CGTAGCTGTT AGAATAACTA GCGAGGATCC
3781 AGATGATGGG TTTAAGCCTA CTGGTGGAAA AGTAAAGGTG CGGTTTCCTG ATGTTAGGTG
3841 TATGAATTGA ACACATTGCT ATATTGCAGC TAGTGAAATG ACTGGATCAT GGTTCTCTTA
3901 TTTTCAGGAG ATAAGTTTCA AGAGTAAACC AAATGTTTGG GCCTATTTCT CAGTAAAGGT
3961 AGTCCTCAAT ATTGTTGCAC TGCCACATTA TTTGAGTTGT CCTAACAATT GTGCTGCAAT
4021 TGTTAGTTTT CAACTATTTG TTGTTCTGTT TGGTTGACTG GTACCCTCTC TTTGCAGTCT
4081 GGTGGAGGCA TCCATGAATT CGCTGATTCT CAGTTCGGTA TGTAAAGTTA AAAGAGTAAT
4141 ATTGTCTTTG CTATTTATGT TTGTCCTCAC TTTTAAAAGA TATTGCCTTC CATTACAGGA
4201 CATGTTTTTG CGTATGGAAC TACTAGATCG GCAGCAATAA CTACCATGGC TCTTGCACTA
4261 AAAGAGGTTC AAATTCGTGG AGAAATTCAT TCAAACGTAG ACTACACAGT TGACCTATTA
4321 AATGTAAGGA CTAAATATCT GCTTATTGAA CCTTGCTTTT TGGTTCCCTA ATGCCATTTT
4381 AGTCTGGCTA CTGAAGAACT TATCCATCAT GCCATTTCTG TTATCTTAAA TTCAGGCCTC
4441 AGATTTTAGA GAAAATAAGA TTCATACTGG TTGGCTGGAT ACCAGGATAG CCATGCGTGT
4501 TCAAGCTGAG AGGCCTCCAT GGTATATTTC AGTCGTTGGA GGGGCTTTAT ATGTAAGACA
4561 AACTATGCCA CTCATTAGCA TTTATGTGAA GCAAATGCGG AAAACATGAT CAATATGTCG
4621 TCTTATTTAA ATTTATTTAT TTTTGTGCTG CAGAAAACAG TAACTGCCAA CACGGCCACT
4681 GTTTCTGATT ATGTTGGTTA TCTTACCAAG GGCCAGATTC CACCAAAGGT ACTATTCTGT
4741 TTTTTCAGGA TATGAATGCT GTTTGAATGT GAAAACCATT GACCATAAAT CCTTGTTTGC
4801 AGCATATATC CCTTGTCTAT ACGACTGTTG CTTTGAATAT AGATGGGAAA AAATATACAG
4861 TAAGTGTGAC ATTCTTAATG GGGAAACTTA ATTTGTTGTA AATAATCAAT ATCATATTGA
```

FIG.26E
(continued)

```
4921 CTCGTGTATG CTGCATCATA GATCGATACT GTGAGGAGTG GACATGGTAG CTACAGATTG
4981 CGAATGAATG GATCAACGGT TGACGCAAAT GTACAAATAT TATGTGATGG TGGGCTTTTA
5041 ATGCAGGTAA TATCTTCTTC CTAGTTAAAG AAGATATATC TTGTTCAAAG AATTCTGATT
5101 ATTGATCTTT TAATGTTTTC AGCTGGATGG AAACAGCCAT GTAATTTATG CTGAAGAAGA
5161 GGCCAGTGGT ACACGACTTC TTATTGATGG AAAGACATGC ATGTTACAGG TAATGATAGC
5221 CTTGTTCTTT TTAGTTCTAG TCACGGTGTT TGCTTGCTAT TTGTTGTATC TATTTAATGC
5281 ATTCACTAAT TACTATATTA GTTGCATCA TCAAGTTAAA ATGGAACTTC TTTCTTGCAG
5341 AATGACCATG ACCCATCAAA GTTATTAGCT GAGACACCAT GCAAACTTCT TCGTTTCTTG
5401 GTTGCTGATG GTGCTCATGT TGATGCTGAT GTACCATATG CGGAAGTTGA GGTTATGAAG
5461 ATGTGCATGC CCCTCTTATC ACCCGCTTCT GGTGTCATAC ATGTTGTAAT GTCTGAGGGC
5521 CAAGCAATGC AGGTACATTC CTACATTCCA TTCATTGTGC TGTGCTGACA TGAACATTTC
5581 AAGTAAATAC CTGTAACTTG TTTATTATTC TAGGCTGGTG ATCTTATAGC TAGGCTGGAT
5641 CTTGATGACC CTTCTGCTGT TAAGAGAGCT GAGCCGTTCG AAGATACTTT TCCACAAATG
5701 GGTCTCCCTA TTGCTGCTTC TGGCCAAGTT CACAAATTAT GTGCTGCAAG TCTGAATGCT
5761 TGTCGAATGA TCCTTGCGGG GTATGAGCAT GATATTGACA AGGTAAACAT CATGTCCTCT
5821 TGTTTTTTCT TTTGTTTATC ATGCATTCTT ATGTTCATCA TGTCCTCTGG CAAATCTAGA
5881 TTCCGCTGTC GTTTCACACA GATTTTTCTC ATTCTCATAA TGGTGCCAAA CATAAATATG
5941 CTGCTATATT CATCAATGTT TTCACTCGAT TTCTAATTTT GCTTTTGAGT TTTAAACTTT
6001 AGTACAATCC ATATCTAATC TCCTTTGGCA ACAGTGAATC CATTATATAT ATTTTTATTA
6061 AACTGCTTTC TTTTTCAGGT TGTGCCAGAG TTGGTATACT GCCTAGACAC TCCGGAGCTT
6121 CCTTTCCTGC AGTGGGAGGA GCTTATGTCT GTTTTAGCAA CTAGACTTCC AAGAAATCTT
6181 AAAAGTGAGG TATATTATGG TTGACAAGAT AGCTAGTCTC ATGCTCTAAG GACTTGTACA
6241 TTTCGCCACA TAGGTTAATT TTCCATATCA AGTTCTAATG TACGATATAA AAGTAGTACT
6301 GGCCTAAAAC AGTATTGGTG GTTGACTATC TTTGTTGTGT AAGATCAAGT ATTTCTTTTT
6361 CATGCTTAGT TTGTCAATAC TTCACATTTA TCACTGACTT GTCGAGCTAA ATGAGATTTT
6421 ATTTGATTTC TGTGCTCCAT TATTTTTGTA TATATATATA TATATTTAAC TATGACTATA
6481 TGTTATGCCT CAAACGTTTC AAACTCTTTC AGTTGGAGGG CAAATATGAG GAATACAAAG
6541 TAAAATTTGA CTCTGGGATA ATCAATGATT TCCCTGCCAA TATGCTACGA GTGATAATTG
6601 AGGTCAGTTA TTCAATTTGT TGTGATAATC ACTGCCTTAA CTGTTCGTTC TTTTAACAAG
6661 CGGTTTTATA GGAAAATCTT GCATGTGGTT CTGAGAAGGA GAAGGCTACA AATGAGAGGC
6721 TTGTTGAGCC TCTTATGAGC CTACTGAAGT CATATGAGGG TGGGAGAGAA AGTCATGCTC
6781 ACTTTGTTGT CAAGTCCCTT TTTGAGGAGT ATCTCTATGT TGAAGAATTG TTCAGTGATG
6841 GAATTCAGGT TAACTTACCT ATTCGCATTA AACAAATCAT CAGTTGTTTT ATGATAAAGT
6901 CAAAATGTTT ATATTTCCCA TTCTTCTGTG GATCAAATAT ATCACGGACA TGATATAGTT
6961 TCCTTAGGCT ATATAATGGT TCTTCATCAA ATAATATTGC AGGAAACAGT ATAGCAAACT
7021 ATTTGTATAT ACTCGAGATG GAAATTGTTA GAAACATCAT TGACTAAATC TGTCCTTTGT
7081 TACGCTGTTT TTGTAGTCTG ATGTGATTGA GCGTCTGCGC CTTCAACATA GTAAAGACCT
7141 ACAGAAGGTC GTAGACATTG TGTTGTCCCA CCAGGTAAAT TTCTTCATGG TCTGATGACT
7201 TCACTGCGAA TGGTTACTGA ACTGTCTTCT TGTTCTGACA ATGTGACTTT TCTTTGTAGA
7261 GTGTTAGAAA TAAAACTAAG CTGATACTAA AACTCATGGA GAGTCTGGTC TATCCAAATC
7321 CTGCTGCCTA CAGGGATCAA TTGATTCGCT TTTCTTCCCT TAATCACAAA GCGTATTACA
7381 AGGTGACCAG GATAAACATA AATAAACGTG AATTTTTCAA TGACCTTTTC TTCTGACATC
```

FIG.26E
(continued)

```
7441 TGAATCTGAT GAATTTCTTG CATATTAATA CAGTTGGCAC TTAAAGCTAG TGAACTTCTT
7501 GAACAAACAA AACTTAGTGA GCTCCGTGCA AGAATAGCAA GGAGCCTTTC AGAGCTGGAG
7561 ATGTTTACTG AGGAAAGCAA GGGTCTCTCC ATGCATAAGC GAGAAATTGC CATTAAGGAG
7621 AGCATGGAAG ATTTAGTCAC TGCTCCACTG CCAGTTGAAG ATGCGCTCAT TTCTTTATTT
7681 GATTGTAGTG ATACAACTGT TCAACAGAGA GTGATTGAGA CTTATATAGC TCGATTATAC
7741 CAGGTATGAG AAGAAAGACC TTTTGAAATT ATTTATATTA ACATATCCTA GTAAAACAGC
7801 ATGCTCATCA TTTCTTAAAA AAAGTTTACA GCACCTGATG TTTGGTTACT GACCGCATCA
7861 TTAAAATAAA GTTACTTGTT GTGGAGAGAT GTATTTTGGA ACTTGTGGCA CATGCAGTAA
7921 CATGCTACTG CTCGATATGT TTGCTAACTT GACAACAATA TTTTTCAGCC TCATCTTGTA
7981 AAGGACAGTA TCAAAATGAA ATGGATAGAA TCGGGTGTTA TTGCTTTATG GGAATTTCCT
8041 GAAGGGCATT TTGATGCAAG AAATGGAGGA GCGGTTCTTG GTGACAAAAG ATGGGGTGCC
8101 ATGGTCATTG TCAAGTCTCT TGAATCACTT TCAATGGCCA TTAGATTTGC ACTAAAGGAG
8161 ACATCACACT ACACTAGCTC TGAGGGCAAT ATGATGCATA TTGCTTTGTT GGGTGCTGAT
8221 AATAAGATGC ATATAATTCA AGAAAGGTAT GTTCATATGC TATGTTGGTG CTGAAATAGT
8281 TATATATGTA GTTAGCTGGT GGAGTTCTGG TAATTAACCT ATCCCATTGT TCAGTGGTGA
8341 TGATGCTGAC AGAATAGCCA AACTTCCCTT GATACTAAAG GATAATGTAA CCGATCTGCA
8401 TGCCTCTGGT GTGAAAACAA TAAGTTTCAT TGTTCAAAGA GATGAAGCAC GGATGACAAT
8461 GCGTCGTACC TTCCTTTGGT CTGATGAAAA GCTTTCTTAT GAGGAAGAGC CAATTCTCCG
8521 GCATGTGGAA CCTCCTCTTT CTGCACTTCT TGAGTTGGTA CGTGATATCA TCAAAATGAT
8581 AATGTTTTGG TATGGCATTG ATTATCTTCT ATGCTCTTTG TATTTATTCA GCCTATTGTG
8641 GATACAGGAC AAGTTGAAAG TGAAAGGATA CAATGAAATG AAGTATACCC CATCACGGGA
8701 TCGTCAATGG CATATCTACA CACTTAGAAA TACTGAAAAC CCCAAAATGT TGCACCGGGT
8761 ATTTTTCCGA ACCCTTGTCA GGCAACCCAG TGTATCCAAC AAGTTTTCTT CGGGCCAGAT
8821 TGGTGACATG GAAGTTGGGA GTGCTGAAGA ACCTCTGTCA TTTACATCAA CCAGCATATT
8881 AAGATCTTTG ATGACTGCTA TAGAGGAATT GGAGCTTCAC GCAATTAGAA CTGGCCATTC
8941 ACACATGTAT TTGCATGTAT TGAAAGAACA AAAGCTTCTT GATCTTGTTC CAGTTTCAGG
9001 GTAAGTGCGC ATATTTCTTT TTGGGAACAT ATGCTTGCTT ATGAGGTTGG TCTTCTCAAT
9061 GATCTTCTTA TCTTACTCAG GAATACAGTT TTGGATGTTG GTCAAGATGA AGCTACTGCA
9121 TATTCACTTT TAAAAGAAAT GGCTATGAAG ATACATGAAC TTGTTGGTGC AAGAATGCAC
9181 CATCTTTCTG TATGCCAATG GGAAGTGAAA CTTAAGTTGG ACTGCGATGG TCCTGCCAGT
9241 GGTACCTGGA GGATTGTAAC AACCAATGTT ACTAGTCACA CTTGCACTGT GGATGTAAGT
9301 TTAATCCTCT AGCATTTTGT TTTCTTTGGA AAAGCATGTG ATTTTAAGCC GGCTGGTCCT
9361 CATACCCAGA CCTAGTGATC TTTATATAGT GTAGACATTT TTCTAACTGC TTTTAATTGT
9421 TTTAGATCTA CCGTGAGATG GAAGATAAAG AATCACGGAA GTTAGTATAC CATCCCGCCA
9481 CTCCGGCGGC TGGTCCTCTG CATGGTGTGG CACTGAATAA TCCATATCAG CCTTTGAGTG
9541 TCATTGATCT CAAACGCTGT TCTGCTAGGA ATAATAGAAC TACATACTGC TATGATTTTC
9601 CACTGGTGAG TTGACTGCTC CCTTATATTC AATGCATTAC CATAGCAAAT TCATATTCGT
9661 TCATGTTGTC AAAATAAGCC GATGAAAATT CAAAACTGTA GGCATTTGAA ACTGCAGTGA
9721 GGAAGTCATG GTCCTCTAGT ACCTCTGGTG CTTCTAAAGG TGTTGAAAAT GCCCAATGTT
9781 ATGTTAAAGC TACAGAGTTG GTATTTGCGG ACAAACATGG GTCATGGGGC ACTCCTTTAG
9841 TTCAAATGGA CCGGCCTGCT GGGCTCAATG ACATTGGTAT GGTAGCTTGG ACCTTGAAGA
9901 TGTCCACTCC TGAATTTCCT AGTGGTAGGG AGATTATTGT TGTTGCAAAT GATATTACGT
```

FIG.26E

```
 9961 TCAGAGCTGG ATCATTTGGC CCAAGGGAAG ATGCATTTTT TGAAGCTGTT ACCAACCTAG
10021 CCTGTGAGAA GAAACTTCCT CTTATTTATT TGGCAGCAAA TTCTGGTGCT CGAATTGGCA
10081 TAGCAGATGA AGTGAAATCT TGCTTCCGTG TTGGGTGGTC TGATGATGGC AGCCCTGAAC
10141 GTGGGTTTCA GTACATTTAT CTAAGCGAAG AAGACTATGC TCGTATTGGC ACTTCTGTCA
10201 TAGCACATAA GATGCAGCTA GACAGTGGTG AAATTAGGTG GGTTATTGAT TCTGTTGTGG
10261 GCAAGGAAGA TGGACTTGGT GTGGAGAATA TACATGGAAG TGCTGCTATT GCCAGTGCTT
10321 ATTCTAGGGC ATATAAGGAG ACATTTACAC TTACATTTGT GACTGGAAGA ACTGTTGGAA
10381 TAGGAGCTTA TCTTGCTCGA CTTGGCATCC GGTGCATACA GCGTCTTGAC CAGCCTATTA
10441 TTCTTACAGG CTATTCTGCA CTGAACAAGC TTCTTGGGCG GGAAGTGTAC AGCTCCCACA
10501 TGCAGTTGGG TGGTCCCAAA ATCATGGCAA CTAATGGTGT TGTCCATCTT ACTGTTTCAG
10561 ATGACCTTGA AGGCGTTTCT AATATATTGA GGTGGCTCAG TTATGTTCCT GCCTACATTG
10621 GTGGACCACT TCCAGTAACA ACACCGTTGG ACCCACCGGA CAGACCTGTT GCATACATTC
10681 CTGAGAACTC GTGTGATCCT CGAGCGGCTA TCCGTGGTGT TGATGACAGC CAAGGGAAAT
10741 GGTTAGGTGG TATGTTTGAT AAAGACAGCT TTGTGGAAAC ATTTGAAGGT TGGGCTAAGA
10801 CAGTGGTTAC TGGCAGAGCA AAGCTTGGTG GAATTCCAGT GGGTGTGATA GCTGTGGAGA
10861 CTCAGACCAT GATGCAAACT ATCCCTGCTG ACCCTGGTCA GCTTGATTCC CGTGAGCAAT
10921 CTGTTCCTCG TGCTGGACAA GTGTGGTTTC CAGATTCTGC AACCAAGACT GCGCAGGCAT
10981 TGCTGGACTT CAACCGTGAA GGATTACCTC TGTTCATCCT CGCTAACTGG AGAGGCTTCT
11041 CTGGTGGACA AAGAGATCTT TTTGAAGGAA TTCTTCAGGC TGGCTCGACT ATTGTTGAGA
11101 ACCTTAGGAC ATACAATCAG CCTGCCTTTG TCTACATTCC CATGGCTGCA GAGCTACGAG
11161 GAGGGGCTTG GGTTGTGGTT GATAGCAAGA TAAACCCAGA CCGCATTGAG TGCTATGCTG
11221 AGAGGACTGC AAAAGGCAAT GTTCTGGAAC CGCAAGGGTT AATTGAGATC AAGTTCAGGT
11281 CAGAGGAACT CCAGGATTGC ATGAGTCGGC TTGACCCAAC ATTAATTGAT CTGAAAGCAA
11341 AACTCGAAGT AGCAAATAAA AATGGAAGTG CTGACACAAA ATCGCTTCAA GAAAATATAG
11401 AAGCTCGAAC AAAACAGTTG ATGCCTCTAT ATACTCAGAT TGCGATACGG TTTGCTGAAT
11461 TGCATGATAC ATCCCTCAGA ATGGCTGCGA AAGGTGTGAT TAAGAAAGTT GTGGACTGGG
11521 AAGAATCACG ATCTTTCTTC TATAAGAGAT TACGGAGGAG GATCTCTGAG GATGTTCTTG
11581 CAAAAGAAAT TAGAGCTGTA GCAGGTGAGC AGTTTTCCCA CCAACCAGCA ATCGAGCTGA
11641 TCAAGAAATG GTATTCAGCT TCACATGCAG CTGAATGGGA TGATGACGAT GCTTTTGTTG
11701 CTTGGATGGA TAACCCTGAA AACTACAAGG ATTATATTCA ATATCTTAAG GCTCAAAGAG
11761 TATCCCAATC CCTCTCAAGT CTTTCAGATT CCAGCTCAGA TTTGCAAGCC CTGCCACAGG
11821 GTCTTTCCAT GTTACTAGAT AAGGTAATTA GCTTACTGAT GCTTATATAA ATTCTTTTTC
11881 ATTACATATG GCTGGAGAAC TATCTAATCA AATAATGATT ATAATTCCAA TCGTTCTTTT
11941 TATGCCATTA TGATCTTCTG AAATTTCCTT CTTTGGACAC TTATTCAGAT GGATCCCTCT
12001 AGAAGAGCTC AACTTGTTGA AGAAATCAGG AAGGTCCTTG GTTGAATCAT ATGATGCCAA
12061 AACTATTATT GGAGGCACAA ATAGCTTGTG GACCCTGTCG GATTGTTGGT GAGTGTATAT
12121 TGGATTTGTT AGTTCTGCCA GATGAAAGTG CAAGTCTGAT GATTCATGAT ACCGTCAGTT
12181 GGCAAGAACA CCGGTTAACC TGAGTGCTTG TTTACAAATG GTCCTTTATG ACAATCGTTG
12241 TTTCGCGCTA GTTCCGTGAT CTACTATCAT CTGTTAGACG CTGTAATTAG TGAGTCTCCG
12301 CGGATCCACA GTATACGGTT GAGCTGTTGA TTCAATTTTG GACACGAATA ATATGATTTT
12361 GTAGGCATAA ATGCGTCTGT ATGTGAAATA AATTGTCTGT TGAGTTAACA CACAAGATGA
12421 CAATATGTTT GTGCTCTACT GCTATTGTCC ATGAATACTG ATTGCGGAAT CAACCACATG
12481 CATTAT
```

FIG.26E (continued)

EAZ33685 - *Oryza sativa* plastidal ACCase Os05g22940 Japonica rice translated protein

```
   1  MTSTHVATLG VGAQAPPRHQ KKSAGTAFVS SGSSRPSYRK NGQRTRSLRE
  51  ESNGGVSDSK KLNHSIRQGL AGIIDLPNDA ASEVDISHGS EDPRGPTVPG
 101  SYQMNGIINE THNGRHASVS KVVEFCTALG GKTPIHSVLV ANNGMAAAKF
 151  MRSVRTWAND TFGSEKAIQL IAMATPEDLR INAEHIRIAD QFVEVPGGTN
 201  NNNYANVQLI VEIAERTGVS AVWPGWGHAS ENPELPDALT AKGIVFLGPP
 251  ASSMHALGDK VGSALIAQAA GVPTLAWSGS HVEVPLECCL DSIPDEMYRK
 301  ACVTTTEEAV ASCQVVGYPA MIKASWGGGG KGIRKVHNDD EVRTLFKQVQ
 351  GEVPGSPIFI MRLAAQSRHL EVQLLCDQYG NVAALHSRDC SVQRRHQKII
 401  EEGPVTVAPR ETVKELEQAA RRLAKAVGYV GAATVEYLYS METGEYYFLE
 451  LNPRLQVEHP VTEWIAEVNL PAAQVAVGMG IPLWQIPEIR RFYGMNHGGG
 501  YDLWRKTAAL ATPFNFDEVD SKWPKGHCVA VRITSEDPDD GFKPTGGKVK
 551  EISFKSKPNV WAYFSVKSGG GIHEFADSQF GHVFAYGTTR SAAITTMALA
 601  LKEVQIRGEI HSNVDYTVDL LNASDFRENK IHTGWLDTRI AMRVQAERPP
 651  WYISVVGGAL YKTVTANTAT VSDYVGYLTK GQIPPKHISL VYTTVALNID
 701  GKKYTIDTVR SGHGSYRLRM NGSTVDANVQ ILCDGGLLMQ LDGNSHVIYA
 751  EEEASGTRLL IDGKTCMLQN DHDPSKLLAE TPCKLLRFLV ADGAHVDADV
 801  PYAEVEVMKM CMPLLSPASG VIHVVMSEGQ AMQAGDLIAR LDLDDPSAVK
 851  RAEPFEDTFP QMGLPIAASG QVHKLCAASL NACRMILAGY EHDIDKVVPE
 901  LVYCLDTPEL PFLQWEELMS VLATRLPRNL KSELEGKYEE YKVKFDSGII
 951  NDFPANMLRV IIEENLACGS EKEKATNERL VEPLMSLLKS YEGGRESHAH
1001  FVVKSLFEEY LYVEELFSDG IQSDVIERLR LQHSKDLQKV VDIVLSHQSV
1051  RNKTKLILKL MESLVYPNPA AYRDQLIRFS SLNHKAYYKL ALKASELLEQ
1101  TKLSELRARI ARSLSELEMF TEESKGLSMH KREIAIKESM EDLVTAPLPV
1151  EDALISLFDC SDTTVQQRVI ETYIARLYQP HLVKDSIKMK WIESGVIALW
1201  EFPEGHFDAR NGGAVLGDKR WGAMVIVKSL ESLSMAIRFA LKETSHYTSS
1251  EGNMMHIALL GADNKMHIIQ ESGDDADRIA KLPLILKDNV TDLHASGVKT
1301  ISFIVQRDEA RMTMRRTFLW SDEKLSYEEE PILRHVEPPL SALLELDKLK
1351  VKGYNEMKYT PSRDRQWHIY TLRNTENPKM LHRVFFRTLV RQPSVSNKFS
1401  SGQIGDMEVG SAEEPLSFTS TSILRSLMTA IEELELHAIR TGHSHMYLHV
1451  LKEQKLLDLV PVSGNTVLDV GQDEATAYSL LKEMAMKIHE LVGARMHHLS
1501  VCQWEVKLKL DCDGPASGTW RIVTTNVTSH TCTVDIYREM EDKESRKLVY
1551  HPATPAAGPL HGVALNNPYQ PLSVIDLKRC SARNNRTTYC YDFPLAFETA
1601  VRKSWSSSTS GASKGVENAQ CYVKATELVQ MDRLAGLNDI GMVAWTLKMS
1651  TPEFLSGREI IVVANDITFR AGSFGPREDA FFEAVTNLAC EKKLPLIYLA
1701  ANSGARIGIA DEVKSCFRVG WSDDGSPERG FQYIYLSEED YARIGTSVIA
1751  HKMQLDSGEI RWVIDSVVGK EDGLGVENIH GSAAIASAYS RAYKETFTLT
1801  FVTGRTVGIG AYLARLGIRC IQRLDQPIIL TGYSALNKLL GREVYSSHMQ
1851  LGGPKIMATN GVVHLTVSDD LEGVSNILRW LSYVPAYIGG PLPVTTPLDP
1901  PDRPVAYIPE NSCDPRAAIR GVDDSQGKWL GGMFDKDSFV ETFEGWAKTV
1951  VTGRAKLGGI PVGVIAVETQ TMMQTIPADP GQLDSREQSV PRAGQVWFPD
2001  SATKTAQALL DFNREGLPLF ILANWRGFSG GQRDLFEGIL QAGSTIVENL
2051  RTYNQPAFVY IPMAAELRGG AWVVVDSKIN PDRIECYAER TAKGNVLEPQ
2101  GLIEIKFRSE ELQDCMSRLD PTLIDLKAKL EVANKNGSAD TKSLQENIEA
2151  RTKQLMPLYT QIAIRFAELH DTSLRMAAKG VIKKVVDWEE SRSFFYKRLR
2201  RRISEDVLAK EIRAVAGEQF SHQPAIELIK KWYSASHAAE WDDDDAFVAW
2251  MDNPENYKDY IQYLKAQRVS QSLSSLSDSS SDLQALPQGL SMLLDKMDPS
2301  RRAQLVEEIR KVLG
```

FIG. 26F

B9FK36 - *Oryza sativa* ACCase protein

```
          10         20         30         40         50         60
   MTSTHVATLG VGAQAPPRHQ KKSAGTAFVS SGSSRPSYRK NGQRTRSLRE ESNGGVSDSK 70         80         90        100        110        120
   KLNHSIRQGL AGIIDLPNDA ASEVDISHGS EDPRGPTVPG SYQMNGIINE THNGRHASVS 130        140        150        160        170        180
   KVVEFCTALG GKTPIHSVLV ANNGMAAAKF MRSVRTWAND TFGSEKAIQL IAMATPEDLR 190        200        210        220        230        240
   INAEHIRIAD QFVEVPGGTN NNNYANVQLI VEIAERTGVS AVWPGWGHAS ENPELPDALT 250        260        270        280        290        300
   AKGIVFLGPP ASSMHALGDK VGSALIAQAA GVPTLAWSGS HVEVPLECCL DSIPDEMYRK 310        320        330        340        350        360
   ACVTTTEEAV ASCQVVGYPA MIKASWGGGG KGIRKVHNDD EVRTLFKQVQ GEVPGSPIFI 370        380        390        400        410        420
   MRLAAQSRHL EVQLLCDQYG NVAALHSRDC SVQRRHQKII EEGPVTVAPR ETVKELEQAA 430        440        450        460        470        480
   RRLAKAVGYV GAATVEYLYS METGEYYFLE LNPRLQVEHP VTEWIAEVNL PAAQVAVGMG 490        500        510        520        530        540
   IPLWQIPEIR RFYGMNHGGG YDLWRKTAAL ATPFNFDEVD SKWPKGHCVA VRITSEDPDD 550        560        570        580        590        600
   GFKPTGGKVK EISFKSKPNV WAYFSVKSGG GIHEFADSQF GHVFAYGTTR SAAITTMALA 610        620        630        640        650        660
   LKEVQIRGEI HSNVDYTVDL LNASDFRENK IHTGWLDTRI AMRVQAERPP WYISVVGGAL 670        680        690        700        710        720
   YKTVTANTAT VSDYVGYLTK GQIPPKHISL VYTTVALNID GKKYTIDTVR SGHGSYRLRM 730        740        750        760        770        780
   NGSTVDANVQ ILCDGGLLMQ LDGNSHVIYA EEEASGTRLL IDGKTCMLQN DHDPSKLLAE
```

FIG.26G

```
       790        800        810        820        830        840
TPCKLLRFLV ADGAHVDADV PYAEVEVMKM CMPLLSPASG VIHVVMSEGQ AMQAGDLIAR 850        860        870        880        890        900
LDLDDPSAVK RAEPFEDTFP QMGLPIAASG QVHKLCAASL NACRMILAGY EHDIDKVVPE 910        920        930        940        950        960
LVYCLDTPEL PFLQWEELMS VLATRLPRNL KSELEGKYEE YKVKFDSGII NDFPANMLRV 970        980        990       1000       1010       1020
IIEENLACGS EKEKATNERL VEPLMSLLKS YEGGRESHAH FVVKSLFEEY LYVEELFSDG 1030       1040       1050       1060       1070       1080
IQSDVIERLR LQHSKDLQKV VDIVLSHQSV RNKTKLILKL MESLVYPNPA AYRDQLIRFS 1090       1100       1110       1120       1130       1140
SLNHKAYYKL ALKASELLEQ TKLSELRARI ARSLSELEMF TEESKGLSMH KREIAIKESM 1150       1160       1170       1180       1190       1200
EDLVTAPLPV EDALISLFDC SDTTVQQRVI ETYIARLYQP HLVKDSIKMK WIESGVIALW 1210       1220       1230       1240       1250       1260
EFPEGHFDAR NGGAVLGDKR WGAMVIVKSL ESLSMAIRFA LKETSHYTSS EGNMMHIALL 1270       1280       1290       1300       1310       1320
GADNKMHIIQ ESGDDADRIA KLPLILKDNV TDLHASGVKT ISFIVQRDEA RMTMRRTFLW 1330       1340       1350       1360       1370       1380
SDEKLSYEEE PILRHVEPPL SALLELDKLK VKGYNEMKYT PSRDRQWHIY TLRNTENPKM 1390       1400       1410       1420       1430       1440
LHRVFFRTLV RQPSVSNKFS SGQIGDMEVG SAEEPLSFTS TSILRSLMTA IEELELHAIR 1450       1460       1470       1480       1490       1500
TGHSHMYLHV LKEQKLLDLV PVSGNTVLDV GQDEATAYSL LKEMAMKIHE LVGARMHHLS 1510       1520       1530       1540       1550       1560
VCQWEVKLKL DCDGPASGTW RIVTTNVTSH TCTVDIYREM EDKESRKLVY HPATPAAGPL 1570       1580       1590       1600       1610       1620
HGVALNNPYQ PLSVIDLKRC SARNNRTTYC YDFPLAFETA VRKSWSSSTS GASKGVENAQ
```

FIG. 26G
(continued)

```
          1630       1640       1650       1660       1670       1680
     CYVKATELVF ADKHGSWGTP LVQMDRPAGL NDIGMVAWTL KMSTPEFPSG REIIVVANDI 1690       1700       1710       1720       1730       1740
     TFRAGSFGPR EDAFFEAVTN LACEKKLPLI YLAANSGARI GIADEVKSCF RVGWSDDGSP 1750       1760       1770       1780       1790       1800
     ERGFQYIYLS EEDYARIGTS VIAHKMQLDS GEIRWVIDSV VGKEDGLGVE NIHGSAAIAS 1810       1820       1830       1840       1850       1860
     AYSRAYKETF TLTFVTGRTV GIGAYLARLG IRCIQRLDQP IILTGYSALN KLLGREVYSS 1870       1880       1890       1900       1910       1920
     HMQLGGPKIM ATNGVVHLTV SDDLEGVSNI LRWLSYVPAY IGGPLPVTTP LDPPDRPVAY 1930       1940       1950       1960       1970       1980
     IPENSCDPRA AIRGVDDSQG KWLGGMFDKD SFVETFEGWA KTVVTGRAKL GGIPVGVIAV 1990       2000       2010       2020       2030       2040
     ETQTMMQTIP ADPGQLDSRE QSVPRAGQVW FPDSATKTAQ ALLDFNREGL PLFILANWRG 2050       2060       2070       2080       2090       2100
     FSGGQRDLFE GILQAGSTIV ENLRTYNQPA FVYIPMAAEL RGGAWVVVDS KINPDRIECY 2110       2120       2130       2140       2150       2160
     AERTAKGNVL EPQGLIEIKF RSEELQDCMS RLDPTLIDLK AKLEVANKNG SADTKSLQEN 2170       2180       2190       2200       2210       2220
     IEARTKQLMP LYTQIAIRFA ELHDTSLRMA AKGVIKKVVD WEESRSFFYK RLRRRISEDV 2230       2240       2250       2260       2270       2280
     LAKEIRAVAG EQFSHQPAIE LIKKWYSASH AAEWDDDDAF VAWMDNPENY KDYIQYLKAQ 2290       2300       2310       2320
     RVSQSLSSLS DSSSDLQALP QGLSMLLDKM DPSRRAQLVE EIRKVLG
```

FIG.26G (continued)

SEQUENCE LISTING

```
<160> NUMBER OF SEQ ID NOS: 253

<210> SEQ ID NO 1
<211> LENGTH: 2320
<212> TYPE: PRT
<213> ORGANISM: Alopecurus myosuroides

<400> SEQUENCE: 1

Met Gly Ser Thr His Leu Pro Ile Val Gly Phe Asn Ala Ser Thr Thr
1               5                   10                  15

Pro Ser Leu Ser Thr Leu Arg Gln Ile Asn Ser Ala Ala Ala Ala Phe
            20                  25                  30

Gln Ser Ser Ser Pro Ser Arg Ser Ser Lys Lys Lys Ser Arg Arg Val
        35                  40                  45

Lys Ser Ile Arg Asp Asp Gly Asp Gly Ser Val Pro Asp Pro Ala Gly
    50                  55                  60
```

```
His Gly Gln Ser Ile Arg Gln Gly Leu Ala Gly Ile Ile Asp Leu Pro
 65                  70                  75                  80

Lys Glu Gly Ala Ser Ala Pro Asp Val Asp Ile Ser His Gly Ser Glu
                 85                  90                  95

Asp His Lys Ala Ser Tyr Gln Met Asn Gly Ile Leu Asn Glu Ser His
            100                 105                 110

Asn Gly Arg His Ala Ser Leu Ser Lys Val Tyr Glu Phe Cys Thr Glu
        115                 120                 125

Leu Gly Gly Lys Thr Pro Ile His Ser Val Leu Val Ala Asn Asn Gly
130                 135                 140

Met Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Met Arg Ile Asn Ala Glu His Ile Arg Ile Ala Asp Gln Phe
            180                 185                 190

Val Glu Val Pro Gly Gly Thr Asn Asn Asn Tyr Ala Asn Val Gln
        195                 200                 205

Leu Ile Val Glu Ile Ala Glu Arg Thr Gly Val Ser Ala Val Trp Pro
210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met Asn Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Ile Pro Leu Glu Leu
        275                 280                 285

Cys Leu Asp Ser Ile Pro Glu Glu Met Tyr Arg Lys Ala Cys Val Thr
290                 295                 300

Thr Ala Asp Glu Ala Val Ala Ser Cys Gln Met Ile Gly Tyr Pro Ala
305                 310                 315                 320

Met Ile Lys Ala Ser Trp Gly Gly Gly Lys Gly Ile Arg Lys Val
                325                 330                 335

Asn Asn Asp Asp Glu Val Lys Ala Leu Phe Lys Gln Val Gln Gly Glu
            340                 345                 350

Val Pro Gly Ser Pro Ile Phe Ile Met Arg Leu Ala Ser Gln Ser Arg
        355                 360                 365

His Leu Glu Val Gln Leu Leu Cys Asp Glu Tyr Gly Asn Val Ala Ala
    370                 375                 380

Leu His Ser Arg Asp Cys Ser Val Gln Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Ser
    450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asp
```

```
                485                 490                 495
Asn Gly Gly Gly Tyr Asp Ile Trp Arg Lys Thr Ala Ala Leu Ala Thr
                500                 505                 510

Pro Phe Asn Phe Asp Glu Val Asp Ser Gln Trp Pro Lys Gly His Cys
                515                 520                 525

Val Ala Val Arg Ile Thr Ser Glu Asn Pro Asp Asp Gly Phe Lys Pro
            530                 535                 540

Thr Gly Lys Val Lys Glu Ile Ser Phe Lys Ser Lys Pro Asn Val
545                 550                 555                 560

Trp Gly Tyr Phe Ser Val Lys Ser Gly Gly Ile His Glu Phe Ala
                565                 570                 575

Asp Ser Gln Phe Gly His Val Phe Ala Tyr Gly Glu Thr Arg Ser Ala
                580                 585                 590

Ala Ile Thr Ser Met Ser Leu Ala Leu Lys Glu Ile Gln Ile Arg Gly
            595                 600                 605

Glu Ile His Thr Asn Val Asp Tyr Thr Val Asp Leu Leu Asn Ala Pro
        610                 615                 620

Asp Phe Arg Glu Asn Thr Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Ile Thr Thr Asn Ala Gly Thr Val Ser
                660                 665                 670

Glu Tyr Val Ser Tyr Leu Ile Lys Gly Gln Ile Pro Pro Lys His Ile
                675                 680                 685

Ser Leu Val His Ser Thr Ile Ser Leu Asn Ile Glu Glu Ser Lys Tyr
        690                 695                 700

Thr Ile Glu Ile Val Arg Ser Gly Gln Gly Ser Tyr Arg Leu Arg Leu
705                 710                 715                 720

Asn Gly Ser Leu Ile Glu Ala Asn Val Gln Thr Leu Cys Asp Gly Gly
                725                 730                 735

Leu Leu Met Gln Leu Asp Gly Asn Ser His Val Ile Tyr Ala Glu Glu
                740                 745                 750

Glu Ala Gly Gly Thr Arg Leu Leu Ile Asp Gly Lys Thr Cys Leu Leu
            755                 760                 765

Gln Asn Asp His Asp Pro Ser Arg Leu Leu Ala Glu Thr Pro Cys Lys
        770                 775                 780

Leu Leu Arg Phe Leu Ile Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ala Gly Val Ile Asn Val Leu Leu Ser Glu Gly Gln Ala Met
            820                 825                 830

Gln Ala Gly Asp Leu Ile Ala Arg Leu Asp Leu Asp Asp Pro Ser Ala
        835                 840                 845

Val Lys Arg Ala Glu Pro Phe Glu Gly Ser Phe Pro Glu Met Ser Leu
        850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
                885                 890                 895

Val Val Gln Asp Leu Val Trp Cys Leu Asp Thr Pro Ala Leu Pro Phe
            900                 905                 910
```

-continued

```
Leu Gln Trp Glu Glu Leu Met Ser Val Leu Ala Thr Arg Leu Pro Arg
        915                 920                 925

Arg Leu Lys Ser Glu Leu Glu Gly Lys Tyr Asn Glu Tyr Lys Leu Asn
        930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Glu Lys Glu Met Val Thr
                965                 970                 975

Ile Glu Arg Leu Val Asp Pro Leu Met Ser Leu Leu Lys Ser Tyr Glu
            980                 985                 990

Gly Gly Arg Glu Ser His Ala His Phe Ile Val Lys Ser Leu Phe Glu
        995                 1000                1005

Glu Tyr Leu Ser Val Glu Glu Leu Phe Ser Asp Gly Ile Gln Ser
    1010                1015                1020

Asp Val Ile Glu Arg Leu Arg Leu Gln Tyr Ser Lys Asp Leu Gln
    1025                1030                1035

Lys Val Val Asp Ile Val Leu Ser His Gln Gly Val Arg Asn Lys
    1040                1045                1050

Thr Lys Leu Ile Leu Ala Leu Met Glu Lys Leu Val Tyr Pro Asn
    1055                1060                1065

Pro Ala Ala Tyr Arg Asp Gln Leu Ile Arg Phe Ser Ser Leu Asn
    1070                1075                1080

His Lys Arg Tyr Tyr Lys Leu Ala Leu Lys Ala Ser Glu Leu Leu
    1085                1090                1095

Glu Gln Thr Lys Leu Ser Glu Leu Arg Thr Ser Ile Ala Arg Asn
    1100                1105                1110

Leu Ser Ala Leu Asp Met Phe Thr Glu Glu Lys Ala Asp Phe Ser
    1115                1120                1125

Leu Gln Asp Arg Lys Leu Ala Ile Asn Glu Ser Met Gly Asp Leu
    1130                1135                1140

Val Thr Ala Pro Leu Pro Val Glu Asp Ala Leu Val Ser Leu Phe
    1145                1150                1155

Asp Cys Thr Asp Gln Thr Leu Gln Gln Arg Val Ile Gln Thr Tyr
    1160                1165                1170

Ile Ser Arg Leu Tyr Gln Pro Gln Leu Val Lys Asp Ser Ile Gln
    1175                1180                1185

Leu Lys Tyr Gln Asp Ser Gly Val Ile Ala Leu Trp Glu Phe Thr
    1190                1195                1200

Glu Gly Asn His Glu Lys Arg Leu Gly Ala Met Val Ile Leu Lys
    1205                1210                1215

Ser Leu Glu Ser Val Ser Thr Ala Ile Gly Ala Ala Leu Lys Asp
    1220                1225                1230

Ala Ser His Tyr Ala Ser Ser Ala Gly Asn Thr Val His Ile Ala
    1235                1240                1245

Leu Leu Asp Ala Asp Thr Gln Leu Asn Thr Thr Glu Asp Ser Gly
    1250                1255                1260

Asp Asn Asp Gln Ala Gln Asp Lys Met Asp Lys Leu Ser Phe Val
    1265                1270                1275

Leu Lys Gln Asp Val Val Met Ala Asp Leu Arg Ala Ala Asp Val
    1280                1285                1290

Lys Val Val Ser Cys Ile Val Gln Arg Asp Gly Ala Ile Met Pro
    1295                1300                1305
```

```
Met Arg Arg Thr Phe Leu Leu Ser Glu Glu Lys Leu Cys Tyr Glu
    1310                1315                1320

Glu Glu Pro Ile Leu Arg His Val Glu Pro Leu Ser Ala Leu
    1325                1330                1335

Leu Glu Leu Asp Lys Leu Lys Val Lys Gly Tyr Asn Glu Met Lys
    1340                1345                1350

Tyr Thr Pro Ser Arg Asp Arg Gln Trp His Ile Tyr Thr Leu Arg
    1355                1360                1365

Asn Thr Glu Asn Pro Lys Met Leu His Arg Val Phe Phe Arg Thr
    1370                1375                1380

Leu Val Arg Gln Pro Ser Ala Gly Asn Arg Phe Thr Ser Asp His
    1385                1390                1395

Ile Thr Asp Val Glu Val Gly His Ala Glu Glu Pro Leu Ser Phe
    1400                1405                1410

Thr Ser Ser Ser Ile Leu Lys Ser Leu Lys Ile Ala Lys Glu Glu
    1415                1420                1425

Leu Glu Leu His Ala Ile Arg Thr Gly His Ser His Met Tyr Leu
    1430                1435                1440

Cys Ile Leu Lys Glu Gln Lys Leu Leu Asp Leu Val Pro Val Ser
    1445                1450                1455

Gly Asn Thr Val Val Asp Val Gly Gln Asp Glu Ala Thr Ala Cys
    1460                1465                1470

Ser Leu Leu Lys Glu Met Ala Leu Lys Ile His Glu Leu Val Gly
    1475                1480                1485

Ala Arg Met His His Leu Ser Val Cys Gln Trp Glu Val Lys Leu
    1490                1495                1500

Lys Leu Val Ser Asp Gly Pro Ala Ser Gly Ser Trp Arg Val Val
    1505                1510                1515

Thr Thr Asn Val Thr Gly His Thr Cys Thr Val Asp Ile Tyr Arg
    1520                1525                1530

Glu Val Glu Asp Thr Glu Ser Gln Lys Leu Val Tyr His Ser Thr
    1535                1540                1545

Ala Leu Ser Ser Gly Pro Leu His Gly Val Ala Leu Asn Thr Ser
    1550                1555                1560

Tyr Gln Pro Leu Ser Val Ile Asp Leu Lys Arg Cys Ser Ala Arg
    1565                1570                1575

Asn Asn Lys Thr Thr Tyr Cys Tyr Asp Phe Pro Leu Thr Phe Glu
    1580                1585                1590

Ala Ala Val Gln Lys Ser Trp Ser Asn Ile Ser Ser Glu Asn Asn
    1595                1600                1605

Gln Cys Tyr Val Lys Ala Thr Glu Leu Val Phe Ala Glu Lys Asn
    1610                1615                1620

Gly Ser Trp Gly Thr Pro Ile Ile Pro Met Gln Arg Ala Ala Gly
    1625                1630                1635

Leu Asn Asp Ile Gly Met Val Ala Trp Ile Leu Asp Met Ser Thr
    1640                1645                1650

Pro Glu Phe Pro Ser Gly Arg Gln Ile Ile Val Ile Ala Asn Asp
    1655                1660                1665

Ile Thr Phe Arg Ala Gly Ser Phe Gly Pro Arg Glu Asp Ala Phe
    1670                1675                1680

Phe Glu Ala Val Thr Asn Leu Ala Cys Glu Lys Lys Leu Pro Leu
    1685                1690                1695

Ile Tyr Leu Ala Ala Asn Ser Gly Ala Arg Ile Gly Ile Ala Asp
```

-continued

```
             1700                    1705                    1710
Glu Val Lys Ser Cys Phe Arg Val Gly Trp Thr Asp Asp Ser Ser
             1715                    1720                    1725
Pro Glu Arg Gly Phe Arg Tyr Ile Tyr Met Thr Asp Glu Asp His
             1730                    1735                    1740
Asp Arg Ile Gly Ser Ser Val Ile Ala His Lys Met Gln Leu Asp
             1745                    1750                    1755
Ser Gly Glu Ile Arg Trp Val Ile Asp Ser Val Val Gly Lys Glu
             1760                    1765                    1770
Asp Gly Leu Gly Val Glu Asn Ile His Gly Ser Ala Ala Ile Ala
             1775                    1780                    1785
Ser Ala Tyr Ser Arg Ala Tyr Glu Glu Thr Phe Thr Leu Thr Phe
             1790                    1795                    1800
Val Thr Gly Arg Thr Val Gly Ile Gly Ala Tyr Leu Ala Arg Leu
             1805                    1810                    1815
Gly Ile Arg Cys Ile Gln Arg Ile Asp Gln Pro Ile Ile Leu Thr
             1820                    1825                    1830
Gly Phe Ser Ala Leu Asn Lys Leu Leu Gly Arg Glu Val Tyr Ser
             1835                    1840                    1845
Ser His Met Gln Leu Gly Gly Pro Lys Ile Met Ala Thr Asn Gly
             1850                    1855                    1860
Val Val His Leu Thr Val Pro Asp Asp Leu Glu Gly Val Ser Asn
             1865                    1870                    1875
Ile Leu Arg Trp Leu Ser Tyr Val Pro Ala Asn Ile Gly Gly Pro
             1880                    1885                    1890
Leu Pro Ile Thr Lys Ser Leu Asp Pro Ile Asp Arg Pro Val Ala
             1895                    1900                    1905
Tyr Ile Pro Glu Asn Thr Cys Asp Pro Arg Ala Ala Ile Ser Gly
             1910                    1915                    1920
Ile Asp Asp Ser Gln Gly Lys Trp Leu Gly Gly Met Phe Asp Lys
             1925                    1930                    1935
Asp Ser Phe Val Glu Thr Phe Glu Gly Trp Ala Lys Thr Val Val
             1940                    1945                    1950
Thr Gly Arg Ala Lys Leu Gly Gly Ile Pro Val Gly Val Ile Ala
             1955                    1960                    1965
Val Glu Thr Gln Thr Met Met Gln Leu Val Pro Ala Asp Pro Gly
             1970                    1975                    1980
Gln Pro Asp Ser His Glu Arg Ser Val Pro Arg Ala Gly Gln Val
             1985                    1990                    1995
Trp Phe Pro Asp Ser Ala Thr Lys Thr Ala Gln Ala Met Leu Asp
             2000                    2005                    2010
Phe Asn Arg Glu Gly Leu Pro Leu Phe Ile Leu Ala Asn Trp Arg
             2015                    2020                    2025
Gly Phe Ser Gly Gly Gln Arg Asp Leu Phe Glu Gly Ile Leu Gln
             2030                    2035                    2040
Ala Gly Ser Thr Ile Val Glu Asn Leu Arg Thr Tyr Asn Gln Pro
             2045                    2050                    2055
Ala Phe Val Tyr Ile Pro Lys Ala Ala Glu Leu Arg Gly Gly Ala
             2060                    2065                    2070
Trp Val Val Ile Asp Ser Lys Ile Asn Pro Asp Arg Ile Glu Cys
             2075                    2080                    2085
Tyr Ala Glu Arg Thr Ala Lys Gly Asn Val Leu Glu Pro Gln Gly
             2090                    2095                    2100
```

```
Leu Ile Glu Ile Lys Phe Arg Ser Glu Leu Lys Glu Cys Met
    2105            2110            2115

Gly Arg Leu Asp Pro Glu Leu Ile Asp Leu Lys Ala Arg Leu Gln
    2120            2125            2130

Gly Ala Asn Gly Ser Leu Ser Asp Gly Glu Ser Leu Gln Lys Ser
    2135            2140            2145

Ile Glu Ala Arg Lys Lys Gln Leu Leu Pro Leu Tyr Thr Gln Ile
    2150            2155            2160

Ala Val Arg Phe Ala Glu Leu His Asp Thr Ser Leu Arg Met Ala
    2165            2170            2175

Ala Lys Gly Val Ile Arg Lys Val Val Asp Trp Glu Asp Ser Arg
    2180            2185            2190

Ser Phe Phe Tyr Lys Arg Leu Arg Arg Arg Leu Ser Glu Asp Val
    2195            2200            2205

Leu Ala Lys Glu Ile Arg Gly Val Ile Gly Glu Lys Phe Pro His
    2210            2215            2220

Lys Ser Ala Ile Glu Leu Ile Lys Lys Trp Tyr Leu Ala Ser Glu
    2225            2230            2235

Ala Ala Ala Ala Gly Ser Thr Asp Trp Asp Asp Asp Ala Phe
    2240            2245            2250

Val Ala Trp Arg Glu Asn Pro Glu Asn Tyr Lys Glu Tyr Ile Lys
    2255            2260            2265

Glu Leu Arg Ala Gln Arg Val Ser Arg Leu Leu Ser Asp Val Ala
    2270            2275            2280

Gly Ser Ser Ser Asp Leu Gln Ala Leu Pro Gln Gly Leu Ser Met
    2285            2290            2295

Leu Leu Asp Lys Met Asp Pro Ser Lys Arg Ala Gln Phe Ile Glu
    2300            2305            2310

Glu Val Met Lys Val Leu Lys
    2315            2320

<210> SEQ ID NO 2
<211> LENGTH: 427
<212> TYPE: PRT
<213> ORGANISM: Escherichia coli

<400> SEQUENCE: 2

Met Glu Ser Leu Thr Leu Gln Pro Ile Ala Arg Val Asp Gly Thr Ile
1               5                   10                  15

Asn Leu Pro Gly Ser Lys Ser Val Ser Asn Arg Ala Leu Leu Leu Ala
                20                  25                  30

Ala Leu Ala His Gly Lys Thr Val Leu Thr Asn Leu Leu Asp Ser Asp
            35                  40                  45

Asp Val Arg His Met Leu Asn Ala Leu Thr Ala Leu Gly Val Ser Tyr
        50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
                85                  90                  95

Thr Ala Met Arg Pro Leu Ala Ala Ala Leu Cys Leu Gly Ser Asn Asp
                100                 105                 110

Ile Val Leu Thr Gly Glu Pro Arg Met Lys Glu Arg Pro Ile Gly His
            115                 120                 125

Leu Val Asp Ala Leu Arg Leu Gly Gly Ala Lys Ile Thr Tyr Leu Glu
```

```
                130             135             140
Gln Glu Asn Tyr Pro Pro Leu Arg Leu Gln Gly Gly Phe Thr Gly Gly
145                 150                 155                 160

Asn Val Asp Val Asp Gly Ser Val Ser Ser Gln Phe Leu Thr Ala Leu
                165                 170                 175

Leu Met Thr Ala Pro Leu Ala Pro Glu Asp Thr Val Ile Arg Ile Lys
            180                 185                 190

Gly Asp Leu Val Ser Lys Pro Tyr Ile Asp Ile Thr Leu Asn Leu Met
        195                 200                 205

Lys Thr Phe Gly Val Glu Ile Glu Asn Gln His Tyr Gln Gln Phe Val
    210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ile Lys
                245                 250                 255

Gly Gly Thr Val Lys Val Thr Gly Ile Gly Arg Asn Ser Met Gln Gly
                260                 265                 270

Asp Ile Arg Phe Ala Asp Val Leu Glu Lys Met Gly Ala Thr Ile Cys
            275                 280                 285

Trp Gly Asp Asp Tyr Ile Ser Cys Thr Arg Gly Glu Leu Asn Ala Ile
        290                 295                 300

Asp Met Asp Met Asn His Ile Pro Asp Ala Ala Met Thr Ile Ala Thr
305                 310                 315                 320

Ala Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
                340                 345                 350

Arg Lys Val Gly Ala Glu Val Glu Glu Gly His Asp Tyr Ile Arg Ile
            355                 360                 365

Thr Pro Pro Glu Lys Leu Asn Phe Ala Glu Ile Ala Thr Tyr Asn Asp
        370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Ile Ser Gln Ala Ala
            420                 425

<210> SEQ ID NO 3
<211> LENGTH: 11
<212> TYPE: PRT
<213> ORGANISM: Unknown
<220> FEATURE:
<223> OTHER INFORMATION: Description of Unknown: OsERF3 repressor domain
      (LxLxPP motif) peptide

<400> SEQUENCE: 3

Leu Asp Leu Asn Arg Pro Pro Val Glu Asn
1               5                   10

<210> SEQ ID NO 4
<211> LENGTH: 6
<212> TYPE: PRT
<213> ORGANISM: Unknown
<220> FEATURE:
<223> OTHER INFORMATION: Description of Unknown: OsERF3 repressor domain
      (LxLxPP motif) peptide
<220> FEATURE:
```

```
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 4

Leu Xaa Leu Xaa Pro Pro
1               5

<210> SEQ ID NO 5
<211> LENGTH: 8
<212> TYPE: PRT
<213> ORGANISM: Unknown
<220> FEATURE:
<223> OTHER INFORMATION: Description of Unknown: AtBRD repressor domain
      (R/KLFGV motif) peptide

<400> SEQUENCE: 5

Leu Arg Leu Phe Gly Val Asn Met
1               5

<210> SEQ ID NO 6
<211> LENGTH: 5
<212> TYPE: PRT
<213> ORGANISM: Unknown
<220> FEATURE:
<223> OTHER INFORMATION: Description of Unknown: AtBRD repressor domain
      (R/KLFGV motif) peptide
<220> FEATURE:
<221> NAME/KEY: MOD_RES
<222> LOCATION: (1)..(1)
<223> OTHER INFORMATION: Arg or Lys

<400> SEQUENCE: 6

Xaa Leu Phe Gly Val
1               5

<210> SEQ ID NO 7
<211> LENGTH: 8
<212> TYPE: PRT
<213> ORGANISM: Unknown
<220> FEATURE:
<223> OTHER INFORMATION: Description of Unknown: AtHsfB1 repressor
      domain (R/KLFGV motif) peptide

<400> SEQUENCE: 7

Leu Lys Leu Phe Gly Val Trp Leu
1               5

<210> SEQ ID NO 8
<211> LENGTH: 10
<212> TYPE: PRT
<213> ORGANISM: Unknown
<220> FEATURE:
<223> OTHER INFORMATION: Description of Unknown: AtSUP repressor domain
      (EAR motif) peptide

<400> SEQUENCE: 8

Leu Asp Leu Glu Leu Arg Leu Gly Phe Ala
1               5                   10

<210> SEQ ID NO 9
<211> LENGTH: 203
<212> TYPE: PRT
<213> ORGANISM: Unknown
<220> FEATURE:
```

<223> OTHER INFORMATION: Description of Unknown: full AtSUP gene
      containing repressor domain (EAR motif) polypeptide

<400> SEQUENCE: 9

Glu Arg Ser Asn Ser Ile Glu Leu Arg Asn Ser Phe Tyr Gly Arg Ala
1               5                   10                  15

Arg Thr Ser Pro Trp Ser Tyr Gly Asp Tyr Asp Asn Cys Gln Gln Asp
            20                  25                  30

His Asp Tyr Leu Leu Gly Phe Ser Trp Pro Pro Arg Ser Tyr Thr Cys
        35                  40                  45

Ser Phe Cys Lys Arg Glu Phe Arg Ser Ala Gln Ala Leu Gly Gly His
    50                  55                  60

Met Asn Val His Arg Arg Asp Arg Ala Arg Leu Arg Leu Gln Gln Ser
65                  70                  75                  80

Pro Ser Ser Ser Thr Pro Ser Pro Pro Tyr Pro Asn Pro Asn Tyr
                85                  90                  95

Ser Tyr Ser Thr Met Ala Asn Ser Pro Pro His His Ser Pro Leu
                100                 105                 110

Thr Leu Phe Pro Thr Leu Ser Pro Pro Ser Ser Pro Arg Tyr Arg Ala
            115                 120                 125

Gly Leu Ile Arg Ser Leu Ser Pro Lys Ser Lys His Thr Pro Glu Asn
    130                 135                 140

Ala Cys Lys Thr Lys Ser Ser Leu Leu Val Glu Ala Gly Glu Ala
145                 150                 155                 160

Thr Arg Phe Thr Ser Lys Asp Ala Cys Lys Ile Leu Arg Asn Asp Glu
                165                 170                 175

Ile Ile Ser Leu Glu Leu Glu Ile Gly Leu Ile Asn Glu Ser Glu Gln
            180                 185                 190

Asp Leu Asp Leu Glu Leu Arg Leu Gly Phe Ala
        195                 200

<210> SEQ ID NO 10
<211> LENGTH: 427
<212> TYPE: PRT
<213> ORGANISM: Escherichia coli

<400> SEQUENCE: 10

Met Glu Ser Leu Thr Leu Gln Pro Ile Ala Arg Val Asp Gly Thr Ile
1               5                   10                  15

Asn Leu Pro Gly Ser Lys Ser Val Ser Asn Arg Ala Leu Leu Leu Ala
            20                  25                  30

Ala Leu Ala His Gly Lys Thr Val Leu Thr Asn Leu Leu Asp Ser Asp
        35                  40                  45

Asp Val Arg His Met Leu Asn Ala Leu Thr Ala Leu Gly Val Ser Tyr
    50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
                85                  90                  95

Thr Ala Met Arg Pro Leu Ala Ala Ala Leu Cys Leu Gly Ser Asn Asp
                100                 105                 110

Ile Val Leu Thr Gly Glu Pro Arg Met Lys Glu Arg Pro Ile Gly His
            115                 120                 125

Leu Val Asp Ala Leu Arg Leu Gly Gly Ala Lys Ile Thr Tyr Leu Glu
    130                 135                 140

-continued

```
Gln Glu Asn Tyr Pro Pro Leu Arg Leu Gln Gly Gly Phe Thr Gly Gly
145                 150                 155                 160

Asn Val Asp Val Asp Gly Ser Val Ser Ser Gln Phe Leu Thr Ala Leu
                165                 170                 175

Leu Met Thr Ala Pro Leu Ala Pro Glu Asp Thr Val Ile Arg Ile Lys
            180                 185                 190

Gly Asp Leu Val Ser Lys Pro Tyr Ile Asp Ile Thr Leu Asn Leu Met
        195                 200                 205

Lys Thr Phe Gly Val Glu Ile Glu Asn Gln His Tyr Gln Gln Phe Val
    210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ile Lys
                245                 250                 255

Gly Gly Thr Val Lys Val Thr Gly Ile Gly Arg Asn Ser Met Gln Gly
            260                 265                 270

Asp Ile Arg Phe Ala Asp Val Leu Glu Lys Met Gly Ala Thr Ile Cys
        275                 280                 285

Trp Gly Asp Asp Tyr Ile Ser Cys Thr Arg Gly Glu Leu Asn Ala Ile
    290                 295                 300

Asp Met Asp Met Asn His Ile Pro Asp Ala Ala Met Thr Ile Ala Thr
305                 310                 315                 320

Ala Ala Leu Phe Ala Lys Gly Thr Thr Arg Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Glu Gly His Asp Tyr Ile Arg Ile
        355                 360                 365

Thr Pro Pro Glu Lys Leu Asn Phe Ala Glu Ile Ala Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Ile Ser Gln Ala Ala
            420                 425
```

<210> SEQ ID NO 11
<211> LENGTH: 518
<212> TYPE: PRT
<213> ORGANISM: Linum usitatissimum

<400> SEQUENCE: 11

```
Met Ala Leu Val Thr Lys Ile Cys Gly Gly Ala Asn Ala Val Ala Leu
1               5                   10                  15

Pro Ala Thr Phe Gly Thr Arg Arg Thr Lys Ser Ile Ser Ser Ser Val
                20                  25                  30

Ser Phe Arg Ser Ser Thr Ser Pro Pro Ser Leu Lys Gln Arg Arg Arg
            35                  40                  45

Ser Gly Asn Val Ala Ala Ala Ala Ala Pro Leu Arg Val Ser Ala
        50                  55                  60

Ser Leu Thr Thr Ala Ala Glu Lys Ala Ser Thr Val Pro Glu Glu Val
65                  70                  75                  80

Val Leu Gln Pro Ile Lys Asp Ile Ser Gly Ile Val Thr Leu Pro Gly
                85                  90                  95
```

```
Ser Lys Ser Leu Ser Asn Arg Ile Leu Leu Ala Ala Leu Ser Glu
            100                 105                 110
Gly Thr Thr Val Val Asp Asn Leu Leu Asn Ser Asp Val His Tyr
            115                 120                 125
Met Leu Gly Ala Leu Lys Thr Leu Gly Leu Asn Val Glu His Ser Ser
130                 135                 140
Glu Gln Lys Arg Ala Ile Val Glu Gly Cys Gly Gly Val Phe Pro Val
145                 150                 155                 160
Gly Lys Leu Ala Lys Asn Asp Ile Glu Leu Phe Leu Gly Asn Ala Gly
                165                 170                 175
Thr Ala Met Arg Pro Leu Thr Ala Val Thr Ala Ala Gly Gly Asn
                180                 185                 190
Ser Ser Tyr Ile Leu Asp Gly Val Pro Arg Met Arg Glu Arg Pro Ile
            195                 200                 205
Gly Asp Leu Val Val Gly Leu Lys Gln Leu Gly Ala Asp Val Thr Cys
            210                 215                 220
Ser Ser Thr Ser Cys Pro Pro Val His Val Asn Gly Gln Gly Gly Leu
225                 230                 235                 240
Pro Gly Gly Lys Val Lys Leu Ser Gly Ser Ile Ser Ser Gln Tyr Leu
                245                 250                 255
Thr Ala Leu Leu Met Ala Ala Pro Leu Ala Leu Gly Asp Val Glu Ile
                260                 265                 270
Glu Ile Val Asp Lys Leu Ile Ser Val Pro Tyr Val Asp Met Thr Leu
            275                 280                 285
Lys Leu Met Glu Arg Phe Gly Val Ala Val Glu His Ser Gly Ser Trp
            290                 295                 300
Asp Arg Phe Phe Val Lys Gly Gly Gln Lys Tyr Lys Ser Pro Gly Asn
305                 310                 315                 320
Ala Tyr Val Glu Gly Asp Ala Ser Ser Ala Ser Tyr Phe Leu Ala Gly
                325                 330                 335
Ala Ala Ile Thr Gly Gly Thr Ile Thr Val Glu Gly Cys Gly Thr Ser
                340                 345                 350
Ser Leu Gln Gly Asp Val Lys Phe Ala Glu Val Leu Glu Lys Met Gly
            355                 360                 365
Ala Lys Val Ile Trp Thr Glu Asn Ser Val Thr Val Thr Gly Pro Pro
370                 375                 380
Arg Asp Ala Ser Gly Arg Lys His Leu Arg Ala Val Asp Val Asn Met
385                 390                 395                 400
Asn Lys Met Pro Asp Val Ala Met Thr Leu Ala Val Val Ala Leu Tyr
                405                 410                 415
Ala Asp Gly Pro Thr Ala Ile Arg Asp Val Ala Ser Trp Arg Val Lys
                420                 425                 430
Glu Thr Glu Arg Met Ile Ala Ile Cys Thr Glu Leu Arg Lys Leu Gly
            435                 440                 445
Ala Thr Val Glu Glu Gly Pro Asp Tyr Cys Ile Ile Thr Pro Pro Glu
            450                 455                 460
Lys Leu Asn Ile Ala Glu Ile Asp Thr Tyr Asp Asp His Arg Met Ala
465                 470                 475                 480
Met Ala Phe Ser Leu Ala Ala Cys Ala Asp Val Pro Val Thr Ile Arg
                485                 490                 495
Asp Pro Gly Cys Thr Lys Lys Thr Phe Pro Asp Tyr Phe Glu Val Leu
            500                 505                 510
```

Glu Arg Tyr Thr Lys His
        515

<210> SEQ ID NO 12
<211> LENGTH: 519
<212> TYPE: PRT
<213> ORGANISM: Linum usitatissimum

<400> SEQUENCE: 12

Met Ala Gln Val Thr Lys Ile Cys Gly Gly Ala Asn Ala Val Ala Leu
1               5                   10                  15

Pro Ala Thr Phe Gly Thr Arg Arg Thr Lys Ser Ile Ser Ser Ser Val
            20                  25                  30

Ser Phe Arg Ser Ser Thr Ser Pro Ser Leu Lys Gln Arg Arg Leu
        35                  40                  45

Leu Gly Asn Val Ala Ala Ala Ala Ala Ala Pro Leu Arg Ile Ser
    50                  55                  60

Ala Ser Leu Ala Thr Ala Ala Glu Lys Ala Ser Thr Val Pro Glu Glu
65                  70                  75                  80

Ile Val Leu Gln Pro Ile Lys Asp Ile Ser Gly Ile Val Thr Leu Pro
                85                  90                  95

Gly Ser Lys Ser Leu Ser Asn Arg Ile Leu Leu Leu Ala Ala Leu Ser
            100                 105                 110

Glu Gly Lys Thr Val Val Asp Asn Leu Leu Asn Ser Asp Asp Val His
            115                 120                 125

Tyr Met Leu Gly Ala Leu Lys Thr Leu Gly Leu Asn Val Glu His Ser
        130                 135                 140

Ser Glu Gln Lys Arg Ala Ile Val Glu Gly Arg Gly Val Phe Pro
145                 150                 155                 160

Val Gly Lys Leu Gly Lys Asn Asp Ile Glu Leu Phe Leu Gly Asn Ala
                165                 170                 175

Gly Thr Ala Met Arg Pro Leu Thr Ala Ala Val Thr Ala Ala Gly Gly
            180                 185                 190

Asn Ser Ser Tyr Ile Leu Asp Gly Val Pro Arg Met Arg Glu Arg Pro
        195                 200                 205

Ile Gly Asp Leu Val Val Gly Leu Lys Gln Leu Gly Ala Asp Val Ser
    210                 215                 220

Cys Ser Ser Thr Ser Cys Pro Pro Val His Val Asn Ala Lys Gly Gly
225                 230                 235                 240

Leu Pro Gly Gly Lys Val Lys Leu Ser Gly Ser Ile Ser Ser Gln Tyr
                245                 250                 255

Leu Thr Ala Leu Leu Met Ala Ala Pro Leu Ala Leu Gly Asp Val Glu
            260                 265                 270

Ile Glu Ile Val Asp Lys Leu Ile Ser Val Pro Tyr Val Asp Met Thr
        275                 280                 285

Leu Lys Leu Met Glu Arg Phe Gly Val Ala Val Glu His Ser Gly Ser
    290                 295                 300

Trp Asp Arg Phe Phe Val Lys Gly Gly Gln Lys Tyr Lys Ser Pro Gly
305                 310                 315                 320

Asn Ala Tyr Val Glu Gly Asp Ala Ser Ser Ala Ser Tyr Phe Leu Ala
                325                 330                 335

Gly Ala Ala Ile Thr Gly Gly Thr Ile Thr Val Glu Gly Cys Gly Thr
            340                 345                 350

Ser Ser Leu Gln Gly Asp Val Lys Phe Ala Glu Val Leu Glu Lys Met
        355                 360                 365

```
Gly Ala Lys Val Thr Trp Thr Glu Thr Ser Val Thr Val Thr Gly Pro
            370                 375                 380
Pro Arg Asp Ala Ser Gly Lys Lys His Leu Arg Ala Val Asp Val Asn
385                 390                 395                 400
Met Asn Lys Met Pro Asp Val Ala Met Thr Leu Ala Val Ala Leu
            405                 410                 415
Tyr Ala Asp Gly Pro Thr Ala Ile Arg Asp Val Ala Ser Trp Arg Val
            420                 425                 430
Lys Glu Thr Glu Arg Met Ile Ala Val Cys Thr Glu Leu Arg Lys Leu
            435                 440                 445
Gly Ala Thr Val Glu Glu Gly Pro Asp Tyr Cys Ile Ile Thr Pro Pro
            450                 455                 460
Glu Lys Leu Ser Ile Ala Glu Ile Asp Thr Tyr Asp His Arg Met
465                 470                 475                 480
Ala Met Ala Phe Ser Leu Ala Ala Cys Ala Asp Val Pro Val Thr Ile
            485                 490                 495
Arg Asp Pro Gly Cys Thr Lys Lys Thr Phe Pro Asp Tyr Phe Glu Val
            500                 505                 510
Leu Glu Arg Tyr Thr Lys His
            515

<210> SEQ ID NO 13
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gtcgtgctgc ttcatgtggt cggggtagcg gctgaagcac tgcacgccgt aggtgaaggt    60
ggtcacgagg gtgggccagg gcacgggcag cttgccggtg g                       101

<210> SEQ ID NO 14
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gtcgtgctgc ttcatgtggt cggggtagcg gctgaagcac tgcacgccgt gggtgaaggt    60
ggtcacgagg gtgggccagg gcacgggcag cttgccggtg g                       101

<210> SEQ ID NO 15
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
ccaccggcaa gctgcccgtg ccctggccca ccctcgtgac caccttcacc tacggcgtgc    60
agtgcttcag ccgctacccc gaccacatga agcagcacga c                       101

<210> SEQ ID NO 16
<211> LENGTH: 101
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ccaccggcaa gctgcccgtg ccctggccca ccctcgtgac caccttcacc cacggcgtgc    60
agtgcttcag ccgctacccc gaccacatga agcagcacga c                       101

<210> SEQ ID NO 17
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
aagatggtgc gctcctggac gtagccttcg ggcatggcgg acttgaagaa gtcgtgctgc    60
ttcatgtggt ctgggtagcg gctgaagcac tgcacgccgt aggtgaaggt ggtcacgagg   120
gtgggccagg gcacgggcag cttgccggtg gtgcagatga acttcagggt cagcttgccg   180
taggtggcat cgccctcgcc c                                             201

<210> SEQ ID NO 18
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
aagtggtgcg ctcctggacg tagccttcgg gcatggcgga cttgaagaag tcgtgctgct    60
tcatgtggtc ggggtagcgg ctgaagcact gcacgccgtg gtgaaggtg gtcacgaggg   120 tgggccaggg cacgggcagc ttgccggtgg tgcagatgaa cttcagggtc agcttgccgt   180
aggtggcatc gccctcgccc                                               200

<210> SEQ ID NO 19
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gggcgagggc gatgccacct acggcaagct gaccctgaag ttcatctgca ccaccggcaa    60
gctgcccgtg ccctggccca ccctcgtgac caccttcacc tacggcgtgc agtgcttcag   120
ccgctacccc gaccacatga agcagcacga cttcttcaag tccgccatgc ccgaaggcta   180
cgtccaggag cgcaccatct t                                             201

<210> SEQ ID NO 20
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
gggcgagggc gatgccacct acggcaagct gaccctgaag ttcatctgca ccaccggcaa      60
gctgcccgtg ccctggccca ccctcgtgac caccttcacc cacggcgtgc agtgcttcag     120
ccgctacccc gaccacatga agcagcacga cttcttcaag tccgccatgc ccgaaggcta    180
cgtccaggag cgcaccatct t                                               201
```

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
tttttttttt                                                            10
```

<210> SEQ ID NO 22
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
gggcgagggc gatgccacct acggcaagct gaccctgaag ttcatctgca ccaccggcaa      60
gctgcccgtg ccctggccca ccctcgtgac caccttcacc tacggcgtgc agtgcttcag     120
ccgctaccca gaccacatga agcagcacga cttcttcaag tccgccatgc ccgaaggcta    180
cgtccaggag cgcaccatct t                                               201
```

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

```
ggtgccgcac gtcacgaagt cgg                                             23
```

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

```
ccctcgtgac caccttcacc tacggcgtgc agtgcttcag c                          41
```

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

```
gtcgtgctgc ttcatgtggt                                                 20
```

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtgaccacct tcacctacgg cgtgcagtgc ttcagccgct acccagacca catgaagcag      60

<210> SEQ ID NO 27
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
ccaccggcaa gctgcccgtg ccctggccca ccctcgtgac caccttcacc tacggcgtgc      60
agtgcttcag ccgctaccca gaccacatga agcagcacga c                        101

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctcgtgacca ccttcaccca                                                 20

<210> SEQ ID NO 29
<211> LENGTH: 71
<212> TYPE: DNA
<213> ORGANISM: Artificial Sequence
<220> FEATURE:
<223> OTHER INFORMATION: Description of Combined DNA/RNA Molecule:
      Synthetic oligonucleotide

<400> SEQUENCE: 29
gcugcccgug ccctggccca ccctcgtgac caccttcacc tacggcgtgc agtgcttcag      60
ccgctacccc g                                                          71

<210> SEQ ID NO 30
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttcatgtggt cggggtagcg gctgaagcac tgcacgccgt aggtgaaggt ggtcacgagg      60
gtgggccagg g                                                          71

<210> SEQ ID NO 31
<211> LENGTH: 71
<212> TYPE: DNA
<213> ORGANISM: Artificial Sequence
<220> FEATURE:
<223> OTHER INFORMATION: Description of Combined DNA/RNA Molecule:

Synthetic oligonucleotide

<400> SEQUENCE: 31
uucauguggu cggggtagcg gctgaagcac tgcacgccgt aggtgaaggt ggtcacgagg    60
gtgggccagg g    71

<210> SEQ ID NO 32
<211> LENGTH: 201
<212> TYPE: DNA
<213> ORGANISM: Artificial Sequence
<220> FEATURE:
<223> OTHER INFORMATION: Description of Combined DNA/RNA Molecule:
      Synthetic oligonucleotide

<400> SEQUENCE: 32
aagauggugc gctcctggac gtagccttcg ggcatggcgg acttgaagaa gtcgtgctgc    60
ttcatgtggt cggggtagcg gctgaagcac tgcacgccgt aggtgaaggt ggtcacgagg    120
gtgggccagg gcacgggcag cttgccggtg gtgcagatga acttcagggt cagcttgccg    180
taggtggcat cgccctcgcc c    201

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tggttatgca attggaagat cgc    23

<210> SEQ ID NO 34
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
agctgctgca aacagcaaca tgttcgggaa tatctcgtcc tcctgagccg gatccccgag    60
aaatgtgtga gctcggttag ctttgtagaa gcgatcttcc aattgcataa ccatgccaag    120
atgctggttg tttaataaaa gtaccttcac tggaagattc tctacacgaa tagtggctag    180
ctcttgcaca ttcattataa a    201

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gtgaccacct tcaccca    17

<210> SEQ ID NO 36
<211> LENGTH: 201
<212> TYPE: DNA
<213> ORGANISM: Artificial Sequence
<220> FEATURE:
<223> OTHER INFORMATION: Description of Artificial Sequence: Synthetic

```
              polynucleotide

<400> SEQUENCE: 36
aagatggtgc gctcctggac gtagccttcg ggcatggcgg acttgaagaa gtcgtgctgc    60
ttcatgtggt cggggtagcg gctgaagcac tgcacgccgt acgtaaacgt ggtcacgagg   120
gtgggccagg gcacgggcag cttgccggtg gtgcagatga acttcagggt cagcttgccg   180
taggtggcat cgccctcgcc c                                             201

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gctgaagcac tgcacgccgt aggtgaaggt ggtcacgagg g                        41

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tggaacagct atgcgtccg                                                 19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgagttgcct ccagcggct                                                 19

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggacgacggc aactacaaga cc                                             22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
taaacggcca caagttcagc                                                20

<210> SEQ ID NO 42
```

```
<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gcatagcagt gagcagaagc                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agaagctgaa aggctggaag                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ggctgaagca ctgcacgccg                                                    20

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tggtcggggt agcggctga                                                     19

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tcgtgaccac cttcaccca                                                     19

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ccctcgtgac caccttcacc tacggcgtgc agtgcttcag cc                           42

<210> SEQ ID NO 48
<211> LENGTH: 201
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
aagatggtgc gctcctggac gtagccttcg ggcatggcgg acttgaagaa gtcgtgctgc    60
ttcatgtggt cggggtagcg gctgaagcac tgcacgccgt aggtgaaggt ggtcacgagg    120
gtgggccagg gcacgggcag cttgccggtg gtgcagatga acttcagggt cagcttgccg    180
taggtggcat cgccctcgcc c                                              201

<210> SEQ ID NO 49
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
cggtcggtaa actggcgaag aacgatattg aacttttcct tggaaatgct ggaatagcta    60
tgcgtgcgct gacagctgct gtaacagccg ctggaggcaa ctcaaggtcc cttccctcaa    120
ctccttccag cctttcagct tcttc                                          145

<210> SEQ ID NO 50
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
cggtcggtaa actggcgaag aacgatattg aacttttcct tggaaatgct ggaatagcta    60
tgcgtgcgct gacagctgct gtaacagccg ctggaggcaa ctcaaggttc cttccctcaa    120
ctccttccag cctttcagct tcttc                                          145

<210> SEQ ID NO 51
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gctgaagcac tgcacgccgt gggtgaaggt ggtcacgagg g                        41

<210> SEQ ID NO 52
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
ctgacctgaa cttgatctca attaacccct gcggttccag aacattgcct tttgcagtcc    60
tctcagcata gcactcaatg cggtctgggt ttatcttgct tccaacgaca acccaagccc    120
ctcctcgtag ctctgcagcc atgggaatgt agacaaaggc aggctgattg tatgtcctaa    180
```
ggttctcaac aatagtcgag ccc 203

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
acgaggaggg gcttgggttg tgg 23

<210> SEQ ID NO 54
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
cauaagaugc agcuagacag 20

<210> SEQ ID NO 55
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
agcuagacag uggugaaauu 20

<210> SEQ ID NO 56
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uagacagugg ugaaauuagg 20

<210> SEQ ID NO 57
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
agacaguggu gaaauuaggu 20

<210> SEQ ID NO 58
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58

```
guggguuauu gauucuguug                                              20

<210> SEQ ID NO 59
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uggguuauug auucuguugu                                              20

<210> SEQ ID NO 60
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uauugauucu guguggggca                                              20

<210> SEQ ID NO 61
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61 ucguugugg gcaaggaaga                                               20

<210> SEQ ID NO 62
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gugggcaagg aagauggacu                                              20

<210> SEQ ID NO 63
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
caaggaagau ggacuuggug                                              20

<210> SEQ ID NO 64
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
cuuggugugg agaauauaca                                              20
```

```
<210> SEQ ID NO 65
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
cuauugccag ugcuuauucu                                              20

<210> SEQ ID NO 66
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
ugcuuauucu agggcauaua                                              20

<210> SEQ ID NO 67
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uuuacacuua cauuugugac                                              20

<210> SEQ ID NO 68
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uuugugacug gaagaacugu                                              20

<210> SEQ ID NO 69
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
acuggaagaa cuguuggaau                                              20

<210> SEQ ID NO 70
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
ggagcuuauc uugcucgacu                                              20
```

```
<210> SEQ ID NO 71
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
auaugcccua gaauaagcac                                                    20

<210> SEQ ID NO 72
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gauaagaugc agcuagacag                                                    20

<210> SEQ ID NO 73
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
ggcuagacag uggugaaauu                                                    20

<210> SEQ ID NO 74
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
gagacagugg ugaaauuagg                                                    20

<210> SEQ ID NO 75
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ggacaguggu gaaauuaggu                                                    20

<210> SEQ ID NO 76
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76 ggggguuauug auucuguugu                                                   20
```

```
<210> SEQ ID NO 77
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
gauugauucu guugugggca                                                   20

<210> SEQ ID NO 78
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
gcuguugugg gcaaggaaga                                                   20

<210> SEQ ID NO 79
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gaaggaagau ggacuuggug                                                   20

<210> SEQ ID NO 80
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
guuggugugg agaauauaca                                                   20

<210> SEQ ID NO 81
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
guauugccag ugcuuauucu                                                   20

<210> SEQ ID NO 82
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
ggcuuauucu agggcauaua                                                   20

<210> SEQ ID NO 83
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
guuacacuua cauuugugac                                                 20

<210> SEQ ID NO 84
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
guugugacug gaagaacugu                                                 20

<210> SEQ ID NO 85
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
gcuggaagaa cuguuggaau                                                 20

<210> SEQ ID NO 86
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
guaugcccua gaauaagcac                                                 20

<210> SEQ ID NO 87
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
cgacuauugu ugagaaccuu                                                 20

<210> SEQ ID NO 88
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ugccuuuguc uacauuccca                                                 20

<210> SEQ ID NO 89
<211> LENGTH: 20
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
cccauggcug cagagcuacg                                              20

<210> SEQ ID NO 90
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
auggcugcag agcuacgagg                                              20

<210> SEQ ID NO 91
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
uggcugcaga gcuacgagga                                              20

<210> SEQ ID NO 92
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
ggcugcagag cuacgaggag                                              20

<210> SEQ ID NO 93
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
cagagcuacg aggaggggcu                                              20

<210> SEQ ID NO 94
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
agagcuacga ggaggggcuu                                              20

<210> SEQ ID NO 95
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 95
acgaggaggg gcuuggguug                                                   20

<210> SEQ ID NO 96
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
gcauugagug cuaugcugag                                                   20

<210> SEQ ID NO 97
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
uaugcugaga ggacugcaaa                                                   20

<210> SEQ ID NO 98
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
gacugcaaaa ggcaauguuc                                                   20

<210> SEQ ID NO 99
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
ggcaauguuc uggaaccgca                                                   20

<210> SEQ ID NO 100
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
gcaauguucu ggaaccgcaa                                                   20

<210> SEQ ID NO 101
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 101
gguuaauuga gaucaaguuc                                                    20

<210> SEQ ID NO 102
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
ugagaucaag uucaggucag                                                    20

<210> SEQ ID NO 103
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
guucagguca gaggaacucc                                                    20

<210> SEQ ID NO 104
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
aacuccagga uugcaugagu                                                    20

<210> SEQ ID NO 105
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
caagccgacu caugcaaucc                                                    20

<210> SEQ ID NO 106
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
uugaucucaa uuaacccuug                                                    20

<210> SEQ ID NO 107
<211> LENGTH: 20
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 107
ucucagcaua gcacucaaug                                                  20

<210> SEQ ID NO 108
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
gcauagcacu caaugcgguc                                                  20

<210> SEQ ID NO 109
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
cauagcacuc aaugcggucu                                                  20

<210> SEQ ID NO 110
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
uccucguagc ucugcagcca                                                  20

<210> SEQ ID NO 111
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
agccauggga auguagacaa                                                  20

<210> SEQ ID NO 112
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
augggaaugu agacaaaggc                                                  20

<210> SEQ ID NO 113
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 113
caggcugauu guauguccua                                            20

<210> SEQ ID NO 114
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
ggacuauugu ugagaaccuu                                            20

<210> SEQ ID NO 115
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
ggccuuuguc uacauuccca                                            20

<210> SEQ ID NO 116
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
gccauggcug cagagcuacg                                            20

<210> SEQ ID NO 117
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
guggcugcag agcuacgagg                                            20

<210> SEQ ID NO 118
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
gggcugcaga gcuacgagga                                            20

<210> SEQ ID NO 119
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
gagagcuacg aggaggggcu                                           20

<210> SEQ ID NO 120
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
ggagcuacga ggaggggcuu                                           20

<210> SEQ ID NO 121
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
gcgaggaggg gcuugggusg                                           20

<210> SEQ ID NO 122
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gaugcugaga ggacugcaaa                                           20

<210> SEQ ID NO 123
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
ggagaucaag uucaggucag                                           20

<210> SEQ ID NO 124
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gacuccagga uugcaugagu                                           20

<210> SEQ ID NO 125
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
gaagccgacu caugcaaucc                                            20

<210> SEQ ID NO 126
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
gugaucucaa uuaacccuug                                            20

<210> SEQ ID NO 127
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gcucagcaua gcacucaaug                                            20

<210> SEQ ID NO 128
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
gauagcacuc aaugcggucu                                            20

<210> SEQ ID NO 129
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gccucguagc ucugcagcca                                            20

<210> SEQ ID NO 130
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ggccauggga auguagacaa                                            20

<210> SEQ ID NO 131
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131

```
gugggaaugu agacaaaggc                                                   20

<210> SEQ ID NO 132
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
gaggcugauu guauguccua                                                   20

<210> SEQ ID NO 133
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
gtcatagcac ataagatgca gctagacagt ggtgaaatta ggtgggttat tgattctgtt       60
gtgggcaagg aagatggact tggtgtggag aatgctcatg gaagtgctgc tattgccagt      120
gcttattcta gggcatataa ggagacattt acacttacat ttgtgactgg aagaactgtt      180
ggaataggag cttatcttgc tcc                                              203

<210> SEQ ID NO 134
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
gagcaagata agctcctatt ccaacagttc ttccagtcac aaatgtaagt gtaaatgtct       60
ccttatatgc cctagaataa gcactggcaa tagcagcact tccatgcaga ttctccacac      120
caagtccatc ttccttgccc acaacagaat caataaccca cctaatttca ccactgtcta      180
gctgcatctt atgtgctatg acc                                              203

<210> SEQ ID NO 135
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
gtcatagcac ataagatgca gctagacagt ggtgaaatta ggtgggttat tgattctgtt       60
gtgggcaagg aagatggact tggtgtggag aatatacatt gcagtgctgc tattgccagt      120
gcttattcta gggcatataa ggagacattt acacttacat ttgtgactgg aagaactgtt      180
ggaataggag cttatcttgc tcc                                              203

<210> SEQ ID NO 136
<211> LENGTH: 203
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 136
gagcaagata agctcctatt ccaacagttc ttccagtcac aaatgtaagt gtaaatgtct    60
ccttatatgc cctagaataa gcactggcaa tagcagcact gcaatgtata ttctccacac   120
caagtccatc ttccttgccc acaacagaat caataaccca cctaatttca ccactgtcta   180
gctgcatctt atgtgctatg acc                                           203

<210> SEQ ID NO 137
<211> LENGTH: 203
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 137
gtcatagcac ataagatgca gctagacagt ggtgaaatta ggtgggttat tgattctgtt    60
gtgggcaagg aagatggact tggtgtggag aatatacatg gaagtgctcc aattgccagt   120
gcttattcta gggcatataa ggagacattt acacttacat ttgtgactgg aagaactgtt   180
ggaataggag cttatcttgc tcc                                           203

<210> SEQ ID NO 138
<211> LENGTH: 203
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 138
gagcaagata agctcctatt ccaacagttc ttccagtcac aaatgtaagt gtaaatgtct    60
ccttatatgc cctagaataa gcactggcaa tggtagcact tccatgtata ttctccacac   120
caagtccatc ttccttgccc acaacagaat caataaccca cctaatttca ccactgtcta   180
gctgcatctt atgtgctatg acc                                           203

<210> SEQ ID NO 139
<211> LENGTH: 203
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 139
ggctcgacta ttgttgagaa ccttaggaca tacaatcagc ctgcctttgt ctacattccc    60
atggctgcag agctacgagg aggggcttgg gttgtggttg gtagcaagat aaacccagac   120
cgcattgagt gctatgctga gaggactgca aaaggcaatg ttctggaacc gcaagggtta   180
attgagatca agttcaggtc agc                                           203

<210> SEQ ID NO 140
<211> LENGTH: 203
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 140
ctgacctgaa cttgatctca attaacccct gcggttccag aacattgcct tttgcagtcc    60
tctcagcata gcactcaatg cggtctgggt ttatcttaaa atcaacgaca acccaagccc   120
ctcctcgtag ctctgcagcc atgggaatgt agacaaaggc aggctgattg tatgtcctaa   180
ggttctcaac aatagtcgag ccc                                          203

<210> SEQ ID NO 141
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
ggctcgacta ttgttgagaa ccttaggaca tacaatcagc ctgcctttgt ctacattccc    60
atggctgcag agctacgagg aggcgcttgg gttgtggttg atagcaagat aaacccagac   120
cgcattgaga ggtatgctga gaggactgca aaaggcaatg ttctggaacc gcaagggtta   180
attgagatca agttcaggtc agc                                          203

<210> SEQ ID NO 142
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
ggctcgacta ttgttgagaa ccttaggaca tacaatcagc ctgcctttgt ctacattccc    60
atggctgcag agctacgagg aggggcttgg gttgtggttg atagcgaaat aaacccagac   120
cgcattgagt gctatgctga gaggactgca aaaggcaatg ttctggaacc gcaagggtta   180
attgagatca agttcaggtc agc                                          203

<210> SEQ ID NO 143
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
ctgacctgaa cttgatctca attaacccct gcggttccag aacattgcct tttgcagtcc    60
tctcagcata gcactcaatg cggtctgggt ttatttcgct atcaaccaca acccaagcgc   120
ctcctcgtag ctctgcagcc atgggaatgt agacaaaggc aggctgattg tatgtcctaa   180
ggttctcaac aatagtcgag ccc                                          203

<210> SEQ ID NO 144
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
ggctcgacta ttgttgagaa ccttaggaca tacaatcagc ctgcctttgt ctacattccc    60
atggctgcag agctacgagg aggggcttgg gttgtggttg atagcaagat aaacccagac    120
cgcattgagc gttatgctga gaggactgca aaaggcaatg ttctggaacc gcaagggtta    180
attgagatca agttcaggtc agc                                            203

<210> SEQ ID NO 145
<211> LENGTH: 203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
ctgacctgaa cttgatctca attaacccttt gcggttccag aacattgcct tttgcagtcc    60
tctcagcata ttgctcaatg cggtctgggt ttatcttgct atcaacgaca acccaagccc    120
ctcctcgtag ctctgcagcc atgggaatgt agacaaaggc aggctgattg tatgtcctaa    180
ggttctcaac aatagtcgag ccc                                            203

<210> SEQ ID NO 146
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
cagaagcgcg ccauuguuga                                                20

<210> SEQ ID NO 147
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
cgcgccauug uugaagguug                                                20

<210> SEQ ID NO 148
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
cgcgccauug uugaaggucg                                                20

<210> SEQ ID NO 149
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
gccauuguug aagguugugg                                                20

```
<210> SEQ ID NO 150
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gccauuguug aaggucgugg                                              20

<210> SEQ ID NO 151
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
agguuguggu ggugugeuuuc                                             20

<210> SEQ ID NO 152
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
aggucguggu ggugugeuuuc                                             20

<210> SEQ ID NO 153
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
ugugguggug uguuccggu                                               20

<210> SEQ ID NO 154
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154 cguggueggug uguuccggu                                              20

<210> SEQ ID NO 155
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155 uguguuccg gucgguaaac                                               20

<210> SEQ ID NO 156
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
uguuuccggu cgguaaacug                                                   20

<210> SEQ ID NO 157
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
aacgauauug aacuuuuccu                                                   20

<210> SEQ ID NO 158
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
aacgauaucg aacuuuuccu                                                   20

<210> SEQ ID NO 159
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
gaacuuuucc uuggaaaugc                                                   20

<210> SEQ ID NO 160
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
acagcugcug uaacagccgc                                                   20

<210> SEQ ID NO 161
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
gcugcuguaa cagccgcugg                                                   20

<210> SEQ ID NO 162
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
aacucaagcu acauacucga                                                 20

<210> SEQ ID NO 163
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
aacucaagcu acauacucga                                                 20

<210> SEQ ID NO 164
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
cgaaugagag agagaccaau                                                 20

<210> SEQ ID NO 165
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
cgaaugagag agagaccgau                                                 20

<210> SEQ ID NO 166
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
agagagacca auggagauu                                                  20

<210> SEQ ID NO 167
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
ccaauuggag auuugguugu                                                 20

<210> SEQ ID NO 168
<211> LENGTH: 20
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 168
ccgauuggag auuuaguugu                                                    20

<210> SEQ ID NO 169
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
ccaacaacca aaucuccaau                                                    20

<210> SEQ ID NO 170
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
ccaacaacua aaucuccaau                                                    20

<210> SEQ ID NO 171
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
auuggucucu cucucauucg                                                    20

<210> SEQ ID NO 172
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
aucggucucu cucucauucg                                                    20

<210> SEQ ID NO 173
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
guagcuugag uugccuccag                                                    20

<210> SEQ ID NO 174
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 174
gcuguuacag cagcugucag                                                    20

<210> SEQ ID NO 175
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uagcuguucc agcauuucca                                                    20

<210> SEQ ID NO 176
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
uucuucgcca guuuaccgac                                                    20

<210> SEQ ID NO 177
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uucuucccca guuuaccgac                                                    20

<210> SEQ ID NO 178
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
accaccacaa ccuucaacaa                                                    20

<210> SEQ ID NO 179
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
accaccacga ccuucaacaa                                                    20

<210> SEQ ID NO 180
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 180
gagaagcgcg ccauuguuga                                                   20

<210> SEQ ID NO 181
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
ggcgccauug uugaagguug                                                   20

<210> SEQ ID NO 182
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
ggcgccauug uugaaggucg                                                   20

<210> SEQ ID NO 183
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
ggguuguggu gguguguuuc                                                   20

<210> SEQ ID NO 184
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
gggucguggu gguguguuuc                                                   20

<210> SEQ ID NO 185
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
ggugguggug uguuccggu                                                    20

<210> SEQ ID NO 186
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 186 gguggugguq uguuuccggu                                             20

<210> SEQ ID NO 187
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
gguguuuccg gucgguaaac                                             20

<210> SEQ ID NO 188
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
gguuuccggu cgguaaacug                                             20

<210> SEQ ID NO 189
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
gacgauauug aacuuuuccu                                             20

<210> SEQ ID NO 190
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
gacgauaucg aacuuuuccu                                             20

<210> SEQ ID NO 191
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
gcagcugcug uaacagccgc                                             20

<210> SEQ ID NO 192
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 192
gacucaagcu acauacucga                                        20

<210> SEQ ID NO 193
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
gacucaagcu acauacucga                                        20

<210> SEQ ID NO 194
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
ggaaugagag agagaccaau                                        20

<210> SEQ ID NO 195
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
ggaaugagag agagaccgau                                        20

<210> SEQ ID NO 196
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
ggagagacca auuggagauu                                        20

<210> SEQ ID NO 197
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
gcaauuggag auuugguugu                                        20

<210> SEQ ID NO 198
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 198
gcgauuggag auuuaguugu                                               20

<210> SEQ ID NO 199
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
gcaacaacca aaucuccaau                                               20

<210> SEQ ID NO 200
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
gcaacaacua aaucuccaau                                               20

<210> SEQ ID NO 201
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
guuggucucu cucucauucg                                               20

<210> SEQ ID NO 202
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
gucggucucu cucucauucg                                               20

<210> SEQ ID NO 203
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
gagcuguucc agcauuucca                                               20

<210> SEQ ID NO 204
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
```

```
gucuucgcca guuuaccgac                                            20

<210> SEQ ID NO 205
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
gucuucccca guuuaccgac                                            20

<210> SEQ ID NO 206
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
gccaccacaa ccuucaacaa                                            20

<210> SEQ ID NO 207
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
gccaccacga ccuucaacaa                                            20

<210> SEQ ID NO 208
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208
cggtcggtaa actggcgaag aacgatattg aacttttcct tggaaatgct gctatagcta     60
tgcgtgcgct gacagctgct gtaacagccg ctggaggcaa ctcaaggtcc cttccctcaa    120
ctccttccag cctttcagct tcttc                                         145

<210> SEQ ID NO 209
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209
aagaagctga aaggctggaa ggagttgagg gaagggacct tgagttgcct ccagcggctg     60
ttacagcagc tgtcagcgga cgcatagctg tggcagcatt tccaaggaaa agttcaatat    120
cgttcttcgc cagtttaccg accgc                                         145

<210> SEQ ID NO 210
<211> LENGTH: 145
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210
aagaagctga aaggctggaa ggagttgagg gaagggacct tgagttgcct ccagcggctg    60
ttacagcagc tgtcagcgca cgcatagcta ttccagcatt tccaaggaaa agttcaatat   120
cgttcttcgc cagtttaccg accgc                                         145

<210> SEQ ID NO 211
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211
cggtcggtaa actggcgaag aacgatattg aacttttcct tggaaatgct ggaattgcta    60
tgcgttctct gacagctgct gtaacagccg ctggaggcaa ctcaaggtcc cttccctcaa   120
ctccttccag cctttcagct tcttc                                         145

<210> SEQ ID NO 212
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212
aagaagctga aaggctggaa ggagttgagg gaagggacct tgagttgcct ccagcggctg    60
ttacagcagc tgtcagtgaa cgcatagcaa ttccagcatt tccaaggaaa agttcaatat   120
cgttcttcgc cagtttaccg accgc                                         145

<210> SEQ ID NO 213
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 213
cggtcggtaa actggcgaag aacgatattg aacttttcct tggaaatgct ggaatcgcta    60
tgcgtactct gacagctgct gtaacagccg ctggaggcaa ctcaaggtcc cttccctcaa   120
ctccttccag cctttcagct tcttc                                         145

<210> SEQ ID NO 214
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214
aagaagctga aaggctggaa ggagttgagg gaagggacct tgagttgcct ccagcggctg    60
ttacagcagc tgtcagtgta cgcatagcaa ttccagcatt tccaaggaaa agttcaatat   120
cgttcttcgc cagtttaccg accgc				145

<210> SEQ ID NO 215
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215
cggtcggtaa actggcgaag aacgatattg aacttttcct tggaaatgct ggaattgcta		60 tgcgtgcgct gacagctgct gtaacagccg ctggaggcaa ctcaaggtcc cttccctcaa		120 ctccttccag cctttcagct tcttc				145

<210> SEQ ID NO 216
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 216
aagaagctga aaggctggaa ggagttgagg gaaggaacct tgagttgcct ccagcggctg		60 ttacagcagc tgtcagcgca cgcatagcta ttccagcatt ccaaggaaa agttcgatat		120 cgttcttccc cagtttaccg accgc				145

<210> SEQ ID NO 217
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 217
cggtcggtaa actggcgaag aacgatattg aacttttcct tggaaatgct ggaatagcta		60 tgcgtgctct gacagctgct gtaacagccg ctggaggcaa ctcaaggtcc cttccctcaa		120 ctccttccag cctttcagct tcttc				145

<210> SEQ ID NO 218
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 218
aagaagctga aaggctggaa ggagttgagg gaagggacct tgagttgcct ccagcggctg		60 ttacagcagc tgtcagcgca cgcatagctg ttccagcatt ccaaggaaa agttcaatat		120 cgttcttcgc cagtttaccg accgc				145

<210> SEQ ID NO 219
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 219
cggtcggtaa actggggaag aacgatatcg aacttttcct tggaaatgct gctatagcta    60
tgcgtgcgct gacagctgct gtaacagccg ctggaggcaa ctcaaggttc cttccctcaa   120
ctccttccag cctttcagct tcttc                                         145

<210> SEQ ID NO 220
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 220
aagaagctga aaggctggaa ggagttgagg gaaggaacct tgagttgcct ccagcggctg    60
ttacagcagc tgtcagcgga cgcatagctg ttgcagcatt ccaaggaaa agttcgatat    120 cgttcttccc cagtttaccg accgc                                         145

<210> SEQ ID NO 221
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221
cggtcggtaa actggggaag aacgatatcg aacttttcct tggaaatgct ggaatagcta    60
tgcgtgcgct gacagctgct gtaacagccg ctggaggcaa ctcaaggttc cttccctcaa   120
ctccttccag cctttcagct tcttc                                         145

<210> SEQ ID NO 222
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222
aagaagctga aaggctggaa ggagttgagg gaaggaacct tgagttgcct ccagcggctg    60
ttacagcagc tgtcagcgca cgcatagcta ttccagcatt ccaaggaaa agttcgatat    120 cgttcttccc cagtttaccg accgc                                         145

<210> SEQ ID NO 223
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223
cggtcggtaa actggggaag aacgatatcg aacttttcct tggaaatgct ggaattgcta    60
tgcgttctct gacagctgct gtaacagccg ctggaggcaa ctcaaggttc cttccctcaa   120
ctccttccag cctttcagct tcttc                                         145

<210> SEQ ID NO 224

<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224
aagaagctga aaggctggaa ggagttgagg gaaggaacct tgagttgcct ccagcggctg    60
ttacagcagc tgtcagtgaa cgcatagcga ttccagcatt tccaaggaaa agttcgatat   120
cgttcttccc cagtttaccg accgc                                         145

<210> SEQ ID NO 225
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225
cggtcggtaa actggggaag aacgatatcg aacttttcct tggaaatgct ggaatcgcta    60
tgcgtactct gacagctgct gtaacagccg ctggaggcaa ctcaaggttc cttccctcaa   120
ctccttccag cctttcagct tcttc                                         145

<210> SEQ ID NO 226
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226
aagaagctga aaggctggaa ggagttgagg gaaggaacct tgagttgcct ccagcggctg    60
ttacagcagc tgtcagtgta cgcatagcta ttccagcatt tccaaggaaa agttcgatat   120
cgttcttccc cagtttaccg accgc                                         145

<210> SEQ ID NO 227
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227
cggtcggtaa actggggaag aacgatatcg aacttttcct tggaaatgct ggaatcgcta    60
tgcgtgcgct gacagctgct gtaacagccg ctggaggcaa ctcaaggttc cttccctcaa   120
ctccttccag cctttcagct tcttc                                         145

<210> SEQ ID NO 228
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 228
aagaagctga aaggctggaa ggagttgagg gaaggaacct tgagttgcct ccagcggctg    60

```
ttacagcagc tgtcagcgga cgcatagcta ttccagcatt tccaaggaaa agttcgatat      120
cgttcttccc cagtttaccg accgc                                            145
```

<210> SEQ ID NO 229
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229

```
cggtcggtaa actggggaag aacgatatcg aactttttcct tggaaatgct ggaatagcta     60
tgcgtgctct gacagctgct gtaacagccg ctggaggcaa ctcaaggttc cttccctcaa     120
ctccttccag cctttcagct tcttc                                           145
```

<210> SEQ ID NO 230
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230

```
aagaagctga aaggctggaa ggagttgagg gaaggaacct tgagttgcct ccagcggctg     60
ttacagcagc tgtcagggaa cgcatagctg ttccagcatt tccaaggaaa agttcgatat    120
cgttcttccc cagtttaccg accgc                                          145
```

<210> SEQ ID NO 231
<211> LENGTH: 71
<212> TYPE: DNA
<213> ORGANISM: Artificial Sequence
<220> FEATURE:
<223> OTHER INFORMATION: Description of Combined DNA/RNA Molecule:
      Synthetic oligonucleotide

<400> SEQUENCE: 231

```
uucauguggu cggggtagcg gctgaagcac tgcacgccgt gggtgaaggt ggtcacgagg     60
gtgggccagg g                                                          71
```

<210> SEQ ID NO 232
<211> LENGTH: 71
<212> TYPE: DNA
<213> ORGANISM: Artificial Sequence
<220> FEATURE:
<223> OTHER INFORMATION: Description of Combined DNA/RNA Molecule:
      Synthetic oligonucleotide

<400> SEQUENCE: 232

```
gcugcccgug ccctggccca ccctcgtgac caccttcacc cacggcgtgc agtgcttcag     60
ccgctacccc g                                                          71
```

<210> SEQ ID NO 233
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
gcugcccgug                                                             10

<210> SEQ ID NO 234
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
gggcgagggc                                                             10

<210> SEQ ID NO 235
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 235
ccctgggaat ctgaaagaag agaagcaggc ccatttatat gggaaagaac aatagtattt      60
cttatatagg cccatttaag ttgaaaacaa tcttcaaaag tcccacatcg c              111

<210> SEQ ID NO 236
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 236
ggagcgagcg gagcgguaca guuuuagagc uagaaauagc aaguuaaaau aaggcuaguc      60
cguuaucaac uugaaaaagu ggcaccgagu cggugcuuuu                           100

<210> SEQ ID NO 237
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(14)
<223> OTHER INFORMATION: a, c, t, g, unknown or other
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: modified_base
<222> LOCATION: (35)..(48)
<223> OTHER INFORMATION: a, c, t, g, unknown or other
<220> FEATURE:
<221> NAME/KEY: misc_feature
<222> LOCATION: (35)..(48)
<223> OTHER INFORMATION: n is a, c, g, or t

<400> SEQUENCE: 237
nnnnnnnnnn nnnntgtacc gctccgctcg ctccnnnnnn nnnnnnnn                   48

<210> SEQ ID NO 238
<211> LENGTH: 48
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(14)
<223> OTHER INFORMATION: a, c, t, g, unknown or other
<220> FEATURE:
<221> NAME/KEY: misc_feature
<222> LOCATION: (1)..(14)
<223> OTHER INFORMATION: n is a, c, g, or t
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: modified_base
<222> LOCATION: (38)..(48)
<223> OTHER INFORMATION: a, c, t, g, unknown or other
<220> FEATURE:
<221> NAME/KEY: misc_feature
<222> LOCATION: (38)..(48)
<223> OTHER INFORMATION: n is a, c, g, or t

<400> SEQUENCE: 238
nnnnnnnnnn nnnnggagcg agcggagcgg tacanggnnn nnnnnnnn              48

<210> SEQ ID NO 239
<211> LENGTH: 177
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 239
ttagataaga aaacgaagct gagtttatat acagctagag tcgaagtagt gattgtcgtg    60
accaccttca cccagtttta gagctagaaa tagcaagtta aaataaggct agtccgttat   120
caacttgaaa aagtggcacc gagtcggtgc ccaggtcaag ttcacgaccc ttttttt     177

<210> SEQ ID NO 240
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
ccaccctcgt gaccaccttc acccacggcg tgcagtgctt cagccgctac cccgaccaca    60
tgaagcagca cgacttcttc a                                             81

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ctcgtgacca ccttcaccca cgg                                           23

<210> SEQ ID NO 242
```

-continued

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ccgaccacat gaagcagcac gac                                            23

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ccacggcgtg cagtgcttca gcc                                            23

<210> SEQ ID NO 244
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ccaccctcgt gaccaccttc acccacggcg tgcagtgctt cagccgctac cccgaccaca    60
tgaagc                                                               66

<210> SEQ ID NO 245
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ggaaatgctg gaacagctat gcgtccgctg acagctgctg taacagccgc tagaggcaac    60
tcaaggttcc                                                           70

<210> SEQ ID NO 246
<211> LENGTH: 7589
<212> TYPE: DNA
<213> ORGANISM: Alopecurus myosuroides

<400> SEQUENCE: 246
tcgataaact tcctgttgca tgtctctatc tctatggact aacggttcct atgtgcatgc    60
atctgtcagg tttccagacc tggggtttac aatcagttta tggcagtctg tgtttgaaga   120
acactgcaac tctgctgtct gtccaaaggg aggacgatgg gatccacaca tctgcccatt   180
gtcgggttta atgcatccac aacaccatcg ctatccactc ttcgccagat aaactcagct   240
gctgctgcat tccaatcttc gtcccttca aggtcatcca agaagaaaag ccgacgtgtt    300
aagtcaataa gggatgatgg cgatggaagc gtgccagacc ctgcaggcca tggccagtct   360
attcgccaag gtctcgctgg catcatcgac ctcccaaagg agggcgcatc agctccagat   420
gtggacattt cacatgggtc tgaagaccac aaggcctcct accaaatgaa tgggatactg   480
aatgaatcac ataacgggag gcacgcctct ctgtctaaag tttatgaatt ttgcacggaa   540
```

```
ttgggtggaa aaacaccaat tcacagtgta ttagtcgcca acaatggaat ggcagcagct    600
aagttcatgc ggagtgtccg gacatgggct aatgatacat ttgggtcaga gaaggcgatt    660
cagttgatag ctatggcaac tccggaagac atgagaataa atgcagagca cattagaatt    720
gctgatcagt ttgttgaagt acctggtgga acaaacaata caactatgc aaatgtccaa     780 ctcatagtgg agatagcaga gagaactggt gtctccgccg tttggcctgg ttggggccat    840
gcatctgaga atcctgaact tccagatgca ctaactgcaa aggaattgt ttttcttggg     900 ccaccagcat catcaatgaa cgcactaggc gacaaggttg gttcagctct cattgctcaa    960
gcagcagggg ttcccactct tgcttggagt ggatcacatg tggaaattcc attagaactt   1020
tgtttggact cgatacctga ggagatgtat aggaaagcct gttgtacaac cgctgatgaa   1080
gcagttgcaa gttgtcagat gattggttac cctgccatga tcaaggcatc ctggggtggt   1140
ggtggtaaag ggattagaaa ggttaataat gatgacgagg tgaaagcact gtttaagcaa   1200
gtacagggtg aagttcctgg ctcccccgata tttatcatga acttgcatc tcagagtcgt   1260 catcttgaag tccagctgct ttgtgatgaa tatggcaatg tagcagcact tcacagtcgt   1320
gattgcagtg tgcaacgacg acaccaaaag attatcgagg aaggaccagt tactgttgct   1380
cctcgtgaaa cagtgaaaga gctagagcaa gcagcaagga ggcttgctaa ggccgtgggt   1440
tacgtcggtc tgctactgt tgaatatctc tacagcatgg agactggtga atactatttt    1500
ctggagctta atccacggtt gcaggttgag cacccagtca ccgagtcgat agctgaagta   1560
aatttgcctg cagcccaagt tgcagttggg atgggtatac ccctttggca gattccagag   1620
atcagacgtt tctacggaat ggacaatgga ggaggctatg atatttggag aaaaacagca   1680
gctctcgcta ctccattcaa ctttgatgaa gtagattctc aatggccgaa gggtcattgt   1740
gtggcagtta ggataaccag tgagaatcca gatgatggat tcaagcctac tggtggaaaa   1800
gtaaaggaga taagttttaa agtaagcca aatgtctggg gatatttctc agttaagtct    1860
ggtggaggca ttcatgaatt tgcggattct cagtttggac acgttttgc ctatggagag    1920 actagatcag cagcaataac cagcatgtct cttgcactaa aagagattca aattcgtgga   1980
gaaattcata caaacgttga ttacacggtt gatctcttga atgccccaga cttcagagaa   2040
aacacgatcc ataccggttg gctggatacc agaatagcta tgcgtgttca agctgagagg   2100
cctccctggt atatttcagt ggttggagga gctctatata aaacaataac caccaatgcg   2160
gagaccgttt ctgaatatgt tagctatctc atcaagggtc agattccacc aaagcacata   2220
tcccttgtcc attcaactat ttcttttgaat atagaggaaa gcaaatatac aattgagatt   2280
gtgaggagtg gacagggtag ctacagattg agactgaatg gatcacttat tgaagccaat   2340
gtacaaacat tatgtgatgg aggccttta atgcagctgg atggaaatag ccatgttatt   2400
tatgctgaag aagaagcggg tggtacacgg cttcttattg atggaaaaac atgcttgcta   2460
cagaatgacc atgatccgtc aaggttatta gctgagacac cctgcaaact tcttcgtttc   2520
ttgattgccg atggtgctca tgttgatgct gatgtaccat acgcggaagt tgaggttatg   2580
aagatgtgca tgccctctt gtcgcctgct gctggtgtca ttaatgtttt gttgtctgag    2640
ggccaggcga tgcaggctgg tgatcttata gcgagcttac atctcgatga cccttctgct   2700
gtgaagagag ccgagccatt tgaaggatct tttccagaaa tgagccttcc tattgctgct   2760
tctggccaag ttcacaaaaag atgtgctgca agtttgaacg ctgctcgaat ggtccttgca   2820
ggatatgacc atgcggccaa caaagttgtg caagatttgg tatggtgcct tgatacacct   2880
```

```
gctcttcctt tcctacaatg ggaagagctt atgtctgttt tagcaactag acttccaaga    2940
cgtcttaaga gcgagttgga gggcaaatac aatgaataca agttaaatgt tgaccatgtg    3000
aagatcaagg atttccctac cgagatgctt agagagacaa tcgaggaaaa tcttgcatgt    3060
gtttccgaga aggaaatggt gacaattgag aggcttgttg accctctgat gagcctgctg    3120
aagtcatacg agggtgggag agaaagccat gcccacttta ttgtcaagtc ccttttttgag   3180
gagtatctct cggttgagga actattcagt gatggcattc agtctgacgt gattgaacgc    3240
ctgcgcctac aatatagtaa agacctccag aaggttgtag acattgtttt gtctcaccag    3300
ggtgtgagaa acaaaacaaa gctgatactc gcgctcatgg agaaactggt ctatccaaac    3360
cctgctgcct acagagatca gttgattcgc ttttcttccc tcaaccataa aagatattat    3420
aagttggctc ttaaagctag tgaacttctt gaacaaacca agctcagcga actccgcaca    3480
agcattgcaa ggaacctttc agcgctggat atgttcaccg aggaaaaggc agatttctcc    3540
ttgcaagaca gaaaattggc cattaatgag agcatgggag atttagtcac tgccccactg    3600
ccagttgaag atgcacttgt ttcttttgttt gattgtactg atcaaactct tcagcagaga    3660
gtgattcaga catacatatc tcgattatac cagcctcaac ttgtgaagga tagcatccag    3720
ctgaaatatc aggattctgg tgttattgct ttatgggaat tcactgaagg aaatcatgag    3780
aagagattgg gtgctatggt tatcctgaag tcactagaat ctgtgtcaac agccattgga    3840
gctgctctaa aggatgcatc acattatgca agctctgcgg gcaacacggt gcatattgct    3900
ttgttggatg ctgataccca actgaataca actgaagata tggtgataa tgaccaagct    3960
caagacaaga tggataaact ttcttttgta ctgaaacaag atgttgtcat ggctgatcta    4020
cgtgctgctg atgtcaaggt tgttagttgc attgttcaaa gagatggagc aatcatgcct    4080
atgcgccgta ccttcctctt gtcagaggaa aaactttgtt acgaggaaga gccgattctt    4140
cggcatgtgg agcctccact ttctgcactt cttgagttgg ataaattgaa agtgaaagga    4200
tacaatgaga tgaagtatac accgtcacgt gatcgtcagt ggcatatata cacacttaga    4260
aatactgaaa atccaaaaat gctgcacagg gtatttttcc gaacacttgt cagacaaccc    4320
agtgcaggca acaggtttac atcagaccat atcactgatg ttgaagtagg acacgcagag    4380
gaacctcttt catttacttc aagcagcata ttaaaatcgt tgaagattgc taaagaagaa    4440
ttggagcttc acgcgatcag gactggccat tctcatatgt acttgtgcat attgaaagag    4500
caaaagcttc ttgaccttgt tcctgtttca gggaacactg ttgtggatgt tggtcaagat    4560
gaagctactg catgctctct tttgaaagaa atggctttaa agatacatga acttgttggt    4620
gcaagaatgc atcatctttc tgtatgccag tgggaagtga aacttaagtt ggtgagcgat    4680
gggcctgcca gtggtagctg gagagttgta acaaccaatg ttactggtca cacctgcact    4740
gtggatatct accgggaggt cgaagataca gaatcacaga aactagtata ccactccacc    4800
gcattgtcat ctggtccttt gcatggtgtt gcactgaata cttcgtatca gccctttgagt   4860
gttattgatt taaacgttg ctctgccagg aacaacaaaa ctacatactg ctatgatttt    4920
ccattgacat ttgaagctgc agtgcagaag tcgtggtcta acatttccag tgaaaacaac    4980
caatgttatg ttaaagcgac agagcttgtg tttgctgaaa agaatgggtc gtggggcact    5040
cctataattc ctatgcagcg tgctgctggg ctgaatgaca ttggtatggt agcctggatc    5100
ttggacatgt ccactcctga atttcccagc ggcagacaga tcattgttat cgcaaatgat    5160
attacattta gagctggatc atttggccca agggaagatg cattttttcga agctgtaacc    5220
aacctggctt gtgagaagaa gcttccactt atctacttgg ctgcaaactc tggtgctcgg    5280
```

```
attggcattg ctgatgaagt aaaatcttgc ttccgtgttg gatggactga tgatagcagc    5340
cctgaacgtg gatttaggta catttatatg actgacgaag accatgatcg tattggctct    5400
tcagttatag cacacaagat gcagctagat agtggcgaga tcaggtgggt tattgattct    5460
gttgtgggaa aagaggatgg actaggtgtg gagaacatac atggaagtgc tgctattgcc    5520
agtgcctatt ctagggcgta cgaggagaca tttacactta cattcgttac tggacgaact    5580
gttggaatcg gagcctatct tgctcgactt ggcatacggt gcatacagcg tattgaccag    5640
cccattattt tgaccgggtt ttctgccctg aacaagcttc ttgggcggga ggtgtacagc    5700
tcccacatgc agttgggtgg tcccaaaatc atggcgacga atggtgttgt ccatctgact    5760
gttccagatg accttgaagg tgtttctaat atattgaggt ggctcagcta tgttcctgca    5820
aacattggtg gacctcttcc tattacaaaa tctttggacc caatagacag acccgttgca    5880
tacatccctg agaatacatg tgatcctcgt gcagccatca gtggcattga tgacagccaa    5940
gggaaatggt tgggtggcat gtttgacaaa gacagttttg tggagacatt tgaaggatgg    6000
gcgaagacag tagttactgg cagagcaaaa cttggaggga ttcctgttgg tgttatagct    6060
gtggagacac agaccatgat gcagctcgtc ccgctgatc caggccagcc tgattcccac    6120
gagcggtctg ttcctcgtgc tgggcaagtt tggtttccag attctgctac caagacagcg    6180
caggcgatgt tggacttcaa ccgtgaagga ttacctctgt tcatacttgc taactggaga    6240
ggcttctctg gagggcaaag agatcttttt gaaggaattc tgcaggctgg gtcaacaatt    6300
gttgagaacc ttaggacata caatcagcct gcctttgtat atatccccaa ggctgcagag    6360
ctacgtggag gagcctgggt cgtgattgat agcaagataa acccagatcg catcgagtgc    6420
tatgctgaga ggactgcaaa gggtaatgtt ctcgaacctc aagggttgat tgagatcaag    6480
ttcaggtcag aggaactcaa agaatgcatg ggtaggcttg atccagaatt gatagatctg    6540
aaagcaagac tccagggagc aaatggaagc ctatctgatg gagaatccct tcagaagagc    6600
atagaagctc ggaagaaaca gttgctgcct ctgtacaccc aaatcgcggt acgttttgcg    6660
gaattgcacg acacttccct tagaatggct gctaaaggtg tgatcaggaa agttgtagac    6720
tgggaagact ctcggtcttt cttctacaag agattacgga ggaggctatc cgaggacgtt    6780
ctggcaaagg agattagagg tgtaattggt gagaagtttc ctcacaaatc agcgatcgag    6840
ctgatcaaga atggtacttt ggcttctgag gcagctgcag caggaagcac cgactgggat    6900
gacgacgatg cttttgtcgc ctggagggag aaccctgaaa actataagga gtatatcaaa    6960
gagcttaggg ctcaaagggt atctcggttg ctctcagatg ttgcaggctc cagttcggat    7020
ttacaagcct gccgcagggg tcttccatg ctactagata agatggatcc ctctaagaga    7080
gcacagttta tcgaggaggt catgaaggtc ctgaaatgat caaatgatac caacacatcc    7140
aatacagtat gtgcatgata tctgtttctc ttgaagtaca tatatagatg gatacaaggc    7200
ggctgtaact gatggtagct aatctgggcc aaccattact tttgtgaact tgctggtggc    7260
ctttattatt caaggcacag ctcgccttcg gaccccctcc ggctggttga tgatgagtgt    7320
aactggatgt gttagttctg ctgccacaga attcgagaag gatagggca tgcgggtttt    7380 gcctcctgtt ggcaagaaca ctggtgattt tgagttcttg ttatgtggac tgtggtagtc    7440
ttgtttcgct gtagttctgt gatgttctat ctcctgtaat tctagtcttg ggagagtgat    7500
tcagatgtcc attcaatttt gaacttgaat aataatatgc tttgtaggcc tatgcgtacc    7560
agtatgtgga ataaatgttc gttgagtta                                       7589
```

<210> SEQ ID NO 247
<211> LENGTH: 2320
<212> TYPE: PRT
<213> ORGANISM: Alopecurus myosuroides

<400> SEQUENCE: 247

```
Met Gly Ser Thr His Leu Pro Ile Val Gly Phe Asn Ala Ser Thr Thr
1               5                   10                  15

Pro Ser Leu Ser Thr Leu Arg Gln Ile Asn Ser Ala Ala Ala Ala Phe
            20                  25                  30

Gln Ser Ser Ser Pro Ser Arg Ser Ser Lys Lys Ser Arg Arg Val
        35                  40                  45

Lys Ser Ile Arg Asp Asp Gly Asp Ser Val Pro Asp Pro Ala Gly
50                  55                  60

His Gly Gln Ser Ile Arg Gln Gly Leu Ala Gly Ile Ile Asp Leu Pro
65                  70                  75                  80

Lys Glu Gly Ala Ser Ala Pro Asp Val Asp Ile Ser His Gly Ser Glu
            85                  90                  95

Asp His Lys Ala Ser Tyr Gln Met Asn Gly Ile Leu Asn Glu Ser His
        100                 105                 110

Asn Gly Arg His Ala Ser Leu Ser Lys Val Tyr Glu Phe Cys Thr Glu
    115                 120                 125

Leu Gly Gly Lys Thr Pro Ile His Ser Val Leu Val Ala Asn Asn Gly
130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Met Arg Ile Asn Ala Glu His Ile Arg Ile Ala Asp Gln Phe
            180                 185                 190

Val Glu Val Pro Gly Gly Thr Asn Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met Asn Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Ile Pro Leu Glu Leu
        275                 280                 285

Cys Leu Asp Ser Ile Pro Glu Glu Met Tyr Arg Lys Ala Cys Val Thr
    290                 295                 300

Thr Ala Asp Glu Ala Val Ala Ser Cys Gln Met Ile Gly Tyr Pro Ala
305                 310                 315                 320

Met Ile Lys Ala Ser Trp Gly Gly Gly Gly Lys Gly Ile Arg Lys Val
                325                 330                 335

Asn Asn Asp Asp Glu Val Lys Ala Leu Phe Lys Gln Val Gln Gly Glu
            340                 345                 350

Val Pro Gly Ser Pro Ile Phe Ile Met Arg Leu Ala Ser Gln Ser Arg
        355                 360                 365

His Leu Glu Val Gln Leu Leu Cys Asp Glu Tyr Gly Asn Val Ala Ala
    370                 375                 380
```

```
Leu His Ser Arg Asp Cys Ser Val Gln Arg His Gln Lys Ile Ile
385                 390                 395                 400

Glu Glu Gly Pro Val Thr Val Ala Pro Arg Glu Thr Val Lys Glu Leu
            405                 410                 415

Glu Gln Ala Ala Arg Arg Leu Ala Lys Ala Val Gly Tyr Val Gly Ala
        420                 425                 430

Ala Thr Val Glu Tyr Leu Tyr Ser Met Glu Thr Gly Glu Tyr Tyr Phe
            435                 440                 445

Leu Glu Leu Asn Pro Arg Leu Gln Val Glu His Pro Val Thr Glu Ser
450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asp
                485                 490                 495

Asn Gly Gly Gly Tyr Asp Ile Trp Arg Lys Thr Ala Ala Leu Ala Thr
            500                 505                 510

Pro Phe Asn Phe Asp Glu Val Asp Ser Gln Trp Pro Lys Gly His Cys
        515                 520                 525

Val Ala Val Arg Ile Thr Ser Glu Asn Pro Asp Gly Phe Lys Pro
530                 535                 540

Thr Gly Gly Lys Val Lys Glu Ile Ser Phe Lys Ser Lys Pro Asn Val
545                 550                 555                 560

Trp Gly Tyr Phe Ser Val Lys Ser Gly Gly Ile His Glu Phe Ala
                565                 570                 575

Asp Ser Gln Phe Gly His Val Phe Ala Tyr Gly Glu Thr Arg Ser Ala
            580                 585                 590

Ala Ile Thr Ser Met Ser Leu Ala Leu Lys Glu Ile Gln Ile Arg Gly
        595                 600                 605

Glu Ile His Thr Asn Val Asp Tyr Thr Val Asp Leu Leu Asn Ala Pro
610                 615                 620

Asp Phe Arg Glu Asn Thr Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Ile Thr Thr Asn Ala Glu Thr Val Ser
            660                 665                 670

Glu Tyr Val Ser Tyr Leu Ile Lys Gly Gln Ile Pro Pro Lys His Ile
        675                 680                 685

Ser Leu Val His Ser Thr Ile Ser Leu Asn Ile Glu Glu Ser Lys Tyr
690                 695                 700

Thr Ile Glu Ile Val Arg Ser Gly Gln Gly Ser Tyr Arg Leu Arg Leu
705                 710                 715                 720

Asn Gly Ser Leu Ile Glu Ala Asn Val Gln Thr Leu Cys Asp Gly Gly
                725                 730                 735

Leu Leu Met Gln Leu Asp Gly Asn Ser His Val Ile Tyr Ala Glu Glu
            740                 745                 750

Glu Ala Gly Gly Thr Arg Leu Leu Ile Asp Gly Lys Thr Cys Leu Leu
        755                 760                 765

Gln Asn Asp His Asp Pro Ser Arg Leu Leu Ala Glu Thr Pro Cys Lys
770                 775                 780

Leu Leu Arg Phe Leu Ile Ala Asp Gly Ala His Val Asp Ala Asp Val
785                 790                 795                 800
```

```
Pro Tyr Ala Glu Val Glu Val Met Lys Met Cys Met Pro Leu Leu Ser
                805                 810                 815

Pro Ala Ala Gly Val Ile Asn Val Leu Leu Ser Glu Gly Gln Ala Met
            820                 825                 830

Gln Ala Gly Asp Leu Ile Ala Arg Leu Asp Leu Asp Asp Pro Ser Ala
        835                 840                 845

Val Lys Arg Ala Glu Pro Phe Glu Gly Ser Phe Pro Glu Met Ser Leu
850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
                885                 890                 895

Val Val Gln Asp Leu Val Trp Cys Leu Asp Thr Pro Ala Leu Pro Phe
            900                 905                 910

Leu Gln Trp Glu Glu Leu Met Ser Val Leu Ala Thr Arg Leu Pro Arg
        915                 920                 925

Arg Leu Lys Ser Glu Leu Glu Gly Lys Tyr Asn Glu Tyr Lys Leu Asn
    930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Glu Lys Glu Met Val Thr
                965                 970                 975

Ile Glu Arg Leu Val Asp Pro Leu Met Ser Leu Leu Lys Ser Tyr Glu
            980                 985                 990

Gly Gly Arg Glu Ser His Ala His Phe Ile Val Lys Ser Leu Phe Glu
        995                 1000                1005

Glu Tyr Leu Ser Val Glu Glu Leu Phe Ser Asp Gly Ile Gln Ser
    1010                1015                1020

Asp Val Ile Glu Arg Leu Arg Leu Gln Tyr Ser Lys Asp Leu Gln
    1025                1030                1035

Lys Val Val Asp Ile Val Leu Ser His Gln Gly Val Arg Asn Lys
    1040                1045                1050

Thr Lys Leu Ile Leu Ala Leu Met Glu Lys Leu Val Tyr Pro Asn
    1055                1060                1065

Pro Ala Ala Tyr Arg Asp Gln Leu Ile Arg Phe Ser Ser Leu Asn
    1070                1075                1080

His Lys Arg Tyr Tyr Lys Leu Ala Leu Lys Ala Ser Glu Leu Leu
    1085                1090                1095

Glu Gln Thr Lys Leu Ser Glu Leu Arg Thr Ser Ile Ala Arg Asn
    1100                1105                1110

Leu Ser Ala Leu Asp Met Phe Thr Glu Glu Lys Ala Asp Phe Ser
    1115                1120                1125

Leu Gln Asp Arg Lys Leu Ala Ile Asn Glu Ser Met Gly Asp Leu
    1130                1135                1140

Val Thr Ala Pro Leu Pro Val Glu Asp Ala Leu Val Ser Leu Phe
    1145                1150                1155

Asp Cys Thr Asp Gln Thr Leu Gln Gln Arg Val Ile Gln Thr Tyr
    1160                1165                1170

Ile Ser Arg Leu Tyr Gln Pro Gln Leu Val Lys Asp Ser Ile Gln
    1175                1180                1185

Leu Lys Tyr Gln Asp Ser Gly Val Ile Ala Leu Trp Glu Phe Thr
    1190                1195                1200

Glu Gly Asn His Glu Lys Arg Leu Gly Ala Met Val Ile Leu Lys
```

```
                1205                1210                1215
Ser Leu Glu Ser Val Ser Thr Ala Ile Gly Ala Ala Leu Lys Asp
    1220                1225                1230

Ala Ser His Tyr Ala Ser Ser Ala Gly Asn Thr Val His Ile Ala
    1235                1240                1245

Leu Leu Asp Ala Asp Thr Gln Leu Asn Thr Thr Glu Asp Ser Gly
    1250                1255                1260

Asp Asn Asp Gln Ala Gln Asp Lys Met Asp Lys Leu Ser Phe Val
    1265                1270                1275

Leu Lys Gln Asp Val Val Met Ala Asp Leu Arg Ala Ala Asp Val
    1280                1285                1290

Lys Val Val Ser Cys Ile Val Gln Arg Asp Gly Ala Ile Met Pro
    1295                1300                1305

Met Arg Arg Thr Phe Leu Leu Ser Glu Glu Lys Leu Cys Tyr Glu
    1310                1315                1320

Glu Glu Pro Ile Leu Arg His Val Glu Pro Pro Leu Ser Ala Leu
    1325                1330                1335

Leu Glu Leu Asp Lys Leu Lys Val Lys Gly Tyr Asn Glu Met Lys
    1340                1345                1350

Tyr Thr Pro Ser Arg Asp Arg Gln Trp His Ile Tyr Thr Leu Arg
    1355                1360                1365

Asn Thr Glu Asn Pro Lys Met Leu His Arg Val Phe Phe Arg Thr
    1370                1375                1380

Leu Val Arg Gln Pro Ser Ala Gly Asn Arg Phe Thr Ser Asp His
    1385                1390                1395

Ile Thr Asp Val Glu Val Gly His Ala Glu Glu Pro Leu Ser Phe
    1400                1405                1410

Thr Ser Ser Ser Ile Leu Lys Ser Leu Lys Ile Ala Lys Glu Glu
    1415                1420                1425

Leu Glu Leu His Ala Ile Arg Thr Gly His Ser His Met Tyr Leu
    1430                1435                1440

Cys Ile Leu Lys Glu Gln Lys Leu Leu Asp Leu Val Pro Val Ser
    1445                1450                1455

Gly Asn Thr Val Val Asp Val Gly Gln Asp Glu Ala Thr Ala Cys
    1460                1465                1470

Ser Leu Leu Lys Glu Met Ala Leu Lys Ile His Glu Leu Val Gly
    1475                1480                1485

Ala Arg Met His His Leu Ser Val Cys Gln Trp Glu Val Lys Leu
    1490                1495                1500

Lys Leu Val Ser Asp Gly Pro Ala Ser Gly Ser Trp Arg Val Val
    1505                1510                1515

Thr Thr Asn Val Thr Gly His Thr Cys Thr Val Asp Ile Tyr Arg
    1520                1525                1530

Glu Val Glu Asp Thr Glu Ser Gln Lys Leu Val Tyr His Ser Thr
    1535                1540                1545

Ala Leu Ser Ser Gly Pro Leu His Gly Val Ala Leu Asn Thr Ser
    1550                1555                1560

Tyr Gln Pro Leu Ser Val Ile Asp Leu Lys Arg Cys Ser Ala Arg
    1565                1570                1575

Asn Asn Lys Thr Thr Tyr Cys Tyr Asp Phe Pro Leu Thr Phe Glu
    1580                1585                1590

Ala Ala Val Gln Lys Ser Trp Ser Asn Ile Ser Ser Glu Asn Asn
    1595                1600                1605
```

-continued

Gln Cys Tyr Val Lys Ala Thr Glu Leu Val Phe Ala Glu Lys Asn
1610             1615                 1620

Gly Ser Trp Gly Thr Pro Ile Ile Pro Met Gln Arg Ala Ala Gly
1625             1630                 1635

Leu Asn Asp Ile Gly Met Val Ala Trp Ile Leu Asp Met Ser Thr
1640             1645                 1650

Pro Glu Phe Pro Ser Gly Arg Gln Ile Ile Val Ile Ala Asn Asp
1655             1660                 1665

Ile Thr Phe Arg Ala Gly Ser Phe Gly Pro Arg Glu Asp Ala Phe
1670             1675                 1680

Phe Glu Ala Val Thr Asn Leu Ala Cys Glu Lys Lys Leu Pro Leu
1685             1690                 1695

Ile Tyr Leu Ala Ala Asn Ser Gly Ala Arg Ile Gly Ile Ala Asp
1700             1705                 1710

Glu Val Lys Ser Cys Phe Arg Val Gly Trp Thr Asp Asp Ser Ser
1715             1720                 1725

Pro Glu Arg Gly Phe Arg Tyr Ile Tyr Met Thr Asp Glu Asp His
1730             1735                 1740

Asp Arg Ile Gly Ser Ser Val Ile Ala His Lys Met Gln Leu Asp
1745             1750                 1755

Ser Gly Glu Ile Arg Trp Val Ile Asp Ser Val Val Gly Lys Glu
1760             1765                 1770

Asp Gly Leu Gly Val Glu Asn Ile His Gly Ser Ala Ala Ile Ala
1775             1780                 1785

Ser Ala Tyr Ser Arg Ala Tyr Glu Glu Thr Phe Thr Leu Thr Phe
1790             1795                 1800

Val Thr Gly Arg Thr Val Gly Ile Gly Ala Tyr Leu Ala Arg Leu
1805             1810                 1815

Gly Ile Arg Cys Ile Gln Arg Ile Asp Gln Pro Ile Ile Leu Thr
1820             1825                 1830

Gly Phe Ser Ala Leu Asn Lys Leu Leu Gly Arg Glu Val Tyr Ser
1835             1840                 1845

Ser His Met Gln Leu Gly Gly Pro Lys Ile Met Ala Thr Asn Gly
1850             1855                 1860

Val Val His Leu Thr Val Pro Asp Asp Leu Glu Gly Val Ser Asn
1865             1870                 1875

Ile Leu Arg Trp Leu Ser Tyr Val Pro Ala Asn Ile Gly Gly Pro
1880             1885                 1890

Leu Pro Ile Thr Lys Ser Leu Asp Pro Ile Asp Arg Pro Val Ala
1895             1900                 1905

Tyr Ile Pro Glu Asn Thr Cys Asp Pro Arg Ala Ala Ile Ser Gly
1910             1915                 1920

Ile Asp Asp Ser Gln Gly Lys Trp Leu Gly Gly Met Phe Asp Lys
1925             1930                 1935

Asp Ser Phe Val Glu Thr Phe Glu Gly Trp Ala Lys Thr Val Val
1940             1945                 1950

Thr Gly Arg Ala Lys Leu Gly Gly Ile Pro Val Gly Val Ile Ala
1955             1960                 1965

Val Glu Thr Gln Thr Met Met Gln Leu Val Pro Ala Asp Pro Gly
1970             1975                 1980

Gln Pro Asp Ser His Glu Arg Ser Val Pro Arg Ala Gly Gln Val
1985             1990                 1995

| | | | | | | | | | | |
|---|---|---|---|---|---|---|---|---|---|---|
| Trp | Phe | Pro | Asp | Ser | Ala | Thr | Lys | Thr | Ala | Gln | Ala | Met | Leu | Asp |
| 2000 | | | | | 2005 | | | | | 2010 | | | | |

Phe Asn Arg Glu Gly Leu Pro Leu Phe Ile Leu Ala Asn Trp Arg
2015                    2020                    2025

Gly Phe Ser Gly Gly Gln Arg Asp Leu Phe Glu Gly Ile Leu Gln
2030                    2035                    2040

Ala Gly Ser Thr Ile Val Glu Asn Leu Arg Thr Tyr Asn Gln Pro
2045                    2050                    2055

Ala Phe Val Tyr Ile Pro Lys Ala Ala Glu Leu Arg Gly Gly Ala
2060                    2065                    2070

Trp Val Val Ile Asp Ser Lys Ile Asn Pro Asp Arg Ile Glu Cys
2075                    2080                    2085

Tyr Ala Glu Arg Thr Ala Lys Gly Asn Val Leu Glu Pro Gln Gly
2090                    2095                    2100

Leu Ile Glu Ile Lys Phe Arg Ser Glu Glu Leu Lys Glu Cys Met
2105                    2110                    2115

Gly Arg Leu Asp Pro Glu Leu Ile Asp Leu Lys Ala Arg Leu Gln
2120                    2125                    2130

Gly Ala Asn Gly Ser Leu Ser Asp Gly Glu Ser Leu Gln Lys Ser
2135                    2140                    2145

Ile Glu Ala Arg Lys Lys Gln Leu Leu Pro Leu Tyr Thr Gln Ile
2150                    2155                    2160

Ala Val Arg Phe Ala Glu Leu His Asp Thr Ser Leu Arg Met Ala
2165                    2170                    2175

Ala Lys Gly Val Ile Arg Lys Val Val Asp Trp Glu Asp Ser Arg
2180                    2185                    2190

Ser Phe Phe Tyr Lys Arg Leu Arg Arg Arg Leu Ser Glu Asp Val
2195                    2200                    2205

Leu Ala Lys Glu Ile Arg Gly Val Ile Gly Glu Lys Phe Pro His
2210                    2215                    2220

Lys Ser Ala Ile Glu Leu Ile Lys Lys Trp Tyr Leu Ala Ser Glu
2225                    2230                    2235

Ala Ala Ala Ala Gly Ser Thr Asp Trp Asp Asp Asp Asp Ala Phe
2240                    2245                    2250

Val Ala Trp Arg Glu Asn Pro Glu Asn Tyr Lys Glu Tyr Ile Lys
2255                    2260                    2265

Glu Leu Arg Ala Gln Arg Val Ser Arg Leu Leu Ser Asp Val Ala
2270                    2275                    2280

Gly Ser Ser Ser Asp Leu Gln Ala Leu Pro Gln Gly Leu Ser Met
2285                    2290                    2295

Leu Leu Asp Lys Met Asp Pro Ser Lys Arg Ala Gln Phe Ile Glu
2300                    2305                    2310

Glu Val Met Lys Val Leu Lys
2315                    2320

<210> SEQ ID NO 248
<211> LENGTH: 7425
<212> TYPE: DNA
<213> ORGANISM: Oryza sativa

<400> SEQUENCE: 248
atgacatcca cacatgtggc gacattggga gttggtgccc aggcacctcc tcgtcaccag     60
aaaaagtcag ctggcactgc atttgtatca tctgggtcat caagaccctc ataccgaaag    120
aatggtcagc gtactcggtc acttagggaa gaaagcaatg gaggagtgtc tgattccaaa    180

| | |
|---|---|
| aagcttaacc actctattcg ccaaggtctt gctggcatca ttgacctccc aaatgacgca | 240 |
| gcttcagaag ttgatatttc acatggttcc gaagatccca gggggcctac ggtcccaggt | 300 |
| tcctaccaaa tgaatgggat tatcaatgaa acacataatg ggaggcatgc ttcagtctcc | 360 |
| aaggttgttg agttttgtac ggcacttggt ggcaaaacac caattcacag tgtattagtg | 420 |
| gccaacaatg gaatggcagc agctaagttc atgcggagtg tccgaacatg ggctaatgat | 480 |
| acttttggat cagagaaggc aattcagctg atagctatgg caactccgga ggatctgagg | 540 |
| ataaatgcag agcacatcag aattgccgat caatttgtag aggtacctgg tggaacaaac | 600 |
| aacaacaact atgcaaatgt ccaactcata gtggagatag cagagagaac aggtgtttct | 660 |
| gctgtttggc ctggttgggg tcatgcatct gagaatcctg aacttccaga tgcgctgact | 720 |
| gcaaaaggaa ttgtttttct tgggccacca gcatcatcaa tgcatgcatt aggagacaag | 780 |
| gttggctcag ctctcattgc tcaagcagct ggagttccaa cacttgcttg gagtggatca | 840 |
| catgtggaag ttcctctgga gtgttgcttg gactcaatac ctgatgagat gtatagaaaa | 900 |
| gcttgtgtta ctaccacaga ggaagcagtt gcaagttgtc aggtggttgg ttatcctgcc | 960 |
| atgattaagg catcttgggg tggtggtggt aaaggaataa ggaaggttca taatgatgat | 1020 |
| gaggttagga cattatttaa gcaagttcaa ggcgaagtac ctggttcccc aatatttatc | 1080 |
| atgaggctag ctgctcagag tcgacatctt gaagttcagt tgctttgtga tcaatatggc | 1140 |
| aacgtagcag cacttcacag tcgagattgc agtgtacaac ggcgacacca aagataatc | 1200 |
| gaggaaggac cagttactgt tgctcctcgt gagactgtga agagcttga gcaggcagca | 1260 |
| cggaggcttg ctaaagctgt gggttatgtt ggtgctgcta ctgttgaata cctttacagc | 1320 |
| atggaaactg gtgaatatta ttttctggaa cttaatccac ggctacaggt tgagcatcct | 1380 |
| gtcactgagt ggatagctga agtaaatttg cctgcggctc aagttgctgt tggaatgggt | 1440 |
| atacccctt ggcagattcc agagatcagg cgcttctacg gaatgaacca tggaggaggc | 1500 |
| tatgaccttt ggaggaaaac agcagctcta gcgactccat ttaactttga tgaagtagat | 1560 |
| tctaaatggc caaaaggcca ctgcgtagct gttagaataa ctagcgagga tccagatgat | 1620 |
| gggtttaagc ctactggtgg aaaagtaaag gagataagtt tcaagagtaa accaaatgtt | 1680 |
| tgggcctatt tctcagtaaa gtctggtgga ggcatccatg aattcgctga ttctcagttc | 1740 |
| ggacatgttt ttgcgtatgg aactactaga tcggcagcaa taactaccat ggctcttgca | 1800 |
| ctaaaagagg ttcaaattcg tggagaaatt cattcaaacg tagactacac agttgaccta | 1860 |
| ttaaatgcct cagattttag agaaaataag attcatactg gttggctgga taccaggata | 1920 |
| gccatgcgtg ttcaagctga gaggcctcca tggtatattt cagtcgttgg aggggcttta | 1980 |
| tataaaacag taactgccaa cacgccact gtttctgatt atgttggtta tcttaccaag | 2040 |
| ggccagattc caccaaagca tatatccctt gtctatacga ctgttgcttt gaatatagat | 2100 |
| gggaaaaaat atacaatcga tactgtgagg agtggacatg gtagctacag attgcgaatg | 2160 |
| aatggatcaa cggttgacgc aaatgtacaa atattatgtg atggtgggct tttaatgcag | 2220 |
| ctggatggaa acagccatgt aatttatgct gaagaagagg ccagtggtac acgacttctt | 2280 |
| attgatggaa agacatgcat gttacagaat gaccatgacc catcaaagtt attagctgag | 2340 |
| acaccatgca aacttcttcg tttcttggtt gctgatggtg ctcatgttga tgctgatgta | 2400 |
| ccatatgcgg aagttgaggt tatgaagatg tgcatgcccc tcttatcacc cgcttctggt | 2460 |
| gtcatacatg ttgtaatgtc tgagggccaa gcaatgcagg ctggtgatct tatagctagg | 2520 |

-continued

| | |
|---|---|
| ctggatcttg atgacccttc tgctgttaag agagctgagc cgttcgaaga tacttttcca | 2580 |
| caaatgggtc tccctattgc tgcttctggc caagttcaca aattatgtgc tgcaagtctg | 2640 |
| aatgcttgtc gaatgatcct tgcggggtat gagcatgata ttgacaaggt tgtgccagag | 2700 |
| ttggtatact gcctagacac tccggagctt ccttttcctgc agtgggagga gcttatgtct | 2760 |
| gttttagcaa ctagacttcc aagaaatctt aaaagtgagt tggagggcaa atatgaggaa | 2820 |
| tacaaagtaa aatttgactc tgggataatc aatgatttcc ctgccaatat gctacgagtg | 2880 |
| ataattgagg aaaatcttgc atgtggttct gagaaggaga aggctacaaa tgagaggctt | 2940 |
| gttgagcctc ttatgagcct actgaagtca tatgagggtg ggagagaaag tcatgctcac | 3000 |
| tttgttgtca agtcccttt tgaggagtat ctctatgttg aagaattgtt cagtgatgga | 3060 |
| attcagtctg atgtgattga gcgtctgcgc cttcaacata gtaaagacct acagaaggtc | 3120 |
| gtagacattg tgttgtccca ccagagtgtt agaaataaaa ctaagctgat actaaaactc | 3180 |
| atggagagtc tggtctatcc aaatcctgct gcctacaggg atcaattgat tcgcttttct | 3240 |
| tcccttaatc acaaagcgta ttacaagttg gcacttaaag ctagtgaact tcttgaacaa | 3300 |
| acaaaactta gtgagctccg tgcaagaata gcaaggagcc tttcagagct ggagatgttt | 3360 |
| actgaggaaa gcaagggtct ctccatgcat aagcgagaaa ttgccattaa ggagagcatg | 3420 |
| gaagatttag tcactgctcc actgccagtt gaagatgcgc tcatttcttt atttgattgt | 3480 |
| agtgatacaa ctgttcaaca gagagtgatt gagacttata tagctcgatt ataccagcct | 3540 |
| catcttgtaa aggacagtat caaaatgaaa tggatagaat cgggtgttat tgctttatgg | 3600 |
| gaatttcctg aagggcattt tgatgcaaga aatggaggag cggttcttgg tgacaaaaga | 3660 |
| tggggtgcca tggtcattgt caagtctctt gaatcacttt caatggccat tagatttgca | 3720 |
| ctaaaggaga catcacacta cactagctct gagggcaata tgatgcatat tgctttgttg | 3780 |
| ggtgctgata ataagatgca tataattcaa gaaagtggtg atgatgctga cagaatagcc | 3840 |
| aaacttccct tgatactaaa ggataatgta accgatctgc atgcctctgg tgtgaaaaca | 3900 |
| ataagtttca ttgttcaaag agatgaagca cggatgacaa tgcgtcgtac cttcctttgg | 3960 |
| tctgatgaaa agcttttctta tgaggaagag ccaattctcc ggcatgtgga acctcctctt | 4020 |
| tctgcacttc ttgagttgga caagttgaaa gtgaaaggat acaatgaaat gaagtatacc | 4080 |
| ccatcacggg atcgtcaatg gcatatctac acacttagaa atactgaaaa ccccaaaatg | 4140 |
| ttgcaccggg tatttttccg aacccttgtc aggcaaccca gtgtatccaa caagttttct | 4200 |
| tcgggccaga ttggtgacat ggaagttggg agtgctgaag aacctctgtc atttacatca | 4260 |
| accagcatat taagatcttt gatgactgct atagaggaat tggagcttca cgcaattaga | 4320 |
| actggccatt cacacatgta tttgcatgta ttgaaagaac aaaagcttct tgatcttgtt | 4380 |
| ccagtttcag ggaatacagt tttggatgtt ggtcaagatg aagctactgc atattcactt | 4440 |
| ttaaaagaaa tggctatgaa gatacatgaa cttgttggtg caagaatgca ccatctttct | 4500 |
| gtatgccaat gggaagtgaa acttaagttg gactgcgatg gtcctgccag tggtacctgg | 4560 |
| aggattgtaa caaccaatgt tactagtcac acttgcactg tggatatcta ccgtgagatg | 4620 |
| gaagataaag aatcacggaa gttagtatac catcccgcca ctccggcggc tggtcctctg | 4680 |
| catggtgtgg cactgaataa tccatatcag cctttgagtg tcattgatct caaacgctgt | 4740 |
| tctgctagga ataatagaac tacatactgc tatgattttc cactggcatt tgaaactgca | 4800 |
| gtgaggaagt catggtcctc tagtacctct ggtgcttcta aaggtgttga aaatgcccaa | 4860 |
| tgttatgtta agctacagaa gttggtattt gcggacaaac atgggtcatg gggcactcct | 4920 |

```
ttagttcaaa tggaccggcc tgctgggctc aatgacattg gtatggtagc ttggaccttg    4980
aagatgtcca ctcctgaatt tcctagtggt agggagatta ttgttgttgc aaatgatatt    5040
acgttcagag ctggatcatt tggcccaagg gaagatgcat tttttgaagc tgttaccaac    5100
ctagcctgtg agaagaaact tcctcttatt tatttggcag caaattctgg tgctcgaatt    5160
ggcatagcag atgaagtgaa atcttgcttc cgtgttgggt ggtctgatga tggcagccct    5220
gaacgtgggt ttcagtacat ttatctaagc gaagaagact atgctcgtat tggcacttct    5280
gtcatagcac ataagatgca gctagacagt ggtgaaatta ggtgggttat tgattctgtt    5340
gtgggcaagg aagatggact tggtgtggag aatatacatg gaagtgctgc tattgccagt    5400
gcttattcta gggcatataa ggagacattt acacttacat tgtgactgg aagaactgtt     5460 ggaataggag cttatcttgc tcgacttggc atccggtgca tacagcgtct tgaccagcct    5520
attattctta caggctattc tgcactgaac aagcttcttg ggcgggaagt gtacagctcc    5580
cacatgcagt gggtggtcc caaaatcatg gcaactaatg gtgttgtcca tcttactgtt     5640
tcagatgacc ttgaaggcgt ttctaatata ttgaggtggc tcagttatgt tcctgcctac    5700
attggtggac cacttccagt aacaacaccg ttggacccac cggacagacc tgttgcatac    5760
attcctgaga actcgtgtga tcctcgagcg gctatccgtg gtgttgatga cagccaaggg    5820
aaatggttag gtggtatgtt tgataaagac agctttgtgg aaacatttga aggttgggct    5880
aagacagtgg ttactggcag agcaaagctt ggtggaattc cagtgggtgt gatagctgtg    5940
gagactcaga ccatgatgca aactatccct gctgaccctg gtcagcttga ttcccgtgag    6000
caatctgttc ctcgtgctgg acaagtgtgg tttccagatt ctgcaaccaa gactgcgcag    6060
gcattgctgg acttcaaccg tgaaggatta cctctgttca tcctcgctaa ctggagaggc    6120
ttctctggtg gacaaagaga tctttttgaa ggaattcttc aggctggctc gactattgtt    6180
gagaacctta ggacatacaa tcagcctgcc tttgtctaca ttcccatggc tgcagagcta    6240
cgaggagggg cttgggttgt ggttgatagc aagataaacc cagaccgcat tgagtgctat    6300
gctgagagga ctgcaaaagg caatgttctg gaaccgcaag ggttaattga gatcaagttc    6360
aggtcagagg aactccagga ttgcatgagt cggcttgacc caacattaat tgatctgaaa    6420
gcaaaactcg aagtagcaaa taaaaatgga agtgctgaca caaaatcgct tcaagaaaat    6480
atagaagctc gaacaaaaca gttgatgcct ctatatactc agattgcgat acggtttgct    6540
gaattgcatg atacatccct cagaatggct gcgaaaggtg tgattaagaa agttgtggac    6600
tgggaagaat cacgatcttt cttctataag agattacgga ggaggatctc tgaggatgtt    6660
cttgcaaaag aaattagagc tgtagcaggt gagcagtttt cccaccaacc agcaatcgag    6720
ctgatcaaga aatggtattc agcttcacat gcagctgaat gggatgatga cgatgctttt    6780
gttgcttgga tggataaccc tgaaaactac aaggattata ttcaatatct taaggctcaa    6840
agagtatccc aatccctctc aagtctttca gattccagct cagatttgca agccctgcca    6900
cagggtcttt ccatgttact agataagatg gatccctcta aagagctca acttgttgaa    6960 gaaatcagga aggtccttgg ttgaatcata tgatgccaaa actattattg gaggcacaaa    7020
tagcttgtgg accctgtcgg attgttggtg agtgtatatt ggatttgtta gttctgccag    7080
atgaaagtgc aagtctgatg attcatgata ccgtcagttg gcaagaacac cggttaacct    7140
gagtgcttgt ttacaaatgg tccttttatga caatcgttgt ttcgcgctag ttccgtgatc    7200
tactatcatc tgttagacgc tgtaattagt gagtctccgc ggatccacag tatacggttg    7260
```

-continued

```
agctgttgat tcaattttgg acacgaataa tatgattttg taggcataaa tgcgtctgta    7320
tgtgaaataa attgtctgtt gagttaacac acaagatgac aatatgtttg tgctctactg    7380
ctattgtcca tgaatactga ttgcggaatc aaccacatgc attat                    7425
```

<210> SEQ ID NO 249
<211> LENGTH: 2327
<212> TYPE: PRT
<213> ORGANISM: Oryza sativa

<400> SEQUENCE: 249

| | | | | | | | | | | | | | | | |
|---|---|---|---|---|---|---|---|---|---|---|---|---|---|---|---|
| Met | Thr | Ser | Thr | His | Val | Ala | Thr | Leu | Gly | Val | Gly | Ala | Gln | Ala | Pro |
| 1 | | | | 5 | | | | | 10 | | | | | 15 | |
| Pro | Arg | His | Gln | Lys | Lys | Ser | Ala | Gly | Thr | Ala | Phe | Val | Ser | Ser | Gly |
| | | | 20 | | | | | 25 | | | | | 30 | | |
| Ser | Ser | Arg | Pro | Ser | Tyr | Arg | Lys | Asn | Gly | Gln | Arg | Thr | Arg | Ser | Leu |
| | | 35 | | | | | 40 | | | | | 45 | | | |
| Arg | Glu | Glu | Ser | Asn | Gly | Gly | Val | Ser | Asp | Ser | Lys | Lys | Leu | Asn | His |
| | 50 | | | | | 55 | | | | | 60 | | | | |
| Ser | Ile | Arg | Gln | Gly | Leu | Ala | Gly | Ile | Ile | Asp | Leu | Pro | Asn | Asp | Ala |
| 65 | | | | | 70 | | | | | 75 | | | | | 80 |
| Ala | Ser | Glu | Val | Asp | Ile | Ser | His | Gly | Ser | Glu | Asp | Pro | Arg | Gly | Pro |
| | | | | 85 | | | | | 90 | | | | | 95 | |
| Thr | Val | Pro | Gly | Ser | Tyr | Gln | Met | Asn | Gly | Ile | Ile | Asn | Glu | Thr | His |
| | | | 100 | | | | | 105 | | | | | 110 | | |
| Asn | Gly | Arg | His | Ala | Ser | Val | Ser | Lys | Val | Val | Glu | Phe | Cys | Thr | Ala |
| | | 115 | | | | | 120 | | | | | 125 | | | |
| Leu | Gly | Gly | Lys | Thr | Pro | Ile | His | Ser | Val | Leu | Val | Ala | Asn | Asn | Gly |
| | 130 | | | | | 135 | | | | | 140 | | | | |
| Met | Ala | Ala | Ala | Lys | Phe | Met | Arg | Ser | Val | Arg | Thr | Trp | Ala | Asn | Asp |
| 145 | | | | | 150 | | | | | 155 | | | | | 160 |
| Thr | Phe | Gly | Ser | Glu | Lys | Ala | Ile | Gln | Leu | Ile | Ala | Met | Ala | Thr | Pro |
| | | | | 165 | | | | | 170 | | | | | 175 | |
| Glu | Asp | Leu | Arg | Ile | Asn | Ala | Glu | His | Ile | Arg | Ile | Ala | Asp | Gln | Phe |
| | | | 180 | | | | | 185 | | | | | 190 | | |
| Val | Glu | Val | Pro | Gly | Gly | Thr | Asn | Asn | Asn | Tyr | Ala | Asn | Val | Gln |
| | | 195 | | | | | 200 | | | | | 205 | | | |
| Leu | Ile | Val | Glu | Ile | Ala | Glu | Arg | Thr | Gly | Val | Ser | Ala | Val | Trp | Pro |
| | 210 | | | | | 215 | | | | | 220 | | | | |
| Gly | Trp | Gly | His | Ala | Ser | Glu | Asn | Pro | Glu | Leu | Pro | Asp | Ala | Leu | Thr |
| 225 | | | | | 230 | | | | | 235 | | | | | 240 |
| Ala | Lys | Gly | Ile | Val | Phe | Leu | Gly | Pro | Pro | Ala | Ser | Ser | Met | His | Ala |
| | | | | 245 | | | | | 250 | | | | | 255 | |
| Leu | Gly | Asp | Lys | Val | Gly | Ser | Ala | Leu | Ile | Ala | Gln | Ala | Ala | Gly | Val |
| | | | 260 | | | | | 265 | | | | | 270 | | |
| Pro | Thr | Leu | Ala | Trp | Ser | Gly | Ser | His | Val | Glu | Val | Pro | Leu | Glu | Cys |
| | | 275 | | | | | 280 | | | | | 285 | | | |
| Cys | Leu | Asp | Ser | Ile | Pro | Asp | Glu | Met | Tyr | Arg | Lys | Ala | Cys | Val | Thr |
| | 290 | | | | | 295 | | | | | 300 | | | | |
| Thr | Thr | Glu | Glu | Ala | Val | Ala | Ser | Cys | Gln | Val | Val | Gly | Tyr | Pro | Ala |
| 305 | | | | | 310 | | | | | 315 | | | | | 320 |
| Met | Ile | Lys | Ala | Ser | Trp | Gly | Gly | Gly | Gly | Lys | Gly | Ile | Arg | Lys | Val |
| | | | | 325 | | | | | 330 | | | | | 335 | |
| His | Asn | Asp | Asp | Glu | Val | Arg | Thr | Leu | Phe | Lys | Gln | Val | Gln | Gly | Glu |
| | | | 340 | | | | | 345 | | | | | 350 | | |

-continued

Val Pro Gly Ser Pro Ile Phe Ile Met Arg Leu Ala Ala Gln Ser Arg
        355                 360                 365

His Leu Glu Val Gln Leu Leu Cys Asp Gln Tyr Gly Asn Val Ala Ala
        370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
                420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Trp
450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asn
                485                 490                 495

His Gly Gly Gly Tyr Asp Leu Trp Arg Lys Thr Ala Ala Leu Ala Thr
                500                 505                 510

Pro Phe Asn Phe Asp Glu Val Asp Ser Lys Trp Pro Lys Gly His Cys
        515                 520                 525

Val Ala Val Arg Ile Thr Ser Glu Asp Pro Asp Gly Phe Lys Pro
        530                 535                 540

Thr Gly Gly Lys Val Lys Glu Ile Ser Phe Lys Ser Lys Pro Asn Val
545                 550                 555                 560

Trp Ala Tyr Phe Ser Val Lys Ser Gly Gly Gly Ile His Glu Phe Ala
                565                 570                 575

Asp Ser Gln Phe Gly His Val Phe Ala Tyr Gly Thr Thr Arg Ser Ala
                580                 585                 590

Ala Ile Thr Thr Met Ala Leu Ala Leu Lys Glu Val Gln Ile Arg Gly
        595                 600                 605

Glu Ile His Ser Asn Val Asp Tyr Thr Val Asp Leu Leu Asn Ala Ser
        610                 615                 620

Asp Phe Arg Glu Asn Lys Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Val Thr Ala Asn Thr Ala Thr Val Ser
                660                 665                 670

Asp Tyr Val Gly Tyr Leu Thr Lys Gly Gln Ile Pro Pro Lys His Ile
        675                 680                 685

Ser Leu Val Tyr Thr Thr Val Ala Leu Asn Ile Asp Gly Lys Lys Tyr
        690                 695                 700

Thr Ile Asp Thr Val Arg Ser Gly His Gly Ser Tyr Arg Leu Arg Met
705                 710                 715                 720

Asn Gly Ser Thr Val Asp Ala Asn Val Gln Ile Leu Cys Asp Gly Gly
                725                 730                 735

Leu Leu Met Gln Leu Asp Gly Asn Ser His Val Ile Tyr Ala Glu Glu
                740                 745                 750

Glu Ala Ser Gly Thr Arg Leu Leu Ile Asp Gly Lys Thr Cys Met Leu
        755                 760                 765

```
Gln Asn Asp His Asp Pro Ser Lys Leu Leu Ala Glu Thr Pro Cys Lys
770                 775                 780

Leu Leu Arg Phe Leu Val Ala Asp Gly Ala His Val Asp Ala Asp Val
785                 790                 795                 800

Pro Tyr Ala Glu Val Glu Val Met Lys Met Cys Met Pro Leu Leu Ser
            805                 810                 815

Pro Ala Ser Gly Val Ile His Val Met Ser Glu Gly Gln Ala Met
        820                 825                 830

Gln Ala Gly Asp Leu Ile Ala Arg Leu Asp Leu Asp Pro Ser Ala
            835                 840                 845

Val Lys Arg Ala Glu Pro Phe Glu Asp Thr Phe Pro Gln Met Gly Leu
850                 855                 860

Pro Ile Ala Ala Ser Gly Gln Val His Lys Leu Cys Ala Ala Ser Leu
865                 870                 875                 880

Asn Ala Cys Arg Met Ile Leu Ala Gly Tyr Glu His Asp Ile Asp Lys
                885                 890                 895

Val Val Pro Glu Leu Val Tyr Cys Leu Asp Thr Pro Glu Leu Pro Phe
            900                 905                 910

Leu Gln Trp Glu Glu Leu Met Ser Val Leu Ala Thr Arg Leu Pro Arg
            915                 920                 925

Asn Leu Lys Ser Glu Leu Glu Gly Lys Tyr Glu Glu Tyr Lys Val Lys
930                 935                 940

Phe Asp Ser Gly Ile Ile Asn Asp Phe Pro Ala Asn Met Leu Arg Val
945                 950                 955                 960

Ile Ile Glu Glu Asn Leu Ala Cys Gly Ser Lys Glu Lys Ala Thr
            965                 970                 975

Asn Glu Arg Leu Val Glu Pro Leu Met Ser Leu Leu Lys Ser Tyr Glu
            980                 985                 990

Gly Gly Arg Glu Ser His Ala His  Phe Val Val Lys Ser  Leu Phe Glu
            995                 1000                1005

Glu Tyr  Leu Tyr Val Glu Glu  Leu Phe Ser Asp Gly  Ile Gln Ser
    1010                1015                1020

Asp Val  Ile Glu Arg Leu Arg  Leu Gln His Ser Lys  Asp Leu Gln
    1025                1030                1035

Lys Val  Val Asp Ile Val Leu  Ser His Gln Ser Val  Arg Asn Lys
    1040                1045                1050

Thr Lys  Leu Ile Leu Lys Leu  Met Glu Ser Leu Val  Tyr Pro Asn
    1055                1060                1065

Pro Ala  Ala Tyr Arg Asp Gln  Leu Ile Arg Phe Ser  Ser Leu Asn
    1070                1075                1080

His Lys  Ala Tyr Tyr Lys Leu  Ala Leu Lys Ala Ser  Glu Leu Leu
    1085                1090                1095

Glu Gln  Thr Lys Leu Ser Glu  Leu Arg Ala Arg Ile  Ala Arg Ser
    1100                1105                1110

Leu Ser  Glu Leu Glu Met Phe  Thr Glu Glu Ser Lys  Gly Leu Ser
    1115                1120                1125

Met His  Lys Arg Glu Ile Ala  Ile Lys Glu Ser Met  Glu Asp Leu
    1130                1135                1140

Val Thr  Ala Pro Leu Pro Val  Glu Asp Ala Leu Ile  Ser Leu Phe
    1145                1150                1155

Asp Cys  Ser Asp Thr Thr Val  Gln Gln Arg Val Ile  Glu Thr Tyr
    1160                1165                1170

Ile Ala  Arg Leu Tyr Gln Pro  His Leu Val Lys Asp  Ser Ile Lys
```

-continued

```
              1175                1180                1185

Met Lys Trp Ile Glu Ser Gly Val Ile Ala Leu Trp Glu Phe Pro
         1190                1195                1200

Glu Gly His Phe Asp Ala Arg Asn Gly Gly Ala Val Leu Gly Asp
         1205                1210                1215

Lys Arg Trp Gly Ala Met Val Ile Val Lys Ser Leu Glu Ser Leu
         1220                1225                1230

Ser Met Ala Ile Arg Phe Ala Leu Lys Glu Thr Ser His Tyr Thr
         1235                1240                1245

Ser Ser Glu Gly Asn Met Met His Ile Ala Leu Leu Gly Ala Asp
         1250                1255                1260

Asn Lys Met His Ile Ile Gln Glu Ser Gly Asp Asp Ala Asp Arg
         1265                1270                1275

Ile Ala Lys Leu Pro Leu Ile Leu Lys Asp Asn Val Thr Asp Leu
         1280                1285                1290

His Ala Ser Gly Val Lys Thr Ile Ser Phe Ile Val Gln Arg Asp
         1295                1300                1305

Glu Ala Arg Met Thr Met Arg Arg Thr Phe Leu Trp Ser Asp Glu
         1310                1315                1320

Lys Leu Ser Tyr Glu Glu Glu Pro Ile Leu Arg His Val Glu Pro
         1325                1330                1335

Pro Leu Ser Ala Leu Leu Glu Leu Asp Lys Leu Lys Val Lys Gly
         1340                1345                1350

Tyr Asn Glu Met Lys Tyr Thr Pro Ser Arg Asp Arg Gln Trp His
         1355                1360                1365

Ile Tyr Thr Leu Arg Asn Thr Glu Asn Pro Lys Met Leu His Arg
         1370                1375                1380

Val Phe Phe Arg Thr Leu Val Arg Gln Pro Ser Val Ser Asn Lys
         1385                1390                1395

Phe Ser Ser Gly Gln Ile Gly Asp Met Glu Val Gly Ser Ala Glu
         1400                1405                1410

Glu Pro Leu Ser Phe Thr Ser Thr Ser Ile Leu Arg Ser Leu Met
         1415                1420                1425

Thr Ala Ile Glu Glu Leu Glu Leu His Ala Ile Arg Thr Gly His
         1430                1435                1440

Ser His Met Tyr Leu His Val Leu Lys Glu Gln Lys Leu Leu Asp
         1445                1450                1455

Leu Val Pro Val Ser Gly Asn Thr Val Leu Asp Val Gly Gln Asp
         1460                1465                1470

Glu Ala Thr Ala Tyr Ser Leu Leu Lys Glu Met Ala Met Lys Ile
         1475                1480                1485

His Glu Leu Val Gly Ala Arg Met His His Leu Ser Val Cys Gln
         1490                1495                1500

Trp Glu Val Lys Leu Lys Leu Asp Cys Asp Gly Pro Ala Ser Gly
         1505                1510                1515

Thr Trp Arg Ile Val Thr Thr Asn Val Thr Ser His Thr Cys Thr
         1520                1525                1530

Val Asp Ile Tyr Arg Glu Met Glu Asp Lys Glu Ser Arg Lys Leu
         1535                1540                1545

Val Tyr His Pro Ala Thr Pro Ala Ala Gly Pro Leu His Gly Val
         1550                1555                1560

Ala Leu Asn Asn Pro Tyr Gln Pro Leu Ser Val Ile Asp Leu Lys
         1565                1570                1575
```

-continued

Arg Cys Ser Ala Arg Asn Asn Arg Thr Thr Tyr Cys Tyr Asp Phe
1580                    1585                    1590

Pro Leu Ala Phe Glu Thr Ala Val Arg Lys Ser Trp Ser Ser Ser
1595                    1600                    1605

Thr Ser Gly Ala Ser Lys Gly Val Glu Asn Ala Gln Cys Tyr Val
1610                    1615                    1620

Lys Ala Thr Glu Leu Val Phe Ala Asp Lys His Gly Ser Trp Gly
1625                    1630                    1635

Thr Pro Leu Val Gln Met Asp Arg Pro Ala Gly Leu Asn Asp Ile
1640                    1645                    1650

Gly Met Val Ala Trp Thr Leu Lys Met Ser Thr Pro Glu Phe Pro
1655                    1660                    1665

Ser Gly Arg Glu Ile Ile Val Val Ala Asn Asp Ile Thr Phe Arg
1670                    1675                    1680

Ala Gly Ser Phe Gly Pro Arg Glu Asp Ala Phe Phe Glu Ala Val
1685                    1690                    1695

Thr Asn Leu Ala Cys Glu Lys Lys Leu Pro Leu Ile Tyr Leu Ala
1700                    1705                    1710

Ala Asn Ser Gly Ala Arg Ile Gly Ile Ala Asp Glu Val Lys Ser
1715                    1720                    1725

Cys Phe Arg Val Gly Trp Ser Asp Asp Gly Ser Pro Glu Arg Gly
1730                    1735                    1740

Phe Gln Tyr Ile Tyr Leu Ser Glu Glu Asp Tyr Ala Arg Ile Gly
1745                    1750                    1755

Thr Ser Val Ile Ala His Lys Met Gln Leu Asp Ser Gly Glu Ile
1760                    1765                    1770

Arg Trp Val Ile Asp Ser Val Val Gly Lys Glu Asp Gly Leu Gly
1775                    1780                    1785

Val Glu Asn Ile His Gly Ser Ala Ala Ile Ala Ser Ala Tyr Ser
1790                    1795                    1800

Arg Ala Tyr Lys Glu Thr Phe Thr Leu Thr Phe Val Thr Gly Arg
1805                    1810                    1815

Thr Val Gly Ile Gly Ala Tyr Leu Ala Arg Leu Gly Ile Arg Cys
1820                    1825                    1830

Ile Gln Arg Leu Asp Gln Pro Ile Ile Leu Thr Gly Tyr Ser Ala
1835                    1840                    1845

Leu Asn Lys Leu Leu Gly Arg Glu Val Tyr Ser Ser His Met Gln
1850                    1855                    1860

Leu Gly Gly Pro Lys Ile Met Ala Thr Asn Gly Val Val His Leu
1865                    1870                    1875

Thr Val Ser Asp Asp Leu Glu Gly Val Ser Asn Ile Leu Arg Trp
1880                    1885                    1890

Leu Ser Tyr Val Pro Ala Tyr Ile Gly Gly Pro Leu Pro Val Thr
1895                    1900                    1905

Thr Pro Leu Asp Pro Pro Asp Arg Pro Val Ala Tyr Ile Pro Glu
1910                    1915                    1920

Asn Ser Cys Asp Pro Arg Ala Ala Ile Arg Gly Val Asp Asp Ser
1925                    1930                    1935

Gln Gly Lys Trp Leu Gly Gly Met Phe Asp Lys Asp Ser Phe Val
1940                    1945                    1950

Glu Thr Phe Glu Gly Trp Ala Lys Thr Val Val Thr Gly Arg Ala
1955                    1960                    1965

-continued

| | | | | | | | | | | |
|---|---|---|---|---|---|---|---|---|---|---|
| Lys | Leu | Gly | Gly | Ile | Pro | Val | Gly | Val | Ile | Ala | Val | Glu | Thr | Gln |
| 1970 | | | | 1975 | | | | 1980 | | |

Thr Met Met Gln Thr Ile Pro Ala Asp Pro Gly Gln Leu Asp Ser
    1985                1990                1995

Arg Glu Gln Ser Val Pro Arg Ala Gly Gln Val Trp Phe Pro Asp
    2000                2005                2010

Ser Ala Thr Lys Thr Ala Gln Ala Leu Leu Asp Phe Asn Arg Glu
    2015                2020                2025

Gly Leu Pro Leu Phe Ile Leu Ala Asn Trp Arg Gly Phe Ser Gly
    2030                2035                2040

Gly Gln Arg Asp Leu Phe Glu Gly Ile Leu Gln Ala Gly Ser Thr
    2045                2050                2055

Ile Val Glu Asn Leu Arg Thr Tyr Asn Gln Pro Ala Phe Val Tyr
    2060                2065                2070

Ile Pro Met Ala Ala Glu Leu Arg Gly Gly Ala Trp Val Val Val
    2075                2080                2085

Asp Ser Lys Ile Asn Pro Asp Arg Ile Glu Cys Tyr Ala Glu Arg
    2090                2095                2100

Thr Ala Lys Gly Asn Val Leu Glu Pro Gln Gly Leu Ile Glu Ile
    2105                2110                2115

Lys Phe Arg Ser Glu Glu Leu Gln Asp Cys Met Ser Arg Leu Asp
    2120                2125                2130

Pro Thr Leu Ile Asp Leu Lys Ala Lys Leu Glu Val Ala Asn Lys
    2135                2140                2145

Asn Gly Ser Ala Asp Thr Lys Ser Leu Gln Glu Asn Ile Glu Ala
    2150                2155                2160

Arg Thr Lys Gln Leu Met Pro Leu Tyr Thr Gln Ile Ala Ile Arg
    2165                2170                2175

Phe Ala Glu Leu His Asp Thr Ser Leu Arg Met Ala Ala Lys Gly
    2180                2185                2190

Val Ile Lys Lys Val Val Asp Trp Glu Glu Ser Arg Ser Phe Phe
    2195                2200                2205

Tyr Lys Arg Leu Arg Arg Arg Ile Ser Glu Asp Val Leu Ala Lys
    2210                2215                2220

Glu Ile Arg Ala Val Ala Gly Glu Gln Phe Ser His Gln Pro Ala
    2225                2230                2235

Ile Glu Leu Ile Lys Lys Trp Tyr Ser Ala Ser His Ala Ala Glu
    2240                2245                2250

Trp Asp Asp Asp Ala Phe Val Ala Trp Met Asp Asn Pro Glu
    2255                2260                2265

Asn Tyr Lys Asp Tyr Ile Gln Tyr Leu Lys Ala Gln Arg Val Ser
    2270                2275                2280

Gln Ser Leu Ser Ser Leu Ser Asp Ser Ser Asp Leu Gln Ala
    2285                2290                2295

Leu Pro Gln Gly Leu Ser Met Leu Leu Asp Lys Met Asp Pro Ser
    2300                2305                2310

Arg Arg Ala Gln Leu Val Glu Glu Ile Arg Lys Val Leu Gly
    2315                2320                2325

<210> SEQ ID NO 250
<211> LENGTH: 12486
<212> TYPE: DNA
<213> ORGANISM: Oryza sativa

<400> SEQUENCE: 250

```
tcattcttat atattttcat ctgtcagatt tcacacatct ggggatttat cttctctttg      60
tatggcacta cacatttgag aaaccgtgca attctactgt ttggtcagca ggacaacaat     120
gacatccaca catgtggcga cattgggagt tggtgcccag gcacctcctc gtcaccagaa     180
aaagtcagct ggcactgcat ttgtatcatc tgggtcatca agaccctcat accgaaagaa     240
tggtcagcgt actcggtcac ttagggaaga aagcaatgga ggagtgtctg attccaaaaa     300
gcttaaccac tctattcgcc aaggtgacca ctagctactt tacatatgct ataatttgtg     360
ccaaacataa acatgcaatg gctgctatta tttaaacgtt aatgttgaaa tagctgctat     420
aggatacagc aaaaatatat aattgactgg gcaagatgca acaattgttt ttcactaaag     480
ttagttatct tttgctgtaa aagacaactg ttttttacat aaaatggtat taataacctt     540
gtaatattca atgcaacatg ttctcaagta aaaaaaaaca ttgcctggtt gtataagcaa     600
atgtgtcgtt gtagacatct tattaaacct ttttgtgata tctattaccg tagggaacag     660
gggagctgtt taaatctgtt atcatagagt aatatgagaa aagtggattg tgcgactttg     720
gcatgtatac ctgctcaatt tcaaatatat gtctatgtgc aggtcttgct ggcatcattg     780
acctcccaaa tgacgcagct tcagaagttg atatttcaca gtaaggactt tatattttat     840
aataattatt ataatttt ctgacatgtt ttgagaacct caaaacatgt gattgcacct     900
tcctttttta tgtctggttc agaaactgat aagttttgac agtgtttagg atggatcttt     960
gatgcgcaca gtgctttcta atgttttcat ttttgaaagt aatgttttag gaagaaatat    1020
ctgattaaat ttatacttta tctttacaaa agtcaaatgc gttctgtatc aattgcggtt    1080
tgtaatatgg caagaacatg ctttcagaat ttgttcatac aatgctttct ttctattatt    1140
atgtagaaca ataccctaat actttgttca ccttttatag tggacacctc tcacagcttt    1200
ttcagtaagt gatgcaattt tgtacatttg taagatgtgt tccagaaacc ttttctcctg    1260
caattctaat gtacccactc aaactggtat caccaaagat ctccatctga ttgaaaaaaa    1320
gctgcgtgaa gtatgcttat ttatgctaac catacatgat ttatactgtt ttatagtaca    1380
atgcttattt atgctaacca tacataattt tattctgttt tctagtacat tatttgtgcc    1440
cctgaccata aatgatcctt tcttttacag tggttccgaa gatcccaggg ggcctacggt    1500
cccaggttcc taccaaatga atgggattat caatgaaaca cataatggga ggcatgcttc    1560
agtctccaag gttgttgagt tttgtacggc acttggtggc aaaacaccaa ttcacagtgt    1620
attagtggcc aacaatggaa tggcagcagc taagttcatg cggagtgtcc gaacatgggc    1680
taatgatact tttggatcag agaaggcaat tcagctgata gctatggcaa ctccggagga    1740
tctgaggata aatgcagagc acatcagaat tgccgatcaa tttgtagagg tacctggtgg    1800
aacaaacaac aacaactatg caaatgtcca actcatagtg gaggttagtt cagctcatcc    1860
ctcaacacaa cattttcgtt tctatttaag ttagggaaaa atctctacga ccctccaatt    1920
tctgaacatc caattttcac catcaactgc aatcacagat agcagagaga acaggtgttt    1980
ctgctgtttg gcctggttgg ggtcatgcat ctgagaatcc tgaacttcca gatgcgctga    2040
ctgcaaaagg aattgttttt cttgggccac cagcatcatc aatgcatgca ttaggagaca    2100
aggttggctc agctctcatt gctcaagcag ctggagttcc aacacttgct tggagtggat    2160
cacatgtgag ccttgtcttc tcttttttag cttatcatct tatctttcg gtgatgcatt    2220 atcccaatga cactaaacca taggtggaag ttcctctgga gtgttgcttg gactcaatac    2280
ctgatgagat gtatagaaaa gcttgtgtta ctaccacaga ggaagcagtt gcaagttgtc    2340
```

```
aggtggttgg ttatcctgcc atgattaagg catcttgggg tggtggtggt aaaggaataa    2400
ggaaggtttg ttcttcttgt agttatcaag agattgtttg gattgcaagt gtttagtgcc    2460
catagttaac tctggtcttt ctaacatgag taactcaact ttcttgcagg ttcataatga    2520
tgatgaggtt aggacattat ttaagcaagt tcaaggcgaa gtacctggtt ccccaatatt    2580
tatcatgagg ctagctgctc aggtggggcc ttttatggaa gttacacctt ttcccttaat    2640
gttgagttat tccggagtta ttatggttat gttctgtatg tttgatctgt aaattattga    2700
aattcacctc cattggttct ccagattagc agacctacaa ttctacatat ggtttatact    2760
ttataaatac taggatttag ggatcttcat atagtttata catggtattt agatttcatt    2820
tgtaacccta ttgaagacat cctgattgtt gtcttatgta gagtcgacat cttgaagttc    2880
agttgctttg tgatcaatat ggcaacgtag cagcacttca cagtcgagat tgcagtgtac    2940
aacggcgaca ccaaaaggtc tgctgtctca gttaaatcac ccctctgaat gatctacttc    3000
ttgcctgctg cgttggtcag aggaataatg gttgtattct actgaacaga taatcgagga    3060
aggaccagtt actgttgctc ctcgtgagac tgtgaaagag cttgagcagg cagcacggag    3120
gcttgctaaa gctgtgggtt atgttggtgc tgctactgtt gaatacctttt acagcatgga    3180
aactggtgaa tattatttttc tggaacttaa tccacggcta caggtcggct cctttgacat    3240
tcttcaggaa ttaatttctg ttgaccacat gatttacatt gtcaaatggt ctcacaggtt    3300
gagcatcctg tcactgagtg gatagctgaa gtaaatttgc ctgcggctca agttgctgtt    3360
ggaatgggta taccccttttg gcagattcca ggtaatgctt cttcatttag ttcctgctct    3420
ttgttaattg aatgagctct tatacagacc atgagacaca ttctactgtt aattcatagt    3480
atcccctgac ttgttagtgt tagagataca gagatgtatc acaaattcat tgtatctcct    3540
caaggactgt aaaaatccta taattaaatt tctgaaaatt tgttcttta agcagaaaaa    3600
aaatctctaa attatctccc tgtatacaga gatcaggcgc ttctacggaa tgaaccatgg    3660
aggaggctat gacctttgga ggaaaacagc agctctagcg actccattta actttgatga    3720
agtagattct aaatggccaa aaggccactg cgtagctgtt agaataacta gcgaggatcc    3780
agatgatggg tttaagccta ctggtggaaa agtaaaggtg cggtttcctg atgttaggtg    3840
tatgaattga acacattgct atattgcagc tagtgaaatg actggatcat ggttctctta    3900
ttttcaggag ataagtttca agagtaaacc aaatgtttgg gcctatttct cagtaaaggt    3960
agtcctcaat attgttgcac tgccacatta tttgagttgt cctaacaatt gtgctgcaat    4020
tgttagtttt caactatttg ttgttctgtt tggttgactg gtaccctctc tttgcagtct    4080
ggtggaggca tccatgaatt cgctgattct cagttcggta tgtaaagtta aaagagtaat    4140
attgtctttg ctatttatgt ttgtcctcac ttttaaaaga tattgccttc cattacagga    4200
catgtttttg cgtatggaac tactagatcg gcagcaataa ctaccatggc tcttgcacta    4260
aaagaggttc aaattcgtgg agaaattcat tcaaacgtag actacacagt tgacctatta    4320
aatgtaagga ctaaatatct gcttattgaa ccttgctttt tggttcccta atgccatttt    4380
agtctggcta ctgaagaact tatccatcat gccatttctg ttatcttaaa ttcaggcctc    4440
agatttttaga gaaataagaa ttcatactgg ttggctggat accaggatag ccatgcgtgt    4500
tcaagctgag aggcctccat ggtatatttc agtcgttgga ggggctttat atgtaagaca    4560
aactatgcca ctcattagca tttatgtgaa gcaaatgcgg aaaacatgat caatatgtcg    4620
tcttatttaa atttatttat ttttgtgctg cagaaaacag taactgccaa cacggccact    4680
gtttctgatt atgttggtta tcttaccaag ggccagattc caccaaaggt actattctgt    4740
```

```
tttttcagga tatgaatgct gtttgaatgt gaaaaccatt gaccataaat ccttgtttgc    4800
agcatatatc ccttgtctat acgactgttg ctttgaatat agatgggaaa aaatatacag    4860
taagtgtgac attcttaatg gggaaactta atttgttgta aataatcaat atcatattga    4920
ctcgtgtatg ctgcatcata gatcgatact gtgaggagtg gacatggtag ctacagattg    4980
cgaatgaatg gatcaacggt tgacgcaaat gtacaaatat tatgtgatgg tgggctttta    5040
atgcaggtaa tatcttcttc ctagttaaag aagatatatc ttgttcaaag aattctgatt    5100
attgatcttt taatgttttc agctggatgg aaacagccat gtaatttatg ctgaagaaga    5160
ggccagtggt acacgacttc ttattgatgg aaagacatgc atgttacagg taatgatagc    5220
cttgttcttt ttagttctag tcacggtgtt tgcttgctat tgttgtatc tatttaatgc     5280
attcactaat tactatatta gtttgcatca tcaagttaaa atggaacttc tttcttgcag    5340
aatgaccatg acccatcaaa gttattagct gagacaccat gcaaacttct tcgtttcttg    5400
gttgctgatg gtgctcatgt tgatgctgat gtaccatatg cggaagttga ggttatgaag    5460
atgtgcatgc ccctcttatc acccgcttct ggtgtcatac atgttgtaat gtctgagggc    5520
caagcaatgc aggtacattc ctacattcca ttcattgtgc tgtgctgaca tgaacatttc    5580
aagtaaatac ctgtaacttg tttattattc taggctggtg atcttatagc taggctggat    5640
cttgatgacc cttctgctgt taagagagct gagccgttcg aagatacttt tccacaaatg    5700
ggtctcccta ttgctgcttc tggccaagtt cacaaattat gtgctgcaag tctgaatgct    5760
tgtcgaatga tccttgcggg gtatgagcat gatattgaca aggtaaacat catgtcctct    5820
tgttttttct tttgtttatc atgcattctt atgttcatca tgtcctctgg caaatctaga    5880
ttccgctgtc gtttcacaca gattttctc attctcataa tggtgccaaa cataaatatg     5940
ctgctatatt catcaatgtt ttcactcgat ttctaatttt gcttttgagt tttaaacttt    6000
agtacaatcc atatctaatc tccttttggca acagtgaatc cattatatat atttttatta   6060
aactgctttc ttttttcaggt tgtgccagag ttggtatact gcctagacac tccggagctt    6120
cctttcctgc agtgggagga gcttatgtct gttttagcaa ctagacttcc aagaaatctt    6180
aaaagtgagg tatattatgg ttgacaagat agctagtctc atgctctaag gacttgtaca    6240
tttcgccaca taggttaatt ttccatatca agttctaatg tacgatataa agtagtact     6300
ggcctaaaac agtattggtg gttgactatc tttgttgtgt aagatcaagt atttcttttt    6360
catgcttagt ttgtcaatac ttcacattta tcactgactt gtcgagctaa atgagatttt    6420
atttgatttc tgtgctccat tattttgta tatatatata tatatttaac tatgactata     6480
tgttatgcct caaacgtttc aaactctttc agttggaggg caaatatgag gaatacaaag    6540
taaaatttga ctctgggata atcaatgatt tccctgccaa tatgctacga gtgataattg    6600
aggtcagtta ttcaatttgt tgtgataatc actgccttaa ctgttcgttc ttttaacaag    6660
cggtttata ggaaaatctt gcatgtggtt ctgagaagga gaaggctaca aatgagaggc      6720
ttgttgagcc tcttatgagc ctactgaagt catatgaggg tgggagagaa agtcatgctc    6780
actttgttgt caagtcccctt tttgaggagt atctctatgt tgaagaattg ttcagtgatg   6840
gaattcaggt taacttacct attcgcatta aacaaatcat cagttgtttt atgataaagt    6900
caaaatgttt atatttccca ttcttctgtg gatcaaatat atcacggaca tgatatagtt    6960
tcctaggct atataatggt tcttcatcaa ataatattgc aggaaacagt atagcaaact     7020
atttgtatat actcgagatg gaaattgtta gaaacatcat tgactaaatc tgtcctttgt    7080
```

```
tacgctgttt ttgtagtctg atgtgattga gcgtctgcgc cttcaacata gtaaagacct    7140
acagaaggtc gtagacattg tgttgtccca ccaggtaaat ttcttcatgg tctgatgact    7200
tcactgcgaa tggttactga actgtcttct tgttctgaca atgtgacttt tcttcgtaga    7260
gtgttagaaa taaaactaag ctgatactaa aactcatgga gagtctggtc tatccaaatc    7320
ctgctgccta cagggatcaa ttgattcgct tttcttccct taatcacaaa gcgtattaca    7380
aggtgaccag gataaacata aataaacgtg aattttttcaa tgacctttttc ttctgacatc   7440
tgaatctgat gaatttcttg catattaata cagttggcac ttaaagctag tgaacttctt    7500
gaacaaacaa aacttagtga gctccgtgca agaatagcaa ggagcctttc agagctggag    7560
atgtttactg aggaaagcaa gggtctctcc atgcataagc gagaaattgc cattaaggag    7620
agcatggaag atttagtcac tgctccactg ccagttgaag atgcgctcat ttctttattt    7680
gattgtagtg atacaactgt tcaacagaga gtgattgaga cttatatagc tcgattatac    7740
caggtatgag aagaaagacc ttttgaaatt atttatatta acatatccta gtaaaacagc    7800
atgctcatca tttcttaaaa aaagtttaca gcacctgatg tttggttact gaccgcatca    7860
ttaaaataaa gttacttgtt gtggagagat gtattttgga acttgtggca catgcagtaa    7920
catgctactg ctcgatatgt ttgctaactt gacaacaata ttttcagcc tcatcttgta    7980
aaggacagta tcaaaatgaa atggatagaa tcgggtgtta ttgctttatg ggaatttcct    8040
gaagggcatt ttgatgcaag aaatggagga gcggttcttg gtgacaaaag atggggtgcc    8100
atggtcattg tcaagtctct tgaatcactt tcaatggcca ttagatttgc actaaaggag    8160
acatcacact acactagctc tgagggcaat atgatgcata ttgctttgtt gggtgctgat    8220
aataagatgc atataattca agaaaggtat gttcatatgc tatgttggtg ctgaaatagt    8280
tatatatgta gttagctggt ggagttctgg taattaacct atcccattgt tcagtggtga    8340
tgatgctgac agaatagcca aacttccctt gatactaaag gataatgtaa ccgatctgca    8400
tgcctctggt gtgaaaacaa taagtttcat tgttcaaaga gatgaagcac ggatgacaat    8460
gcgtcgtacc ttcctttggt ctgatgaaaa gctttcttat gaggaagagc caattctccg    8520
gcatgtggaa cctcctcttt ctgcacttct tgagttggta cgtgatatca tcaaaatgat    8580
aatgttttgg tatggcattg attatcttct atgctctttg tatttattca gcctattgtg    8640
gatacaggac aagttgaaag tgaaaggata caatgaaatg aagtataccc catcacggga    8700
tcgtcaatgg catatctaca cacttagaaa tactgaaaac cccaaaatgt tgcaccgggt    8760
attttttccga acccttgtca ggcaacccag tgtatccaac aagttttctt cgggccagat    8820
tggtgacatg gaagttggga gtgctgaaga acctctgtca tttacatcaa ccagcatatt    8880
aagatctttg atgactgcta tagaggaatt ggagcttcac gcaattagaa ctggccattc    8940
acacatgtat ttgcatgtat tgaaagaaca aaagcttctt gatcttgttc cagtttcagg    9000
gtaagtgcgc atatttcttt ttgggaacat atgcttgctt atgaggttgg tcttctcaat    9060
gatcttctta tcttactcag gaatacagtt ttggatgttg gtcaagatga agctactgca    9120
tattcacttt taaaagaaat ggctatgaag atacatgaac ttgttggtgc aagaatgcac    9180
catctttctg tatgccaatg ggaagtgaaa cttaagttgg actgcgatgg tcctgccagt    9240
ggtacctgga ggattgtaac aaccaatgtt actagtcaca cttgcactgt ggatgtaagt    9300
ttaatcctct agcattttgt tttctttgga aaagcatgtg attttaagcc ggctggtcct    9360
catacccaga cctagtgatc tttatatagt gtagacattt ttctaactgc ttttaattgt    9420
tttagatcta ccgtgagatg gaagataaag aatcacggaa gttagtatac catcccgcca    9480
```

```
ctccggcggc tggtcctctg catggtgtgg cactgaataa tccatatcag cctttgagtg    9540
tcattgatct caaacgctgt tctgctagga ataatagaac tacatactgc tatgattttc    9600
cactggtgag ttgactgctc ccttatattc aatgcattac catagcaaat tcatattcgt    9660
tcatgttgtc aaaataagcc gatgaaaatt caaaactgta ggcatttgaa actgcagtga    9720
ggaagtcatg gtcctctagt acctctggtg cttctaaagg tgttgaaaat gcccaatgtt    9780
atgttaaagc tacagagttg gtatttgcgg acaaacatgg gtcatggggc actccttag    9840
ttcaaatgga ccggcctgct gggctcaatg acattggtat ggtagcttgg accttgaaga    9900
tgtccactcc tgaatttcct agtggtaggg agattattgt tgttgcaaat gatattacgt    9960
tcagagctgg atcatttggc ccaagggaag atgcattttt tgaagctgtt accaacctag   10020
cctgtgagaa gaaacttcct cttatttatt tggcagcaaa ttctggtgct cgaattggca   10080
tagcagatga agtgaaatct tgcttccgtg ttgggtggtc tgatgatggc agccctgaac   10140
gtgggtttca gtacatttat ctaagcgaag aagactatgc tcgtattggc acttctgtca   10200
tagcacataa gatgcagcta gacagtggtg aaattaggtg ggttattgat tctgttgtgg   10260
gcaaggaaga tggacttggt gtggagaata tacatggaag tgctgctatt gccagtgctt   10320
attctagggc atataaggag acatttacac ttacatttgt gactggaaga actgttggaa   10380
taggagctta tcttgctcga cttggcatcc ggtgcataca gcgtcttgac cagcctatta   10440
ttcttacagg ctattctgca ctgaacaagc ttcttgggcg ggaagtgtac agctcccaca   10500
tgcagttggg tggtcccaaa atcatggcaa ctaatggtgt tgtccatctt actgtttcag   10560
atgaccttga aggcgtttct aatatattga ggtggctcag ttatgttcct gcctacattg   10620
gtggaccact tccagtaaca acaccgttgg acccaccgga cagacctgtt gcatacattc   10680
ctgagaactc gtgtgatcct cgagcggcta tccgtgtgt tgatgacagc caagggaaat   10740
ggttaggtgg tatgtttgat aaagacagct ttgtggaaac atttgaaggt tgggctaaga   10800
cagtggttac tggcagagca aagcttggtg gaattccagt gggtgtgata gctgtggaga   10860
ctcagaccat gatgcaaact atccctgctg accctggtca gcttgattcc cgtgagcaat   10920
ctgttcctcg tgctggacaa gtgtggtttc cagattctgc aaccaagact gcgcaggcat   10980
tgctggactt caaccgtgaa ggattacctc tgttcatcct cgctaactgg agaggcttct   11040
ctggtggaca aagagatctt tttgaaggaa ttcttcaggc tggctcgact attgttgaga   11100
accttaggac atacaatcag cctgcctttg tctacattcc catggctgca gagctacgag   11160
gaggggcttg ggttgtggtt gatagcaaga taaacccaga ccgcattgag tgctatgctg   11220
agaggactgc aaaaggcaat gttctggaac cgcaagggtt aattgagatc aagttcaggt   11280
cagaggaact ccaggattgc atgagtcggc ttgacccaac attaattgat ctgaaagcaa   11340
aactcgaagt agcaaataaa aatggaagtg ctgacacaaa atcgcttcaa gaaaatatag   11400
aagctcgaac aaaacagttg atgcctctat atactcagat tgcgatacgg tttgctgaat   11460
tgcatgatac atccctcaga atggctgcga aaggtgtgat taagaaagtt gtggactggg   11520
aagaatcacg atctttcttc tataagagat tacggaggag gatctctgag gatgttcttg   11580
caaaagaaat tagagctgta gcaggtgagc agttttccca ccaaccagca atcgagctga   11640
tcaagaaatg gtattcagct tcacatgcag ctgaatggga tgatgacgat gcttttgttg   11700
cttggatgga taaccctgaa aactacaagg attatattca atatcttaag gctcaaagag   11760
tatcccaatc cctctcaagt ctttcagatt ccagctcaga tttgcaagcc ctgccacagg   11820
```

```
gtctttccat gttactagat aaggtaatta gcttactgat gcttatataa attcttttc    11880
attacatatg gctggagaac tatctaatca aataatgatt ataattccaa tcgttctttt    11940
tatgccatta tgatcttctg aaatttcctt ctttggacac ttattcagat ggatccctct    12000
agaagagctc aacttgttga agaaatcagg aaggtccttg gttgaatcat atgatgccaa    12060
aactattatt ggaggcacaa atagcttgtg gaccctgtcg gattgttggt gagtgtatat    12120
tggatttgtt agttctgcca gatgaaagtg caagtctgat gattcatgat accgtcagtt    12180
ggcaagaaca ccggttaacc tgagtgcttg tttacaaatg gtcctttatg acaatcgttg    12240
tttcgcgcta gttccgtgat ctactatcat ctgttagacg ctgtaattag tgagtctccg    12300
cggatccaca gtatacggtt gagctgttga ttcaattttg gacacgaata atatgatttt    12360
gtaggcataa atgcgtctgt atgtgaaata aattgtctgt tgagttaaca cacaagatga    12420
caatatgttt gtgctctact gctattgtcc atgaatactg attgcggaat caaccacatg    12480
cattat                                                                12486
```

<210> SEQ ID NO 251
<211> LENGTH: 2314
<212> TYPE: PRT
<213> ORGANISM: Oryza sativa

<400> SEQUENCE: 251

```
Met Thr Ser Thr His Val Ala Thr Leu Gly Val Gly Ala Gln Ala Pro
1               5                   10                  15

Pro Arg His Gln Lys Lys Ser Ala Gly Thr Ala Phe Val Ser Ser Gly
            20                  25                  30

Ser Ser Arg Pro Ser Tyr Arg Lys Asn Gly Gln Arg Thr Arg Ser Leu
        35                  40                  45

Arg Glu Glu Ser Asn Gly Gly Val Ser Asp Ser Lys Lys Leu Asn His
    50                  55                  60

Ser Ile Arg Gln Gly Leu Ala Gly Ile Ile Asp Leu Pro Asn Asp Ala
65                  70                  75                  80

Ala Ser Glu Val Asp Ile Ser His Gly Ser Glu Asp Pro Arg Gly Pro
                85                  90                  95

Thr Val Pro Gly Ser Tyr Gln Met Asn Gly Ile Ile Asn Glu Thr His
            100                 105                 110

Asn Gly Arg His Ala Ser Val Ser Lys Val Val Glu Phe Cys Thr Ala
        115                 120                 125

Leu Gly Gly Lys Thr Pro Ile His Ser Val Leu Val Ala Asn Asn Gly
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Leu Arg Ile Asn Ala Glu His Ile Arg Ile Ala Asp Gln Phe
            180                 185                 190

Val Glu Val Pro Gly Gly Thr Asn Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met His Ala
                245                 250                 255
```

```
Leu Gly Asp Lys Val Gly Ser Ala Leu Ile Ala Gln Ala Ala Gly Val
            260                 265                 270

Pro Thr Leu Ala Trp Ser Gly Ser His Val Glu Val Pro Leu Glu Cys
        275                 280                 285

Cys Leu Asp Ser Ile Pro Asp Glu Met Tyr Arg Lys Ala Cys Val Thr
    290                 295                 300

Thr Thr Glu Glu Ala Val Ala Ser Cys Gln Val Val Gly Tyr Pro Ala
305                 310                 315                 320

Met Ile Lys Ala Ser Trp Gly Gly Gly Lys Gly Ile Arg Lys Val
                325                 330                 335

His Asn Asp Asp Glu Val Arg Thr Leu Phe Lys Gln Val Gln Gly Glu
            340                 345                 350

Val Pro Gly Ser Pro Ile Phe Ile Met Arg Leu Ala Ala Gln Ser Arg
        355                 360                 365

His Leu Glu Val Gln Leu Leu Cys Asp Gln Tyr Gly Asn Val Ala Ala
    370                 375                 380

Leu His Ser Arg Asp Cys Ser Val Gln Arg His Gln Lys Ile Ile
385                 390                 395             400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Trp
    450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asn
                485                 490                 495

His Gly Gly Gly Tyr Asp Leu Trp Arg Lys Thr Ala Ala Leu Ala Thr
            500                 505                 510

Pro Phe Asn Phe Asp Glu Val Asp Ser Lys Trp Pro Lys Gly His Cys
        515                 520                 525

Val Ala Val Arg Ile Thr Ser Glu Asp Pro Asp Gly Phe Lys Pro
    530                 535                 540

Thr Gly Gly Lys Val Lys Glu Ile Ser Phe Lys Ser Lys Pro Asn Val
545                 550                 555                 560

Trp Ala Tyr Phe Ser Val Lys Ser Gly Gly Ile His Glu Phe Ala
                565                 570                 575

Asp Ser Gln Phe Gly His Val Phe Ala Tyr Gly Thr Thr Arg Ser Ala
            580                 585                 590

Ala Ile Thr Thr Met Ala Leu Ala Leu Lys Glu Val Gln Ile Arg Gly
        595                 600                 605

Glu Ile His Ser Asn Val Asp Tyr Thr Val Asp Leu Leu Asn Ala Ser
    610                 615                 620

Asp Phe Arg Glu Asn Lys Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Val Thr Ala Asn Thr Ala Thr Val Ser
            660                 665                 670
```

```
Asp Tyr Val Gly Tyr Leu Thr Lys Gly Gln Ile Pro Lys His Ile
            675                 680                 685

Ser Leu Val Tyr Thr Thr Val Ala Leu Asn Ile Asp Gly Lys Lys Tyr
        690                 695                 700

Thr Ile Asp Thr Val Arg Ser Gly His Gly Ser Tyr Arg Leu Arg Met
705                 710                 715                 720

Asn Gly Ser Thr Val Asp Ala Asn Val Gln Ile Leu Cys Asp Gly Gly
                725                 730                 735

Leu Leu Met Gln Leu Asp Gly Asn Ser His Val Ile Tyr Ala Glu Glu
            740                 745                 750

Glu Ala Ser Gly Thr Arg Leu Leu Ile Asp Gly Lys Thr Cys Met Leu
        755                 760                 765

Gln Asn Asp His Asp Pro Ser Lys Leu Leu Ala Glu Thr Pro Cys Lys
770                 775                 780

Leu Leu Arg Phe Leu Val Ala Asp Gly Ala His Val Asp Ala Asp Val
785                 790                 795                 800

Pro Tyr Ala Glu Val Glu Val Met Lys Met Cys Met Pro Leu Leu Ser
            805                 810                 815

Pro Ala Ser Gly Val Ile His Val Val Met Ser Glu Gly Gln Ala Met
        820                 825                 830

Gln Ala Gly Asp Leu Ile Ala Arg Leu Asp Leu Asp Asp Pro Ser Ala
            835                 840                 845

Val Lys Arg Ala Glu Pro Phe Glu Asp Thr Phe Pro Gln Met Gly Leu
            850                 855                 860

Pro Ile Ala Ala Ser Gly Gln Val His Lys Leu Cys Ala Ala Ser Leu
865                 870                 875                 880

Asn Ala Cys Arg Met Ile Leu Ala Gly Tyr Glu His Asp Ile Asp Lys
                885                 890                 895

Val Val Pro Glu Leu Val Tyr Cys Leu Asp Thr Pro Glu Leu Pro Phe
            900                 905                 910

Leu Gln Trp Glu Glu Leu Met Ser Val Leu Ala Thr Arg Leu Pro Arg
            915                 920                 925

Asn Leu Lys Ser Glu Leu Glu Gly Lys Tyr Glu Glu Tyr Lys Val Lys
            930                 935                 940

Phe Asp Ser Gly Ile Ile Asn Asp Phe Pro Ala Asn Met Leu Arg Val
945                 950                 955                 960

Ile Ile Glu Glu Asn Leu Ala Cys Gly Ser Glu Lys Glu Lys Ala Thr
                965                 970                 975

Asn Glu Arg Leu Val Glu Pro Leu Met Ser Leu Leu Lys Ser Tyr Glu
                980                 985                 990

Gly Gly Arg Glu Ser His Ala His  Phe Val Val Lys Ser Leu Phe Glu
            995                 1000                1005

Glu Tyr Leu Tyr Val Glu Glu  Leu Phe Ser Asp Gly  Ile Gln Ser
    1010                1015                1020

Asp Val Ile Glu Arg Leu Arg  Leu Gln His Ser Lys  Asp Leu Gln
            1025                1030                1035

Lys Val Val Asp Ile Val Leu  Ser His Gln Ser Val  Arg Asn Lys
    1040                1045                1050

Thr Lys Leu Ile Leu Lys Leu  Met Glu Ser Leu Val  Tyr Pro Asn
    1055                1060                1065

Pro Ala Ala Tyr Arg Asp Gln  Leu Ile Arg Phe Ser  Ser Leu Asn
    1070                1075                1080

His Lys Ala Tyr Tyr Lys Leu  Ala Leu Lys Ala Ser  Glu Leu Leu
```

```
                1085                1090                1095
Glu Gln Thr Lys Leu Ser Glu Leu Arg Ala Arg Ile Ala Arg Ser
        1100                1105                1110
Leu Ser Glu Leu Glu Met Phe Thr Glu Glu Ser Lys Gly Leu Ser
        1115                1120                1125
Met His Lys Arg Glu Ile Ala Ile Lys Glu Ser Met Glu Asp Leu
        1130                1135                1140
Val Thr Ala Pro Leu Pro Val Glu Asp Ala Leu Ile Ser Leu Phe
        1145                1150                1155
Asp Cys Ser Asp Thr Thr Val Gln Gln Arg Val Ile Glu Thr Tyr
        1160                1165                1170
Ile Ala Arg Leu Tyr Gln Pro His Leu Val Lys Asp Ser Ile Lys
        1175                1180                1185
Met Lys Trp Ile Glu Ser Gly Val Ile Ala Leu Trp Glu Phe Pro
        1190                1195                1200
Glu Gly His Phe Asp Ala Arg Asn Gly Gly Ala Val Leu Gly Asp
        1205                1210                1215
Lys Arg Trp Gly Ala Met Val Ile Val Lys Ser Leu Glu Ser Leu
        1220                1225                1230
Ser Met Ala Ile Arg Phe Ala Leu Lys Glu Thr Ser His Tyr Thr
        1235                1240                1245
Ser Ser Glu Gly Asn Met Met His Ile Ala Leu Leu Gly Ala Asp
        1250                1255                1260
Asn Lys Met His Ile Ile Gln Glu Ser Gly Asp Asp Ala Asp Arg
        1265                1270                1275
Ile Ala Lys Leu Pro Leu Ile Leu Lys Asp Asn Val Thr Asp Leu
        1280                1285                1290
His Ala Ser Gly Val Lys Thr Ile Ser Phe Ile Val Gln Arg Asp
        1295                1300                1305
Glu Ala Arg Met Thr Met Arg Arg Thr Phe Leu Trp Ser Asp Glu
        1310                1315                1320
Lys Leu Ser Tyr Glu Glu Glu Pro Ile Leu Arg His Val Glu Pro
        1325                1330                1335
Pro Leu Ser Ala Leu Leu Glu Leu Asp Lys Leu Lys Val Lys Gly
        1340                1345                1350
Tyr Asn Glu Met Lys Tyr Thr Pro Ser Arg Asp Arg Gln Trp His
        1355                1360                1365
Ile Tyr Thr Leu Arg Asn Thr Glu Asn Pro Lys Met Leu His Arg
        1370                1375                1380
Val Phe Phe Arg Thr Leu Val Arg Gln Pro Ser Val Ser Asn Lys
        1385                1390                1395
Phe Ser Ser Gly Gln Ile Gly Asp Met Glu Val Gly Ser Ala Glu
        1400                1405                1410
Glu Pro Leu Ser Phe Thr Ser Thr Ser Ile Leu Arg Ser Leu Met
        1415                1420                1425
Thr Ala Ile Glu Glu Leu Glu Leu His Ala Ile Arg Thr Gly His
        1430                1435                1440
Ser His Met Tyr Leu His Val Leu Lys Glu Gln Lys Leu Leu Asp
        1445                1450                1455
Leu Val Pro Val Ser Gly Asn Thr Val Leu Asp Val Gly Gln Asp
        1460                1465                1470
Glu Ala Thr Ala Tyr Ser Leu Leu Lys Glu Met Ala Met Lys Ile
        1475                1480                1485
```

-continued

His Glu Leu Val Gly Ala Arg Met His His Leu Ser Val Cys Gln
    1490            1495            1500

Trp Glu Val Lys Leu Lys Leu Asp Cys Asp Gly Pro Ala Ser Gly
    1505            1510            1515

Thr Trp Arg Ile Val Thr Thr Asn Val Thr Ser His Thr Cys Thr
    1520            1525            1530

Val Asp Ile Tyr Arg Glu Met Glu Asp Lys Glu Ser Arg Lys Leu
    1535            1540            1545

Val Tyr His Pro Ala Thr Pro Ala Ala Gly Pro Leu His Gly Val
    1550            1555            1560

Ala Leu Asn Asn Pro Tyr Gln Pro Leu Ser Val Ile Asp Leu Lys
    1565            1570            1575

Arg Cys Ser Ala Arg Asn Asn Arg Thr Thr Tyr Cys Tyr Asp Phe
    1580            1585            1590

Pro Leu Ala Phe Glu Thr Ala Val Arg Lys Ser Trp Ser Ser Ser
    1595            1600            1605

Thr Ser Gly Ala Ser Lys Gly Val Glu Asn Ala Gln Cys Tyr Val
    1610            1615            1620

Lys Ala Thr Glu Leu Val Gln Met Asp Arg Leu Ala Gly Leu Asn
    1625            1630            1635

Asp Ile Gly Met Val Ala Trp Thr Leu Lys Met Ser Thr Pro Glu
    1640            1645            1650

Phe Leu Ser Gly Arg Glu Ile Ile Val Val Ala Asn Asp Ile Thr
    1655            1660            1665

Phe Arg Ala Gly Ser Phe Gly Pro Arg Glu Asp Ala Phe Phe Glu
    1670            1675            1680

Ala Val Thr Asn Leu Ala Cys Glu Lys Lys Leu Pro Leu Ile Tyr
    1685            1690            1695

Leu Ala Ala Asn Ser Gly Ala Arg Ile Gly Ile Ala Asp Glu Val
    1700            1705            1710

Lys Ser Cys Phe Arg Val Gly Trp Ser Asp Asp Gly Ser Pro Glu
    1715            1720            1725

Arg Gly Phe Gln Tyr Ile Tyr Leu Ser Glu Glu Asp Tyr Ala Arg
    1730            1735            1740

Ile Gly Thr Ser Val Ile Ala His Lys Met Gln Leu Asp Ser Gly
    1745            1750            1755

Glu Ile Arg Trp Val Ile Asp Ser Val Val Gly Lys Glu Asp Gly
    1760            1765            1770

Leu Gly Val Glu Asn Ile His Gly Ser Ala Ala Ile Ala Ser Ala
    1775            1780            1785

Tyr Ser Arg Ala Tyr Lys Glu Thr Phe Thr Leu Thr Phe Val Thr
    1790            1795            1800

Gly Arg Thr Val Gly Ile Gly Ala Tyr Leu Ala Arg Leu Gly Ile
    1805            1810            1815

Arg Cys Ile Gln Arg Leu Asp Gln Pro Ile Ile Leu Thr Gly Tyr
    1820            1825            1830

Ser Ala Leu Asn Lys Leu Leu Gly Arg Glu Val Tyr Ser Ser His
    1835            1840            1845

Met Gln Leu Gly Gly Pro Lys Ile Met Ala Thr Asn Gly Val Val
    1850            1855            1860

His Leu Thr Val Ser Asp Asp Leu Glu Gly Val Ser Asn Ile Leu
    1865            1870            1875

```
Arg Trp Leu Ser Tyr Val Pro Ala Tyr Ile Gly Gly Pro Leu Pro
    1880                1885                1890

Val Thr Thr Pro Leu Asp Pro Asp Arg Pro Val Ala Tyr Ile
    1895                1900                1905

Pro Glu Asn Ser Cys Asp Pro Arg Ala Ala Ile Arg Gly Val Asp
    1910                1915                1920

Asp Ser Gln Gly Lys Trp Leu Gly Gly Met Phe Asp Lys Asp Ser
    1925                1930                1935

Phe Val Glu Thr Phe Glu Gly Trp Ala Lys Thr Val Val Thr Gly
    1940                1945                1950

Arg Ala Lys Leu Gly Gly Ile Pro Val Gly Val Ile Ala Val Glu
    1955                1960                1965

Thr Gln Thr Met Met Gln Thr Ile Pro Ala Asp Pro Gly Gln Leu
    1970                1975                1980

Asp Ser Arg Glu Gln Ser Val Pro Arg Ala Gly Gln Val Trp Phe
    1985                1990                1995

Pro Asp Ser Ala Thr Lys Thr Ala Gln Ala Leu Leu Asp Phe Asn
    2000                2005                2010

Arg Glu Gly Leu Pro Leu Phe Ile Leu Ala Asn Trp Arg Gly Phe
    2015                2020                2025

Ser Gly Gly Gln Arg Asp Leu Phe Glu Gly Ile Leu Gln Ala Gly
    2030                2035                2040

Ser Thr Ile Val Glu Asn Leu Arg Thr Tyr Asn Gln Pro Ala Phe
    2045                2050                2055

Val Tyr Ile Pro Met Ala Ala Glu Leu Arg Gly Gly Ala Trp Val
    2060                2065                2070

Val Val Asp Ser Lys Ile Asn Pro Asp Arg Ile Glu Cys Tyr Ala
    2075                2080                2085

Glu Arg Thr Ala Lys Gly Asn Val Leu Glu Pro Gln Gly Leu Ile
    2090                2095                2100

Glu Ile Lys Phe Arg Ser Glu Glu Leu Gln Asp Cys Met Ser Arg
    2105                2110                2115

Leu Asp Pro Thr Leu Ile Asp Leu Lys Ala Lys Leu Glu Val Ala
    2120                2125                2130

Asn Lys Asn Gly Ser Ala Asp Thr Lys Ser Leu Gln Glu Asn Ile
    2135                2140                2145

Glu Ala Arg Thr Lys Gln Leu Met Pro Leu Tyr Thr Gln Ile Ala
    2150                2155                2160

Ile Arg Phe Ala Glu Leu His Asp Thr Ser Leu Arg Met Ala Ala
    2165                2170                2175

Lys Gly Val Ile Lys Lys Val Val Asp Trp Glu Glu Ser Arg Ser
    2180                2185                2190

Phe Phe Tyr Lys Arg Leu Arg Arg Arg Ile Ser Glu Asp Val Leu
    2195                2200                2205

Ala Lys Glu Ile Arg Ala Val Ala Gly Glu Gln Phe Ser His Gln
    2210                2215                2220

Pro Ala Ile Glu Leu Ile Lys Lys Trp Tyr Ser Ala Ser His Ala
    2225                2230                2235

Ala Glu Trp Asp Asp Asp Asp Ala Phe Val Ala Trp Met Asp Asn
    2240                2245                2250

Pro Glu Asn Tyr Lys Asp Tyr Ile Gln Tyr Leu Lys Ala Gln Arg
    2255                2260                2265

Val Ser Gln Ser Leu Ser Ser Leu Ser Asp Ser Ser Ser Asp Leu
```

```
             2270                2275                2280
     Gln Ala Leu Pro Gln Gly Leu Ser Met Leu Leu Asp Lys Met Asp
         2285                2290                2295

Pro Ser Arg Arg Ala Gln Leu Val Glu Glu Ile Arg Lys Val Leu
         2300                2305                2310

Gly

<210> SEQ ID NO 252
<211> LENGTH: 2327
<212> TYPE: PRT
<213> ORGANISM: Oryza sativa

<400> SEQUENCE: 252

Met Thr Ser Thr His Val Ala Thr Leu Gly Val Gly Ala Gln Ala Pro
1               5                   10                  15

Pro Arg His Gln Lys Lys Ser Ala Gly Thr Ala Phe Val Ser Ser Gly
            20                  25                  30

Ser Ser Arg Pro Ser Tyr Arg Lys Asn Gly Gln Arg Thr Arg Ser Leu
        35                  40                  45

Arg Glu Glu Ser Asn Gly Gly Val Ser Asp Ser Lys Lys Leu Asn His
    50                  55                  60

Ser Ile Arg Gln Gly Leu Ala Gly Ile Ile Asp Leu Pro Asn Asp Ala
65                  70                  75                  80

Ala Ser Glu Val Asp Ile Ser His Gly Ser Glu Asp Pro Arg Gly Pro
                85                  90                  95

Thr Val Pro Gly Ser Tyr Gln Met Asn Gly Ile Ile Asn Glu Thr His
            100                 105                 110

Asn Gly Arg His Ala Ser Val Ser Lys Val Val Glu Phe Cys Thr Ala
        115                 120                 125

Leu Gly Gly Lys Thr Pro Ile His Ser Val Leu Val Ala Asn Asn Gly
130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Leu Arg Ile Asn Ala Glu His Ile Arg Ile Ala Asp Gln Phe
            180                 185                 190

Val Glu Val Pro Gly Gly Thr Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met His Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Val Pro Leu Glu Cys
        275                 280                 285

Cys Leu Asp Ser Ile Pro Asp Glu Met Tyr Arg Lys Ala Cys Val Thr
    290                 295                 300

Thr Thr Glu Glu Ala Val Ala Ser Cys Gln Val Val Gly Tyr Pro Ala
305                 310                 315                 320

Met Ile Lys Ala Ser Trp Gly Gly Gly Gly Lys Gly Ile Arg Lys Val
```

325                 330                 335
His Asn Asp Asp Glu Val Arg Thr Leu Phe Lys Gln Val Gln Gly Glu
            340                 345                 350
Val Pro Gly Ser Pro Ile Phe Ile Met Arg Leu Ala Ala Gln Ser Arg
            355                 360                 365
His Leu Glu Val Gln Leu Leu Cys Asp Gln Tyr Gly Asn Val Ala Ala
            370                 375                 380
Leu His Ser Arg Asp Cys Ser Val Gln Arg Arg His Gln Lys Ile Ile
385                 390                 395                 400
Glu Glu Gly Pro Val Thr Val Ala Pro Arg Glu Thr Val Lys Glu Leu
            405                 410                 415
Glu Gln Ala Ala Arg Arg Leu Ala Lys Ala Val Gly Tyr Val Gly Ala
            420                 425                 430
Ala Thr Val Glu Tyr Leu Tyr Ser Met Glu Thr Gly Glu Tyr Tyr Phe
            435                 440                 445
Leu Glu Leu Asn Pro Arg Leu Gln Val Glu His Pro Val Thr Glu Trp
            450                 455                 460
Ile Ala Glu Val Asn Leu Pro Ala Ala Gln Val Ala Val Gly Met Gly
465                 470                 475                 480
Ile Pro Leu Trp Gln Ile Pro Glu Ile Arg Arg Phe Tyr Gly Met Asn
            485                 490                 495
His Gly Gly Gly Tyr Asp Leu Trp Arg Lys Thr Ala Ala Leu Ala Thr
            500                 505                 510
Pro Phe Asn Phe Asp Glu Val Asp Ser Lys Trp Pro Lys Gly His Cys
            515                 520                 525
Val Ala Val Arg Ile Thr Ser Glu Asp Pro Asp Asp Gly Phe Lys Pro
            530                 535                 540
Thr Gly Gly Lys Val Lys Glu Ile Ser Phe Lys Ser Lys Pro Asn Val
545                 550                 555                 560
Trp Ala Tyr Phe Ser Val Lys Ser Gly Gly Gly Ile His Glu Phe Ala
            565                 570                 575
Asp Ser Gln Phe Gly His Val Phe Ala Tyr Gly Thr Thr Arg Ser Ala
            580                 585                 590
Ala Ile Thr Thr Met Ala Leu Ala Leu Lys Glu Val Gln Ile Arg Gly
            595                 600                 605
Glu Ile His Ser Asn Val Asp Tyr Thr Val Asp Leu Leu Asn Ala Ser
            610                 615                 620
Asp Phe Arg Glu Asn Lys Ile His Thr Gly Trp Leu Asp Thr Arg Ile
625                 630                 635                 640
Ala Met Arg Val Gln Ala Glu Arg Pro Pro Trp Tyr Ile Ser Val Val
            645                 650                 655
Gly Gly Ala Leu Tyr Lys Thr Val Thr Ala Asn Thr Ala Thr Val Ser
            660                 665                 670
Asp Tyr Val Gly Tyr Leu Thr Lys Gly Gln Ile Pro Pro Lys His Ile
            675                 680                 685
Ser Leu Val Tyr Thr Thr Val Ala Leu Asn Ile Asp Gly Lys Lys Tyr
            690                 695                 700
Thr Ile Asp Thr Val Arg Ser Gly His Gly Ser Tyr Arg Leu Arg Met
705                 710                 715                 720
Asn Gly Ser Thr Val Asp Ala Asn Val Gln Ile Leu Cys Asp Gly Gly
            725                 730                 735
Leu Leu Met Gln Leu Asp Gly Asn Ser His Val Ile Tyr Ala Glu Glu
            740                 745                 750

-continued

```
Glu Ala Ser Gly Thr Arg Leu Leu Ile Asp Gly Lys Thr Cys Met Leu
            755                 760                 765
Gln Asn Asp His Asp Pro Ser Lys Leu Leu Ala Glu Thr Pro Cys Lys
        770                 775                 780
Leu Leu Arg Phe Leu Val Ala Asp Gly Ala His Val Asp Ala Asp Val
785                 790                 795                 800
Pro Tyr Ala Glu Val Glu Val Met Lys Met Cys Met Pro Leu Leu Ser
                805                 810                 815
Pro Ala Ser Gly Val Ile His Val Val Met Ser Glu Gly Gln Ala Met
            820                 825                 830
Gln Ala Gly Asp Leu Ile Ala Arg Leu Asp Leu Asp Asp Pro Ser Ala
        835                 840                 845
Val Lys Arg Ala Glu Pro Phe Glu Asp Thr Phe Pro Gln Met Gly Leu
850                 855                 860
Pro Ile Ala Ala Ser Gly Gln Val His Lys Leu Cys Ala Ala Ser Leu
865                 870                 875                 880
Asn Ala Cys Arg Met Ile Leu Ala Gly Tyr Glu His Asp Ile Asp Lys
                885                 890                 895
Val Val Pro Glu Leu Val Tyr Cys Leu Asp Thr Pro Glu Leu Pro Phe
            900                 905                 910
Leu Gln Trp Glu Glu Leu Met Ser Val Leu Ala Thr Arg Leu Pro Arg
        915                 920                 925
Asn Leu Lys Ser Glu Leu Glu Gly Lys Tyr Glu Glu Tyr Lys Val Lys
930                 935                 940
Phe Asp Ser Gly Ile Ile Asn Asp Phe Pro Ala Asn Met Leu Arg Val
945                 950                 955                 960
Ile Ile Glu Glu Asn Leu Ala Cys Gly Ser Lys Glu Lys Ala Thr
                965                 970                 975
Asn Glu Arg Leu Val Glu Pro Leu Met Ser Leu Leu Lys Ser Tyr Glu
            980                 985                 990
Gly Gly Arg Glu Ser His Ala His Phe Val Val Lys Ser Leu Phe Glu
        995                 1000                1005
Glu Tyr Leu Tyr Val Glu Leu Phe Ser Asp Gly Ile Gln Ser
    1010                1015                1020
Asp Val Ile Glu Arg Leu Arg Leu Gln His Ser Lys Asp Leu Gln
    1025                1030                1035
Lys Val Val Asp Ile Val Leu Ser His Gln Ser Val Arg Asn Lys
    1040                1045                1050
Thr Lys Leu Ile Leu Lys Leu Met Glu Ser Leu Val Tyr Pro Asn
    1055                1060                1065
Pro Ala Ala Tyr Arg Asp Gln Leu Ile Arg Phe Ser Ser Leu Asn
    1070                1075                1080
His Lys Ala Tyr Tyr Lys Leu Ala Leu Lys Ala Ser Glu Leu Leu
    1085                1090                1095
Glu Gln Thr Lys Leu Ser Glu Leu Arg Ala Arg Ile Ala Arg Ser
    1100                1105                1110
Leu Ser Glu Leu Glu Met Phe Thr Glu Glu Ser Lys Gly Leu Ser
    1115                1120                1125
Met His Lys Arg Glu Ile Ala Ile Lys Glu Ser Met Glu Asp Leu
    1130                1135                1140
Val Thr Ala Pro Leu Pro Val Glu Asp Ala Leu Ile Ser Leu Phe
    1145                1150                1155
```

```
Asp Cys Ser Asp Thr Thr Val Gln Gln Arg Val Ile Glu Thr Tyr
    1160                1165                1170
Ile Ala Arg Leu Tyr Gln Pro His Leu Val Lys Asp Ser Ile Lys
    1175                1180                1185
Met Lys Trp Ile Glu Ser Gly Val Ile Ala Leu Trp Glu Phe Pro
    1190                1195                1200
Glu Gly His Phe Asp Ala Arg Asn Gly Gly Ala Val Leu Gly Asp
    1205                1210                1215
Lys Arg Trp Gly Ala Met Val Ile Val Lys Ser Leu Glu Ser Leu
    1220                1225                1230
Ser Met Ala Ile Arg Phe Ala Leu Lys Glu Thr Ser His Tyr Thr
    1235                1240                1245
Ser Ser Glu Gly Asn Met Met His Ile Ala Leu Leu Gly Ala Asp
    1250                1255                1260
Asn Lys Met His Ile Ile Gln Glu Ser Gly Asp Asp Ala Asp Arg
    1265                1270                1275
Ile Ala Lys Leu Pro Leu Ile Leu Lys Asp Asn Val Thr Asp Leu
    1280                1285                1290
His Ala Ser Gly Val Lys Thr Ile Ser Phe Ile Val Gln Arg Asp
    1295                1300                1305
Glu Ala Arg Met Thr Met Arg Arg Thr Phe Leu Trp Ser Asp Glu
    1310                1315                1320
Lys Leu Ser Tyr Glu Glu Glu Pro Ile Leu Arg His Val Glu Pro
    1325                1330                1335
Pro Leu Ser Ala Leu Leu Glu Leu Asp Lys Leu Lys Val Lys Gly
    1340                1345                1350
Tyr Asn Glu Met Lys Tyr Thr Pro Ser Arg Asp Arg Gln Trp His
    1355                1360                1365
Ile Tyr Thr Leu Arg Asn Thr Glu Asn Pro Lys Met Leu His Arg
    1370                1375                1380
Val Phe Phe Arg Thr Leu Val Arg Gln Pro Ser Val Ser Asn Lys
    1385                1390                1395
Phe Ser Ser Gly Gln Ile Gly Asp Met Glu Val Gly Ser Ala Glu
    1400                1405                1410
Glu Pro Leu Ser Phe Thr Ser Thr Ser Ile Leu Arg Ser Leu Met
    1415                1420                1425
Thr Ala Ile Glu Glu Leu Glu Leu His Ala Ile Arg Thr Gly His
    1430                1435                1440
Ser His Met Tyr Leu His Val Leu Lys Glu Gln Lys Leu Leu Asp
    1445                1450                1455
Leu Val Pro Val Ser Gly Asn Thr Val Leu Asp Val Gly Gln Asp
    1460                1465                1470
Glu Ala Thr Ala Tyr Ser Leu Leu Lys Glu Met Ala Met Lys Ile
    1475                1480                1485
His Glu Leu Val Gly Ala Arg Met His His Leu Ser Val Cys Gln
    1490                1495                1500
Trp Glu Val Lys Leu Lys Leu Asp Cys Asp Gly Pro Ala Ser Gly
    1505                1510                1515
Thr Trp Arg Ile Val Thr Thr Asn Val Thr Ser His Thr Cys Thr
    1520                1525                1530
Val Asp Ile Tyr Arg Glu Met Glu Asp Lys Glu Ser Arg Lys Leu
    1535                1540                1545
Val Tyr His Pro Ala Thr Pro Ala Ala Gly Pro Leu His Gly Val
```

```
            1550                1555                1560

Ala Leu Asn Asn Pro Tyr Gln Pro Leu Ser Val Ile Asp Leu Lys
1565                1570                1575

Arg Cys Ser Ala Arg Asn Asn Arg Thr Thr Tyr Cys Tyr Asp Phe
1580                1585                1590

Pro Leu Ala Phe Glu Thr Ala Val Arg Lys Ser Trp Ser Ser Ser
1595                1600                1605

Thr Ser Gly Ala Ser Lys Gly Val Glu Asn Ala Gln Cys Tyr Val
1610                1615                1620

Lys Ala Thr Glu Leu Val Phe Ala Asp Lys His Gly Ser Trp Gly
1625                1630                1635

Thr Pro Leu Val Gln Met Asp Arg Pro Ala Gly Leu Asn Asp Ile
1640                1645                1650

Gly Met Val Ala Trp Thr Leu Lys Met Ser Thr Pro Glu Phe Pro
1655                1660                1665

Ser Gly Arg Glu Ile Ile Val Val Ala Asn Asp Ile Thr Phe Arg
1670                1675                1680

Ala Gly Ser Phe Gly Pro Arg Glu Asp Ala Phe Phe Glu Ala Val
1685                1690                1695

Thr Asn Leu Ala Cys Glu Lys Lys Leu Pro Leu Ile Tyr Leu Ala
1700                1705                1710

Ala Asn Ser Gly Ala Arg Ile Gly Ile Ala Asp Glu Val Lys Ser
1715                1720                1725

Cys Phe Arg Val Gly Trp Ser Asp Asp Gly Ser Pro Glu Arg Gly
1730                1735                1740

Phe Gln Tyr Ile Tyr Leu Ser Glu Glu Asp Tyr Ala Arg Ile Gly
1745                1750                1755

Thr Ser Val Ile Ala His Lys Met Gln Leu Asp Ser Gly Glu Ile
1760                1765                1770

Arg Trp Val Ile Asp Ser Val Val Gly Lys Glu Asp Gly Leu Gly
1775                1780                1785

Val Glu Asn Ile His Gly Ser Ala Ala Ile Ala Ser Ala Tyr Ser
1790                1795                1800

Arg Ala Tyr Lys Glu Thr Phe Thr Leu Thr Phe Val Thr Gly Arg
1805                1810                1815

Thr Val Gly Ile Gly Ala Tyr Leu Ala Arg Leu Gly Ile Arg Cys
1820                1825                1830

Ile Gln Arg Leu Asp Gln Pro Ile Ile Leu Thr Gly Tyr Ser Ala
1835                1840                1845

Leu Asn Lys Leu Leu Gly Arg Glu Val Tyr Ser Ser His Met Gln
1850                1855                1860

Leu Gly Gly Pro Lys Ile Met Ala Thr Asn Gly Val Val His Leu
1865                1870                1875

Thr Val Ser Asp Asp Leu Glu Gly Val Ser Asn Ile Leu Arg Trp
1880                1885                1890

Leu Ser Tyr Val Pro Ala Tyr Ile Gly Gly Pro Leu Pro Val Thr
1895                1900                1905

Thr Pro Leu Asp Pro Pro Asp Arg Pro Val Ala Tyr Ile Pro Glu
1910                1915                1920

Asn Ser Cys Asp Pro Arg Ala Ala Ile Arg Gly Val Asp Asp Ser
1925                1930                1935

Gln Gly Lys Trp Leu Gly Gly Met Phe Asp Lys Asp Ser Phe Val
1940                1945                1950
```

-continued

```
Glu Thr Phe Glu Gly Trp Ala Lys Thr Val Val Thr Gly Arg Ala
    1955                1960                1965

Lys Leu Gly Gly Ile Pro Val Gly Val Ile Ala Val Glu Thr Gln
    1970                1975                1980

Thr Met Met Gln Thr Ile Pro Ala Asp Pro Gly Gln Leu Asp Ser
    1985                1990                1995

Arg Glu Gln Ser Val Pro Arg Ala Gly Gln Val Trp Phe Pro Asp
    2000                2005                2010

Ser Ala Thr Lys Thr Ala Gln Ala Leu Leu Asp Phe Asn Arg Glu
    2015                2020                2025

Gly Leu Pro Leu Phe Ile Leu Ala Asn Trp Arg Gly Phe Ser Gly
    2030                2035                2040

Gly Gln Arg Asp Leu Phe Glu Gly Ile Leu Gln Ala Gly Ser Thr
    2045                2050                2055

Ile Val Glu Asn Leu Arg Thr Tyr Asn Gln Pro Ala Phe Val Tyr
    2060                2065                2070

Ile Pro Met Ala Ala Glu Leu Arg Gly Gly Ala Trp Val Val Val
    2075                2080                2085

Asp Ser Lys Ile Asn Pro Asp Arg Ile Glu Cys Tyr Ala Glu Arg
    2090                2095                2100

Thr Ala Lys Gly Asn Val Leu Glu Pro Gln Gly Leu Ile Glu Ile
    2105                2110                2115

Lys Phe Arg Ser Glu Glu Leu Gln Asp Cys Met Ser Arg Leu Asp
    2120                2125                2130

Pro Thr Leu Ile Asp Leu Lys Ala Lys Leu Glu Val Ala Asn Lys
    2135                2140                2145

Asn Gly Ser Ala Asp Thr Lys Ser Leu Gln Glu Asn Ile Glu Ala
    2150                2155                2160

Arg Thr Lys Gln Leu Met Pro Leu Tyr Thr Gln Ile Ala Ile Arg
    2165                2170                2175

Phe Ala Glu Leu His Asp Thr Ser Leu Arg Met Ala Ala Lys Gly
    2180                2185                2190

Val Ile Lys Lys Val Val Asp Trp Glu Glu Ser Arg Ser Phe Phe
    2195                2200                2205

Tyr Lys Arg Leu Arg Arg Arg Ile Ser Glu Asp Val Leu Ala Lys
    2210                2215                2220

Glu Ile Arg Ala Val Ala Gly Glu Gln Phe Ser His Gln Pro Ala
    2225                2230                2235

Ile Glu Leu Ile Lys Lys Trp Tyr Ser Ala Ser His Ala Ala Glu
    2240                2245                2250

Trp Asp Asp Asp Ala Phe Val Ala Trp Met Asp Asn Pro Glu
    2255                2260                2265

Asn Tyr Lys Asp Tyr Ile Gln Tyr Leu Lys Ala Gln Arg Val Ser
    2270                2275                2280

Gln Ser Leu Ser Ser Leu Ser Asp Ser Ser Ser Asp Leu Gln Ala
    2285                2290                2295

Leu Pro Gln Gly Leu Ser Met Leu Leu Asp Lys Met Asp Pro Ser
    2300                2305                2310

Arg Arg Ala Gln Leu Val Glu Glu Ile Arg Lys Val Leu Gly
    2315                2320                2325

<210> SEQ ID NO 253
<211> LENGTH: 59
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
ccttcaccca cggcgtgcag tgcttcagcc gctaccccga ccacatgaag cagcacgac      59
```

METHODS AND COMPOSITIONS FOR TARGETED GENE MODIFICATION

CROSS REFERENCE TO RELATED APPLICATIONS

This application is a continuation-in-part application of International Patent Application No. PCT/US2015/020622, filed Mar. 14, 2015, which claims priority to U.S. Provisional Application No. 61/953,333, filed Mar. 14, 2014; U.S. Provisional Application No. 62/051,579, filed Sep. 17, 2014; U.S. Provisional Application No. 62/075,811, filed Nov. 5, 2014; U.S. Provisional Application No. 62/075,816, filed Nov. 5, 2014; and U.S. Provisional Application No. 62/133,129, filed Mar. 13, 2015; and is a continuation-in-part application of U.S. patent application Ser. No. 14/777,357, which is a U.S. National Phase Application of International Patent Application No. PCT/US2014/029566, filed Mar. 14, 2014, which claims priority to U.S. Provisional Application No. 61/801,333, filed Mar. 15, 2013, each of which is hereby incorporated by reference in its entirety including all tables, figures and claims.

SEQUENCE LISTING

The instant application contains a Sequence Listing which has been submitted electronically in ASCII format and is hereby incorporated by reference in its entirety. Said ASCII copy, created on Nov. 2, 2016, is named CIBUS029CIPTR1_SeqListing.txt and is 220 kilobytes in size.

FIELD OF THE INVENTION

The instant disclosure relates at least in part to targeted genetic mutations and modifications, including methods and compositions for making such mutations and modifications.

BACKGROUND

The following discussion is merely provided to aid the reader in understanding and is not admitted to describe or constitute prior art to the present disclosure.

U.S. Pat. No. 6,271,360 discloses methods and compositions for the introduction of predetermined genetic changes in target genes of a living cell by introducing an oligodeoxynucleoticle encoding the predetermined change. The oligodeoxynucleotides are effective in mammalian, avian, plant and bacterial cells.

U.S. Pat. No. 8,771,945 discloses vectors and vector systems, some of which encode one or more components of a CRISPR complex, as well as methods for the design and use of such vectors.

U.S. Pat. No. 8,470,973 "refers to methods for selectively recognizing a base pair in a DNA sequence by a polypeptide, to modified polypeptides which specifically recognize one or more base pairs in a DNA sequence and, to DNA which is modified so that it can be specifically recognized by a polypeptide and to uses of the polypeptide and DNA in specific DNA targeting as well as to methods of modulating expression of target genes in a cell."

SUMMARY

Provided herein include methods and compositions for effecting a targeted genetic change in DNA in a cell. Certain aspects and embodiments relate to improving the efficiency of the targeting of modifications to specific locations in genomic or other nucleotide sequences. As described herein, nucleic acids which direct specific changes to the genome may be combined with various approaches to enhance the availability of components of the natural repair systems present in the cells being targeted for modification.

In a first aspect, provided are methods for introducing a gene repair oligonucleobase (GRON)-mediated mutation into a target deoxyribonucleic acid (DNA) sequence in a plant cell. In certain embodiments the methods may include, inter alia, culturing the plant cell under conditions that increase one or more cellular DNA repair processes prior to, and/or coincident with, delivery of a GRON into the plant cell; and/or delivery of a GRON into the plant cell greater than 15 bases in length, the GRON optionally comprising one or more; or two or more; mutation sites for introduction into the target DNA.

A "gene repair oligonucleotide" or "GRON" as used herein means an oligonucleobase (e.g., mixed duplex oligonucleotides, non-nucleotide containing molecules, single stranded oligodeoxynucleotides, double stranded oligodeoxynucleotides and other gene repair molecules) that can under certain conditions direct single, or in some embodiments multiple, nucleotide deletions, insertions or substitutions in a DNA sequence. This oligonucleotide-mediated gene repair editing of the genome may comprise both non-homology based repair systems (e.g., non-homologous end joining) and homology-based repair systems (e.g., homology-directed repair). The GRON is typically designed to align in register with a genomic target except for the designed mismatch(es). These mismatches can be recognized and corrected by harnessing one or more of the cell's endogenous DNA repair systems. In some embodiments a GRON or oligonucleotide can be designed to contain multiple differences when compared to the organisms target sequence. These differences may not all affect the protein sequence translated from said target sequence and in one or more cases be known as silent changes. Numerous variations of GRON structure, chemistry and function are described elsewhere herein. In various embodiments, a GRON as used herein may have one or more modifications. For example, a GRON as used herein may have one or more modifications that attract DNA repair machinery to the targeted (mismatch) site and/or that prevent recombination of part or all of the GRON (other than the desired targeted deletion(s), insertion(s), substitution(s) or the like) into the genomic DNA of the target DNA sequence and/or that increase the stability of the GRON.

In various embodiments, a GRON may have both RNA and DNA nucleotides and/or other types of nucleobases. In some embodiments, one or more of the DNA or RNA nucleotides comprise a modification.

In one aspect, provided is a method of causing a genetic change in a plant cell, wherein the method involves exposing the cell to a DNA cutter and a GRON, for example a GRON that is modified as contemplated herein. In some embodiments the GRON may be modified such as with a Cy3 group, 3P5 group, a 2'O-methyl group or other modification such as contemplated herein. In another aspect, provided is a plant cell that includes a DNA cutter and a GRON, for example where the GRON is modified such as with a Cy3 group, 3P5 group, a 2'O-methyl group or other modification. In some embodiments, the DNA cutter is one or more selected from a CRISPR, a TALEN, a zinc finger, meganuclease, and a DNA-cutting antibiotic. In some embodiments, the DNA cutter is a CRISPR. In some embodiments, the DNA cutter is a TALEN. In some embodiments, the GRON is between 15 and 60 nucleobases in length; or between 30 and 40 nucleobases in length; or between 35 and 45 nucleobases in length; or between 20 and 70 nucleobases in length; or between 20 and 200 nucleobases in length; or between 30 and 180 nucleobases in length; or between 50 and 160 nucleobases in length; or between 70 and 150 nucleobases in length; or between 70 and 210 nucleobases in length; or between 80 and 120 nucleobases in length; or between 90 and 110 nucleobases in length; or between 95 and 105 nucleobases in length; or between 80 and 300 nucleobases in length; or between 90 and 250 nucleobases in length; or between 100 and 150 nucleobases in length; or between 100 and 200 nucleobases in length; or between 100 and 210 nucleobases in length; or between 100 and 300 nucleobases in length; or between 150 and 200 nucleobases in length; or between 200 and 300 nucleobases in length; or between 250 and 350 nucleobases in length; or between 50 and 110 nucleobases in length; or between 50 and 200 nucleobases in length; or between 150 and 210 nucleobases in length; or between 20 and 1000 nucleobases in length; or between 100 and 1000 nucleobases in length; or between 200 and 1000 nucleobases in length; or between 300 and 1000 nucleobases in length; or between 400 and 1000 nucleobases in length; or between 500 and 1000 nucleobases in length; or between 600 and 1000 nucleobases in length; or between 700 and 1000 nucleobases in length; or between 800 and 1000 nucleobases in length; or between 900 and 1000 nucleobases in length; or between 300 and 800 nucleobases in length; or between 400 and 600 nucleobases in length; or between 500 and 700 nucleobases in length; or between 600 and 800 nucleobases in length; or longer than 30 nucleobases in length; or longer than 35 nucleobases in length; or longer than 40 nucleobases in length; or longer than 50 nucleobases in length; or longer than 60 nucleobases in length; or longer than 65 nucleobases in length; or longer than 70 nucleobases in length; or longer than 75 nucleobases in length; or longer than 80 nucleobases in length; or longer than 85 nucleobases in length; or longer than 90 nucleobases in length; or longer than 95 nucleobases in length; or longer than 100 nucleobases in length; or longer than 110 nucleobases in length; or longer than 125 nucleobases in length; or longer than 150 nucleobases in length; or longer than 165 nucleobases in length; or longer than 175 nucleobases in length; or longer than 200 nucleobases in length; or longer than 250 nucleobases in length; or longer than 300 nucleobases in length; or longer than 350 nucleobases in length; or longer than 400 nucleobases in length; or longer than 450 nucleobases in length; or longer than 500 nucleobases in length; or longer than 550 nucleobases in length; or longer than 600 nucleobases in length; or longer than 700 nucleobases in length; or longer than 800 nucleobases in length; or longer than 900 nucleobases in length.

GRONs may be targeted at both non-coding (NC) and coding (C) regions of a target gene. By way of example, FIGS. 27 and 28 respectively depict C-GRONs and NC-GRONs suitable for introducing mutations into the rice genome in order to introduce one or more of the following amino acid substitions to the ACCase gene. The convention is to use the amino acid numbering system for the plastidal ACCase from blackgrass (*Alopecurus myosuroides*; Am) as the reference. The ACCase numbering used herein is based on the numbering for the blackgrass reference sequence ACCase protein (SEQ ID NO: 1) or at an analogous amino acid residue in an ACCase paralog (V=CY3; H=3'DMT dC CPG). The following table lists ACCase mutations that produce one or more of alloxydim, butroxydim, clethodim, cloproxydim, cycloxydim, sethoxydim, tepraloxydim, tralkoxydim, chlorazifop, clodinafop, clofop, diclofop, fenoxaprop, fenoxaprop-P, fenthiaprop, fluazifop, fluazifop-P, haloxyfop, haloxyfop-P, isoxapyrifop, propaquizafop, quizalofop, quizalofop-P, trifop, pinoxaden, agronomically acceptable salts and esters of any of these herbicides, and combinations thereof resistant phenotype.

| Amino Acid Change | Codon Change |
|---|---|
| I1781A | ATA > GCT |
| | ATA > GCC |
| | ATA > GCA |
| | ATA > GCG |
| I1781L | ATA > CTT |
| | ATA > CTC |
| | ATA > CTA |
| | ATA > CTG |
| | ATA > TTA |
| | ATA > TTG |
| I1781M | ATA > ATG |
| I1781N | ATA > AAT |
| | ATA > AAC |
| I1781S | ATA > TCT |
| | ATA > TCC |
| | ATA > TCA |
| | ATA > TCG |
| I1781T | ATA > ACT |
| | ATA > ACC |
| | ATA > ACA |
| | ATA > ACG |
| I1781V | ATA > GTT |
| | ATA > GTC |
| | ATA > GTA |
| | ATA > GTG |
| G1783C | GGA > TGT |
| | GGA > TGC |
| A1786P | GCT > CCT |
| | GCT > CCC |
| | GCT > CCA |
| | GCT > CCG |
| D2078G | GAT > GGT |
| | GAT > GGC |
| | GAT > GGA |
| | GAT > GGG |
| D2078K | GAT > AAA |
| | GAT > AAG |
| D2078T | GAT > ACT |
| | GAT > ACC |
| | GAT > ACA |
| | GAT > ACG |
| S2079F | AGC > TTT |
| | AGC > TTC |
| K2080E | AAG > GAA |
| | AAG > GAG |
| C2088F | TGC > TTT |
| | TGC > TTC |
| C2088G | TGC > GGT |
| | TGC > GGC |
| | TGC > GGA |
| | TGC > GGG |
| C2088H | TGC > CAT |
| | TGC > CAC |
| C2088K | TGC > AAA |
| | TGC > AAG |
| C2088L | TGC > CTT |
| | TGC > CTC |
| | TGC > CTA |
| | TGC > CTG |
| | TGC > TTA |
| | TGC > TTG |
| C2088N | TGC > AAT |
| | TGC > AAC |
| C2088P | TGC > CCT |
| | TGC > CCC |
| | TGC > CCA |
| | TGC > CCG |

-continued

| Amino Acid Change | Codon Change |
|---|---|
| C2088Q | TGC > CAA |
| | TGC > CAG |
| C2088R | TGC > CGT |
| | TGC > CGC |
| | TGC > CGA |
| | TGC > CGG |
| | TGC > AGA |
| | TGC > AGG |
| C2088S | TGC > TCT |
| | TGC > TCC |
| | TGC > TCA |
| | TGC > TCG |
| C2088T | TGC > ACT |
| | TGC > ACC |
| | TGC > ACA |
| | TGC > ACG |
| C2088V | TGC > GTT |
| | TGC > GTC |
| | TGC > GTA |
| | TGC > GTG |
| C2088W | TGC > TGG |

Similarly, FIGS. 29 and 30 respectively depict (coding) C-GRONs and (non-coding) NC-GRONs suitable for introducing mutations into the flax genome in order to introduce one or more of the following amino acid substitions to the EPSPS gene (with all numbering relative to the amino acid sequence of the *E. coli* AroA protein (prokaryotic EPSPS equivalent) (such as those described in U.S. Pat. No. 8,268,622). (V=CY3; H=3'DMT dC CPG). The following table lists EPSPS mutations that produce glyphosate agronomically acceptable salts and esters of any of these herbicides, and combinations thereof resistant phenotype.

| Amino Acid Change | Codon Change |
|---|---|
| G96A | GGA > GCT |
| | GGA > GCC |
| | GGA > GCA |
| | GGA > GCG |
| T97I | ACA > ATT |
| | ACA > ATC |
| | ACA > ATA |
| P101A | CCG > GCT |
| | CCG > GCC |
| | CCG > GCA |
| | CCG > GCG |
| P101S | CCG > TCT |
| | CCG > TCC |
| | CCG > TCA |
| | CCG > TCG |
| P101T | CCG > ACT |
| | CCG > ACC |
| | CCG > ACA |
| | CCG > ACG |

The term "CRISPR" as used herein refers to elements; i.e., a cas (CRISPR associated) gene, transcript (e.g., mRNA) or protein and at least one CRISPR spacer sequence (Clustered Regularly Interspaced Short Palindromic Repeats, also known as SPIDRs—SPacer Interspersed Direct Repeats); that when effectively present or expressed in a cell could effect cleavage of a target DNA sequence via CRISPR/CAS cellular machinery such as described in e.g., Cong, L. et al., Science, vol. 339 no 6121 pp. 819-823 (2013); Jinek et al, Science, vol. 337:816-821 (2013); Wang et al., RNA, vol. 14, pp. 903-913 (2008); Zhang et al., Plant Physiology, vol. 161, pp. 20-27 (2013), Zhang et al, PCT Application No. PCT/U52013/074743; and Charpentier et al., PCT Application No. PCT/U52013/032589. In some embodiments, such as for example a CRISPR for use in a eukaryotic cell, a CRISPR as contemplated herein may also include an additional element that includes a sequence for one or more functional nuclear localization signals. CRISPRs as contemplated herein can be expressed in, administered to and/or present in a cell (such as a plant cell) in any of many ways or manifestations. For example a CRISPR as contemplated herein may include or involve one or more of a CRISPR on a plasmid, a CRISPR nickase on a plasmid, a CRISPRa on a plasmid, or a CRISPRi on a plasmid as follows:

CRISPR on a Plasmid:

A recombinant expression vector comprising:

(i) a nucleotide sequence encoding a DNA-targeting RNA (e.g., guide RNA), wherein the DNA-targeting RNA comprises:
  a. a first segment comprising a nucleotide sequence that is complementary to a sequence in a target DNA (e.g., protospacer, spacer, or crRNA); and
  b. a second segment that interacts with a site-directed modifying polypeptide (e.g., trans-activating crRNA or tracrRNA); and
(ii) a nucleotide sequence encoding the site-directed modifying polypeptide (e.g., cas gene), wherein the site-directed polypeptide comprises:
  a. an RNA-binding portion that interacts with the DNA-targeting RNA (e.g., REC lobe); and
  b. an activity portion that causes double-stranded breaks within the target DNA (e.g., NUC lobe), wherein the site of the double-stranded breaks within the target DNA is determined by the DNA-targeting RNA.

CRISPR nickase on a plasmid. A recombinant expression vector comprising:

(i) a nucleotide sequence encoding a DNA-targeting RNA (e.g., guide RNA), wherein the DNA-targeting RNA comprises:
  a. a first segment comprising a nucleotide sequence that is complementary to a sequence in a target DNA (e.g., protospacer, spacer, or crRNA); and
  b. a second segment that interacts with a site-directed modifying polypeptide (e.g., trans-activating crRNA or tracrRNA); and
(ii) a nucleotide sequence encoding the site-directed modifying polypeptide (e.g., cas gene), wherein the site-directed polypeptide comprises:
  a. an RNA-binding portion that interacts with the DNA-targeting RNA (e.g., REC lobe); and
  b. an activity portion that causes single-stranded breaks within the target DNA (e.g., NUC lobe), wherein the site of the single-stranded breaks within the target DNA is determined by the DNA-targeting RNA.

CRISPRa on a plasmid. A recombinant expression vector comprising:

(i) a nucleotide sequence encoding a DNA-targeting RNA (e.g., guide RNA), wherein the DNA-targeting RNA comprises:
  a. a first segment comprising a nucleotide sequence that is complementary to a sequence in a target DNA (e.g., protospacer, spacer, or crRNA); and
  b. a second segment that interacts with a site-directed modifying polypeptide (e.g., trans-activating crRNA or tracrRNA); and (ii) a nucleotide sequence encoding the site-directed modifying polypeptide (e.g., cas gene), wherein the site-directed polypeptide comprises:
a. an RNA-binding portion that interacts with the DNA-targeting RNA (e.g., REC lobe); and
b. an activity portion that modulates transcription (e.g., NUC lobe; in certain embodiments increases transcription) within the target DNA, wherein the site of the transcriptional modulation within the target DNA is determined by the DNA-targeting RNA.

CRISPRi on a plasmid. A recombinant expression vector comprising:
(i) a nucleotide sequence encoding a DNA-targeting RNA (e.g., guide RNA), wherein the DNA-targeting RNA comprises:
a. a first segment comprising a nucleotide sequence that is complementary to a sequence in a target DNA (e.g., protospacer, spacer, or crRNA); and
b. a second segment that interacts with a site-directed modifying polypeptide (e.g., trans-activating crRNA or tracrRNA); and
(ii) a nucleotide sequence encoding the site-directed modifying polypeptide (e.g., cas gene), wherein the site-directed polypeptide comprises:
a. an RNA-binding portion that interacts with the DNA-targeting RNA (e.g., REC lobe); and
b. an activity portion that modulates transcription/ translation (e.g., NUC lobe; in some embodiments decreases transcription/translation) within the target DNA, wherein the site of transcriptional/translational modulation within the target DNA is determined by the DNA-targeting RNA.

Each of the CRISPR on a plasmid, CRISPR nickase on a plasmid, CRISPRa on a plasmid, and CRISPRi on a plasmid may in some embodiments alternatively have one or more appropriate elements be administered, expressed or present in a cell as an RNA (e.g., mRNA) or a protein rather than on a plasmid. Delivery of protected mRNA may be as described in Kariko, et al, U.S. Pat. No. 8,278,036.

In some embodiments, each of the CRISPRi and CRISPRa may include a deactivated cas9 (dCas9). A deactivated cas9 still binds to target DNA, but does not have cutting activity. Nuclease-deficient Cas9 can result from D10A and H840A point mutations which inactivates its two catalytic domains.

In some embodiments, a CRISPRi inhibits transcription initiation or elongation via steric hindrance of RNA Polymerase II. CRISPRi can optionally be enhanced (CRISPRei) by fusion of a strong repressor domain to the C-terminal end of a dCas9 protein. In some embodiments, a repressor domain recruits and employs chromatin modifiers. In some embodiments, the repressor domain may include, but is not limited to domains as described in Kagale, S. et al., Epigenetics, vol. 6 no 2 pp 141-146 (2011):

```
                                        (SEQ ID NO: 3)
1.  LDLNRPPPVEN (SEQ ID NO: 4)
    - OsERF3 repressor domain (LxLxPP motif)

(SEQ ID NO: 5)
2.  LRLFGVNM (R/KLFGV motif (SEQ ID NO: 6))
    - AtBRD repressor domain
```

```
                                        (SEQ ID NO: 7)
3.  LKLFGVWL (R/KLFGV motif (SEQ ID NO: 6))
    - AtHsfB1 repressor domain (SEQ ID NO: 8)
4.  LDLELRLGFA
    - AtSUP repressor domain (EAR motif)

5.  ERSNSIELRNSFYGRARTSPWSYGDYDNCQQDHDYLLGFSWPPRSY

TCSFCKREFRSAQALGGHMNVHRRDRARLRLQQSPSSSSTPSPPYP

NPNYSYSTMANSPPPHHSPLTLFPTLSPPSSPRYRAGLIRSLSPKS

KHTPENACKTKKSSLLVEAGEATRFTSKDACKILRNDEIISLELEI

GLINESEQDLDLELRLGFA*

(SEQ ID NO: 9)
    - full AtSUP gene containing repressor domain
      (EAR motif)
```

In some embodiments, a CRISPRa activation of transcription achieved by use of dCas9 protein containing a fused C-terminal end transcriptional activator. In some embodiments, an activation may include, but is not limited to VP64 (4×VP16), AtERF98 activation domain, or AtERF98×4 concatemers such as described in Cheng, A W et al., Cell Research, pp 1-9 (2013); Perez-Pinera, P. et al., Nature Methods, vol. 10 pp 913-976 (2013); Maeder, M L. et al., Nature Methods, vol. 10 pp 977-979 (2013) and Mali, P., et al., Nature Biotech., vol. 31 pp 833-838 (2013).

In some embodiments the CRISPR includes a nickase. In certain embodiments, two or more CRISPR nickases are used. In some embodiments, the two or more nickases cut on opposite strands of target nucleic acid. In other embodiments, the two or more nickases cut on the same strand of target nucleic acid.

As used herein, "repressor protein" or "repressor" refers to a protein that binds to operator of DNA or to RNA to prevent transcription or translation, respectively.

As used herein, "repression" refers to inhibition of transcription or translation by binding of repressor protein to specific site on DNA or mRNA. In some embodiments, repression includes a significant change in transcription or translation level of at least 1.5 fold, in other embodiments at least two fold, and in other embodiments at least five fold.

As used herein, an "activator protein" or "activator" with regard to gene transcription and/or translation, refers to a protein that binds to operator of DNA or to RNA to enhance or increase transcription or translation, respectively.

As used herein with regard to gene transcription and/or translation, "activation" with regard to gene transcription and/or translation, refers to enhancing or increasing transcription or translation by binding of activator protein to specific site on DNA or mRNA. In some embodiments, activation includes a significant change in transcription or translation level of at least 1.5 fold, in some embodiments at least two fold, and in some embodiments at least five fold.

In certain embodiments, conditions that increase one or more cellular DNA repair processes may include one or more of: introduction of one or more sites into the GRON or into the plant cell DNA that are targets for base excision repair, introduction of one or more sites into the GRON or into the plant cell DNA that are targets for non-homologous end joining, introduction of one or more sites into the GRON or into the plant cell DNA that are targets for microhomology-mediated end joining, introduction of one or more sites into the GRON or into the plant cell DNA that are targets for homologous recombination, and introduction of one or more sites into the GRON or into the plant cell DNA that are targets for effecting repair (e.g., base-excision repair (BER); homologous recombination repair (HR); mismatch repair (MMR); non-homologous end-joining repair (NHEJ) which include classical and alternative NHEJ; and nucleotide excision repair (NER)).

As described herein, GRONs for use herein may include one or more of the following alterations from conventional RNA and DNA nucleotides:
  one or more abasic nucleotides;
  one or more 8'oxo dA and/or 8'oxo dG nucleotides;
  a reverse base at the 3' end thereof;
  one or more 2'O-methyl nucleotides;
  one or more RNA nucleotides;
  one or more RNA nucleotides at the 5' end thereof, and in some embodiments 2, 3, 4, 5, 6, 7, 8, 9, 10, or more; wherein one or more of the RNA nucleotides may further be modified; one or more RNA nucleotides at the 3' end thereof, and in some embodiments 2, 3, 4, 5, 6, 7, 8, 9, 10, or more; wherein one or more of the RNA nucleotides may further be modified;
  one or more 2'O-methyl RNA nucleotides at the 5' end thereof, and in some embodiments 2, 3, 4, 5, 6, 7, 8, 9, 10, or more;
  an intercalating dye;
  a 5' terminus cap;
  a backbone modification selected from the group consisting of a phosphothioate modification, a methyl phosphonate modification, a locked nucleic acid (LNA) modification, a O-(2-methoxyethyl) (MOE) modification, a di PS modification, and a peptide nucleic acid (PNA) modification;
  one or more intrastrand crosslinks;
  one or more fluorescent dyes conjugated thereto, and in some embodiments at the 5' or 3' end of the GRON; and
  one or more bases which increase hybridization energy.
This list is not meant to be limiting.

The term "wobble base" as used herein refers to a change in a one or more nucleotide bases of a reference nucleotide sequence wherein the change does not change the sequence of the amino acid coded by the nucleotide relative to the reference sequence.

The term "non-nucleotide" or "abasic nucleotide" as use herein refers to any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine. It may have substitutions for a 2' or 3' H or OH as described in the art and herein.

As described herein, in certain embodiments GRON quality and conversion efficiency may be improved by synthesizing all or a portion of the GRON using nucleotide multimers, such as dimers, trimers, tetramers, etc. improving its purity.

In certain embodiments, the target deoxyribonucleic acid (DNA) sequence is within a plant cell, for example the target DNA sequence is in the plant cell genome. The plant cell may be non-transgenic or transgenic, and the target DNA sequence may be a transgene or an endogenous gene of the plant cell.

In certain embodiments, the conditions that increase one or more cellular DNA repair processes comprise introducing one or more compounds which induce single or double DNA strand breaks into the plant cell prior to, or coincident to, or after delivering the GRON into the plant cell. Exemplary compounds are described herein.

The methods and compositions described herein are applicable to plants generally. By way of example only, a plant species may be selected from the group consisting of canola, sunflower, corn, tobacco, sugar beet, cotton, maize, wheat (including but not limited to *Triticum* spp., *Triticum aestivum*, *Triticum durum Triticum timopheevii*, *Triticum monococcum*, *Triticum spelta*, *Triticum zhukovskyi* and *Triticum urartu* and hybrids thereof), barley (including but not limited to *Hordeum vulgare* L., *Hordeum comosum*, *Hordeum depressum*, *Hordeum intercedens*, *Hordeum jubatum*, *Hordeum marinum*, *Hordeum marinum*, *Hordeum parodii*, *Hordeum pusillum*, *Hordeum secalinum*, and *Hordeum spontaneum*), rice (including but not limited to *Oryza sativa* subsp. *indica*, *Oryza sativa* subsp. *japonica*, *Oryza sativa* subsp. *javanica*, *Oryza sativa* subsp. *glutinosa* (glutinous rice), *Oryza sativa Aromatica* group (e.g., basmati), and *Oryza sativa* (floating rice group)), alfalfa, barley, sorghum, tomato, mango, peach, apple, pear, strawberry, banana, melon, cassava, potato, carrot, lettuce, onion, soy bean, soya spp, sugar cane, pea, chickpea, field pea, fava bean, lentils, turnip, rutabaga, brussel sprouts, lupin, cauliflower, kale, field beans, poplar, pine, eucalyptus, grape, citrus, triticale, alfalfa, rye (including but not limited to *Secale sylvestre*, *Secale strictum*, *Secale cereale*, *Secale vavilovii*, *Secale africanum*, *Secale ciliatoglume*, *Secale ancestrale*, and *Secale montanum*), oats, turf (including but not limited to Turf grass include *Zoysia japonica*, *Agrostris palustris*, *Poa pratensis*, *Poa annua*, *Digitaria sanguinalis*, *Cyperus rotundus*, *Kyllinga brevifolia*, *Cyperus amuricus*, *Erigeron canadensis*, *Hydrocotyle sibthorpioides*, *Kummerowia striata*, *Euphorbia humifusa*, and *Viola arvensis*) and forage grasses, flax, oilseed rape, cotton, mustard, cucumber, morning glory, balsam, pepper, eggplant, marigold, lotus, cabbage, daisy, carnation, tulip, iris, lily, nut-producing plants insofar as they are not already specifically mentioned. These may also apply in whole or in part to all other biological systems including but not limited to bacteria, yeast, fungi, algae, and mammalian cells and even their organelles (e.g., mitochondria and chloroplasts). In some embodiments, the organism or cell is of a species selected from the group consisting of *Escherichia coli*, *Mycobacterium smegmatis*, *Baccillus subtilis*, *Chlorella*, *Bacillus thuringiensis*, *Saccharomyces cerevisiae*, *Yarrowia lipolytica*, *Chlamydamonas rhienhardtii*, *Pichia pastoris*, *Corynebacterium*, *Aspergillus niger*, and *Neurospora crassa*. In some embodiments, the yeast is *Yarrowia lypolitica*. In other embodiments, the yeast is not *Saccharomyces cerevisiae*. In some embodiments, the plant or plant cell is of a species selected from the group consisting of *Arabidopsis thaliana*, *Solanum tuberosum*, *Solanum phureja*, *Oryza sativa*, *Glycine max*, *Amaranthus tuberculatus*, *Linum usitatissimum*, and *Zea mays*. The plant species may be selected from the group consisting of monocotyledonous plants of the grass family Poaceae. The family Poaceae may be divided into two major clades, the clade containing the subfamilies Bambusoideae, Ehrhartoideae, and Pooideae (the BEP clade) and the clade containing the subfamilies Panicoideae, Arundinoideae, Chloridoideae, Centothecoideae, Micrairoideae, Aristidoideae, and Danthonioideae (the PACCMAD clade). The subfamily Bambusoideae includes tribe Oryzeae. The plant species may relate to plants of the BEP clade, in particular plants of the subfamilies Bambusoideae and Ehrhartoideae. The BET clade includes subfamilies Bambusoideae, Ehrhartoideae, and group Triticodae and no other subfamily Pooideae groups. BET crop plants are plants grown for food or forage that are members of BET subclade, for example barley, corn, etc.

In certain embodiments, the methods further comprise regenerating a plant having a mutation introduced by the GRON from the plant cell, and may comprise collecting seeds from the plant.

In related aspects, the present disclosure relates to plant cells comprising a genomic modification introduced by a GRON according to the methods described herein, a plant comprising a genomic modification introduced by a GRON according to the methods described herein, or a seed comprising a genomic modification introduced by a GRON according to the methods described herein; or progeny of a seed comprising a genomic modification introduced by a GRON according to the methods described herein.

Other embodiments of the disclosure will be apparent from the following detailed description, exemplary embodiments, and claims.

BRIEF DESCRIPTION OF THE FIGURES

FIG. 2A depicts GRONs (SEQ ID NOS 31, 231, 29, and 232, respectively, in order of appearance) comprising RNA/DNA, referred to herein as "2'-O-methyl GRONs." FIG. 2B depicts GRONs (SEQ ID NOS 31, 231, 29, and 232, respectively, in order of appearance) comprising RNA/DNA, referred to herein as "2'-O-methyl GRONs.".

FIG. 3 is a schematic of the location on the bfp gene where the BFP5 CRISPRs target. Figure discloses SEQ ID NO: 253.

FIG. 14 shows the results of next generation sequencing of 3- and 6-week old *Linum usitatissimum* (flax) microcalli derived from shoot tip protoplasts PEG treated with CRISPR plasmid at T=0.

FIG. 15 shows the results of next generation sequencing of 3- and 6-week old *Linum usitatissimum* microcalli derived from shoot tip protoplasts PEG treated with CRISPR plasmid at T=0.

FIG. 16A shows the distribution of indels based on size as determined by deep sequencing in protoplasts treated with CRISPR-Cas plasmid (BC-1) at 72 h post delivery. Indels represented 0.79% of the total reads. FIG. 16B shows BFP to GFP editing measured by the percentage of GFP fluorescing protoplasts identified by flow cytometry 72 h post delivery of plasmid (BC-1) and GRON (CG-6). Represented data is not normalized for transfection efficiency. Error bars are s.e.m. (n=9).

FIG. 23 shows the amino acid sequence of *Alopecurus myosuroides* (blackgrass) ACCase gene product (SEQ ID NO:1).

FIG. 24 shows the amino acid sequence of *Escherichia coli* EPSPS gene product (SEQ ID NO:2).

FIG. 25 shows exemplary analogous EPSPS positions.

FIG. 26A (SEQ ID NO: 246) shows an *Alopecurus myosuroides* plastidal ACCase cDNA sequence. FIG. 26B (SEQ ID NO: 247) shows an *Alopecurus myosuroides* plastidal ACCase amino acid sequence. FIG. 26C (SEQ ID NO: 248) shows an *Oryza sativa* plastidal ACCase cDNA sequence. FIG. 26D (SEQ ID NO: 249) shows an *Oryza sativa* plastidal ACCase amino acid sequence. FIG. 26E (SEQ ID NO: 250) shows an *Oryza sativa* plastidal ACCase genomic DNA sequence. FIG. 26F (SEQ ID NO: 251) shows an *Oryza sativa* plastidal ACCase protein sequence. FIG. 26G (SEQ ID NO: 252) shows an *Oryza sativa* ACCase protein sequence.

DETAILED DESCRIPTION

Figure 1:
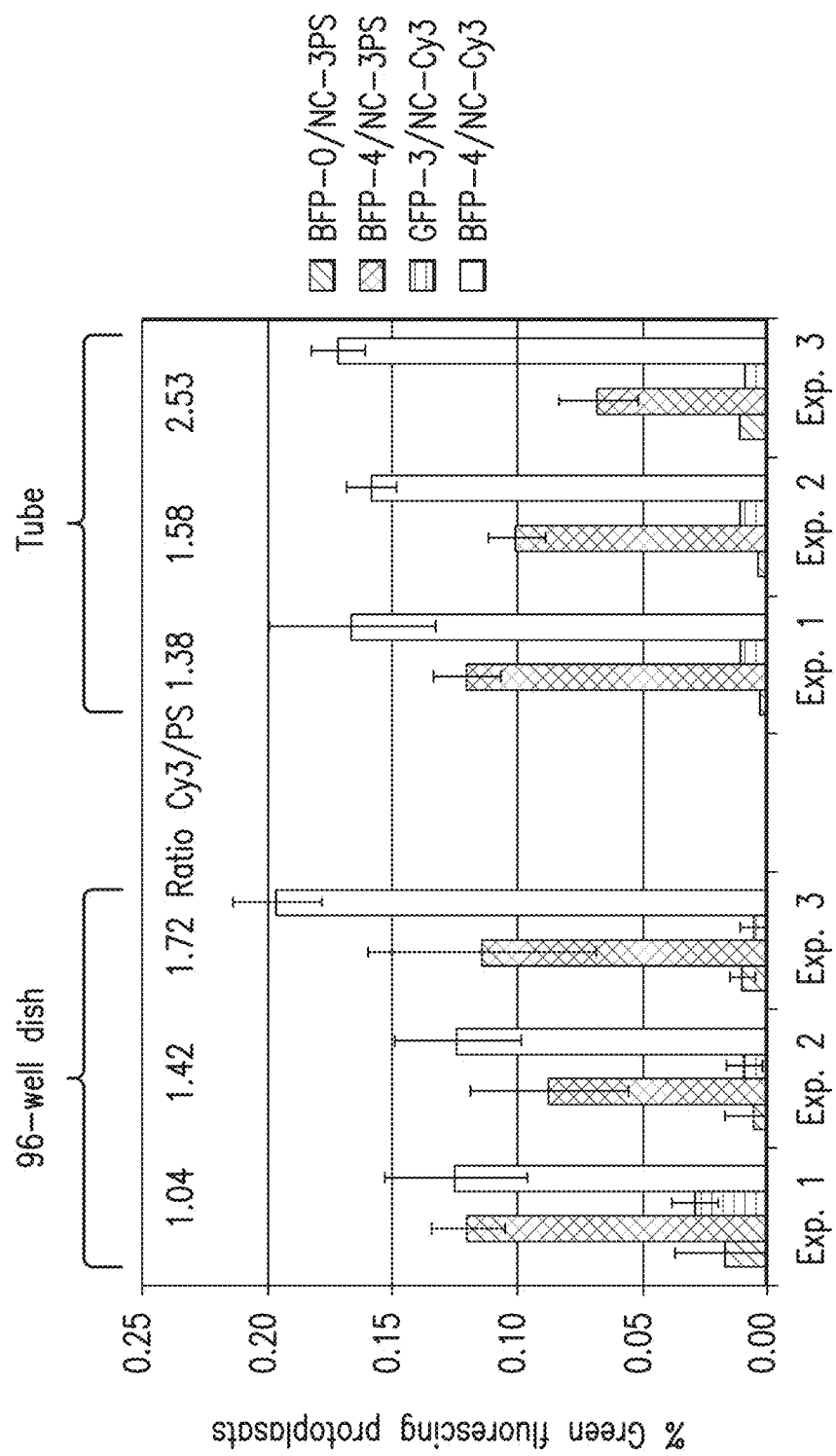
FIG. 1 depicts BFP to GFP conversion mediated by phosphothioate (PS) labeled GRONs (having 3 PS moieties at each end of the GRON) and 5'Cy3/3'idC labeled GRONs.

Targeted genetic modification mediated by oligonucleotides is a valuable technique for use in the specific alteration of short stretches of DNA to create deletions, short insertions, and point mutations. These methods involve DNA pairing/annealing, followed by a DNA repair/recombination event. First, the nucleic acid anneals with its complementary strand in the double-stranded DNA in a process mediated by cellular protein factors. This annealing creates a centrally located mismatched base pair (in the case of a point mutation), resulting in a structural perturbation that most likely stimulates the endogenous protein machinery to initiate the second step in the repair process: site-specific modification of the chromosomal sequence and/or that in organelles (e.g., mitochondria and chloroplasts). This newly introduced mismatch induces the DNA repair machinery to perform a second repair event, leading to the final revision of the target site. The present methods and compositions in various aspects and embodiments disclosed herein, may improve the methods by providing novel approaches which increase the availability of DNA repair components, thus increasing the efficiency and reproducibility of gene repair-mediated modifications to targeted nucleic acids.

Efficient methods for site-directed genomic modifications are desirable for research, clinical gene therapy, industrial microbiology and agriculture. One approach utilizes triplex-forming oligonucleotides (TFO) which bind as third strands to duplex DNA in a sequence-specific manner, to mediate directed mutagenesis. Such TFO can act either by delivering a tethered mutagen, such as psoralen or chlorambucil (Havre et al., Proc Nat'l Acad Sci, U.S.A. 90:7879-7883, 1993; Havre et al., J Virol 67:7323-7331, 1993; Wang et al., Mol Cell Biol 15:1759-1768, 1995; Takasugi et al., Proc Nat'l Acad Sci, U.S.A. 88; 5602-5606, 1991; Belousov et al., Nucleic Acids Res 25:3440-3444, 1997), or by binding with sufficient affinity to provoke error-prone repair (Wang et al., Science 271:802-805, 1996).

Another strategy for genomic modification involves the induction of homologous recombination between an exogenous DNA fragment and the targeted gene. This approach has been used successfully to target and disrupt selected genes in mammalian cells and has enabled the production of transgenic mice carrying specific gene knockouts (Capeechi et al., Science 244:1288-1292, 1989; Wagner, U.S. Pat. No. 4,873,191). This approach involves the transfer of selectable markers to allow isolation of the desired recombinants. Without selection, the ratio of homologous to non-homologous integration of transfected DNA in typical gene transfer experiments is low, usually in the range of 1:1000 or less (Sedivy et al., Gene Targeting, W. H. Freeman and Co., New York, 1992). This low efficiency of homologous integration limits the utility of gene transfer for experimental use or gene therapy. The frequency of homologous recombination can be enhanced by damage to the target site from UV irradiation and selected carcinogens (Wang et al., Mol Cell Biol 8:196-202, 1988) as well as by site-specific endonucleases (Sedivy et al, Gene Targeting, W. H. Freeman and Co., New York, 1992; Rouet et al., Proc Nat'l Acad Sci, U.S.A. 91:6064-6068, 1994; Segal et al., Proc Nat'l Acad Sci, U.S.A. 92:806-810, 1995). In addition, DNA damage induced by triplex-directed psoralen photoadducts can stimulate recombination within and between extrachromosomal vectors (Segal et al., Proc Nat'l Acad. Sci, U.S.A. 92:806-810, 1995; Faruqi et al., Mol Cell Biol 16:6820-6828, 1996; Glazer, U.S. Pat. No. 5,962,426).

Linear donor fragments are more recombinogenic than their circular counterparts (Folger et al., Mol Cell Biol. 2:1372-1387, 1982). Recombination can in certain embodiments also be influenced by the length of uninterrupted homology between both the donor and target sites, with short fragments often appearing to be ineffective substrates for recombination (Rubnitz et al., Mol Cell Biol. 4:2253-2258, 1984). Nonetheless, the use of short fragments of DNA or DNA/RNA hybrids for gene correction is the focus of various strategies. (Kunzelinann et al., Gene Ther 3:859-867, 1996).

"Nucleic acid sequence," "nucleotide sequence" and "polynucleotide sequence" as used herein refer to an oligonucleotide or polynucleotide, and fragments or portions thereof, and to DNA or RNA of genomic or synthetic origin which may be single- or double-stranded, and represent the sense or antisense strand.

As used herein, the terms "oligonucleotide" and "oligomer" refer to a polymer of nucleobases of at least about 10 nucleobases and as many as about 1000 nucleobases.

The terms "DNA-modifying molecule" and "DNA-modifying reagent" as used herein refer to a molecule which is capable of recognizing and specifically binding to a nucleic acid sequence in the genome of a cell, and which is capable of modifying a target nucleotide sequence within the genome, wherein the recognition and specific binding of the DNA-modifying molecule to the nucleic acid sequence is protein-independent. The term "protein-independent" as used herein in connection with a DNA-modifying molecule means that the DNA-modifying molecule does not require the presence and/or activity of a protein and/or enzyme for the recognition of, and/or specific binding to, a nucleic acid sequence. DNA-modifying molecules are exemplified, but not limited to triplex forming oligonucleotides, peptide nucleic acids, polyamides, and oligonucleotides which are intended to promote gene conversion. The DNA-modifying molecules of the present disclosure are in certain embodiments distinguished from the prior art's nucleic acid sequences which are used for homologous recombination (Wong & Capecchi, Molec. Cell. Biol. 7:2294-2295, 1987) in that the prior art's nucleic acid sequences which are used for homologous recombination are protein-dependent. The term "protein-dependent" as used herein in connection with a molecule means that the molecule requires the presence and/or activity of a protein and/or enzyme for the recognition of, and/or specific binding of the molecule to, a nucleic acid sequence. Methods for determining whether a DNA-modifying molecule requires the presence and/or activity of a protein and/or enzyme for the recognition of, and/or specific binding to, a nucleic acid sequence are within the skill in the art (see, e.g., Dennis et al. Nucl. Acids Res. 27:4734-4742, 1999). For example, the DNA-modifying molecule may be incubated in vitro with the nucleic acid sequence in the absence of any proteins and/or enzymes. The detection of specific binding between the DNA-modifying molecule and the nucleic acid sequence demonstrates that the DNA-modifying molecule is protein-independent. On the other hand, the absence of specific binding between the DNA-modifying molecule and the nucleic acid sequence demonstrates that the DNA-modifying molecule is protein-dependent and/or requires additional factors.

"Triplex forming oligonucleotide" (TFO) is defined as a sequence of DNA or RNA that is capable of binding in the major grove of a duplex DNA or RNA helix to form a triple helix. Although the TFO is not limited to any particular length, a preferred length of the TFO is 250 nucleotides or less, 200 nucleotides or less, or 100 nucleotides or less, or from 5 to 50 nucleotides, or from 10 to 25 nucleotides, or from 15 to 25 nucleotides. Although a degree of sequence specificity between the TFO and the duplex DNA is necessary for formation of the triple helix, no particular degree of specificity is required, as long as the triple helix is capable of forming. Likewise, no specific degree of avidity or affinity between the TFO and the duplex helix is required as long as the triple helix is capable of forming. While not intending to limit the length of the nucleotide sequence to which the TFO specifically binds in one embodiment, the nucleotide sequence to which the TFO specifically binds is from 1 to 100, in some embodiments from 5 to 50, yet other embodiments from 10 to 25, and in other embodiments from 15 to 25, nucleotides. Additionally, "triple helix" is defined as a double-helical nucleic acid with an oligonucleotide bound to a target sequence within the double-helical nucleic acid. The "double-helical" nucleic acid can be any double-stranded nucleic acid including double-stranded DNA, double-stranded RNA and mixed duplexes of DNA and RNA. The double-stranded nucleic acid is not limited to any particular length. However, in preferred embodiments it has a length of greater than 500 bp, in some embodiments greater than 1 kb and in some embodiments greater than about 5 kb. In many applications the double-helical nucleic acid is cellular, genomic nucleic acid. The triplex forming oligonucleotide may bind to the target sequence in a parallel or anti-parallel manner.

"Peptide Nucleic Acids," "polyamides" or "PNA" are nucleic acids wherein the phosphate backbone is replaced with an N-aminoethylglycine-based polyamide structure. PNAs have a higher affinity for complementary nucleic acids than their natural counter parts following the Watson-Crick base-pairing rules. PNAs can form highly stable triple helix structures with DNA of the following stoichiometry: (PNA)2.DNA. Although the peptide nucleic acids and polyamides are not limited to any particular length, a preferred length of the peptide nucleic acids and polyamides is 200 nucleotides or less, in some embodiments 100 nucleotides or less, and in some embodiments from 5 to 50 nucleotides long. While not intending to limit the length of the nucleotide sequence to which the peptide nucleic acid and polyamide specifically binds, in one embodiment, the nucleotide sequence to which the peptide nucleic acid and polyamide specifically bind is from 1 to 100, in some embodiments from 5 to 50, yet other embodiments from 5 to 25, and other embodiments from 5 to 20, nucleotides.

The term "cell" refers to a single cell. The term "cells" refers to a population of cells. The population may be a pure population comprising one cell type. Likewise, the population may comprise more than one cell type. In the present disclosure, there is no limit on the number of cell types that a cell population may comprise. A cell as used herein includes without limitation plant callus cells, cells with and without cell walls, prokaryotic cells and eukaryotic cells.

The term "synchronize" or "synchronized," when referring to a sample of cells, or "synchronized cells" or "synchronized cell population" refers to a plurality of cells which have been treated to cause the population of cells to be in the same phase of the cell cycle. It is not necessary that all of the cells in the sample be synchronized. A small percentage of cells may not be synchronized with the majority of the cells in the sample. A preferred range of cells that are synchronized is between 10-100%. A more preferred range is between 30-100%. Also, it is not necessary that the cells be a pure population of a single cell type. More than one cell type may be contained in the sample. In this regard, only one of cell types may be synchronized or may be in a different phase of the cell cycle as compared to another cell type in the sample.

The term "synchronized cell" when made in reference to a single cell means that the cell has been manipulated such that it is at a cell cycle phase which is different from the cell cycle phase of the cell prior to the manipulation. Alternatively, a "synchronized cell" refers to a cell that has been manipulated to alter (i.e., increase or decrease) the duration of the cell cycle phase at which the cell was prior to the manipulation when compared to a control cell (e.g., a cell in the absence of the manipulation).

The term "cell cycle" refers to the physiological and morphological progression of changes that cells undergo when dividing (i.e. proliferating). The cell cycle is generally recognized to be composed of phases termed "interphase," "prophase," "metaphase," "anaphase," and "telophase". Additionally, parts of the cell cycle may be termed "M (mitosis)," "S (synthesis)," "G0," "G1 (gap 1)" and "G2 (gap2)". Furthermore, the cell cycle includes periods of progression that are intermediate to the above named phases.

The term "cell cycle inhibition" refers to the cessation of cell cycle progression in a cell or population of cells. Cell cycle inhibition is usually induced by exposure of the cells to an agent (chemical, proteinaceous or otherwise) that interferes with aspects of cell physiology to prevent continuation of the cell cycle.

"Proliferation" or "cell growth" refers to the ability of a parent cell to divide into two daughter cells repeatably thereby resulting in a total increase of cells in the population. The cell population may be in an organism or in a culture apparatus.

The term "capable of modifying DNA" or "DNA modifying means" refers to procedures, as well as endogenous or exogenous agents or reagents that have the ability to induce, or can aid in the induction of, changes to the nucleotide sequence of a targeted segment of DNA. Such changes may be made by the deletion, addition or substitution of one or more bases on the targeted DNA segment. It is not necessary that the DNA sequence changes confer functional changes to any gene encoded by the targeted sequence. Furthermore, it is not necessary that changes to the DNA be made to any particular portion or percentage of the cells.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences that do not encode an mRNA or protein product (e.g., promoter sequence, enhancer sequence, polyadenylation sequence, termination sequence, regulatory RNAs such as miRNA, etc.).

"Amino acid sequence," "polypeptide sequence," "peptide sequence" and "peptide" are used interchangeably herein to refer to a sequence of amino acids.

"Target sequence," as used herein, refers to a double-helical nucleic acid comprising a sequence greater than 8 nucleotides in length but less than 201 nucleotides in length. In some embodiments, the target sequence is between 8 to 30 bases. The target sequence, in general, is defined by the nucleotide sequence on one of the strands on the double-helical nucleic acid.

As used herein, a "purine-rich sequence" or "polypurine sequence" when made in reference to a nucleotide sequence on one of the strands of a double-helical nucleic acid sequence is defined as a contiguous sequence of nucleotides wherein greater than 50% of the nucleotides of the target sequence contain a purine base. However, it is preferred that the purine-rich target sequence contain greater than 60% purine nucleotides, in some embodiments greater than 75% purine nucleotides, in other embodiments greater than 90% purine nucleotides and yet other embodiments 100% purine nucleotides.

As used herein, a "pyrimidine-rich sequence" or "polypyrimidine sequence" when made in reference to a nucleotide sequence on one of the strands of a double-helical nucleic acid sequence is defined as a contiguous sequence of nucleotides wherein greater that 50% of the nucleotides of the target sequence contain a pyrimidine base. However, it is preferred that the pyrimidine-rich target sequence contain greater than 60% pyrimidine nucleotides and in some embodiments greater than 75% pyrimidine nucleotides. In some embodiments, the sequence contains greater than 90% pyrimidine nucleotides and, in other embodiments, is 100% pyrimidine nucleotides.

A "variant" of a first nucleotide sequence is defined as a nucleotide sequence which differs from the first nucleotide sequence (e.g., by having one or more deletions, insertions, or substitutions that may be detected using hybridization assays or using DNA sequencing). Included within this definition is the detection of alterations or modifications to the genomic sequence of the first nucleotide sequence. For example, hybridization assays may be used to detect (1) alterations in the pattern of restriction enzyme fragments capable of hybridizing to the first nucleotide sequence when comprised in a genome (i.e., RFLP analysis), (2) the inability of a selected portion of the first nucleotide sequence to hybridize to a sample of genomic DNA which contains the first nucleotide sequence (e.g., using allele-specific oligonucleotide probes), (3) improper or unexpected hybridization, such as hybridization to a locus other than the normal chromosomal locus for the first nucleotide sequence (e.g., using fluorescent in situ hybridization (FISH) to metaphase chromosomes spreads, etc.). One example of a variant is a mutated wild type sequence.

The terms "nucleic acid" and "unmodified nucleic acid" as used herein refer to any one of the known four deoxyribonucleic acid bases (i.e., guanine, adenine, cytosine, and thymine). The term "modified nucleic acid" refers to a nucleic acid whose structure is altered relative to the structure of the unmodified nucleic acid. Illustrative of such modifications would be replacement covalent modifications of the bases, such as alkylation of amino and ring nitrogens as well as saturation of double bonds.

As used herein, the terms "mutation" and "modification" and grammatical equivalents thereof when used in reference to a nucleic acid sequence are used interchangeably to refer to a deletion, insertion, substitution, strand break, and/or introduction of an adduct. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is a different molecule from the replaced one or more nucleotides. For example, a nucleic acid may be replaced by a different nucleic acid as exemplified by replacement of a thymine by a cytosine, adenine, guanine, or uridine. Pyrimidine to pyrimidine (e.g. C to T or T to C nucleotide substitutions) or purine to purine (e.g. G to A or A to G nucleotide substitutions) are termed transitions, whereas pyrimidine to purine or purine to pyrimidine (e.g. G to T or G to C or A to T or A to C) are termed transversions. Alternatively, a nucleic acid may be replaced by a modified nucleic acid as exemplified by replacement of a thymine by thymine glycol. Mutations may result in a mismatch. The term "mismatch" refers to a non-covalent interaction between two nucleic acids, each nucleic acid residing on a different polynucleic acid sequence, which does not follow the base-pairing rules. For example, for the partially complementary sequences 5'-AGT-3' and 5'-AAT-3', a G-A mismatch (a transition) is present. The terms "introduction of an adduct" or "adduct formation" refer to the covalent or non-covalent linkage of a molecule to one or more nucleotides in a DNA sequence such that the linkage results in a reduction (in some embodiments from 10% to 100%, in other embodiments from 50% to 100%, and in some embodiments from 75% to 100%) in the level of DNA replication and/or transcription.

The term "DNA cutter" refers to a moiety that effects a strand break. Non-limited examples include meganucleases, TALEs/TALENs, antibiotics, zinc fingers and CRISPRs or CRISPR/cas systems.

The term "strand break" when made in reference to a double stranded nucleic acid sequence includes a single-strand break and/or a double-strand break. A single-strand break (a nick) refers to an interruption in one of the two strands of the double stranded nucleic acid sequence. This is in contrast to a double-strand break which refers to an interruption in both strands of the double stranded nucleic acid sequence, which may result in blunt or staggered ends. Strand breaks may be introduced into a double stranded nucleic acid sequence either directly (e.g., by ionizing radiation or treatment with certain chemicals) or indirectly (e.g., by enzymatic incision at a nucleic acid base).

The terms "mutant cell" and "modified cell" refer to a cell which contains at least one modification in the cell's genomic sequence.

The term "portion" when used in reference to a nucleotide sequence refers to fragments of that nucleotide sequence. The fragments may range in size from 5 nucleotide residues to the entire nucleotide sequence minus one nucleic acid residue.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

As used herein, the terms "vector" and "vehicle" are used interchangeably in reference to nucleic acid molecules that transfer DNA segment(s) from one cell to another.

The terms "in operable combination," "in operable order" and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that a functional protein is produced.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofectin, protoplast fusion, retroviral infection, biolistics (i.e., particle bombardment) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total". "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids. For the sake of convenience, the terms "polynucleotides" and "oligonucleotides" include molecules which include nucleosides.

The terms "homology" and "homologous" as used herein in reference to nucleotide sequences refer to a degree of complementarity with other nucleotide sequences. There may be partial homology or complete homology (i.e., identity). When used in reference to a double-stranded nucleic acid sequence such as a cDNA or genomic clone, the term "substantially homologous" refers to any nucleic acid sequence (e.g., probe) which can hybridize to either or both strands of the double-stranded nucleic acid sequence under conditions of low stringency as described above. A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 68° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 m/ml denatured salmon sperm DNA followed by washing in a solution comprising 2.0×SSPE, 0.1% SDS at room temperature when a probe of about 100 to about 1000 nucleotides in length is employed.

In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5×SSPE, 1% SDS, 5×Denhardt's reagent and 100 µg/ml denatured salmon sperm DNA followed by washing in a solution comprising 0.1×SSPE and 0.1% SDS at 68° C. when a probe of about 100 to about 1000 nucleotides in length is employed.

It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with the other nucleic acid sequences that have from 50% to 70% homology to the first nucleic acid sequence.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids.

As used herein the term "hybridization complex" refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: Tm=81.5+0.41 (% G+C), when a nucleic acid is in aqueous solution at 1 M NaCl (see e.g., Anderson and Young, Quantitative Filter Hybridization, in Nucleic Acid Hybridization, 1985). Other references include more sophisticated computations which take structural as well as sequence characteristics into account for the calculation of Tm.

As used herein the term "stringency" is used in reference to the conditions of temperature, ionic strength, and the presence of other compounds such as organic solvents, under which nucleic acid hybridizations are conducted. "Stringency" typically occurs in a range from about Tm–5° C. (5° C. below the melting temperature of the probe) to about 20° C. to 25° C. below Tm. As will be understood by those of skill in the art, a stringent hybridization can be used to identify or detect identical polynucleotide sequences or to identify or detect similar or related polynucleotide sequences.

The terms "specific binding," "binding specificity," and grammatical equivalents thereof when made in reference to the binding of a first nucleotide sequence to a second nucleotide sequence, refer to the preferential interaction between the first nucleotide sequence with the second nucleotide sequence as compared to the interaction between the second nucleotide sequence with a third nucleotide sequence. Specific binding is a relative term that does not require absolute specificity of binding; in other words, the term "specific binding" does not require that the second nucleotide sequence interact with the first nucleotide sequence in the absence of an interaction between the second nucleotide sequence and the third nucleotide sequence. Rather, it is sufficient that the level of interaction between the first nucleotide sequence and the second nucleotide sequence is greater than the level of interaction between the second nucleotide sequence with the third nucleotide sequence. "Specific binding" of a first nucleotide sequence with a second nucleotide sequence also means that the interaction between the first nucleotide sequence and the second nucleotide sequence is dependent upon the presence of a particular structure on or within the first nucleotide sequence; in other words the second nucleotide sequence is recognizing and binding to a specific structure on or within the first nucleotide sequence rather than to nucleic acids or to nucleotide sequences in general. For example, if a second nucleotide sequence is specific for structure "A" that is on or within a first nucleotide sequence, the presence of a third nucleic acid sequence containing structure A will reduce the amount of the second nucleotide sequence which is bound to the first nucleotide sequence.

As used herein, the term "amplifiable nucleic acid" is used in reference to nucleic acids which may be amplified by any amplification method. It is contemplated that "amplifiable nucleic acid" will usually comprise "sample template."

The terms "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

"Amplification" is defined as the production of additional copies of a nucleic acid sequence and is generally carried out using polymerase chain reaction technologies well known in the art (Dieffenbach C W and G S Dveksler (1995) PCR Primer, a Laboratory Manual, Cold Spring Harbor Press, Plainview, N.Y.). As used herein, the term "polymerase chain reaction" ("PCR") refers to the method of K. B. Mullis U.S. Pat. Nos. 4,683,195, and 4,683,202, hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

One such preferred method, particularly for commercial applications, is based on the widely used TaqMan® real-time PCR technology, and combines Allele-Specific PCR with a Blocking reagent (ASB-PCR) to suppress amplification of the wildtype allele. ASB-PCR can be used for detection of germ line or somatic mutations in either DNA or RNA extracted from any type of tissue, including formalin-fixed paraffin-embedded tumor specimens. A set of reagent design rules are developed enabling sensitive and selective detection of single point substitutions, insertions, or deletions against a background of wild-type allele in thousand-fold or greater excess. (Morlan J, Baker J, Sinicropi D Mutation Detection by Real-Time PCR: A Simple, Robust and Highly Selective Method. PLoS ONE 4(2): e4584, 2009)

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). In some embodiments, the primer is single stranded for maximum efficiency in amplification, but may alternatively be double stranded. If double stranded, the primer is first treated to separate its strands before being used to prepare extension products. In some embodiments, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present disclosure will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present disclosure be limited to any particular detection system or label.

As used herein, the terms "restriction endonucleases" and "restriction enzymes" refer to bacterial enzymes, each of which cut or nick double- or single-stranded DNA at or near a specific nucleotide sequence, for example, an endonuclease domain of a type IIS restriction endonuclease (e.g., FokI can be used, as taught by Kim et al., 1996, Proc. Nat'l. Acad. Sci. USA, 6:1 156-60).

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Additionally "an oligonucleotide having a nucleotide sequence encoding a gene" may include suitable control elements such as enhancers, promoters, splice junctions, polyadenylation signals, etc. if needed to permit proper initiation of transcription and/or correct processing of the primary RNA transcript. Further still, the coding region of the present disclosure may contain endogenous enhancers, splice junctions, intervening sequences, polyadenylation signals, etc.

Transcriptional control signals in eukaryotes comprise "enhancer" elements. Enhancers consist of short arrays of DNA sequences that interact specifically with cellular proteins involved in transcription (Maniatis, T. et al., Science 236:1237, 1987). Enhancer elements have been isolated from a variety of eukaryotic sources including genes in plant, yeast, insect and mammalian cells and viruses. The selection of a particular enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site (Sambrook, J. et al., Molecular Cloning: A Laboratory Manual, 2nd ed., Cold Spring Harbor Laboratory Press, New York, pp. 16.7-16.8, 1989). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The term "promoter," "promoter element" or "promoter sequence" as used herein, refers to a DNA sequence which when placed at the 5' end of (i.e., precedes) an oligonucleotide sequence is capable of controlling the transcription of the oligonucleotide sequence into mRNA. A promoter is typically located 5' (i.e., upstream) of an oligonucleotide sequence whose transcription into mRNA it controls, and provides a site for specific binding by RNA polymerase and for initiation of transcription.

The term "promoter activity" when made in reference to a nucleic acid sequence refers to the ability of the nucleic acid sequence to initiate transcription of an oligonucleotide sequence into mRNA.

The term "tissue specific" as it applies to a promoter refers to a promoter that is capable of directing selective expression of an oligonucleotide sequence to a specific type of tissue in the relative absence of expression of the same oligonucleotide in a different type of tissue. Tissue specificity of a promoter may be evaluated by, for example, operably linking a reporter gene to the promoter sequence to generate a reporter construct, introducing the reporter construct into the genome of a plant or an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic plant or animal. Selectivity need not be absolute. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter which is capable of directing selective expression of an oligonucleotide sequence in a specific type of cell in the relative absence of expression of the same oligonucleotide sequence in a different type of cell within the same tissue. The term "cell type specific" when applied to a promoter also means a promoter capable of promoting selective expression of an oligonucleotide in a region within a single tissue. Again, selectivity need not be absolute. Cell type specificity of a promoter may be assessed using methods well known in the art, e.g., immunohistochemical staining as described herein. Briefly, tissue sections are embedded in paraffin, and paraffin sections are reacted with a primary antibody which is specific for the polypeptide product encoded by the oligonucleotide sequence whose expression is controlled by the promoter. As an alternative to paraffin sectioning, samples may be cryosectioned. For example, sections may be frozen prior to and during sectioning thus avoiding potential interference by residual paraffin. A labeled (e.g., peroxidase conjugated) secondary antibody which is specific for the primary antibody is allowed to bind to the sectioned tissue and specific binding detected (e.g., with avidin/biotin) by microscopy.

The terms "selective expression," "selectively express" and grammatical equivalents thereof refer to a comparison of relative levels of expression in two or more regions of interest. For example, "selective expression" when used in connection with tissues refers to a substantially greater level of expression of a gene of interest in a particular tissue, or to a substantially greater number of cells which express the gene within that tissue, as compared, respectively, to the level of expression of, and the number of cells expressing, the same gene in another tissue (i.e., selectivity need not be absolute). Selective expression does not require, although it may include, expression of a gene of interest in a particular tissue and a total absence of expression of the same gene in another tissue. Similarly, "selective expression" as used herein in reference to cell types refers to a substantially greater level of expression of, or a substantially greater number of cells which express, a gene of interest in a particular cell type, when compared, respectively, to the expression levels of the gene and to the number of cells expressing the gene in another cell type.

The term "contiguous" when used in reference to two or more nucleotide sequences means the nucleotide sequences are ligated in tandem either in the absence of intervening sequences, or in the presence of intervening sequences which do not comprise one or more control elements.

As used herein, the terms "nucleic acid molecule encoding," "nucleotide encoding," "DNA sequence encoding" and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or double-stranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein, the term "purified" or "to purify" refers to the removal of one or more (undesired) components from a sample. For example, where recombinant polypeptides are expressed in bacterial host cells, the polypeptides are purified by the removal of host cell proteins thereby increasing the percent of recombinant polypeptides in the sample.

As used herein, the term "substantially purified" refers to molecules, either nucleic or amino acid sequences, that are removed from their natural environment, isolated or separated, and are at least 60% free, in some embodiments 75% free and other embodiments 90% free from other components with which they are naturally associated. An "isolated polynucleotide" is, therefore, a substantially purified polynucleotide.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side generally by the nucleotide triplet "ATG" which encodes the initiator methionine and on the 3' side by one of the three triplets which specify stop codons (i.e., TAA, TAG, TGA).

By "coding sequence" is meant a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the eel Vs biochemical machinery to provide a mature mRNA. The anti-sense strand is the complement of such a nucleic acid, and the encoding sequence can be deduced therefrom.

By "non-coding sequence" is meant a sequence of a nucleic acid or its complement, or a part thereof that is not transcribed into amino acid in vivo, or where tRNA does not interact to place or attempt to place an amino acid. Non-coding sequences include both intron sequences in genomic DNA. or immature primary RNA transcripts, and gene-associated sequences such as promoters, enhancers, silencers, etc.

As used herein, the term "structural gene" or "structural nucleotide sequence" refers to a DNA sequence coding for RNA or a protein which does not control the expression of other genes. In contrast, a "regulatory gene" or "regulatory sequence" is a structural gene which encodes products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements include splicing signals, polyadenylation signals, termination signals, etc.

As used herein, the term "peptide transcription factor binding site" or "transcription factor binding site" refers to a nucleotide sequence which binds protein transcription factors and, thereby, controls some aspect of the expression of nucleic acid sequences. For example, Sp-1 and AP1 (activator protein 1) binding sites are examples of peptide transcription factor binding sites.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. A gene is generally a single locus. In a normal diploid organism, a gene has two alleles. In tetraploid potato, however, each gene has 4 alleles. In sugarcane, which is dodecaploid there can be 12 alleles per gene. Particular examples include flax which has two EPSPS loci each with two alleles and rice which has a single homomeric plastidal ACCase with two alleles.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

A "non-human animal" refers to any animal which is not a human and includes vertebrates such as rodents, non-human primates, ovines, bovines, ruminants, lagomorphs, porcines, caprines, equines, canines, felines, ayes, etc. Preferred non-human animals are selected from the order Rodentia. "Non-human animal" additionally refers to amphibians (e.g. *Xenopus*), reptiles, insects (e.g. *Drosophila*) and other non-mammalian animal species.

As used herein, the term "transgenic" refers to an organism or cell that has DNA derived from another organism inserted into which becomes integrated into the genome either of somatic and/or germ line cells of the plant or animal. A "transgene" means a DNA sequence which is partly or entirely heterologous (i.e., not present in nature) to the plant or animal in which it is found, or which is homologous to an endogenous sequence (i.e., a sequence that is found in the animal in nature) and is inserted into the plant' or animal's genome at a location which differs from that of the naturally occurring sequence. Transgenic plants or animals which include one or more transgenes are within the scope of this disclosure. Additionally, a "transgenic" as used herein refers to an organism that has had one or more genes modified and/or "knocked out" (made non-functional or made to function at reduced level, i.e., a "knockout" mutation) by the disclosure's methods, by homologous recombination, TFO mutation or by similar processes. For example, in some embodiments, a transgenic organism or cell includes inserted DNA that includes a foreign promoter and/or coding region.

A "transformed cell" is a cell or cell line that has acquired the ability to grow in cell culture for multiple generations, the ability to grow in soft agar, and/or the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, nucleofection and lipofection (liposome-mediated gene transfer). Transformation may be accomplished through use of any expression vector. For example, the use of baculovirus to introduce foreign nucleic acid into insect cells is contemplated. The term "transformation" also includes methods such as P-element mediated germline transformation of whole insects. Additionally, transformation refers to cells that have been transformed naturally, usually through genetic mutation.

As used herein "exogenous" means that the gene encoding the protein is not normally expressed in the cell. Additionally, "exogenous" refers to a gene transfected into a cell to augment the normal (i.e. natural) level of expression of that gene.

A peptide sequence and nucleotide sequence may be "endogenous" or "heterologous" (i.e., "foreign"). The term "endogenous" refers to a sequence which is naturally found in the cell into which it is introduced so long as it does not contain some modification relative to the naturally-occurring sequence. The term "heterologous" refers to a sequence which is not endogenous to the cell into which it is introduced. For example, heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell into which it is introduced and which contains some modification relative to the naturally-occurring sequence. Generally, although not necessarily, heterologous DNA encodes heterologous RNA and heterologous proteins that are not normally produced by the cell into which it is introduced. Examples of heterologous DNA include reporter genes, transcriptional and translational regulatory sequences, DNA sequences which encode selectable marker proteins (e.g., proteins which confer drug resistance), etc.

Constructs

The nucleic acid molecules disclosed herein (e.g., site specific nucleases, or guide RNA for CRISPRs) can be used in the production of recombinant nucleic acid constructs. In one embodiment, the nucleic acid molecules of the present disclosure can be used in the preparation of nucleic acid constructs, for example, expression cassettes for expression in the plant, microorganism, or animal of interest. This expression may be transient for instance when the construct is not integrated into the host genome or maintained under the control offered by the promoter and the position of the construct within the host's genome if it becomes integrated.

Expression cassettes may include regulatory sequences operably linked to the site specific nuclease or guide RNA sequences disclosed herein. The cassette may additionally contain at least one additional gene to be co-transformed into the organism. Alternatively, the additional gene(s) can be provided on multiple expression cassettes.

The nucleic acid constructs may be provided with a plurality of restriction sites for insertion of the site specific nuclease coding sequence to be under the transcriptional regulation of the regulatory regions. The nucleic acid constructs may additionally contain nucleic acid molecules encoding for selectable marker genes.

Any promoter can be used in the production of the nucleic acid constructs. The promoter may be native or analogous, or foreign or heterologous, to the plant, microbial, or animal host nucleic acid sequences disclosed herein. Additionally, the promoter may be the natural sequence or alternatively a synthetic sequence. Where the promoter is "foreign" or "heterologous" to the plant, microbial, or animal host, it is intended that the promoter is not found in the native plant, microbial, or animal into which the promoter is introduced. As used herein, a chimeric gene comprises a coding sequence operably linked to a transcription initiation region that is heterologous to the coding sequence.

The site directed nuclease sequences disclosed herein may be expressed using heterologous promoters.

Any promoter can be used in the preparation of constructs to control the expression of the site directed nuclease sequences, such as promoters providing for constitutive, tissue-preferred, inducible, or other promoters for expression in plants, microbes, or animals. Constitutive promoters include, for example, the core promoter of the Rsyn7 promoter and other constitutive promoters disclosed in WO 99/43 838 and U.S. Pat. No. 6,072,050; the core CaMV 35S promoter (Odell et al. Nature 313:810-812; 1985); rice actin (McElroy et al., Plant Cell 2:163-171, 1990); ubiquitin (Christensen et al., Plant Mol. Biol. 12:619-632, 1989 and Christensen et al., Plant Mol. Biol. 18:675-689, 1992); pEMU (Last et al., Theor. Appl. Genet. 81:581-588, 1991); MAS (Velten et al., EMBO J. 3:2723-2730, 1984); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to direct site directed nuclease expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al., Plant J. 12(2): 255-265, 1997; Kawamata et al., Plant Cell Physiol. 38(7): 792-803, 1997; Hansen et al., Mol. Gen Genet. 254(3):337-343, 1997; Russell et al., Transgenic Res. 6(2):157-168, 1997; Rinehart et al., Plant Physiol. 1 12(3):1331-1341, 1996; Van Camp et al., Plant Physiol. 1 12(2):525-535, 1996; Canevascini et al., Plant Physiol. 112(2): 513-524, 1996; Yamamoto et al., Plant Cell Physiol. 35(5):773-778, 1994; Lam, Results Probl. Cell Differ. 20:181-196, 1994; Orozco et al. Plant Mol Biol. 23(6):1129-1138, 1993; Matsuoka et al., Proc Nat'l. Acad. Sci. USA 90(20):9586-9590, 1993; and Guevara-Garcia et al., Plant J. 4(3):495-505, 1993.

The nucleic acid constructs may also include transcription termination regions. Where transcription terminations regions are used, any termination region may be used in the preparation of the nucleic acid constructs. For example, the termination region may be derived from another source (i.e., foreign or heterologous to the promoter). Examples of termination regions that are available for use in the constructs of the present disclosure include those from the Ti-plasmid of *A. tumefaciens*, such as the octopine synthase and nopaline synthase termination regions. See also Guerineau et al., Mol. Gen. Genet. 262:141-144, 1991; Proudfoot, Cell 64:671-674, 1991; Sanfacon et al., Genes Dev. 5:141-149, 1991; Mogen et al., Plant Cell 2:1261-1272, 1990; Munroe et al., Gene 91:151-158, 1990; Ballas et al., Nucleic Acids Res. 17:7891-7903, 1989; and Joshi et al., Nucleic Acid Res. 15:9627-9639, 1987.

In conjunction with any of the aspects, embodiments, methods and/or compositions disclosed herein, the nucleic acids may be optimized for increased expression in the transformed plant. That is, the nucleic acids encoding the site directed nuclease proteins can be synthesized using plant-preferred codons for improved expression. See, for example, Campbell and Gown, (Plant Physiol. 92:1-11, 1990) for a discussion of host-preferred codon usage. Methods are available in the art for synthesizing plant-preferred genes. See, for example, U.S. Pat. Nos. 5,380,831, and 5,436,391, and Murray et al., Nucleic Acids Res. 17:477-498, 1989. See also e.g., Lanza et al., BMC Systems Biology 8:33-43, 2014; Burgess-Brown et al., Protein Expr. Purif. 59:94-102, 2008; Gustafsson et al., Trends Biotechnol 22:346-353, 2004.

In addition, other sequence modifications can be made to the nucleic acid sequences disclosed herein. For example, additional sequence modifications are known to enhance gene expression in a cellular host. These include elimination of sequences encoding spurious polyadenylation signals, exon/intron splice site signals, transposon-like repeats, and other such well-characterized sequences that may be deleterious to gene expression. The G-C content of the sequence may also be adjusted to levels average for a target cellular host, as calculated by reference to known genes expressed in the host cell. In addition, the sequence can be modified to avoid predicted hairpin secondary mRNA structures.

Other nucleic acid sequences may also be used in the preparation of the constructs of the present disclosure, for example to enhance the expression of the site directed nuclease coding sequence. Such nucleic acid sequences include the introns of the maize AdhI, intron1 gene (Callis et al., Genes and Development 1:1183-1200, 1987), and leader sequences, (W-sequence) from the Tobacco Mosaic virus (TMV), Maize Chlorotic Mottle Virus and Alfalfa Mosaic Virus (Gallie et al., Nucleic Acid Res. 15:8693-8711, 1987; and Skuzeski et al., Plant Mol. Biol. 15:65-79, 1990). The first intron from the shrunken-1 locus of maize has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize site directed nuclease gene expression, the plant expression vectors disclosed herein may also contain DNA sequences containing matrix attachment regions (MARs). Plant cells transformed with such modified expression systems, then, may exhibit overexpression or constitutive expression of a nucleotide sequence of the disclosure.

The expression constructs disclosed herein can also include nucleic acid sequences capable of directing the expression of the site directed nuclease sequence to the chloroplast or other organelles and structures in both prokaryotes and eukaryotes. Such nucleic acid sequences include chloroplast targeting sequences that encodes a chloroplast transit peptide to direct the gene product of interest to plant cell chloroplasts. Such transit peptides are known in the art. With respect to chloroplast-targeting sequences, "operably linked" means that the nucleic acid sequence encoding a transit peptide (i.e., the chloroplast-targeting sequence) is linked to the site directed nuclease nucleic acid molecules disclosed herein such that the two sequences are contiguous and in the same reading frame. See, for example, Von Heijne et al., Plant Mol. Biol. Rep. 9:104-126, 1991; Clark et al., J. Biol. Chem. 264:17544-17550, 1989; Della-Cioppa et al., Plant Physiol. 84:965-968, 1987; Romer et al., Biochem. Biophys. Res. Commun. 196:1414-1421, 1993; and Shah et al., Science 233:478-481, 1986.

Chloroplast targeting sequences are known in the art and include the chloroplast small subunit of ribulose-1,5-bisphosphate carboxylase (Rubisco) (de Castro Silva Filho et al., Plant Mol. Biol. 30:769-780, 1996; Schnell et al., J. Biol. Chem. 266(5):3335-3342, 1991); 5-(enolpyruvyl)shikimate-3-phosphate synthase (EPSPS) (Archer et al., J. Bioenerg. Biomemb. 22(6):789-810, 1990); tryptophan synthase (Zhao et al., J. Biol. Chem. 270(11):6081-6087, 1995); plastocyanin (Lawrence et al., J. Biol. Chem. 272(33):20357-20363, 1997); chorismate synthase (Schmidt et al., J. Biol. Chem. 268(36):27447-27457, 1993); and the light harvesting chlorophyll a/b binding protein (LHBP) (Lamppa et al., J. Biol. Chem. 263:14996-14999, 1988). See also Von Heijne et al., Plant Mol. Biol. Rep. 9:104-126, 1991; Clark et al., J. Biol. Chem. 264:17544-17550, 1989; Della-Cioppa et al., Plant Physiol. 84:965-968, 1987; Romer et al., Biochem. Biophys. Res. Commun. 196:1414-1421, 1993; and Shah et al., Science 233: 478-481, 1986.

In conjunction with any of the aspects, embodiments, methods and/or compositions disclosed herein, the nucleic acid constructs may be prepared to direct the expression of the mutant site directed nuclease coding sequence from the plant cell chloroplast. Methods for transformation of chloroplasts are known in the art. See, for example, Svab et al., Proc. Nat'l. Acad. Sci. USA 87:8526-8530, 1990; Svab and Maliga, Proc. Nat'l. Acad. Sci. USA 90:913-917, 1993; Svab and Maliga, EMBO J. 12:601-606, 1993. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. Proc. Nat'l. Acad. Sci. USA 91:7301-7305, 1994.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

The nucleic acid constructs can be used to transform plant cells and regenerate transgenic plants comprising the site directed nuclease coding sequences. Numerous plant transformation vectors and methods for transforming plants are available. See, for example, U.S. Pat. No. 6,753,458, An, G. et al., Plant Physiol., 81:301-305, 1986; Fry, J. et al., Plant Cell Rep. 6:321-325, 1987; Block, M., Theor. Appl Genet. 76:767-774, 1988; Hinchee et al., Stadler. Genet. Symp. 203212.203-212, 1990; Cousins et al., Aust. J. Plant Physiol. 18:481-494, 1991; Chee, P. P. and Slightom, J. L., Gene. 118:255-260, 1992; Christou et al., Trends. Biotechnol. 10:239-246, 1992; D'Halluin et al., Bio/Technol. 10:309-3 14, 1992; Dhir et al., Plant Physiol. 99:81-88, 1992; Casas et al., Proc. Nat'l. Acad Sci. USA 90:11212-11216, 1993; Christou, P., In Vitro Cell. Dev. Biol. Plant 29P:1 19-124, 1993; Davies, et al., Plant Cell Rep. 12:180-183, 1993;

Dong, J. A. and Mc Hughen, A., Plant Sci. 91:139-148, 1993; Franklin, C. I. and Trieu, T. N., Plant. Physiol. 102:167, 1993; Golovkin et al., Plant Sci. 90:41-52, 1993; Guo Chin Sci. Bull. 38:2072-2078; Asano, et al., Plant Cell Rep. 13, 1994; Ayeres N. M. and Park, W. D., Crit. Rev. Plant. Sci. 13:219-239, 1994; Barcelo et al., Plant. J. 5:583-592, 1994; Becker, et al., Plant. J. 5:299-307, 1994; Borkowska et al., Acta. Physiol Plant. 16:225-230, 1994; Christou, P., Agro. Food. Ind. Hi Tech. 5:17-27, 1994; Eapen et al., Plant Cell Rep. 13:582-586, 1994; Hartman et al., Bio-Technology 12:919923, 1994; Ritala et al., Plant. Mol. Biol. 24:317-325, 1994; and Wan, Y. C. and Lemaux, P. G., Plant Physiol. 104:3748, 1994. The constructs may also be transformed into plant cells using homologous recombination.

The term "wild-type" when made in reference to a peptide sequence and nucleotide sequence refers to a peptide sequence and nucleotide sequence (locus/gene/allele), respectively, which has the characteristics of that peptide sequence and nucleotide sequence when isolated from a naturally occurring source. A wild-type peptide sequence and nucleotide sequence is that which is most frequently observed in a population and is thus arbitrarily designated the "normal" or "wild-type" form of the peptide sequence and nucleotide sequence, respectively. "Wild-type" may also refer to the sequence at a specific nucleotide position or positions, or the sequence at a particular codon position or positions, or the sequence at a particular amino acid position or positions.

"Consensus sequence" is defined as a sequence of amino acids or nucleotides that contain identical amino acids or nucleotides or functionally equivalent amino acids or nucleotides for at least 25% of the sequence. The identical or functionally equivalent amino acids or nucleotides need not be contiguous.

The term "*Brassica*" as used herein refers to plants of the *Brassica* genus. Exemplary *Brassica* species include, but are not limited to, *B. carinata, B. elongate, B. fruticulosa, B. juncea, B. napus, B. narinosa, B. nigra, B. oleracea, B. perviridis, B. rapa* (syn *B. campestris*), *B. rupestris, B. septiceps,* and *B. tournefortii.*

A nucleobase is a base, which in certain preferred embodiments is a purine, pyrimidine, or a derivative or analog thereof. Nucleosides are nucleobases that contain a pentosefuranosyl moiety, e.g., an optionally substituted riboside or T-deoxyriboside. Nucleosides can be linked by one of several linkage moieties, which may or may not contain phosphorus. Nucleosides that are linked by unsubstituted phosphodiester linkages are termed nucleotides. The term "nucleobase" as used herein includes peptide nucleobases, the subunits of peptide nucleic acids, and morpholine nucleobases as well as nucleosides and nucleotides.

An oligonucleobase is a polymer comprising nucleobases; in some embodiments at least a portion of which can hybridize by Watson-Crick base pairing to a DNA having the complementary sequence. An oligonucleobase chain may have a single 5' and 3 terminus, which are the ultimate nucleobases of the polymer. A particular oligonucleobase chain can contain nucleobases of all types. An oligonucleobase compound is a compound comprising one or more oligonucleobase chains that may be complementary and hybridized by Watson-Crick base pairing. Ribo-type nucleobases include pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

In certain embodiments, an oligonucleobase strand may include both oligonucleobase chains and segments or regions of oligonucleobase chains. An oligonucleobase strand may have a 3 end and a 5' end and when an oligonucleobase strand is coextensive with a chain, the 3' and 5' ends of the strand are also 3' and 5' termini of the chain.

As used herein the term codon refers to a sequence of three adjacent nucleotides (either RNA or DNA) constituting the genetic code that determines the insertion of a specific amino acid in a polypeptide chain during protein synthesis or the signal to stop protein synthesis. The term "codon" also used to refer to the corresponding (and complementary) sequences of three nucleotides in the messenger RNA into which the original DNA is transcribed.

As used herein, the term "homology" refers to sequence similarity among proteins and DNA. The term "homology" or "homologous" refers to a degree of identity. There may be partial homology or complete homology. A partially homologous sequence is one that has less than 100% sequence identity when compared to another sequence.

"Heterozygous" refers to having different alleles at one or more genetic loci in homologous chromosome segments. As used herein "heterozygous" may also refer to a sample, a cell, a cell population or an organism in which different alleles at one or more genetic loci may be detected. Heterozygous samples may also be determined via methods known in the art such as, for example, nucleic acid sequencing. For example, if a sequencing electropherogram shows two peaks at a single locus and both peaks are roughly the same size, the sample may be characterized as heterozygous. Or, if one peak is smaller than another, but is at least about 25% the size of the larger peak, the sample may be characterized as heterozygous. In some embodiments, the smaller peak is at least about 15% of the larger peak. In other embodiment, the smaller peak is at least about 10% of the larger peak. In other embodiments, the smaller peak is at least about 5% of the larger peak. In other embodiments, a minimal amount of the smaller peak is detected.

As used herein, "homozygous" refers to having identical alleles at one or more genetic loci in homologous chromosome segments. "Homozygous" may also refer to a sample, a cell, a cell population or an organism in which the same alleles at one or more genetic loci may be detected. Homozygous samples may be determined via methods known in the art, such as, for example, nucleic acid sequencing. For example, if a sequencing electropherogram shows a single peak at a particular locus, the sample may be termed "homozygous" with respect to that locus.

The term "hemizygous" refers to a gene or gene segment being present only once in the genotype of a cell or an organism because the second allele is deleted, or is not present on homologous chromosome segment. As used herein "hemizygous" may also refer to a sample, a cell, a cell population or an organism in which an allele at one or more genetic loci may be detected only once in the genotype.

The term "zygosity status" as used herein refers to a sample, a cell population, or an organism as appearing heterozygous, homozygous, or hemizygous as determined by testing methods known in the art and described herein. The term "zygosity status of a nucleic acid" means determining whether the source of nucleic acid appears heterozygous, homozygous, or hemizygous. The "zygosity status" may refer to differences in at a single nucleotide position in a sequence. In some methods, the zygosity status of a sample with respect to a single mutation may be categorized as homozygous wild-type, heterozygous (i.e., one wild-type allele and one mutant allele), homozygous mutant, or hemizygous (i.e., a single copy of either the wild-type or mutant allele).

As used herein, the term "RTDS'" refers to The Rapid Trait Development System™ (RTDS) developed by Cibus. RTDS is a site-specific gene modification system that is effective at making precise changes in a gene sequence without the incorporation of foreign genes or control sequences.

The term "about" as used herein means in quantitative terms plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

RTDS and Repair Oligonucleotides (GRONs)

This disclosure generally relates to novel methods to improve the efficiency of the targeting of modifications to specific locations in genomic or other nucleotide sequences. Additionally, this disclosure relates to target DNA that has been modified, mutated or marked by the approaches disclosed herein. The disclosure also relates to cells, tissue, and organisms which have been modified by the disclosure's methods. The present disclosure builds on the development of compositions and methods related in part to the successful conversion system, the Rapid Trait Development System (RTDS™, Cibus US LLC).

RTDS is based on altering a targeted gene by utilizing the cell's own gene repair system to specifically modify the gene sequence in situ and not insert foreign DNA and gene expression control sequences. This procedure effects a precise change in the genetic sequence while the rest of the genome is left unaltered. In contrast to conventional transgenic GM Os, there is no integration of foreign genetic material, nor is any foreign genetic material left in the plant. The changes in the genetic sequence introduced by RTDS are not randomly inserted. Since affected genes remain in their native location, no random, uncontrolled or adverse pattern of expression occurs.

The RTDS that effects this change is a chemically synthesized oligonucleotide (GRON) as described herein which may be composed of both DNA and modified RNA bases as well as other chemical moieties, and is designed to hybridize at the targeted gene location to create a mismatched base-pair(s). This mismatched base-pair acts as a signal to attract the cell's own natural gene repair system to that site and correct (replace, insert or delete) the designated nucleotide (s) within the gene. Once the correction process is complete the RTDS molecule is degraded and the now-modified or repaired gene is expressed under that gene's normal endogenous control mechanisms.

The methods and compositions disclosed herein can be practiced or made with "gene repair oligonucleobases" (GRON) having the conformations and chemistries as described in detail herein and below. The "gene repair oligonucleobases" as contemplated herein have also been described in published scientific and patent literature using other names including "recombinagenic oligonucleobases;" "RNA/DNA chimeric oligonucleotides;" "chimeric oligonucleotides;" "mixed duplex oligonucleotides" (MDONs); "RNA DNA oligonucleotides (RDOs);" "gene targeting oligonucleotides;" "genoplasts;" "single stranded modified oligonucleotides;" "Single stranded oligodeoxynucleotide mutational vectors" (SSOMVs); "duplex mutational vectors;" and "heteroduplex mutational vectors." The gene repair oligonucleobase can be introduced into a plant cell using any method commonly used in the art, including but not limited to, microcarriers (biolistic delivery), microfibers, polyethylene glycol. (PEG)-mediated uptake, electroporation, and microinjection.

In one embodiment, the gene repair oligonucleobase is a mixed duplex oligonucleotides (MDON) in which the RNA-type nucleotides of the mixed duplex oligonucleotide are made RNase resistant by replacing the 2-hydroxyl with a fluoro, chloro or bromo functionality or by placing a substituent on the 2'-O. Suitable substituents include the substituents taught by the Kmiec if. Alternative substituents include the substituents taught by U.S. Pat. No. 5,334,711 (Sproat) and the substituents taught by patent publications EP 629 387 and EP 679 657 (collectively, the Martin Applications), which are hereby incorporated by reference. As used herein, a 2'-fluoro, chloro or bromo derivative of a ribonucleotide or a ribonucleotide having a T-OH substituted with a substituent described in the Martin Applications or Sproat is termed a "T-Substituted Ribonucleotide." As used herein the term "RNA-type nucleotide" means a T-hydroxyl or 2'-Substituted Nucleotide that is linked to other nucleotides of a mixed duplex oligonucleotide by an unsubstituted phosphodiester linkage or any of the non-natural linkages taught by Kmiec 1 or Kmiec II. As used herein the term "deoxyribo-type nucleotide" means a nucleotide having a T-H, which can be linked to other nucleotides of a gene repair oligonucleobase by an unsubstituted phosphodiester linkage or any of the non-natural linkages taught by Kmiec I or Kmiec II.

In a particular embodiment of the present disclosure, the gene repair oligonucleobase is a mixed duplex oligonucleotide (MDON) that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-Substituted Nucleotide. Particular preferred embodiments of 2-Substituted Ribonucleotides are T-fluoro, T-methoxy, 2'-propyloxy, T-allyloxy, 2'-hydroxylethyloxy, T-methoxyethyloxy, T-fluoropropyloxy and T-trifluoropropyloxy substituted ribonucleotides. More preferred embodiments of 2'-Substituted Ribonucleotides are 2-fluoro, 2'-methoxy, 2'-methoxyethyloxy, and T-allyloxy substituted nucleotides. In another embodiment the mixed duplex oligonucleotide is linked by unsubstituted phosphodiester bonds.

Although mixed duplex oligonucleotides (MDONs) having only a single type of 2-substituted RNA-type nucleotide are more conveniently synthesized, the methods of the disclosure can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses terms such as "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides in some embodiments have fewer than 100 nucleotides and other embodiments fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3 and 5' ends can be protected by the addition of a "hairpin cap" whereby the 3' and 5° terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target gene/allele, i.e., have the same sequence as the target gene/allele. A homologous region contains the nucleotides of an RNA segment and rimy contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene/allele. Alternatively, the heterologous region can also contain an insertion or one, two, three or of five or fewer nucleotides. Alternatively, the sequence of the mixed duplex oligonucleotide may differ from the sequence of the target gene/allele only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identical to the length of the heterologous region where a substitution or substitutions is intended. When the heterologous region contains an insertion, the homologous regions are thereby separated in the mixed duplex oligonucleotide farther than their complementary homologous fragments are in the gene/allele, and the converse is applicable when the heterologous region encodes a deletion.

The RNA segments of the mixed duplex oligonucleotides are each a part of a homologous region, i.e., a region that is identical in sequence to a fragment of the target gene, which segments together in some embodiments contain at least 13 RNA-type nucleotides and in some embodiments from 16 to 25 RNA-type nucleotides or yet other embodiments 18-22 RNA-type nucleotides or in some embodiments 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

In another embodiment of the present disclosure, the gene repair oligonucleobase (GRON) is a single stranded oligodeoxynucleotide mutational vector (SSOMV), such as disclosed in International Patent Application PCT/USOO/23457, U.S. Pat. Nos. 6,271,360, 6,479,292, and 7,060,500 which is incorporated by reference in its entirety. The sequence of the SSOMV is based on the same principles as the mutational vectors described in U.S. Pat. Nos. 5,756, 325; 5,871,984; 5,760,012; 5,888,983; 5,795,972; 5,780, 296; 5,945,339; 6,004,804; and 6,010,907 and in international Publication Nos. WO 98/49350; WO 99/07865; WO 99/58723; WO 99/58702; and WO 99/40789. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region can cause a substitution. Alternatively, the homologous regions in the SSOMV can be contiguous to each other, while the regions in the target gene having the same sequence are separated by one, two or more nucleotides. Such an SSOMV causes a deletion from the target gene of the nucleotides that are absent from the SSOMV. Lastly, the sequence of the target gene that is identical to the homologous regions may be adjacent in the target gene but separated by one, two, or more nucleotides in the sequence of the SSOMV. Such an SSOMV causes an insertion in the sequence of the target gene. In certain embodiments, a SSOMV does not anneal to itself.

The nucleotides of the SSOMV are deoxyribonucleotides that are linked by unmodified phosphodiester bonds except that the 3' terminal and/or 5 terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotide and the targeted nucleotide be a pyrimidine. To the extent that is consistent with achieving the desired functional result, it is preferred that both the mutator nucleotide and the targeted nucleotide in the complementary strand be pyrimidines. Particularly preferred are SSON/Vs that encode transversion mutations, i.e., a C or T mutator nucleotide is mismatched, respectively, with a C or T nucleotide in the complementary strand.

Okazaki Fragment/2'-OME GRON Design. In various embodiments, a GRON may have both RNA and DNA nucleotides and/or other types of nucleobases. In some embodiments, one or more of the DNA or RNA nucleotides comprise a modification. In certain embodiments, the first 5' nucleotide is an RNA nucleotide and the remainder of the nucleotides are DNA. In still further embodiments, the first 5' RNA nucleotide is modified with a 2-O-Me. In other embodiments, the first two, three, four, five, six, seven, eight, nine, ten or more 5' nucleotides are an RNA nucleotide and the remainder of the nucleotides are DNA. In still further embodiments, one or more of the first two, three, four, five, six, seven, eight, nine, ten or more 5' RNA nucleotide are modified with a 2-O-Me. In plant cells, double-strand beaks in DNA are typically repaired by the NHEJ DNA repair pathway. This pathway does not require a template to repair the DNA and is therefore error prone. The advantage of using this pathway to repair DNA for a plant cell is that it is quick, ubiquitous and most importantly can occur at times when a cell is not undergoing DNA replication. Another DNA repair pathway that functions in repairing double-strand breaks outside of the replication fork in plant cells is called homologous recombination (HR); however, unlike the NHEJ pathway this type of repair is precise and requires the use of a DNA template (GRON). Since these GRONs mimic Okazaki fragments at the DNA replication fork of targeted genes, it is not obvious to use them with a double-strand DNA cutter to those skilled in the art.

Improving Efficiency

The present disclosure provides a number of approaches to increase the effectiveness of conversion of a target gene using repair oligonucleotides, and which may be used alone or in combination with one another. These include:

1. Introducing modifications to the repair oligonucleotides which attract DNA repair machinery to the targeted (mismatch) site.
    A. Introduction of one or more abasic sites in the oligonucleotide (e.g., within 10 bases, and in some embodiments with 5 bases of the desired mismatch site) generates a lesion which is an intermediate in base excision repair (BER), and which attracts BER machinery to the vicinity of the site targeted for conversion by the repair oligonucleotide. dSpacer (abasic furan) modified oligonucleotides may be prepared as described in, for example, Takeshita et al., *J. Biol. Chem.,* 262:10171-79, 1987.
    B. Inclusion of compounds which induce single or double strand breaks, either into the oligonucleotide or together with the oligonucleotide, generates a lesion which is repaired by NHEJ, microhomology-mediated end joining (MMEJ), and homologous recombination. By way of example, the bleomycin family of antibiotics, zinc fingers, FokI (or any type IIS class of restriction enzyme) and other nucleases may be covalently coupled to the 3' or 5' end of repair oligonucleotides, in order to introduce double strand breaks in the vicinity of the site targeted for conversion by the repair oligonucleotide. The bleomycin family of antibiotics are DNA cleaving glycopeptides which include bleomycin, zeocin, phleomycin, tallysomycin, pepleomycin and others.
    C. Introduction of one or more 8'oxo dA or dG incorporated in the oligonucleotide (e.g., within 10 bases, and in some embodiments with 5 bases of the desired mismatch site) generates a lesion which is similar to lesions created by reactive oxygen species. These lesions induce the so-called "pushing repair" system. See, e.g., Kim et al., J. Biochem. Mol. Biol. 37:657-62, 2004.
2. Increase stability of the repair oligonucleotides:
    Introduction of a reverse base (idC) at the 3' end of the oligonucleotide to create a 3' blocked end on the repair oligonucleotide.
    Introduction of one or more 2'O-methyl nucleotides or bases which increase hybridization energy (see, e.g., WO2007/073149) at the 5' and/or 3' of the repair oligonucleotide.
    Introduction of one or a plurality of 2'O-methyl RNA nucleotides at the 5' end of the repair oligonucleotide, leading into DNA bases which provide the desired mismatch site, thereby creating an Okazaki Fragment-like nucleic acid structure.
    Conjugated (5' or 3') intercalating dyes such as acridine, psoralen, ethidium bromide and Syber stains.
    Introduction of a 5' terminus cap such as a T/A clamp, a cholesterol moiety, SIMA (HEX), riboC and amidite.
    Backbone modifications such as phosphothioate, 2'-0 methyl, methyl phosphonates, locked nucleic acid (LNA), MOE (methoxyethyl), di PS and peptide nucleic acid (PNA).
    Crosslinking of the repair oligonucleotide, e.g., with intrastrand crosslinking reagents agents such as cisplatin and mitomycin C.
    Conjugation with fluorescent dyes such as Cy3, DY547, Cy3.5, Cy3B, Cy5 and DY647.
3. Increase hybridization energy of the repair oligonucleotide through incorporation of bases which increase hybridization energy (see, e.g., WO2007/073149).
4. Increase the quality of repair oligonucleotide synthesis by using nucleotide multimers (dimers, trimers, tetramers, etc.) as building blocks for synthesis. This results in fewer coupling steps and easier separation of the full length products from building blocks.
5. Use of long repair oligonucleotides (i.e., greater than 55 nucleotides in length, for example such as the lengths described herein, for example having one or more mutations or two or more mutations targeted in the repair oligonucleotide.

Examples of the foregoing approaches are provided in Table 1.

TABLE 1

Exemplary GRON chemistries.

| | Oligo type | Modifications |
| --- | --- | --- |
| 5' mods | T/A clamp | T/A clamp |
| Backbone modifications | Phosphothioate | PS |
| Intercalating dyes | 5' Acridine 3' | idC Acridine, idC |
| 2'-O-methyl | | DNA/RNA |
| Cy3 replacements | | DY547 |
| Facilitators | 2'-O-Me oligos designed 5' and 3' of the converting oligo | 2'-O-Me |
| Abasic | Abasic site placed in various locations 5' and 3' to the converting base. 44 mer | Abasic 2 |
| Assist | Assist approach Overlap: 2 oligos: 1 with Cy3/idC, 1 unmodified repair oligo | Cy3, idC on one, none on the other: |

TABLE 1-continued

Exemplary GRON chemistries.

| | Oligo type | Modifications |
|---|---|---|
| Assist | Assist approach No overlap: 2 oligos: 1 with Cy3/idC, 1 unmodified repair oligo | only make the unmodified oligo |
| Abasic | THF site placed in various locations 5' and 3' to the converting base. 44 mer | Tetrahydrofuran (dspacer) |
| Backbone modifications | 9 | 2'-O-Me |
| Trimers | | Trimer amidites, Cy3. idC |
| Pushing repair | | 8'oxo dA, 5' Cy3, idC |
| Pushing repair | | 8'oxo dA, 5' Cy3, idC |
| Double Strand Break | | Bleomycin |
| Crosslinker | | Cisplatin |
| Crosslinker | | Mitomycin C |
| Facilitators | super bases 5' and 3' of converting oligo | 2 amino dA and 2-thio T |
| Super oligos | | 2'amino d, 5' Cy3, idC |
| Super oligos | | 2-thio T, 5' Cy3, idC |
| Super oligos | | 7-deaza A, 5' Cy3, idC |
| Super oligos | | 7-deaza G, 5' Cy3, idC |
| Super oligos | | propanyl dC, 5' Cy3, idC |
| Intercalating dyes | 5' Psoralen/3' idC | Psoralen, idC |
| Intercalating dyes | 5' Ethidium bromide | Ethidium bromide |
| Intercalating dyes | 5' Syber stains | Syber stains |
| 5' mods | 5' Chol/3' idC | Cholesterol |
| Double mutation | Long oligo (55+ bases) w/ 2 mutation | Any modification |
| 5' mods | 5' SIMA HEX/3'idC | SIMA HEX, idC |
| Backbone modifications | 9 | Methyl phosphonates |
| Backbone modifications | | LNA |
| Backbone modifications | 1 | MOE (methoxyethyl) |
| Cy3 replacements | | Cy3.5 |
| Cy3 replacements | | Cy5 |
| Backbone modifications | | di PS |
| 5' mods | | riboC for branch nm |
| Backbone modifications | | PNA |
| Cy3 replacements | | DY647 |
| 5' mods | 5' branch | symmetric branch amidite/idC |

The foregoing modifications may also include known nucleotide modifications such as methylation, 5' intercalating dyes, modifications to the 5' and 3' ends, backbone modifications, crosslinkers, cyclization and 'caps' and substitution of one or more of the naturally occurring nucleotides with an analog such as inosine. Modifications of nucleotides include the addition of acridine, amine, biotin, cascade blue, cholesterol, Cy3@, Cy5 @, Cy5.5@ Daboyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S", SE, BODIPY®, Marina Blue@, Pacific Blue@, Oregon Green@, Rhodamine Green@, Rhodamine Red@, Rhodol Green@ and Texas Red@. Polynucleotide backbone modifications include methylphosphonate, 2'-OMe-methylphosphonate RNA, phosphorothioate, RNA, 2'-0MeRNA. Base modifications include 2-amino-dA, 2-aminopurine, 3'-(ddA), 3'dA (cordycepin), 7-deaza-dA, 8-Br-dA, 8-oxo-dA, N6-Me-dA, abasic site (dSpacer), biotin dT, 2'-OMe-5Me-C, 2'-OMe-propynyl-C, 3'-(5-Me-dC), 3'-(ddC), 5-Br-dC, 5-1-duc, 5-Me-dC, 5-F-dC, carboxy-dT, convertible dA, convertible dC, convertible dG, convertible dT, convertible dU, 7-deaza-dG, 8-Br-dG, 8-oxo-dG, 06-Me-dG, S6-DNP-dG, 4-methyl-indole, 5-nitroindole, 2'-OMe-inosine, 2'-dI, o6-phenyl-dl, 4-methyl-indole, 2'-deoxynebularine, 5-nitroindole, 2-aminopurine, dP (purine analogue), dK (pyrimidine analogue), 3-nitropyrrole, 2-thio-dT, 4-thio-dT, biotin-dT, carboxy-dT, 04-Me-dT, 04-triazol dT, 2'-OMe-propynyl-U, 5-Br-dU, 2'-dU, 5-F-dU, 5-1-dU, 04-triazol dU. Said terms also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors.

Oligonucleobases may have nick(s), gap(s), modified nucleotides such as modified oligonucleotide backbones, abasic nucleotides, or other chemical moieties. In a further embodiment, at least one strand of the oligonucleobase includes at least one additional modified nucleotide, e.g., a 2'-O-methyl modified nucleotide such as a MOE (methoxyethyl), a nucleotide having a 5'-phosphorothioate group, a terminal nucleotide linked to a cholesteryl derivative, a 2'-deoxy-2'-fluoro modified nucleotide, a 2'-deoxy-modified nucleotide, a locked nucleotide, an abasic nucleotide (the nucleobase is missing or has a hydroxyl group in place thereof (see, e.g., Glen Research, http://www.glenresearch.com/GlenReports/GR21-14.html)), a 2'-amino-modified nucleotide, a 2'-alkyl-modified nucleotide, a morpholino nucleotide, a phosphoramidite, and a non-natural base comprising nucleotide. Various salts, mixed salts and free acid forms are also included.

Preferred modified oligonucleotide backbones include, for example, phosphorothioates, chiral phosphorothioates, phosphoro-dithioates, phosphotriesters, amino alkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and amino alkylphosphoramidates, thionophosphoramidates, thionoalkylphosphonates, thionoalkylphosphotriesters, selenophosphates and boranophosphates having normal 3'-5'linkages, 2'-5'linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). The most common use of a linkage inversion is to add a 3'-3' linkage to the end of an antisense oligonucleotide with a phosphorothioate backbone. The 3'-3' linkage further stabilizes the antisense oligonucleotide to exonuclease degradation by creating an oligonucleotide with two 5'-OH ends and no 3'-OH end. Linkage inversions can be introduced into specific locations during oligonucleotide synthesis through use of "reversed phosphoramidites". These reagents have the phosphoramidite groups on the 5'-OH position and the dimethoxytrityl (DMT) protecting group on the 3'-OH position. Normally, the DMT protecting group is on the 5'-OH and the phosphoramidite is on the 3'-OH.

Examples of modified bases include, but are not limited to, 2-aminopurine, 2'-amino-butyryl pyrene-uridine, 2'-aminouridine, 2'-deoxyuridine, 2'-fluoro-cytidine, 2'-fluorouridine, 2,6-diaminopurine, 4-thio-uridine, 5-bromo-uridine, 5-fluoro-cytidine, 5-fluorouridine, 5-indo-uridine, 5-methyl-cytidine, inosine, N3-methyl-uridine, 7-deaza-guanine, 8-aminohexyl-amino-adenine, 6-thio-guanine, 4-thio-thymine, 2-thio-thymine, 5-iodo-uridine, 5-iodo-cytidine, 8-bromo-guanine, 8-bromo-adenine, 7-deaza-adenine, 7-diaza-guanine, 8-oxo-guanine, 5,6-dihydro-uridine, and 5-hydroxymethyl-uridine. These synthetic units are commercially available; (for example, purchased from Glen Research Company) and can be incorporated into DNA by chemical synthesis.

Examples of modification of the sugar moiety are 3'-deoxylation, 2'-fluorination, and arabanosidation, however, it is not to be construed as being limited thereto. Incorporation of these into DNA is also possible by chemical synthesis.

Examples of the 5' end modification are 5'-amination, 5'-biotinylation, 5'-fluoresceinylation, 5'-tetrafluoro-fluoreceinyaltion, 5'-thionation, and 5'-dabsylation, however it is not to be construed as being limited thereto.

Examples of the 3' end modification are 3'-amination, 3'-biotinylation, 2,3-dideoxidation, 3'-thionation, 3'-dabsylation, 3'-carboxylation, and 3'-cholesterylation, however, it is not to be construed as being limited thereto.

In one preferred embodiment, the oligonucleobase can contain a 5 blocking substituent that is attached to the 5' terminal carbons through a linker. The chemistry of the linker is not critical other than its length, which should in some embodiments be at least 6 atoms long and that the linker should be flexible. A variety of non-toxic substituents such as biotin, cholesterol or other steroids or a non-intercalating cationic fluorescent dye can be used. Particularly preferred reagents to make oligonucleobases are the reagents sold as Cy3™ and Cy5™ by Glen Research, Sterling Va. (now GE Healthcare), which are blocked phosphoroamidites that upon incorporation into an oligonucleotide yield 3,3,3',3'-tetramethyl N,N'-isopropyl substituted indomonocarbocyanine and indodicarbocyanine dyes, respectively. Cy3 is particularly preferred. When the indocarbocyanine is N-oxyalkyl substituted it can be conveniently linked to the 5' terminal of the oligodeoxynucleotide as a phosphodiester with a 5' terminal phosphate. When the commercially available Cy3 phosphoramidite is used as directed, the resulting 5' modification consists of a blocking substituent and linker together which are a N-hydroxypropyl, N'-phosphatidylpropyl 3,3,3',3'-tetramethyl indomonocarbocyanine. Other dyes contemplated include Rhodamine6G, Tetramethylrhodamine, Sulforhodamine 101, Merocyanine 540, Atto565, Atto550 26, Cy3.5, Dy547, Dy548, Dy549, Dy554, Dy555, Dy556, Dy560, mStrawberry and mCherry.

In a preferred embodiment the indocarbocyanine dye is tetra substituted at the 3 and 3' positions of the indole rings. Without limitations as to theory these substitutions prevent the dye from being an intercalating dye. The identity of the substituents at these positions is not critical.

The oligo designs herein described might also be used as more efficient donor templates in combination with other DNA editing or recombination technologies including, but not limited to, gene targeting using site-specific homologous recombination by zinc finger nucleases, Transcription Activator-Like Effector Nucleases (TALENs) or Clustered Regularly Interspaced Short Palindromic Repeats (CRISPRs).

The present disclosure in certain aspects and embodiments generally relates to methods for the efficient modification of genomic cellular DNA and/or recombination of DNA into the genomic DNA of cells. Although not limited to any particular use, some methods provided herein may in certain embodiments be useful in, for example, introducing a modification into the genome of a cell for the purpose of determining the effect of the modification on the cell. For example, a modification may be introduced into the nucleotide sequence which encodes an enzyme to determine whether the modification alters the enzymatic activity of the enzyme, and/or determine the location of the enzyme's catalytic region. Alternatively, the modification may be introduced into the coding sequence of a DNA-binding protein to determine whether the DNA binding activity of the protein is altered, and thus to delineate the particular DNA-binding region within the protein. Yet another alternative is to introduce a modification into a non-coding regulatory sequence (e.g., promoter, enhancer, regulatory RNA sequence (miRNA), etc.) in order to determine the effect of the modification on the level of expression of a second sequence which is operably linked to the non-coding regulatory sequence. This may be desirable to, for example, define the particular sequence which possesses regulatory activity.

DNA Cutters

One strategy for producing targeted gene disruption is through the generation of single strand or double strand DNA breaks using a DNA cutter such as a site-specific endonuclease. Endonucleases are most often used for targeted gene disruption in organisms that have traditionally been refractive to more conventional gene targeting methods, such as algae, plants, and large animal models, including humans. For example, there are currently human clinical trials underway involving zinc finger nucleases for the treatment and prevention of HIV infection. Additionally, endonuclease engineering is currently being used in attempts to disrupt genes that produce undesirable phenotypes in crops.

Zinc Fingers

One class of artificial endonucleases is the zinc finger endonucleases. Zinc finger endonucleases combine a non-specific cleavage domain, typically that of FoId endonuclease, with zinc finger protein domains that are engineered to bind to specific DNA sequences. The modular structure of the zinc finger endonucleases makes them a versatile platform for delivering site-specific double-strand breaks to the genome. As FokI endonuclease cleaves as a dimer, one strategy to prevent off-target cleavage events has been to design zinc finger domains that bind at adjacent 9 base pair sites. See also U.S. Pat. Nos. 7,285,416; 7,521,241; 7,361,635; 7,273,923; 7,262,054; 7,220,719; 7,070,934; 7,013,219; 6,979,539; 6,933,113; 6,824,978; each of which is hereby herein incorporated by reference in its entirety.

TALENs

TALENs are targetable nucleases are used to induce single- and double-strand breaks into specific DNA sites, which are then repaired by mechanisms that can be exploited to create sequence alterations at the cleavage site.

The fundamental building block that is used to engineer the DNA-binding region of TALENs is a highly conserved repeat domain derived from naturally occurring TALEs encoded by *Xanthomonas* spp. proteobacteria. DNA binding by a TALEN is mediated by arrays of highly conserved 33-35 amino acid repeats that are flanked by additional TALE-derived domains at the amino-terminal and carboxy-terminal ends of the repeats.

These TALE repeats specifically bind to a single base of DNA, the identity of which is determined by two hypervariable residues typically found at positions 12 and 13 of the repeat, with the number of repeats in an array corresponded to the length of the desired target nucleic acid, the identity of the repeat selected to match the target nucleic acid sequence. In some embodiments, the target nucleic acid is between 15 and 20 base pairs in order to maximize selectivity of the target site. Cleavage of the target nucleic acid typically occurs within 50 base pairs of TALEN binding. Computer programs for TALEN recognition site design have been described in the art. See, e.g., Cermak et al., Nucleic Acids Res. 2011 July; 39(12): e82.

Once designed to match the desired target sequence, TALENs can be expressed recombinantly and introduced into protoplasts as exogenous proteins, or expressed from a plasmid within the protoplast or administered as mRNA.

Meganucleases

The homing endonucleases, also known as meganucleases, are sequence specific endonucleases that generate double strand breaks in genomic DNA with a high degree of specificity due to their large (e.g., >14 bp) cleavage sites. While the specificity of the homing endonucleases for their target sites allows for precise targeting of the induced DNA breaks, homing endonuclease cleavage sites are rare and the probability of finding a naturally occurring cleavage site in a targeted gene is low.

Another class of artificial endonucleases is the engineered meganucleases. Engineered homing endonucleases are generated by modifying the specificity of existing homing endonucleases. In one approach, variations are introduced in the amino acid sequence of naturally occurring homing endonucleases and then the resultant engineered homing endonucleases are screened to select functional proteins which cleave a targeted binding site. In another approach, chimeric homing endonucleases are engineered by combining the recognition sites of two different homing endonucleases to create a new recognition site composed of a half-site of each homing endonuclease. See e.g., U.S. Pat. No. 8,338,157.

CRISPRs or CRISPR/cas Systems

CRISPR-Cas system contains three basic design components: 1) Cas gene, transcript (e.g., mRNA) or protein; 2) guide RNA (gRNA); and 3) crRNAs (CRISPR RNA) are RNA segments processed from RNA transcripts encoding the CRISPR repeat arrays, which harbor a "protospacer" region that are complementary to a foreign DNA site (e.g., endogenous DNA target region) and a part of the CRISPR repeat. See e.g., PCT Application Nos. WO/2014/093661 and WO/2013/176772.

Cas (CRISPR Associated) Gene, Transcript (e.g., mRNA) or Protein

Transient Cas expression from a plasmid vector, direct delivery of Cas protein and or direct delivery of Cas mRNA into plant cells. Cas genes are codon optimized for expression in higher plants, algae or yeast and are driven by either a constitutive, inducible, tissue-specific or species-specific promoter when applicable. Cas transcript termination and polyadenlyation signals are either NosT, RBCT, HSP18.2T or other gene specific or speciesspecific terminators. Cas gene cassettes or mRNA may contain introns, either native or in combination with gene-specific promoters and or synthetic promoters. Cas protein may contain one or more nuclear localization signal sequences (NLS), mutations, deletions, alterations or truncations. In transient expression systems, Cas gene cassettes may be combined with other components of the CRISPR-Cas system such as gRNA cassettes on the same transient expression vector. Alternatively, Cas gene cassettes may be located and expressed from constructs independent of gRNA cassettes or from other components of the CRISPR-Cas system. CRISPR associated (Cas) gene—encode for proteins with a variety of predicted nucleic acid-manipulating activities such as nucleases, helicases and polymerase. Cas genes include cas9. Cas9 is a gene encoding a large protein containing a predicted RuvC-like and HNH endonuclease domains and is associated with the CRISPR adaptive immunity system that is present in most archaea and many bacteria. Cas9 protein consists of two lobes:

1) Recognition (REC) lobe—consists of three domains:
   a) BH (bridge helix)
   b) REC1—facilitates RNA-guided DNA targeting
   c) REC2—facilitates RNA-guided DNA targeting
2) Nuclease (NUC) lobe—consists of three domains:
   a) RuvC—facilitates RNA-guided DNA targeting; endonuclease activity
   b) HNH—endonuclease activity
   c) PI— PAM interacting In other embodiments, the cas gene may be a homolog of cas9 in which the RuvC, HNH, REC and BH domains are highly conserved. In some embodiments, cas genes are those from the following species.

Guide RNA (gRNA)

gRNA or sgRNA (single guide RNA) is engineered as a fusion between a crRNA and part of the transactivating CRISPR RNA (tracrRNA) sequence, which guides the Cas9 to a specific target DNA sequence that is complementary to the protospacer region. Guide RNA may include an expression cassette containing a chimeric RNA design with a long tracerRNA hybrid, short tracrRNA hybrid or a native CRISPR array+tracrRNA conformation. Chimeric gRNA combines the targeting specificity of the crRNA with the scaffolding properties of the tracrRNA into a single transcript. gRNA transient expression is controlled by speciesspecific higher plant RNA Polymerase III promoters such as those from the U6 or U3 snRNA gene family (Wang et al 2008). gRNA transcript termination is controlled by a 6-20 nucleotide tract of poly dT as per Wang et al 2008. gRNA expression cassettes are located on the same or different transient expression vectors from other components of the CRISPR-Cas system. gRNA transcripts may be synthesized in-vitro and delivered directly into plant cells, independent of or in combination with gRNA transient expression vectors.

Target Region

Guide RNAs contain two components that define specificity to a DNA target region, a proto-spacer and a proto-spacer adjacent motif (PAM). Proto-spacer sequence, typically 20 nucleotides but can vary based on the DNA target, provides DNA sequence specificity for the CRISPR-Cas complex. DNA targets also contain a NNG or NAG trinucleotide sequence (PAM) where N denotes any nucleotide, immediately 3' or downstream of the proto-spacer.

One Component Approach

Similar to Le Cong et al. (2013) and others, a simplified "one component approach" to CRISPR-Cas gene editing wherein a single transient expression construct contains all components of the CRISPR-Cas complex, i.e. both the gRNA and the Cas expressions cassettes. This allows for an easy modular design for targeting single or multiple loci in any given plant or crop. Targeting multiple loci can be achieved by simply swapping in the target-specific gRNA cassettes. Additionally, species specific promoters, terminators or other expressing enhancing elements can easily be shuttled in and out of "one component approach" transient vectors allowing for optimal expression of both gRNA and Cas protein in a species specific manner.

Two Component Approach

In the two component approach, Cas and gRNA expression cassettes are located on different transient expression vectors. This allows for delivery of a CRISPR-Cas editing components separately, allowing for different ratios of gRNA to Cas within the same cell. Similar to the one component approach, the two component approach also allows for promoters, terminators or other elements affecting expression of CRISPRCas components to be easily altered and allow targeting of DNA in a species-specific manner.

Antibiotics

Another class of endonucleases are antibiotics which are DNA cleaving glycopeptides such as the bleomycin family of antibiotics are DNA cleaving glycopeptides which include bleomycin, zeocin, phleomycin, tallysomycin, pepleomycin and others which are further described herein.

Other DNA-modifying molecules may be used in targeted gene recombination. For example, peptide nucleic acids may be used to induce modifications to the genome of the target cell or cells (see, e.g., Ecker, U.S. Pat. No. 5,986,053 herein incorporated by reference). In brief, synthetic nucleotides comprising, at least, a partial peptide backbone are used to target a homologous genomic nucleotide sequence. Upon binding to the double-helical DNA, or through a mutagen ligated to the peptide nucleic acid, modification of the target DNA sequence and/or recombination is induced to take place. Targeting specificity is determined by the degree of sequence homology between the targeting sequence and the genomic sequence.

Furthermore, the present disclosure is not limited to the particular methods which are used herein to execute modification of genomic sequences. Indeed, a number of methods are contemplated. For example, genes may be targeted using triple helix forming oligonucleotides (TFO). TFOs may be generated synthetically, for example, by PCR or by use of a gene synthesizer apparatus. Additionally, TFOs may be isolated from genomic DNA if suitable natural sequences are found. TFOs may be used in a number of ways, including, for example, by tethering to a mutagen such as, but not limited to, psoralen or chlorambucil (see, e.g., Havre et al., Proc Nat'l Acad Sci, U.S.A. 90:7879-7883, 1993; Havre et al., 0.1 Virol 67:7323-7331, 1993; Wang et al., Mol Cell Biol 15:1759-1768, 1995; Takasugi et al., Proc Nat'l Acad Sci, U.S.A. 88:5602-5606, 1991; Belousov et al., Nucleic Acids Res 25:3440-3444, 1997). Furthermore, for example, TFOs may be tethered to donor duplex DNA (see, e.g., Chan et al., J Biol Chem 272:11541-11548, 1999). TFOs can also act by binding with sufficient affinity to provoke error-prone repair (Wang et al., Science 271:802-805, 1996).

The methods disclosed herein are not necessarily limited to the nature or type of DNA-modifying reagent which is used. For example, such DNA-modifying reagents release radicals which result in DNA strand breakage. Alternatively, the reagents alkylate DNA to form adducts which would block replication and transcription. In another alternative, the reagents generate crosslinks or molecules that inhibit cellular enzymes leading to strand breaks. Examples of DNA-modifying reagents which have been linked to oligonucleotides to form TFOs include, but are not limited to, indolocarbazoles, napthalene diimide (NDI), transplatin, bleomycin, analogues of cyclopropapyrroloindole, and phenanthodihydrodioxins. In particular, indolocarbazoles are topoisomerase I inhibitors. Inhibition of these enzymes results in strand breaks and DNA protein adduct formation (Arimondo et al., Bioorganic and Medicinal Chem. 8, 777, 2000). NIX is a photooxidant that can oxidize guanines which could cause mutations at sites of guanine residues (Nunez, et al., Biochemistry, 39, 6190, 2000). Transplatin has been shown to react with DNA in a triplex target when the TFO is linked to the reagent. This reaction causes the formation of DNA adducts which would be mutagenic (Colurnbier, et at, Nucleic Acids Research, 24: 4519, 1996). Bleomycin is a DNA breaker, widely used as a radiation mimetic. It has been linked to oligonucleotides and shown to be active as a breaker in that format (Sergeyev, Nucleic Acids Research 23, 4400, 1995: Kane, et al., Biochemistry, 34, 16715, 1995). Analogues of cyclopropapyrroloindole have been linked to TFOs and shown to alkylate DNA in a triplex target sequence. The alkylated DNA would then contain chemical adducts which would be mutagenic (Lukhtanov, et al., Nucleic Acids Research, 25, 5077, 1997). Phenanthodihydrodioxins are masked quinones that release radical species upon photoactivation. They have been linked to TFOs and have been shown to introduce breaks into duplex DNA on photoactivation (Bendinskas et at, Bioconjugate Chem. 9, 555, 1998).

Other methods of inducing modifications and/or recombination are contemplated by the present disclosure. For example, another embodiment involves the induction of homologous recombination between an exogenous DNA fragment and the targeted gene (see e.g., Capecchi et al., Science 244:1288-1292, 1989) or by using peptide nucleic acids (PNA) with affinity for the targeted site. Still other methods include sequence specific DNA recognition and targeting by polyamides (see e.g., Dervan et al., Curr Opin Chem Biol 3:688-693, 1999 Biochemistry 38:2143-2151, 1999) and the use nucleases with site specific activity (e.g., zinc finger proteins, TALENs, Meganucleases and/or CRISPRs).

The present disclosure is not limited to any particular frequency of modification and/or recombination. In some embodiments the methods disclosed herein result in a frequency of modification in the target nucleotide sequence of from 0.2% to 3%. Nonetheless, any frequency (i.e., between 0% and 100%) of modification and/or recombination is contemplated to be within the scope of the present disclosure. The frequency of modification and/or recombination is dependent on the method used to induce the modification and/or recombination, the cell type used, the specific gene targeted and the DNA mutating reagent used, if any. Additionally, the method used to detect the modification and/or recombination, due to limitations in the detection method, may not detect all occurrences of modification and/or recombination. Furthermore, some modification and/or recombination events may be silent, giving no detectable indication that the modification and/or recombination has taken place. The inability to detect silent modification and/or recombination events gives an artificially low estimate of modification and/or recombination. Because of these reasons, and others, the disclosure is not necessarily limited to any particular modification and/or recombination frequency. In one embodiment, the frequency of modification and/or recombination is between 0.01% and 100%. In another embodiment, the frequency of modification and/or recombination is between 0.01% and 50%. In yet another embodiment, the frequency of modification and/or recombination is between 0.1% and 10%. In still yet another embodiment, the frequency of modification and/or recombination is between 0.1.% and 5%.

The term "frequency of mutation." as used herein in reference to a population of cells which are treated with a DNA-modifying molecule that is capable of introducing a mutation into a target site in the cells genome, refers to the number of cells in the treated population which contain the mutation at the target site as compared to the total number of cells which are treated with the DNA-modifying molecule. For example, with respect to a population of cells which is treated with the DNA-modifying molecule TFO tethered to psoralen which is designed to introduce a mutation at a target site in the cells' genome, a frequency of mutation of 5% means that of a total of 100 cells which are treated with TFO-psoralen, 5 cells contain a mutation at the target site.

Although the present disclosure is not necessarily limited to any degree of precision in the modification and/or recombination of DNA in the cell, it is contemplated that some embodiments of the present disclosure require higher degrees of precision, depending on the desired result. For example, the specific sequence changes required for gene repair (e.g., particular base changes) require a higher degree of precision as compared to producing a gene knockout wherein only the disruption of the gene is necessary. With the methods of the present disclosure, achievement of higher levels of precision in modification and/or homologous recombination techniques is greater than with prior art methods.

Delivery of Gene Repair Oligonueleobases into Plant Cells

Any commonly known method used to transform a plant cell can be used for delivering the gene repair oligonucleobases. Illustrative methods are listed below. The methods and compositions herein may involve any of many methods to transfect the cells with the DNA-modifying reagent or reagents. Methods for the introduction of DNA modifying reagents into a cell or cells are well known in the art and include, but are not limited to, microinjection, electroporation, passive adsorption, calcium phosphate-DNA co-precipitation, DEAE-dextran-mediated transfection, polybrene-mediated transfection, liposome fusion, lipofectin, nucleofection, protoplast fusion, retroviral infection, biolistics (i.e., particle bombardment) and the like.

The use of metallic microcarriers (microspheres) for introducing large fragments of DNA into plant cells having cellulose cell walls by projectile penetration is well known to those skilled in the relevant art (henceforth Holistic delivery). U.S. Pat. Nos. 4,945,050; 5,100,792 and 5,204,253 describe general techniques for selecting microcarriers and devices for projecting them.

Specific conditions for using microcarriers in the methods disclosed herein may include the conditions described in International Publication WO 99/07865. In an illustrative technique, ice cold microcarriers (60 mg/mL), mixed duplex oligonucleotide (60 mg/mL) 2.5 M $CaCl_2$ and OA M spermidine are added in that order; the mixture gently agitated, e.g., by vortexing, for 10 minutes and then left at room temperature for 10 minutes, whereupon the microcarriers are diluted in 5 volumes of ethanol, centrifuged and resuspended in 100% ethanol. Good results can be obtained with a concentration in the adhering solution of 8-10 µg/pt microcarriers, 14-17 µg/mL mixed duplex oligonucleotide, 1.1-1.4 M $CaCl_2$ and 18-22 mM spermidine. Optimal results were observed under the conditions of 8 µg/µL microcarriers, 16.5 µg/mL, mixed duplex oligonucleotide, 1.3 M $CaCl_2$ and 21 mM spermidine.

Gene repair oligonucleobases can also be introduced into plant cells using microfibers to penetrate the cell wall and cell membrane. U.S. Pat. No. 5,302,523 to Coffee et al describes the use of silicon carbide fibers to facilitate transformation of suspension maize cultures of Black Mexican Sweet. Any mechanical technique that can be used to introduce DNA for transformation of a plant cell using microfibers can be used to deliver gene repair oligonucleobases for transmutation.

An illustrative technique for microfiber delivery of a gene repair oligonucleobase is as follows: Sterile microfibers (2 µg) are suspended in 150 µL of plant culture medium containing about 10 µg of a mixed duplex oligonucleotide. A suspension culture is allowed to settle and equal volumes of packed cells and the sterile fiber/nucleotide suspension are vortexed for 10 minutes and plated. Selective media are applied immediately or with a delay of up to about 120 h as is appropriate for the particular trait.

In an alternative embodiment, the gene repair oligonucleobases can be delivered to the plant cell by electroporation of a protoplast derived from a plant part. The protoplasts are formed by enzymatic treatment of a plant part, particularly a leaf, according to techniques well known to those skilled in the art. See, e.g., Gallois et al, 1996, in Methods in Molecular Biology 55:89-107, Humana Press, Totowa, N.J.; Kipp et al., 1999, in Methods in Molecular Biology 133: 213-221, Humana Press, Totowa, N.J. The protoplasts need not be cultured in growth media prior to electroporation. Illustrative conditions or electroporation are 300,000 protoplasts in a total volume of 0.3 mL with a concentration of gene repair oligonucleobase of between 0.6-4 µg/mL.

In an alternative embodiment. nucleic acids are taken up by plant protoplasts in the presence of the membrane-modifying agent polyethylene glycol, according to techniques well. known to those skilled in the art. In another alternative embodiment, the gene repair oligonucleobases can be delivered injecting it with a microcapillary into plant cells or into protoplasts.

In an alternative embodiment, nucleic acids are embedded in microbeads composed of calcium alginate and taken up by plant protoplasts in the presence of the membrane-modifying agent polyethylene glycol (see, e.g., Sone et at, 2002. Liu et al., 2004).

In an alternative embodiment, nucleic acids frozen in water and introduced into plant cells by bombardment in the form of microparticles (see, e.g., Gilmore, 1991, U.S. Pat. No. 5,219,746; Winegar et al.).

In an alternative embodiment, nucleic acids attached to nanoparticles are introduced into intact plant cells by incubation of the cells in a suspension containing the nanoparticle (see, e.g., Pasupathy et al., 2008) or by delivering them into intact cells through particle bombardment or into protoplasts by co-incubation (see, e.g., Tomey et al., 2007).

In an alternative embodiment, nucleic acids complexed with penetrating peptides and delivered into cells by co-incubation see, e.g., (Chugh et al. 2008. WO 2008148223 A1; Eudes and Chugh).

In an alternative embodiment, nucleic acids are introduced into intact cells through electroporation (see, e.g., He et al., 1998. US 2003/0115641 A1, Dobres et al.).

In an alternative embodiment, nucleic acids are delivered into cells of dry embryos by soaking them in a solution with nucleic acids (see, e.g., Töpfer et al., 1989. Senaratna et at, 1991) or in other embodiments are introduced by Cellsqueeze (SQZ Biotech).

Selection of Plants

In various embodiments. plants as disclosed herein can be of any species of dicotyledonous, monocotyledonous or gymnospermous plant, including any woody plant species that grows as a tree or shrub, any herbaceous species, or any species that produces edible fruits, seeds or vegetables, or any species that produces colorful or aromatic flowers. For example, the plant maybe selected from a species of plant from the group consisting of canola, sunflower, corn, tobacco, sugar beet, cotton, maize, wheat, barley, rice, alfalfa, barley, sorghum, tomato, mango, peach, apple, pear, strawberry, banana, melon, cassava, potato carrot, lettuce, onion, soy bean, soya spp, sugar cane, pea, chickpea, field pea, fava bean, lentils, turnip, rutabaga, brussel sprouts, lupin, cauliflower, kale, field beans, poplar, pine, eucalyptus, grape, citrus, triticale, alfalfa, rye, oats, turf and forage grasses, flax, oilseed rape, mustard, cucumber, morning glory, balsam, pepper, eggplant, marigold, lotus, cabbage, daisy, carnation, tulip, iris, lily, and nut producing plants insofar as they are not already specifically mentioned.

Plants and plant cells can be tested for resistance or tolerance to an herbicide using commonly known methods in the art, e.g., by growing the plant or plant cell in the presence of an herbicide and measuring the rate of growth as compared to the growth rate in the absence of the herbicide.

As used herein, substantially normal growth of a plant, plant organ, plant tissue or plant cell is defined as a growth rate or rate of cell division of the plant, plant organ, plant tissue, or plant cell that is at least 35%, at least 50%, at least 60%, or at least 75% of the growth rate or rate of cell division in a corresponding plant, plant organ, plant tissue or plant cell expressing the wild-type protein of interest.

As used herein, substantially normal development of a plant, plant organ, plant tissue or plant cell is defined as the occurrence of one or more development events in the plant, plant organ, plant tissue or plant cell that are substantially the same as those occurring in a corresponding plant, plant organ, plant tissue or plant cell expressing the wild-type protein.

In certain embodiments plant organs provided herein include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.

Plants are substantially "tolerant" to a relevant herbicide when they are subjected to it and provide a dose/response curve which is shifted to the right when compared with that provided by similarly subjected non-tolerant like plant. Such dose/response curves have "dose" plotted on the X-axis and "percentage kill", "herbicidal effect", etc., plotted on the y-axis. Tolerant plants will require more herbicide than non-tolerant like plants in order to produce a given herbicidal effect. Plants that are substantially "resistant" to the herbicide exhibit few, if any, necrotic, lytic, chlorotic or other lesions, when subjected to herbicide at concentrations and rates which are typically employed by the agrochemical community to kill weeds in the field. Plants which are resistant an herbicide are also tolerant of the herbicide.

Generation of Plants

Tissue culture of various tissues of plant species and regeneration of plants therefrom is known. For example, the propagation of a canola cultivar by tissue culture is described in any of the following but not limited to any of the following: Chuong et al., "A Simple Culture Method for *Brassica* hypocotyls Protoplasts," Plant Cell Reports 4:4-6, 1985; Barsby, T. L., et al., "A Rapid and Efficient Alternative Procedure for the Regeneration of Plants from Hypocotyl Protoplasts of *Brassica napus*," Plant Cell Reports (Spring, 1996); Kartha, K., et al., "In vitro Plant Formation from Stem Explants of Rape," Physiol. Plant, 31:217-220, 1974; Narasimhulu, S., et al., "Species Specific Shoot Regeneration Response of Cotyledonary Explants of Brassicas," Plant Cell Reports (Spring 1988); Swanson, E., "Microspore Culture in *Brassica*," Methods in Molecular Biology, Vol. 6, Chapter 17, p. 159, 1990.

Further reproduction of the variety can occur by tissue culture and regeneration. Tissue culture of various tissues of soybeans and regeneration of plants therefrom is well known and widely published. For example, reference may be had to Komatsuda, T. et al., "Genotype X Sucrose Interactions for Somatic Embryogenesis in Soybeans," Crop Sci. 31:333-337, 1991; Stephens, P. A., et al., "Agronomic Evaluation of Tissue-Culture-Derived Soybean Plants," Theor. Appl. Genet. 82:633-635, 1991; Komatsuda, T. et al., "Maturation and Germination of Somatic Embryos as Affected by Sucrose and Plant Growth Regulators in Soybeans *Glycine gracilis* Skvortz and *Glycine max* (L.) Merr." Plant Cell, Tissue and Organ Culture, 28:103-113, 1992; Dhir, S. et al., "Regeneration of Fertile Plants from Protoplasts of Soybean (*Glycine max* L. Merr.); Genotypic Differences in Culture Response," Plant Cell Reports 11:285-289, 1992; Pandey, P. et al., "Plant Regeneration from Leaf and Hypocotyl Explants of *Glycine wightii* (W. and A.) VERDC. var. longicauda," Japan J. Breed. 42:1-5, 1992; and Shetty, K., et al., "Stimulation of In Vitro Shoot Organogenesis in *Glycine max* (Merrill.) by Allantoin and Amides," Plant Science 81:245-251, 1992. The disclosures of U.S. Pat. No. 5,024,944 issued Jun. 18, 1991 to Collins et al., and U.S. Pat. No. 5,008,200 issued Apr. 16, 1991 to Ranch et al., are hereby incorporated herein in their entirety by reference.

Exemplary Embodiments

In addition to the aspects and embodiments described and provided elsewhere in this disclosure, the following non-limiting list of particular embodiments are specifically contemplated.
1. A method of causing a genetic change in a cell, said method comprising exposing said cell to a DNA cutter and a modified GRON.
2. A cell comprising a DNA cutter and a GRON.
3. The method or cell of any of the preceding embodiments, wherein said cells is one or more species of cell selected from the group consisting of plant, bacteria, yeast, fungi, algae, and mammalian.
4. The method or cell of any of the preceding embodiments, wherein said cells is one or more species of cell selected from the group consisting of *Escherichia coli*, *Mycobacterium smegmatis*, *Bacillus subtilis*, *Chlorella*, *Bacillus thuringiensis*, *Saccharomyces cerevisiae*, *Yarrowia lipolytica*, *Chlamydamonas rhienhardtii*, *Pichia pastoris*, *Corynebacterium*, *Aspergillus niger*, and *Neurospora crassa*. *Arabidopsis thaliana*, *Solanum tuberosum*, *Solanum phureja*, *Oryza sativa*, *Glycine max*, *Amaranthus tuberculatus*, *Linum usitatissimum*, and *Zea mays*
5. The method or cell of any of the preceding embodiments, wherein said cell is *Yarrowia lipolytica*.
6. The method or cell of any of the preceding embodiments, wherein said cell is a yeast cell that is not *Saccharomyces cerevisiae*.
7. A method of causing a genetic change in a plant cell, said method comprising exposing said cell to a DNA cutter and a modified GRON.
8. A plant cell comprising a DNA cutter and a modified GRON.
9. A method of causing a genetic change in a plant cell, said method comprising exposing said cell to a DNA cutter and a GRON that comprises DNA and RNA.
10. A plant cell comprising a DNA cutter that comprises DNA and RNA.
11. A method of causing a genetic change in a Acetyl-Coenzyme A carboxylase (ACCase) gene in a cell, wherein said genetic change causes a change in the Acetyl-Coenzyme A carboxylase (ACCase) protein at one or more amino acid positions, said positions selected from the group consisting of 1781, 1783, 1786, 2078, 2079, 2080 and 2088 based on the numbering of the blackgrass reference sequence SEQ ID NO:1 or at an analogous amino acid residue in an ACCase paralog said method comprising exposing said cell to a modified GRON.
12. A method of causing a genetic change in a Acetyl-Coenzyme A carboxylase (ACCase) gene in a cell, wherein said genetic change causes a change in the Acetyl-Coenzyme A carboxylase (ACCase) protein at one or more amino acid positions, said positions selected from the group consisting of 1781, 1783, 1786, 2078, 2079, 2080 and 2088 based on the numbering of the blackgrass reference sequence SEQ ID NO:1 or at an analogous amino acid residue in an ACCase paralog said method comprising exposing said cell to a DNA cutter and a modified GRON.
13. A method for producing a plant or plant cell, comprising introducing into a plant cell a gene repair oligonucleobase (GRON) with a targeted mutation in an Acetyl-Coenzyme A carboxylase (ACCase) gene to produce a plant cell with an ACCase gene that expresses an ACCase protein comprising a mutation at one or more amino acid positions corresponding to a position selected from the group consisting of 1781, 1783, 1786, 2078, 2079, 2080 and 2088 based on the numbering of the blackgrass reference sequence SEQ ID NO:1 or at an analogous amino acid residue in an ACCase paralog.
14. A method for producing a plant or plant cell, comprising introducing into a plant cell a DNA cutter and a gene repair oligonucleobase (GRON) with a targeted mutation in an Acetyl-Coenzyme A carboxylase (ACCase) gene to produce a plant cell with an ACCase gene that expresses an ACCase protein comprising a mutation at one or more amino acid positions corresponding to a position selected from the group consisting of 1781, 1783, 1786, 2078, 2079, 2080 and 2088 based on the numbering of the blackgrass reference sequence SEQ ID NO:1 or at an analogous amino acid residue in an ACCase paralog.
15. A fertile plant comprising an Acetyl-Coenzyme A carboxylase (ACCase) gene that encodes a protein comprising a mutation at position 2078 based on the numbering of the blackgrass reference sequence SEQ ID NO:1 or at an analogous amino acid residue in an ACCase paralog.
16. A fertile rice plant comprising an Acetyl-Coenzyme A carboxylase (ACCase) gene that encodes a protein comprising a mutation at position 2078 based on the numbering of the blackgrass reference sequence SEQ ID NO:1 or at an analogous amino acid residue in an ACCase paralog.
17. A plant cell comprising an Acetyl-Coenzyme A carboxylase (ACCase) gene that encodes a protein comprising a mutation at position 2078 based on the numbering of the blackgrass reference sequence SEQ ID NO:1 or at an analogous amino acid residue in an ACCase paralog and that further comprises an Acetyl-Coenzyme A carboxylase (ACCase) gene that encodes a protein comprising a mutation at one or more amino acid positions, said positions selected from the group consisting of 1781, 1783, 1786, 2079, 2080 and 2088 based on the numbering of the blackgrass reference sequence SEQ ID NO:1 or at an analogous amino acid residue in an ACCase paralog.
18. A fertile plant comprising an Acetyl-Coenzyme A carboxylase (ACCase) gene that encodes a protein comprising a mutation at position 2078 based on the numbering of the blackgrass reference sequence SEQ ID NO:1 or at an analogous amino acid residue in an ACCase paralog and that further comprises an Acetyl-Coenzyme A carboxylase (ACCase) gene that encodes a protein comprising a mutation at one or more amino acid positions, said positions selected from the group consisting of 1781, 1783, 1786, 2079, 2080 and 2088 based on the numbering of the blackgrass reference sequence SEQ ID NO:1 or at an analogous amino acid residue in an ACCase paralog.
19. A method of causing a genetic change in a Acetyl-Coenzyme A carboxylase (ACCase) gene in a cell, wherein said genetic change causes a change in the Acetyl-Coenzyme A carboxylase (ACCase) protein at position 2078 based on the numbering of the blackgrass reference sequence SEQ ID NO:1 or at an analogous amino acid residue in an ACCase paralog said method comprising exposing said cell to a modified GRON.
20. A method of causing a genetic change in a Acetyl-Coenzyme A carboxylase (ACCase) gene in a cell, wherein said genetic change causes a change in the Acetyl-Coenzyme A carboxylase (ACCase) protein at position 2078 based on the numbering of the blackgrass reference sequence SEQ ID NO:1 or at an analogous amino acid residue in an ACCase paralog said method comprising exposing said cell to a DNA cutter and a modified GRON.

21. The method, plant or cell of any of the preceding embodiments, wherein said mutation or change in an Acetyl-Coenzyme A carboxylase (ACCase) gene, if present results in an Acetyl-Coenzyme A carboxylase (ACCase) protein comprising one or more selected from the group consisting of an isoleucine to alanine at a position corresponding to position 1781 of SEQ ID NO:1; an isoleucine to leucine at a position corresponding to position 1781 of SEQ ID NO:1; an isoleucine to methionine at a position corresponding to position 1781 of SEQ ID NO:1; an isoleucine to asparagine at a position corresponding to position 1781 of SEQ ID NO:1; an isoleucine to serine at a position corresponding to position 1781 of SEQ ID NO:1; an isoleucine to threonine at a position corresponding to position 1781 of SEQ ID NO:1; an isoleucine to valine at a position corresponding to position 1781 of SEQ ID NO:1; a glycine to cysteine at a position corresponding to position 1783 of SEQ ID NO:1; an alanine to proline at a position corresponding to position 1786 of SEQ ID NO:1; an aspartate to glycine at a position corresponding to position 2078 of SEQ ID NO:1; an aspartate to lysine at a position corresponding to position 2078 of SEQ ID NO:1; an aspartate to threonine at a position corresponding to position 2078 of SEQ ID NO:1; a serine to phenylalanine at a position corresponding to position 2079 of SEQ ID NO:1; a lysine to glutamate at a position corresponding to position 2080 of SEQ ID NO:1; a cysteine to phenylalanine at a position corresponding to position 2088 of SEQ ID NO:1; a cysteine to glycine at a position corresponding to position 2088 of SEQ ID NO:1; a cysteine to histidine at a position corresponding to position 2088 of SEQ ID NO:1; a cysteine to lysine at a position corresponding to position 2088 of SEQ ID NO:1; a cysteine to leucine at a position corresponding to position 2088 of SEQ ID NO:1; a cysteine to asparagine at a position corresponding to position 2088 of SEQ ID NO:1; a cysteine to proline at a position corresponding to position 2088 of SEQ ID NO:1; a cysteine to glutamine at a position corresponding to position 2088 of SEQ ID NO:1; a cysteine to arginine at a position corresponding to position 2088 of SEQ ID NO:1; a cysteine to serine at a position corresponding to position 2088 of SEQ ID NO:1; a cysteine to threonine at a position corresponding to position 2088 of SEQ ID NO:1; a cysteine to valine at a position corresponding to position 2088 of SEQ ID NO:1; and a cysteine to a tryptophan at a position corresponding to position 2088 of SEQ ID NO: 1.

22. The plant or cell of any of the preceding embodiments, or a plant or plant cell made by any of the methods of the preceding embodiments, wherein said plant or cell comprises an Acetyl-Coenzyme A carboxylase (ACCase) protein comprising one or more selected from the group consisting of an isoleucine to alanine at a position corresponding to position 1781 of SEQ ID NO:1; an isoleucine to leucine at a position corresponding to position 1781 of SEQ ID NO:1; an isoleucine to methionine at a position corresponding to position 1781 of SEQ ID NO:1; an isoleucine to asparagine at a position corresponding to position 1781 of SEQ ID NO:1; an isoleucine to serine at a position corresponding to position 1781 of SEQ ID NO:1; an isoleucine to threonine at a position corresponding to position 1781 of SEQ ID NO:1; an isoleucine to valine at a position corresponding to position 1781 of SEQ ID NO:1; a glycine to cysteine at a position corresponding to position 1783 of SEQ ID NO:1; an alanine to proline at a position corresponding to position 1786 of SEQ ID NO:1; an aspartate to glycine at a position corresponding to position 2078 of SEQ ID NO:1; an aspartate to lysine at a position corresponding to position 2078 of SEQ ID NO:1; an aspartate to threonine at a position corresponding to position 2078 of SEQ ID NO:1; a serine to phenylalanine at a position corresponding to position 2079 of SEQ ID NO:1; a lysine to glutamate at a position corresponding to position 2080 of SEQ ID NO:1; a cysteine to phenylalanine at a position corresponding to position 2088 of SEQ ID NO:1; a cysteine to glycine at a position corresponding to position 2088 of SEQ ID NO:1; a cysteine to histidine at a position corresponding to position 2088 of SEQ ID NO:1; a cysteine to lysine at a position corresponding to position 2088 of SEQ ID NO:1; a cysteine to leucine at a position corresponding to position 2088 of SEQ ID NO:1; a cysteine to asparagine at a position corresponding to position 2088 of SEQ ID NO:1; a cysteine to proline at a position corresponding to position 2088 of SEQ ID NO:1; a cysteine to glutamine at a position corresponding to position 2088 of SEQ ID NO:1; a cysteine to arginine at a position corresponding to position 2088 of SEQ ID NO:1; a cysteine to serine at a position corresponding to position 2088 of SEQ ID NO:1; a cysteine to threonine at a position corresponding to position 2088 of SEQ ID NO:1; a cysteine to valine at a position corresponding to position 2088 of SEQ ID NO:1; and a cysteine to a tryptophan at a position corresponding to position 2088 of SEQ ID NO: 1.

23. The plant or cell of any of the preceding embodiments, or a plant or cell made by any of the methods of the preceding embodiments, wherein said plant or plant cell comprises an Acetyl-Coenzyme A carboxylase (ACCase) gene that encodes a protein comprising a mutation at one or more amino acid positions, said positions selected from the group consisting of 1781, 1783, 1786, 2078, 2079, 2080 and 2088 based on the numbering of the blackgrass reference sequence SEQ ID NO:1 or at an analogous amino acid residue in an ACCase paralog.

24. The plant or cell of any of the preceding embodiments, or a plant or cell made by any of the methods of the preceding embodiments, wherein said plant or cell comprises an Acetyl-Coenzyme A carboxylase (ACCase) gene that encodes a protein comprising a mutation at position 2078 based on the numbering of the blackgrass reference sequence SEQ ID NO:1 or at an analogous amino acid residue in an ACCase paralog and that further comprises an Acetyl-Coenzyme A carboxylase (ACCase) gene that encodes a protein comprising a mutation at one or more amino acid positions, said positions selected from the group consisting of 1781, 1783, 1786, 2079, 2080 and 2088 based on the numbering of the blackgrass reference sequence SEQ ID NO:1 or at an analogous amino acid residue in an ACCase paralog.

In each of the foregoing ACCase embodiments 11-24, whether methods, plants, cells, or otherwise, the following are suitable mutations for use therein:

| Amino Acid Change | Codon Change |
|---|---|
| I1781A | ATA > GCT |
|  | ATA > GCC |
|  | ATA > GCA |
|  | ATA > GCG |

| Amino Acid Change | Codon Change |
|---|---|
| I1781L | ATA > CTT |
|  | ATA > CTC |
|  | ATA > CTA |
|  | ATA > CTG |
|  | ATA > TTA |
|  | ATA > TTG |
| I1781M | ATA > ATG |
| I1781N | ATA > AAT |
|  | ATA > AAC |
| I1781S | ATA > TCT |
|  | ATA > TCC |
|  | ATA > TCA |
|  | ATA > TCG |
| I1781T | ATA > ACT |
|  | ATA > ACC |
|  | ATA > ACA |
|  | ATA > ACG |
| I1781V | ATA > GTT |
|  | ATA > GTC |
|  | ATA > GTA |
|  | ATA > GTG |
| G1783C | GGA > TGT |
|  | GGA > TGC |
| A1786P | GCT > CCT |
|  | GCT > CCC |
|  | GCT > CCA |
|  | GCT > CCG |
| D2078G | GAT > GGT |
|  | GAT > GGC |
|  | GAT > GGA |
|  | GAT > GGG |
| D2078K | GAT > AAA |
|  | GAT > AAG |
| D2078T | GAT > ACT |
|  | GAT > ACC |
|  | GAT > ACA |
|  | GAT > ACG |
| S2079F | AGC > TTT |
|  | AGC > TTC |
| K2080E | AAG > GAA |
|  | AAG > GAG |
| C2088F | TGC > TTT |
|  | TGC > TTC |
| C2088G | TGC > GGT |
|  | TGC > GGC |
|  | TGC > GGA |
|  | TGC > GGG |
| C2088H | TGC > CAT |
|  | TGC > CAC |
| C2088K | TGC > AAA |
|  | TGC > AAG |
| C2088L | TGC > CTT |
|  | TGC > CTC |
|  | TGC > CTA |
|  | TGC > CTG |
|  | TGC > TTA |
|  | TGC > TTG |
| C2088N | TGC > AAT |
|  | TGC > AAC |
| C2088P | TGC > CCT |
|  | TGC > CCC |
|  | TGC > CCA |
|  | TGC > CCG |
| C2088Q | TGC > CAA |
|  | TGC > CAG |
| C2088R | TGC > CGT |
|  | TGC > CGC |
|  | TGC > CGA |
|  | TGC > CGG |
|  | TGC > AGA |
|  | TGC > AGG |
| C2088S | TGC > TCT |
|  | TGC > TCC |
|  | TGC > TCA |
|  | TGC > TCG |

| Amino Acid Change | Codon Change |
|---|---|
| C2088T | TGC > ACT |
|  | TGC > ACC |
|  | TGC > ACA |
|  | TGC > ACG |
| C2088V | TGC > GTT |
|  | TGC > GTC |
|  | TGC > GTA |
|  | TGC > GTG |
| C2088W | TGC > TGG |

Alternative mutations include, but are not limited to, the following:

| Amino Acid Change | | Codon Change | |
|---|---|---|---|
| S2079A | AGC | > | GCT |
|  | AGC | > | GCC |
|  | AGC | > | GCA |
|  | AGC | > | GCG |
| G1783A | GGA | > | GCT |
|  | GGA | > | GCC |
|  | GGA | > | GCA |
|  | GGA | > | GCG |
| A1786G | GCT | > | GGT |
|  | GCT | > | GGC |
|  | GCT | > | GGA |
|  | GCT | > | GGG |

With regard to embodiments 11-24, corresponding positions to 1781m 1783, 1786, 2078, 2079, and 2080 based on the numbering of the blackgrass reference sequence are well known in the art and readily obtainable from appropriate sequence databases. By way of example, the following table shows the corresponding positions in the rice ACCase sequence:

| Am | OsI | OsJ |
|---|---|---|
| I1781 | I1792 | I1779 |
| G1783 | G1794 | G1781 |
| A1786 | A1797 | A1784 |
| D2078 | D2089 | D2076 |
| S2079 | S2090 | S2077 |
| K2080 | K2091 | K2078 |
| C2088 | C2099 | C2086 |

Am: *Alopecurus myosuroide*;
OsI: *Oryza sativa indica* variety;
OsJ: *Oryza sativa japonica* variety 25. A method for producing a plant or plant cell with a mutated EPSPS gene, comprising introducing into a plant cell a gene repair oligonucleobase (GRON) with a targeted mutation in an 5-enol pyruvylshikimate-3-phosphate synthase (EPSPS) gene to produce a plant cell with an EPSPS gene that expresses an EPSPS protein comprising a mutation at one or more amino acid positions corresponding to a position selected from the group consisting of 96, 97 and 101 based on the numbering of the amino acid sequence for the *Escherichia coli* reference sequence SEQ ID NO:2 or at an analogous amino acid residue in an EPSPS paralog.

26. A method for producing a plant or plant cell with a mutated EPSPS gene, comprising introducing into a plant cell a DNA cutter and a gene repair oligonucleobase (GRON) with a targeted mutation in an 5-enol pyruvylshikimate-3-phosphate synthase (EPSPS) gene to produce a plant cell with an EPSPS gene that expresses an EPSPS protein comprising a mutation at one or more amino acid positions corresponding to a position selected from the group consisting of 96, 97 and 101 based on the numbering of the amino acid sequence for the *Escherichia coli* reference sequence SEQ ID NO:2 or at an analogous amino acid residue in an EPSPS paralog.

27. A plant or cell with a mutated EPSPS gene, wherein said plant or cell is made by a method introducing into a plant cell a DNA cutter and a gene repair oligonucleobase (GRON) with a targeted mutation in an 5-enol pyruvyl-shikimate-3-phosphate synthase (EPSPS) gene to produce a plant cell with an EPSPS gene that expresses an EPSPS protein comprising a mutation at one or more amino acid positions corresponding to a position selected from the group consisting of 96, 97 and 101 based on the numbering of the amino acid sequence for the *Escherichia coli* reference sequence SEQ ID NO:2 or at an analogous amino acid residue in an EPSPS paralog.

28. The plant or cell of any of the preceding embodiments, or a plant or cell made by any of the methods of the preceding embodiments, wherein the plant or plant cell expresses an EPSPS protein comprising a mutation at one or more amino acid positions are selected from the group consisting of a glycine to alanine at a position corresponding to position 96 of SEQ ID NO:2; a threonine to isoleucine at a position corresponding to position 97 of SEQ ID NO:2; a proline to alanine at a position corresponding to position 101 of SEQ ID NO:2; a proline to serine at a position corresponding to position 101 of SEQ ID NO:2; and a proline to threonine at a position corresponding to position 101 of SEQ ID NO:2.

29. The plant or cell of any of the preceding embodiments, or a plant or cell made by any of the methods of the preceding embodiments, wherein the plant or plant cell expresses an EPSPS protein comprising mutation combinations selected from the group consisting of a threonine to isoleucine at a position corresponding to position 97 of SEQ ID NO:2 and a proline to alanine at a position corresponding to position 101 of SEQ ID NO:2; a threonine to isoleucine at a position corresponding to position 97 of SEQ ID NO:2 and a proline to alanine at a position corresponding to position 101 of SEQ ID NO:2; a threonine to isoleucine at a position corresponding to position 97 of SEQ ID NO:2 and a proline to serine at a position corresponding to position 101 of SEQ ID NO:2; and a threonine to isoleucine at a position corresponding to position 97 of SEQ ID NO:2 and a proline to threonine at a position corresponding to position 101 of SEQ ID NO:2.

With regard to embodiments 25-30, corresponding positions to 96, 97 and 101 based on the numbering of the *Escherichia coli* reference sequence SEQ ID NO:2 are well known in the art and readily obtainable from appropriate sequence databases. See e.g., U.S. Pat. No. 8,268,622. By way of example, the following table shows the corresponding positions in the flax EPSPS sequence:[A1][A2]

|  | Flax EPSPS | |
| --- | --- | --- |
| *E. coli* EPSPS | Gene1 | Gene2 |
| G96 | G176 | G177 |
| T97 | T177 | T178 |
| P101 | P181 | P182 |

*E. coli* EPSPS sequence is AroA having the sequence
(SEQ ID NO: 10)
MESLTLQPIARVDGTINLPGSKTVSNRALLLAALAHGKTVLTNLLDSDDV
RHMLNALTALGVSYTLSADRTRCEIIGNGGPLHAEGALELFLGNAGTAMR
PLAAALCLGSNDIVLTGEPRMKERPIGHLVDALRLGGAKITYLEQENYPP
LRLQGGFTGGNVDVDGSVSSQFLTALLMTAPLAPEDTVIRIKGDLVSKPY
IDITLNLMKTFGVEIENQHYQQFVVKGGQSYQSPGTYLVEGDASSASYFL
AAAAIKGGTVKVTGIGRNSMQGDIRFADVLEKMGATICWGDDYISCTRGE
LNAIDMDMNHIPDAAMTIATAALFAKGTTRLRNIYNWRVKETDRLFAMAT
ELRKVGAEVEEGHDYIRITPPEKLNFAEIATYNDHRMAMCFSLVALSDTP
VTILDPKCTAKTFPDYFEQLARISQAA Flax gene 1 sequence is lcl - g41452_1333 having the sequence
(SEQ ID NO: 11)
MALVTKICGGANAVALPATFGTRRTKSISSSVSFRSSTSPPSLKQRRRSG
NVAAAAAAPLRVSASLTTAAEKASTVPEEVVLQPIKDISGIVTLPGSKSL
SNRILLLAALSEGTTVVDNLLNSDDVHYMLGALKTLGLNVEHSSEQKRAI
VEGCGGVFPVGKLAKNDIELFLGNAGTAMRPLTAAVTAAGGNSSYILDGV
PRMRERPIGDLVVGLKQLGADVTCSSTSCPPVHVNGQGGLPGGKVKLSGS
ISSQYLTALLMAAPLALGDVEIEIVDKLISVPYVDMTLKLMERFGVAVEH
SGSWDRFFVKGGQKYKSPGNAYVEGDASSASYFLAGAAITGGTITVEGCG
TSSLQGDVKFAEVLEKMGAKVIWTENSVTVTGPPRDASGRKHLRAVDVNM
NKMPDVAMTLAVVALYADGPTAIRDVASWRVKETERMIAICTELRKLGAT
VEEGPDYCIITPPEKLNIAEIDTYDDHRMAMAFSLAACADVPVTIRDPGC
TKKTFPDYFEVLERYTKH Flax gene 2 sequence is lcl - g40547_1271 having the sequence
(SEQ ID NO: 12)
MAQVTKICGGANAVALPATFGTRRTKSISSSVSFRSSTSPPSLKQRRLLG
NVAAAAAAPLRISASLATAAEKASTVPEEIVLQPIKDISGIVTLPGSKS
LSNRILLLAALSEGKTVVDNLLNSDDVHYMLGALKTLGLNVEHSSEQKRA
IVEGRGGVFPVGKLGKNDIELFLGNAGTAMRPLTAAVTAAGGNSSYILDG
VPRMRERPIGDLVVGLKQLGADVSCSSTSCPPVHVNAKGGLPGGKVKLSG
SISSQYLTALLMAAPLALGDVEIEIVDKLISVPYVDMTLKLMERFGVAVE
HSGSWDRFFVKGGQKYKSPGNAYVEGDASSASYFLAGAAITGGTITVEGC
GTSSLQGDVKFAEVLEKMGAKVTWTETSVTVTGPPRDASGKKHLRAVDVN
MNKMPDVAMTLAVVALYADGPTAIRDVASWRVKETERMIAVCTELRKLGA
TVEEGPDYCIITPPEKLSIAEIDTYDDHRMAMAFSLAACADVPVTIRDPG
CTKKTFPDYFEVLERYTKH 30. The method or cell of any of the preceding embodiments, wherein said DNA cutter is one or more selected from a CRISPR, a TALEN, a zinc finger, meganuclease, and a DNA-cutting antibiotic.

31. The method or cell of any of the preceding embodiments, wherein said DNA cutter is a CRISPR or a TALEN.

32. The method or cell of any of the preceding embodiments, wherein said DNA cutter is a CRISPR.

33. The method or cell of any of the preceding embodiments, wherein said DNA cutter is a TALEN.
34. The method or cell of any of the preceding embodiments, wherein said DNA cutter is one or more DNA-cutting antibiotics selected from the group consisting of bleomycin, zeocin, phleomycin, tallysomycin and pepleomycin.
35. The method or cell of any of the preceding embodiments, wherein said DNA cutter is zeocin.
36. The method or cell of any of the preceding embodiments, wherein said GRON is single stranded.
37. The method or cell of any of the preceding embodiments, wherein the GRON is a chemically protected oligonucleotide.
38. The method or cell of any of the preceding embodiments, wherein the GRON comprises a chemically protected oligonucleotide protected at the 5' end.
39. The method or cell of any of the preceding embodiments, wherein the GRON comprises a chemically protected oligonucleotide protected at the 3' end.
40. The method or cell of any of the preceding embodiments, wherein the GRON comprises a chemically protected oligonucleotide protected at the 5' and 3' ends.
41. The method or cell of any of the preceding embodiments, wherein the GRON comprises one or more selected from a Cy3 group, a 3P5 group, and a 2'-O-methyl group.
42. The method or cell of any of the preceding embodiments, wherein the GRON comprises a Cy3 group.
43. The method or cell of any of the preceding embodiments, wherein the GRON comprises a Cy3 group at the first base on the 5' end.
44. The method or cell of any of the preceding embodiments, wherein the GRON comprises a Cy3 group at the first base on the 3' end.
45. The method or cell of any of the preceding embodiments, wherein the GRON comprises a 3P5 group.
46. The method or cell of any of the preceding embodiments, wherein the GRON comprises two or more 3P5 groups.
47. The method or cell of any of the preceding embodiments, wherein the GRON comprises three or more 3P5 groups.
48. The method or cell of any of the preceding embodiments, wherein the GRON comprises a 3P5 group at the first base on the 5' end.
49. The method or cell of any of the preceding embodiments, wherein the GRON comprises a 3P5 group at the first base on the 3' end.
50. The method or cell of any of the preceding embodiments, wherein the GRON comprises a 2'-O-methyl group.
51. The method or cell of any of the preceding embodiments, wherein the GRON comprises two or more 2'-O-methyl groups.
52. The method or cell of any of the preceding embodiments, wherein the GRON comprises a 2'-O-methyl group at the first base on the 5' end.
53. The method or cell of any of the preceding embodiments, wherein the GRON has a 2'-O-methyl group at the first base on the 5' end and does not have any other 2'-O-methyl groups.
54. The method or cell of any of the preceding embodiments, wherein the GRON comprises a 2'-O-methyl group on each of the first two or more bases at the 5' end.
55. The method or cell of any of the preceding embodiments, wherein the GRON comprises a 2'-O-methyl group on each of the first three or more bases at the 5' end.
56. The method or cell of any of the preceding embodiments, wherein the GRON comprises a 2'-O-methyl group on each of the first four or more bases at the 5' end.
57. The method or cell of any of the preceding embodiments, wherein the GRON comprises a 2'-O-methyl group on each of the first five or more bases at the 5' end.
58. The method or cell of any of the preceding embodiments, wherein the GRON comprises a 2'-O-methyl group on each of the first six or more bases at the 5' end.
59. The method or cell of any of the preceding embodiments, wherein the GRON comprises a 2'-O-methyl group on each of the first seven or more bases at the 5' end.
60. The method or cell of any of the preceding embodiments, wherein the GRON comprises a 2'-O-methyl group on each of the eight four or more bases at the 5' end.
61. The method or cell of any of the preceding embodiments, wherein the GRON comprises a 2'-O-methyl group on each of the first nine or more bases at the 5' end.
62. The method or cell of any of the preceding embodiments, wherein the GRON comprises a 2'-O-methyl group on each of the first ten or more bases at the 5' end.
63. The method or cell of any of the preceding embodiments, wherein the GRON comprises 1, 2, 3, 4, 5, 6, 7, 8, 9, or 10 RNA base at the 5' end.
64. The method or cell of any of the preceding embodiments, wherein said GRON has a wobble base pair relative to the target sequence for the genetic change.
65. The method or cell of any of the preceding embodiments, wherein said GRON is between 15 and 60 nucleotides in length.
66. The method or cell of any of the preceding embodiments, wherein said GRON is 41 nucleotides in length.
67. The method or cell of any of the preceding embodiments, wherein said GRON is between 50 and 110 nucleotides in length.
68. The method or cell of any of the preceding embodiments, wherein said GRON is 101 nucleotides in length.
69. The method or cell of any of the preceding embodiments, wherein said GRON is between 150 and 210 nucleotides in length.
70. The method or cell of any of the preceding embodiments, wherein said GRON is 201 nucleotides in length.
71. The method or cell of any of the preceding embodiments, wherein said GRON is between 70 and 210 nucleotides in length.
72. The method or cell of any of the preceding embodiments, wherein said GRON is longer than 70 nucleotides in length.
73. The method or cell of any of the preceding embodiments, wherein said GRON is longer than 100 nucleotides in length.
74. The method or cell of any of the preceding embodiments, wherein said GRON is longer than 165 nucleotides in length.
75. The method or cell of any of the preceding embodiments, wherein said GRON is longer than 175 nucleotides in length.
76. The method or cell of any of the preceding embodiments, wherein said GRON is longer than 185 nucleotides in length.
77. The method or cell of any of the preceding embodiments, wherein said GRON is longer than 195 nucleotides in length.
78. The method or cell of any of the preceding embodiments, wherein said GRON is longer than 200 nucleotides in length.
79. The method or cell of any of the preceding embodiments, wherein said GRON is longer than 210 nucleotides in length.

80. The method or cell of any of the preceding embodiments, wherein said GRON is longer than 220 nucleotides in length.
81. The method or cell of any of the preceding embodiments, wherein said GRON is longer than 230 nucleotides in length.
82. The method or cell of any of the preceding embodiments, wherein said GRON is longer than 240 nucleotides in length.
83. The method or cell of any of the preceding embodiments, wherein said GRON is longer than 250 nucleotides in length.
84. The method or cell of any of the preceding embodiments, wherein said GRON is longer than 260 nucleotides in length.
85. The method or cell of any of the preceding embodiments, wherein said GRON is longer than 270 nucleotides in length.
86. The method or cell of any of the preceding embodiments, wherein said GRON is longer than 280 nucleotides in length.
87. The method or cell of any of the preceding embodiments, wherein said GRON is longer than 290 nucleotides in length.
88. The method or cell of any of the preceding embodiments, wherein said GRON is longer than 300 nucleotides in length.
89. The method or cell of any of the preceding embodiments, wherein said GRON is longer than 400 nucleotides in length.
90. The method or cell of any of the preceding embodiments, wherein said GRON is longer than 500 nucleotides in length.
91. The method or cell of any of the preceding embodiments, wherein said GRON is longer than 600 nucleotides in length.
92. The method or cell of any of the preceding embodiments, wherein said GRON is longer than 700 nucleotides in length.
93. The method or cell of any of the preceding embodiments, wherein said GRON is longer than 800 nucleotides in length.
94. The method or cell of any of the preceding embodiments, wherein said GRON is longer than 900 nucleotides in length.
95. The method or cell of any of the preceding embodiments, wherein said GRON is longer than 1000 nucleotides in length.
96. The method or cell of any of the preceding embodiments wherein said plant is selected from the group consisting of canola, sunflower, corn, tobacco, sugar beet, cotton, maize, wheat, barley, rice, alfalfa, barley, sorghum, tomato, mango, peach, apple, pear, strawberry, banana, melon, cassava, potato, carrot, lettuce, onion, soy bean, soya spp, sugar cane, pea, chickpea, field pea, fava bean, lentils, turnip, rutabaga, brussel sprouts, lupin, cauliflower, kale, field beans, poplar, pine, eucalyptus, grape, citrus, triticale, alfalfa, rye, oats, turf and forage grasses, flax, oilseed rape, mustard, cucumber, morning glory, balsam, pepper, eggplant, marigold, lotus, cabbage, daisy, carnation, tulip, iris, and lily.
97. The method or cell of any of the preceding embodiments wherein said plant is canola.
98. The method or cell of any of the preceding embodiments wherein said plant is corn
99. The method or cell of any of the preceding embodiments wherein said plant is maize.
100. The method or cell of any of the preceding embodiments wherein said plant is rice.
101. The method or cell of any of the preceding embodiments wherein said plant is sorghum.
102. The method or cell of any of the preceding embodiments wherein said plant is potato.
103. The method or cell of any of the preceding embodiments wherein said plant is soy bean.
104. The method or cell of any of the preceding embodiments wherein said plant is flax.
105. The method or cell of any of the preceding embodiments wherein said plant is oilseed rape.
106. The method or cell of any of the preceding embodiments wherein said plant is cassava.
107. The method or cell of any of the preceding embodiments wherein said plant is sunflower.
108. A method of causing a genetic change in a plant cell, said method comprising exposing said cell to a CRISPR and a modified GRON.
109. The method or cell of any of the preceding embodiments wherein multiple genetic changes are made.
110. The method or cell of any of the preceding embodiments wherein two or more guide RNAs are used.
111. The method or cell of any of the preceding embodiments wherein each of the more than one guide RNAs is complimentary to a different target for genetic change.
112. The method or cell of any of the preceding embodiments wherein the CRISPR includes a nickase.
113. The method or cell of any of the preceding embodiments wherein the DNA cutter includes two or more nickases.
114. The method or cell of any of the preceding embodiments wherein two or more nickases cuts on opposite strands of the target nucleic acid sequence.
115. The method or cell of any of the preceding embodiments wherein two or more nickases cuts on the same strand of the target nucleic acid sequence.
116. A non-transgenic herbicide resistant or tolerant[A3][A4] plant made by the method or from the cell of one any of the preceding embodiments.
117. The method or cell of any of the preceding embodiments, wherein said plant cell has a genetic change or mutation in Acetyl-Coenzyme A carboxylase (ACCase) and is selected from the group consisting of barley, maize, millet, oats, rye, rice, sorghum, sugarcane, turf grasses, and wheat.
118. The method or cell of any of the preceding embodiments, wherein said plant cell has a genetic change or mutation in Acetyl-Coenzyme A carboxylase (ACCase) and is resistant or tolerant to one or more herbicides.
119. The method or cell of any of the preceding embodiments, wherein said plant cell has a genetic change or mutation in Acetyl-Coenzyme A carboxylase (ACCase), is resistant to one or more ACCase-inhibiting herbicides.
120. The method Or ell of any of the preceding embodiments, wherein said plant cell has a genetic change or mutation in Acetyl-Coenzyme A carboxylase (ACCase), is resistant to one or more herbicides selected from the group consisting of alloxydim, butroxydim, clethodim, cloproxydim, cycloxydim, sethoxydim, tepraloxydim, tralkoxydim, chlorazifop, cloclinafop, clofop, diclofop, fenoxaprop, fenoxaprop-P, fenthiaprop, fluazifop, fluazifop-P, haloxyfop, haloxyfop-P, isoxapyrifop, propaquizafop, quizalofop, quizalofop-P, trifop, pinoxaden, agronomically acceptable salts and esters of any of these herbicides, and combinations thereof. [A5][A6]

121. The method or cell of any of the preceding embodiments, wherein said plant cell has a genetic change or mutation in 5-enolpyruvylshikimate-3-phosphate synthase (EPSPS), and wherein said plant cell is selected from the group consisting of corn, wheat, rice, barley, sorghum, oats, rye, sugarcane, soybean, cotton, sugarbeet, oilseed rape, canola, flax, cassava, sunflower, potato, tobacco, tomato, alfalfa, poplar, pine, eucalyptus, apple, lettuce, peas, lentils, grape and turf grasses.

122. The method or cell of any of the preceding embodiments, wherein said plant or plant cell has a genetic change or mutation in 5-enolpyruvylshikimate-3-phosphate synthase (EPSPS), and wherein plant or plant cell is resistant to at least one herbicide.

123. The method or cell of any of the preceding embodiments, wherein said plant or plant cell has a genetic change or mutation in 5-enolpyruvylshikimate-3-phosphate synthase (EPSPS), and wherein plant or plant cell is resistant to a herbicide of the phosphonomethylglycine family.

124. The method or cell of any of the preceding embodiments, wherein said plant or plant cell has a genetic change or mutation in 5-enolpyruvylshikimate-3-phosphate synthase (EPSPS), and wherein plant or plant cell is resistant to glyphosate.

125. The method or cell of any of the preceding embodiments, wherein said plant or plant cell has a genetic change or mutation in 5-enolpyruvylshikimate-3-phosphate synthase (EPSPS), and wherein plant or plant cell is selected from the group consisting of corn, wheat, rice, barley, sorghum, oats, rye, sugarcane, soybean, cotton, sugarbeet, oilseed rape, canola, flax, cassava, sunflower, potato, tobacco, tomato, alfalfa, poplar, pine, eucalyptus, apple, lettuce, peas, lentils, grape and turf grasses.

126. The method or cell of any of the preceding embodiments, wherein the genetic change or mutation in the cell occurs at one allele of the gene.

127. The method or cell of any of the preceding embodiments, wherein the genetic change or mutation in the cell occurs at two alleles of the gene [A7].

128. The method or cell of any of the preceding embodiments, wherein the genetic change or mutation in the cell occurs at three alleles of the gene.

129. The method or cell of any of the preceding embodiments, wherein the genetic change or mutation in the cell occurs at four alleles of the gene.

130. The method or cell of any of the preceding embodiments, wherein the genetic change or mutation in the cell occurs at one, two, three, four, five, six, seven, eight, nine, ten, eleven, or twelve alleles of the gene.

131. The method or cell of any of the preceding embodiments, wherein the genetic change or mutation in the cell comprises a deletion or insertion resulting in a knockout of one allele of the gene.

132. The method or cell of any of the preceding embodiments, wherein the genetic change or mutation in the cell comprises a deletion or insertion resulting in a knockout of two alleles of the gene.

133. The method or cell of any of the preceding embodiments, wherein the genetic change or mutation in the cell comprises a deletion or insertion resulting in a knockout of three alleles of the gene.

134. The method or cell of any of the preceding embodiments, wherein the genetic change or mutation in the cell comprises a deletion or insertion resulting in a knockout of four alleles of the gene.

135. The method or cell of any of the preceding embodiments, wherein the genetic change or mutation in the cell comprises a deletion or insertion resulting in a knockout of one, two, three, four, five, six, seven, eight, nine, ten, eleven, or twelve alleles of the gene.

136. The method or cell of any of the preceding embodiments, wherein the genetic change or mutation in the cell occurs at one allele of the gene and a second allele of the gene comprises a deletion or insertion resulting in a knockout of said second allele.

137. The method or cell of any of the preceding embodiments, wherein the genetic change or mutation in the cell occurs at one allele of the gene and a second allele and third allele of the gene comprises a deletion or insertion resulting in a knockout of said second allele and said third allele.

138. The method or cell of any of the preceding embodiments, wherein the genetic change or mutation in the cell occurs at one allele of the gene and a second allele, third allele, and fourth allele of the gene comprises a deletion or insertion resulting in a knockout of said second allele, said third allele and said fourth allele.

139. The method or cell of any of the preceding embodiments, wherein the genetic change in the cell comprises at least one mutation at one allele and at least one knockout in another allele.

140. The method or cell of any of the preceding embodiments, wherein the genetic change in the cell comprises at least one mutation at one allele and at least one knockout in at least one other allele.

141. The method or cell of any of the preceding embodiments, wherein the genetic change in the cell comprises at least one mutation at one allele and at least one knockout in at least two other alleles.

142. The method or cell of any of the preceding embodiments, wherein the genetic change in the cell comprises at least one mutation at one allele and at least one knockout in at least three other alleles.

143. The method or cell of any of the preceding embodiments, wherein the genetic change in the cell comprises at least one mutation at one allele and a knockout in all other alleles.

EXAMPLES

The following are examples, which illustrate procedures for practicing the methods and compositions described herein. These examples should not be construed as limiting.

Example 1: GRON Length

Sommer et al., (Mol Biotechnol. 33:115-22, 2006) describes a reporter system for the detection of in vivo gene conversion which relies upon a single nucleotide change to convert between blue and green fluorescence in green fluorescent protein (GFP) variants. This reporter system was adapted for use in the following experiments using *Arabidopsis thaliana* as a model species in order to assess efficiency of GRON conversion following modification of the GRON length.

In short, for this and the subsequent examples an *Arabidopsis thaliana* line with multiple copies of a blue fluorescent protein gene was created by methods known to those skilled in the art (see, e.g., Clough and Brent, 1998). Root-derived meristematic tissue cultures were established with this line, which was used for protoplast isolation and culture (see, e.g., Mathur et al., 1995). GRON delivery into protoplasts was achieved through polyethylene glycol (PEG) mediated GRON uptake into protoplasts. A method using a 96-well format, similar to that described by similar to that described by Fujiwara and Kato (2007) was used. In the following the protocol is briefly described. The volumes given are those applied to individual wells of a 96-well dish.

1. Mix 6.25 µl of GRON (80 µM) with 25 µl of *Arabidopsis thaliana* BFP transgenic root meristematic tissue-derived protoplasts at $5 \times 10^6$ cells/ml in each well of a 96 well plate.
2. 31.25 µl of a 40% PEG solution was added and the protoplasts were mixed.
3. Treated cells were incubated on ice for 30 min.
4. To each well 200 µl of W5 solution was added and the cells mixed.
5. The plates were allowed to incubate on ice for 30 min allowing the protoplasts to settle to the bottom of each well.
6. 200 µl of the medium above the settled protoplasts was removed.
7. 85 µl of culture medium (MSAP, see Mathur et al., 1995) was added.
8. The plates were incubated at room temperate in the dark for 48 hours. The final concentration of GRON after adding culture medium is 8 µM.

Forty eight hours after GRON delivery samples were analyzed by flow cytometry in order to detect protoplasts whose green and yellow fluorescence is different from that of control protoplasts (BFP0 indicates non-targeting GRONs with no change compared to the BFP target; C is the coding strand design and NC is the non-coding strand design). A single C to T nucleotide difference (coding strand) or G to A nucleotide targeted mutation (non-coding strand) in the center of the BFP4 molecules. The green fluorescence is caused by the introduction of a targeted mutation in the BFP gene, resulting in the synthesis of GFP. The results are shown in FIG. 1.

Table 2 shows the sequences of exemplary 101-mer and 201-mer BFP4/NC 5'-3P5/3'-3P5 GRONs designed for the conversion of a blue fluorescent protein (BFP) gene to green fluorescence. "3P5" denotes 3 phosphothioate linkages at each of the 5' and 3' oligo ends.

TABLE 2

Exemplary GRON Nucleotide Sequences for BFP to GFP conversion

| GRON Name | GRON Nucleotide Sequence |
|---|---|
| BFP4/NC 101-mer | G* T*C*G TGC TGC TTC ATG TGG TCG GGG TAG CGG CTG AAG CAC TGC ACG CCG TAG GTG AAG GTG GTC ACG AGG GTG GGC CAG GGC ACG GGC AGC TTG CCG G*T*G* G (SEQ ID NO: 13) |
| BFP0/NC 101-mer | G* T*C*G TGC TGC TTC ATG TGG TCG GGG TAG CGG CTG AAG CAC TGC ACG CCG TGG GTG AAG GTG GTC ACG AGG GTG GGC CAG GGC ACG GGC AGC TTG CCG G*T*G *G (SEQ ID NO: 14) |
| BFP4/C 101-mer | C *C*A*C CGG CAA GCT GCC CGT GCC CTG GCC CAC CCT CGT GAC CAC CTT CAC CTA CGG CGT GCA GTG CTT CAG CCG CTA CCC CGA CCA CAT GAA GCA GCA C*G*A *C (SEQ ID NO: 15) |

TABLE 2-continued

Exemplary GRON Nucleotide Sequences for BFP to GFP conversion

| GRON Name | GRON Nucleotide Sequence |
|---|---|
| BFP0/C 101-mer | C*C*A*CCGGCAAGCTGCCCGTGCCCTGGCCCACC CTCGTGACCACCTTCACCCACGGCGTGCAGTGCTT CAGCCGCTACCCCGACCACATGAAGCAGCAC*G*A* C (SEQ ID NO: 16) |
| BFP4/NC 201-mer | A*A*G*ATGGTGCGCTCCTGGACGTAGCCTTCGGG CATGGCGGACTTGAAGAAGTCGTGCTGCTTCATGT GGTCTGGGTAGCGGCTGAAGCACTGCACGCCGTAG GTGAAGGTGGTCACGAGGGTGGGCCAGGGCACGGG CAGCTTGCCGGTGGTGCAGATGAACTTCAGGGTCA GCTTGCCG TAGGTGGCATCGCCCTCG *C*C*C (SEQ ID NO: 17) |
| BFP0/NC 201-mer | A*A*G*TGGTGCGCTCCTGGACGTAGCCTTCGGGC ATGGCGGACTTGAAGAAGTCGTGCTGCTTCATGTG GTCGGGGTAGCGGCTGAAGCACTGCACGCCGTGGG TGAAGGTGGTCACGAGGGTGGGCCAGGGCACGGGC AGCTTGCCGGTGTGCAGATGAACTTCAGGGTCAG CTTGCCG TAGGTGGCATCGCCCTCG *C*C*C (SEQ ID NO: 18) |
| BFP4/C 201-mer | G*G*G*CGAGGGCGATGCCACCTACGGCAAGCTGA CCCTGAAGTTCATCTGCACCACCGGCAAGCTGCCC GTGCCCTGGCCCACCCTCGTGACCACCTTCACCTA CGGCGTGCAGTGCTTCAGCCGCTACCCCGACCACA TGAAGCAGCACGACTTCTTCAAGTCCGCCATGCCC GAAGGCTACGTCCAGGA GCGCACCAT *C*T*T (SEQ ID NO: 19) |
| BFP0/C 201-mer | G*G*G*CGAGGGCGATGCCACCTACGGCAAGCTGA CCCTGAAGTTCATCTGCACCACCGGCAAGCTGCCC GTGCCCTGGCCCACCCTCGTGACCACCTTCACCCA CGGCGTGCAGTGCTTCAGCCGCTACCCCGACCACA TGAAGCAGCACGACTTCTTCAAGTCCGCCATGCCC GAAGGCTACGTCCAGGA GCGCACCAT*C*T*T (SEQ ID NO: 20) |

* = PS linkage (phosphothioate)

Example 2: Conversion Rates Using 5'Cy3/3'idC Labeled GRONs

The purpose of this series of examples is to compare the efficiencies of phosphothioate (PS) labeled GRONs (having 3 PS moieties at each end of the GRON) to the 5'Cy3/3'idC labeled GRONs. The 5'Cy3/3'idC labeled GRONs have a 5' Cy3 fluorophore (amidite) and a 3' idC reverse base. Efficiency was assessed using conversion of blue fluorescent protein (BFP) to green fluorescence.

In all three examples, done either by PEG delivery of GRONs into protoplasts in individual Falcon tubes (labeled "Tubes") or in 96-well plates (labeled "96-well dish"), there was no significant difference between the different GRON chemistries in BFP to GFP conversion efficiency as determined by cytometry (FIG. 1).

Example 3: Comparison Between 41-Mer BFP4/NC 5'-3PS/3'-3PS GRON and 2'-O-Me GRONs The purpose of this series of examples is to compare the conversion efficiencies of the phosphothioate (PS) labeled GRONs with 3P5 moieties at each end of the GRON to 2'-O-Me or "Okazaki fragment GRONs" in the presence and absence of a member of the bleomycin family, Zeocin™ (1 mg/ml) to induce DNA breaks. The designs of these GRONs are depicted in FIG. 2. GRONs were delivered into *Arabidopsis thaliana* BFP protoplasts by PEG treatment and BFP to GFP conversion was determined at 24 h post treatment by cytometry. Samples treated with zeocin (1 mg/ml) were incubated with zeocin for 90 min on ice prior to PEG treatment.

In general the presence of zeocin (1 mg/ml) increased BFP to GFP conversion as determined by cytometry (Table 3). In both the presence and absence of zeocin, the NC Okazaki GRON containing one 2'-OMe group on the first RNA base at the 5' end of the GRON was more efficacious at converting BFP to GFP when compared to the NC Okazaki GRON containing one 2'-OMe group on each of the first nine 5' RNA bases (FIG. 2 and Table 3).

In all examples, there was no significant difference between the 41-mer BFP4/NC 5'3P5/3'3P5 and the 71-mer Okazaki Fragment BFP4/NC GRON that contains one 5' 2'-0 me group on the first 5' RNA base (denoted as BFP4 71-mer (1) NC) in BFP to GFP conversion in both the presence or absence of 1 mg/ml of zeocin as determined by cytometry (FIG. 2 and Table 3). It is important to note that in the presence of zeocin (and expected for bleomycin, phleomycin, tallysomycin, pepleomycin and other members of this family of antibiotics) that conversion becomes strand independent (i.e., both coding (C) and non-coding (NC) GRONs with the designs tested in these examples display approximately equal activity).

TABLE 3

Comparison of a standard GRON design with Okazaki fragment GRON designs in the presence and absence of a glycopeptide antibiotic zeocin.

| Exp. | BFP4 41-mer | | BFP4 71-mer (0) | | BFP4 71-mer (1) | | BFP4 71-mer (9) | |
| --- | --- | --- | --- | --- | --- | --- | --- | --- |
| Name | NC | C | NC | C | NC | C | NC | C |
| Zeocin (+) | | | | | | | | |
| APT043 | 0.13 | 0.0875 | 0.2275 | 0.2075 | 0.355 | 0.2275 | 0.2325 | 0.195 |
| APT066 | 1.9 | 0.713 | 0.762 | 0.683 | 1.318 | 0.7103 | 0.769 | 0.883 |
| Mean | 1.015 | 0.40025 | 0.49475 | 0.44525 | 0.8365 | 0.4689 | 0.50075 | 0.539 |
| Std Dev | 1.251579 | 0.442295 | 0.377949 | 0.336229 | 0.680944 | 0.341391 | 0.379363 | 0.486489 |
| SE | 0.885134 | 0.312797 | 0.26729 | 0.237786 | 0.481573 | 0.241436 | 0.268291 | 0.344052 |
| Zeocin (−) | | | | | | | | |
| APT043 | nd | nd | 0.1875 | 0.0175 | 0.21 | 0.025 | 0.1 | 0.0225 |
| APT066 | 0.109 | 0.007 | 0.112 | 0.005 | 0.141 | 0.023 | 0.065 | 0.021 |
| Mean | 0.109 | 0.007 | 0.14975 | 0.01125 | 0.1755 | 0.024 | 0.0825 | 0.02175 |
| Std Dev | na | na | 0.053387 | 0.008839 | 0.04879 | 0.001414 | 0.024749 | 0.001061 |
| SE | na | na | 0.037756 | 0.006251 | 0.034505 | 0.001 | 0.017503 | 0.00075 |

| | | |
| --- | --- | --- |
| BFP4 71-mer (0) NC / C | | 5' first 10 bp are RNA and GRON has no protection |
| BFP4 71-mer (1) NC / C | | 5' first 10 bp are RNA and first bp on the 5' end has a 2' O—Me |
| BFP4 71-mer (9) NC / C | | 5' first 10 bp are RNA and first nine bp on the 5' end has a 2' O—Me |

Example 4: Comparison Between 41-Mer, 101-Mer and 201-Mer BFP4/NC 5'-3PS/3'-3PS GRONs The purpose of this series of examples was to compare the conversion efficiencies (in the presence and absence of zeocin) of the phosphothioate (PS) labeled GRONs with 3P5 moieties at each end of the GRON of different lengths: 41-mer, 101-mer and 201-mer shown in Table 2. Again, the presence of zeocin (1 mg/ml) increased BFP to GFP conversion rates as determined by cytometry (Table 4). The overall trend in all three examples was linear with increasing NC GRON length in both the presence and absence of zeocin. Except for the BFP-4/NC/101 and BFP-4/C/101 in the presence of zeocin, this had conversion rates that were close to equal but lower than the 41-mer NC GRON. This is in contrast to all previous examples in which the BFP-4/41 coding and non-coding GRONs were used, where the non-coding was always far superior to the coding GRON. This asymmetry in conversion frequency also applies to the BFP-4/201 GRONs used in this example series.

TABLE 4

| Exp. | BFP4 41-mer | | BFP4 101-mer | | BFP4 201-mer | |
| --- | --- | --- | --- | --- | --- | --- |
| Name | NC | C | NC | C | NC | C |
| Zeocin (+) | | | | | | |
| APT038 | 0.2425 | 0.1275 | 0.3025 | 0.2575 | 0.97 | 0.245 |
| APT043 | 0.13 | 0.0875 | 0.185 | 0.2275 | 0.66 | 0.1875 |

TABLE 4-continued

| Exp. | BFP4 41-mer | | BFP4 101-mer | | BFP4 201-mer | |
|---|---|---|---|---|---|---|
| Name | NC | C | NC | C | NC | C |
| APT047 | 0.3975 | 0.145 | 0.19 | 0.125 | 0.235 | 0.085 |
| APT052 | 0.3275 | nd | 0.17 | 0.21 | 0.585 | 0.225 |
| APT052 | nd | nd | 0.3225 | 0.3175 | 0.5075 | 0.3125 |
| APT058 | 1.4275 | nd | 1.2 | nd | 1.9 | nd |
| APT066 | 1.9 | 0.713 | 0.992 | 1.05 | 1.7 | 0.916 |
| Mean | 0.7375 | 0.26825 | 0.480286 | 0.364583 | 0.936786 | 0.3285 |
| Std Dev | 0.7382801 | 0.297475 | 0.428968 | 0.341634 | 0.630943 | 0.297412 |
| SE | 0.30146186 | 0.148738 | 0.162119 | 0.139499 | 0.238452 | 0.121442 |
| Zeocin (−) | | | | | | |
| APT038 | 0.05 | 0.01 | 0.1025 | 0.025 | 0.5725 | 0.025 |
| APT066 | 0.109 | 0.007 | 0.214 | 0.047 | 0.566 | 0.035 |
| Mean | 0.0795 | 0.0085 | 0.15825 | 0.036 | 0.56925 | 0.03 |
| Std Dev | 0.0417193 | 0.002121 | 0.078842 | 0.015556 | 0.004596 | 0.007071 |
| SE | 0.02950446 | 0.0015 | 0.055758 | 0.011002 | 0.00325 | 0.005001 |

Example 5: Delivery of Cas9 Protein into Plants

This example makes use of direct delivery of recombinant Cas9 protein to plant cells as an alternative to delivery of CRISPR-Cas expression plasmids. This method employs carriers such as cell penetrating peptides (CPP), transfection liposome reagents, poly(ethylene glycol) (PEG) either alone or in combination to allow for delivery of active recombinant Cas9 protein to cells.

Methods

BFP transgenic *Arabidopsis thaliana* protoplasts derived from induced root tissue are seeded on a flat-bottom 96-well plate at 250,000 cells per well at a cell density of $1 \times 10^7$ cells/ml. Fluorescently-tagged recombinant Cas9 protein (1 μg) pre-coated with CPPs at 20:1, 10: or 5:1 and other CPP to cargo ratio (TAT, Penetratin, Chariot™, PEP-1 or others for example) or encapsulated with liposome reagents are then mixed with the seeded protoplasts and incubated at 23° C. for 2-6 h to allow for Cas9/carrier complexes to penetrate the cells. In another series of treatments fluorescently-tagged recombinant Cas9 protein (1 μg) either pre-coated with CPPs as described above or not coated are introduced to protoplasts using PEG methodology. Protoplasts were then analyzed by flow cytometry 24 h after treatment in order to determine the percentage of Cas9 positive protoplasts within a given treatment.

Example 6: CRISPR with 201-Mer±Wobble Base GRONs

The purpose of this series of examples is to demonstrate BFP to GFP conversion in our *Arabidopsis thaliana* BFP transgenic model system using CRISPRs to create targeted double-stranded breaks in the bfp gene and the 201-mer GRONs to mediate conversion. The BFP CRISPR targets the coding strand of the bfp gene and the conversion site is 27 bp upstream of the PAM sequence (FIG. 3). The GRON is used as a template to repair the double-stranded break in the bfp gene created by the CRISPR and along with converting the targeted gene from BFP to GFP, it introduces a wobble base in the bfp gene that corresponds to the PAM sequence of the BFP CRISPR as well. A wobble base in the PAM sequence of the BFP CRISPR is hypothesized to minimize re-cutting of the bfp gene by the CRISPRs once conversion has happened. This series of examples will help to address whether or not introducing a wobble base into the PAM sequence of the BFP CRISPR in converted bfp genes will increase conversion efficiencies.

Methods

BFP transgenic *Arabidopsis thaliana* protoplasts derived from induced root tissue were seeded on a flat-bottom 96-well plate, at 250,000 cells per well at a cell density of 1×107 cells/ml. The CRISPR encoded plasmids contain the mannopine synthase (MAS) promoter driving the Cas9 coding sequence with an rbcSE9 terminator and the *Arabidopsis* U6 promoter driving the sgRNA with a poly-T10 terminator ("T10" disclosed as SEQ ID NO:21). The CRISPR plasmids along with GRON were introduced into protoplasts by PEG mediated delivery at a final concentration of 0.05 μg/μl and 0.16 μM respectively. Protoplasts were incubated in the dark at 23° C. for 72 hours, and then they were analyzed by flow cytometer in order to determine the percentage of GFP positive protoplasts within a given treatment.

The CRISPR consists of two components: the plant codon-optimized *Streptococcus pyogenes* Cas9 (SpCas9) and sgRNA both of which were expressed from the same plasmid. The sgRNA is a fusion of CRISPR RNA (crRNA) and trans-activating crRNA (tracrRNA). The crRNA region contains the spacer sequence used to guide the Cas9 nuclease to the BFP target gene. In this example the BFP targets the bfp gene (FIG. 3). 201-mer GRONs targeting BFP with or without wobble bases were used to determine their effect on the rate of BFP to GFP conversion. Table 5 gives a list of the GRONs and their corresponding sequences.

TABLE 5

List of GRONs used in these examples (SEQ ID NOS: 17, 19, 17, and 22, respectively, in order of appearance)

| GRON Name | GRON Chemistry | GRON Sequence |
| --- | --- | --- |
| BFP4/NC 201-mer | 3PS | 5' AAGATGGTGCGCTCCTGGACGTAGCCTTCGGGCATGGCGGACTTGAAGAAGTCGTGCTGCTT CATGTGGTCTGGGTAGCGGCTGAAGCACTGCACGCCGTAGGTGAAGGTGGTCACGAGGGTGGG CCAGGGCACGGGCAGCTTGCCGGTGGTGCAGATGAACTTCAGGGTCAGCTTGCCGTAGGTGGC ATCGCCCTCGCCC 3' |
| BFP4/C 201-mer | 3PS | 5' GGGCGAGGGCGATGCCACCTACGGCAAGCTGACCCTGAAGTTCATCTGCACCACCGGCAAGC TGCCCGTGCCCTGGCCCACCCTCGTGACCACCTTCACCTACGGCGTGCAGTGCTTCAGCCGCTA CCCCGACCACATGAAGCAGCACGACTTCTTCAAGTCCGCCATGCCCGAAGGCTACGTCCAGGA GCGCACCATCTT 3' |
| BFP4/NC 201-mer (1 wobble) | 3PS | 5' AAGATGGTGCGCTCCTGGACGTAGCCTTCGGGCATGGCGGACTTGAAGAAGTCG TGCTGCTTCATGTGGTCTGGGTAGCGGCTGAAGCACTGCACGCCGTAGGTGAAGGTGGTCACG AGGGTGGGCCAGGGCACGGGCAGCTTGCCGGTGGTGCAGATGAACTTCAGGGTCAGCTTGCCG TAGGTGGCATCGCCCTCGCCC 3' |
| BFP4/C 201-mer (1 wobble) | 3PS | 5' GGGCGAGGGCGATGCCACCTACGGCAAGCTGACCCTGAAGTTCATCTGCACCACCG GCAAGCTGCCCGTGCCCTGGCCCACCCTCGTGACCACCTTCACCTACGGCGTGCAGTGCTTCAG CCGCTACCCAGACCACATGAAGCAGCACGACTTCTTCAAGTCCGCCATGCCCGAAGGCTACGTC CAGGAGCGCACCATCTT 3' |

Results

Using the BFP CRISPR, the BFP4/C GRON with the wobble bases is up to a 3.5-fold more efficacious in BFP to GFP conversion when compared to the BFP4/C GRON without the wobble bases (Table 6). There is up to a 5.9-fold increase in BFP to GFP conversion when the BFP4/C GRON with the wobble base is used instead of the BFP4/NC GRON with the wobble base (Table 6). Therefore, the BFP4/C GRON with the wobble base is most efficacious in BFP to GFP conversion when used with the BFP CRISPR.

Conclusions

Including a wobble base in the GRON that changes the PAM sequence of the BFP CRISPR in the converted target gene increases BFP to GFP conversion. BFP to GFP conversion by the BFP CRISPR along with the wobble-based GRON was confirmed by Next Generation Sequencing (data not shown). Additionally, the ability of the BFP CRISPR to cleave the DNA and produce indels in the bfp gene was confirmed by Next Generation Sequencing (data not shown).

TABLE 6

The percentage of BFP to GFP conversion as determine by cytometry at 72 h post PEG delivery of the BFP CRISPR and GRON into protoplasts derived from the *Arabidopsis thaliana* BFP transgenic line 21-15-09.

| | Percentage of GFP Positive Cells (std dev) CRISPR: BFP5 | | | |
| --- | --- | --- | --- | --- |
| | BFP4/C GRON | | BFP4/NC GRON | |
| Exp. Name | (−) Wobbles | (+) 1 wobbles | (−) Wobbles | (+) 1 wobbles |
| Exp 1 | 0.46 (0.07) | 1.59 (0.06) | 0.08 (0.02) | 0.27 (0.04) |
| Exp 2 | 0.24 (0.03) | 0.61 (0.05) | 0.04 (0.01) | 0.16 (0.04) |

Example 7: CRISPR with Cy3 Modified GRONs

The purpose of this series of examples is to demonstrate BFP to GFP conversion in our *Arabidopsis thaliana* BFP transgenic model system using CRISPRs to create targeted double-stranded breaks in the bfp gene and GRONs to mediate conversion. The BFP6 CRISPR (CR:BFP6) used in these examples targets the bfp gene and causes a double-stranded break in the DNA near the site of conversion. The GRONs used with the BFP6 CRISPR, contains the coding sequence of the bfp gene around the site of conversion and are labeled at the 5' end with Cy3 and at the 3' end with an idC reverse base and are herein referred to as Cy3 GRONs. These GRONs are tested at three different lengths of 41-mers, 101-mers and 201-mers and they are directly compared to the 3P5 GRONs which only differ from the Cy3 GRONs in that they have 3 phosphothioate linkages on both the 5' and 3' ends of the GRON. These GRONs are herein referred to as 3P5 GRONs. See Table 7 for the list of GRONs used in these examples.

Methods

BFP transgenic *Arabidopsis thaliana* protoplasts derived from induced root tissue were seeded on a flat-bottom 96-well plate, at 250,000 cells per well at a cell density of 1×107 cells/ml. The CRISPR encoded plasmids contain the MAS promoter driving the Cas9 coding sequence with an rbcSE9 terminator and the *Arabidopsis thaliana* U6 promoter driving the sgRNA with a poly-T10 terminator ("T10" disclosed as SEQ ID NO:21). The CRISPR plasmids along with GRON were introduced into protoplasts by PEG mediated delivery at a final concentration of 0.05 μg/μl for the CRISPR and 8.0 μM for the 41-mer, 0.32 μM for the 101-mer and 0.16 μM 201-mer GRONs. GRON treatments alone received a final GRON concentration after PEG delivery of 8.0 μM for the 41-mer, 5.0 μM for the 101-mer and 2.5 μM for the 201-mer. Protoplasts were incubated in the dark at 23° C. for 72 hours, and then they were analyzed by flow cytometer in order to determine the percentage of GFP positive protoplasts within a given treatment.

The CRISPR consists of two components: the plant codon-optimized *Streptococcus pyogenes* Cas9 (SpCas9) and sgRNA both of which were expressed from the same plasmid. The sgRNA is a fusion of CRISPR RNA (crRNA) and trans-activating crRNA (tracrRNA). The crRNA region contains the spacer sequence used to guide the Cas9 nuclease to the BFP target gene. In this experiment the BFP6 CRISPR (5'GGTGCCGCACGTCACGAAGTCGG 3' (SEQ ID N023)) was used which targets the bfp gene. The GRONs contain the coding sequence of the bfp gene near the site of conversion. Table 7 gives a list of the GRONs used.

96-well plate, at 250,000 cells per well at a cell density of 1×107 cells/ml. The CRISPR encoded plasmids contain the MAS promoter driving the Cas9 coding sequence with an

TABLE 7

List of GRONs used in these examples (SEQ ID NOS 24, 15, and 19, respectively, in order of appearance)

| GRON Name | GRON Chemistry | GRON Sequence | CRISPR |
|---|---|---|---|
| BFP4/C 41-mer | Cy3 or 3PS | 5' CCCTCGTGACCACCTTCACCTACGGCGTGCAGTGCTTCAGC 3' | BFP6 |
| BFP4/C 101-mer | Cy3 or 3PS | 5' CCACCGGCAAGCTGCCCGTGCCCTGGCCCACCCTCGTGACCACCTTCACCTACGGCGTGCAGTGCTTCAGCCGCTACCCCGACCACATGAAGCAGCACGAC 3' | BFP6 |
| BFP4/C 201-mer | Cy3 or 3PS | 5' GGGCGAGGGCGATGCCACCTACGGCAAGCTGACCCTGAAGTTCATCTGCACCACCGGCAAGCTGCCCGTGCCCTGGCCCACCCTCGTGACCACCTTCACCTACGGCGTGCAGTGCTTCAGCCGCTACCCCGACCACATGAAGCAGCACGACTTCTTCAAGTCCGCCATGCCCGAAGGCTACGTCCAGGAGCGCACCATCTT 3' | BFP6 |

Results

Figure 4:
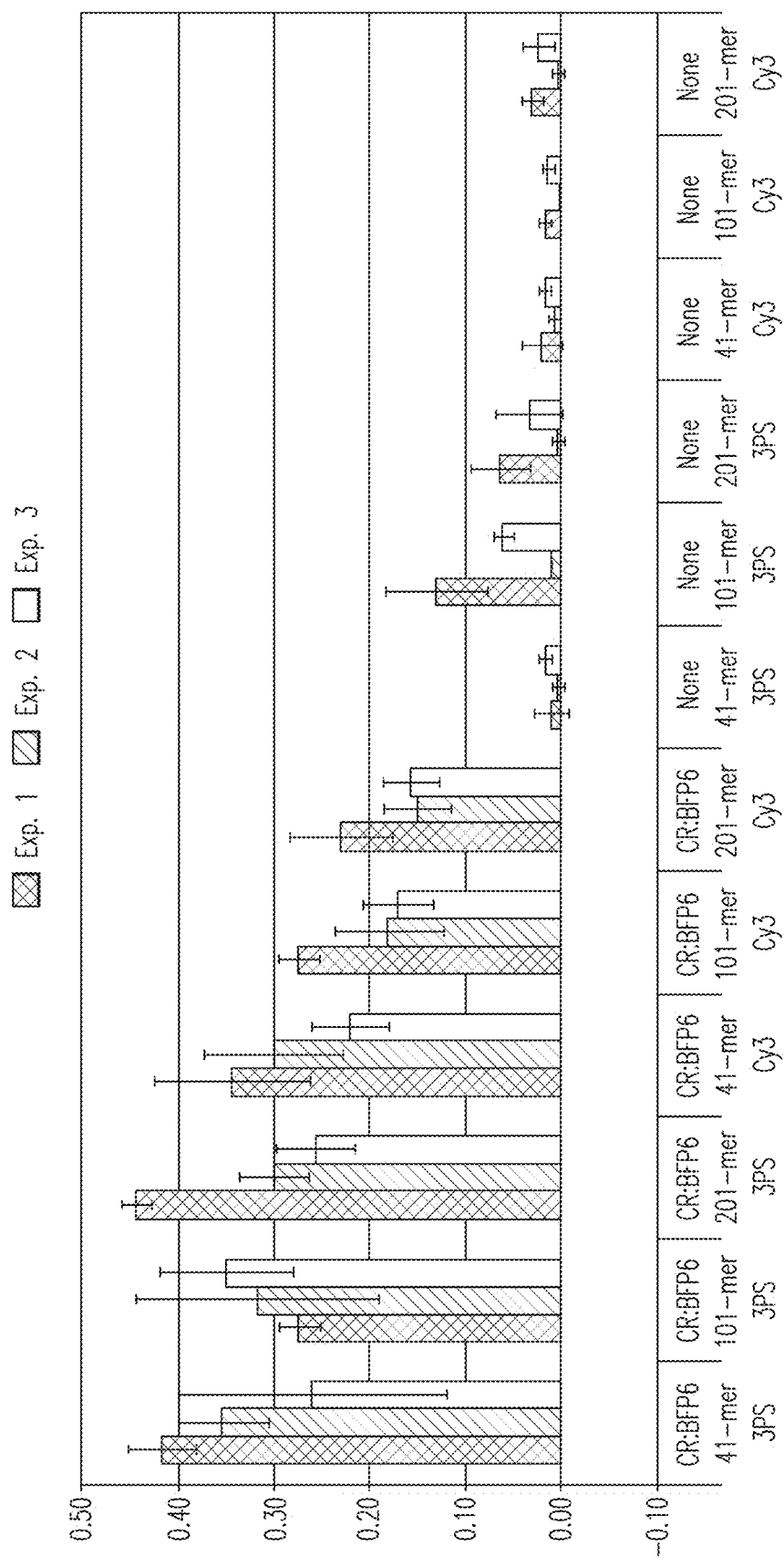
FIG. 4 shows the results of the effect of CRISPRs introduced with either the Cy3 or 3P5 GRONs at various lengths, on the percentage of BFP to GFP conversion in a BFP transgenic *Arabidopsis thaliana* model system.

Using the BFP6 CRISPR, the Cy3 GRONs at all lengths tested are able to mediate BFP to GFP conversion as efficiently as the 3P5 GRONs (FIG. 4). Overall, the samples containing the BFP6 CRISPR and GRON have higher levels of BFP to GFP conversion when compared to the GRON only samples (FIG. 4), demonstrating the positive impact CRISPRs have on increasing conversion rates.

Example 8: CRISPR with GRONs of Varying Size

The purpose of this series of examples is to demonstrate BFP to GFP conversion in our *Arabidopsis thaliana* BFP transgenic model system using CRISPRs to create targeted double-stranded breaks in the bfp gene and GRONs of varying lengths to mediate conversion. The BFP CRISPR used in these examples targets the bfp gene and causes a double-stranded break in the DNA near the site of conversion. The GRONs used with the BFP CRISPR, contains the coding sequence of the bfp gene around the site of conversion and are labeled at both the 5' end and the 3' end with 3 phosphothioate linkages and are herein referred to as 3P5 GRONs. These GRONs are tested at three different lengths of 60-mers, 101-mers and 201-mers and they are directly compared to the GRON only treatments. See Table 8 for the list of GRONs used in these examples.

rbcSE9 terminator and the *Arabidopsis thaliana* U6 promoter driving the sgRNA with a poly-T10 terminator ("T10" disclosed as SEQ ID NO: 21). The CRISPR plasmids along with GRON were introduced into protoplasts by PEG mediated delivery at a final concentration of 0.05 µg/µl for the CRISPR and 0.547 µM for the 60-mer, 0.32 µM for the 101-mer and 0.16 µM 201-mer GRONs. GRON treatments alone received a final GRON concentration after PEG delivery of 7.5 µM for the 60-mer, 5.0 µM for the 101-mer and 2.5 µM for the 201-mer. Protoplasts were incubated in the dark at 23° C. for 72 hours, and then they were analyzed by flow cytometry in order to determine the percentage of GFP positive protoplasts within a given treatment.

The CRISPR consists of two components: the plant codon-optimized *Streptococcus pyogenes* Cas9 (SpCas9) and sgRNA both of which were expressed from the same plasmid. The sgRNA is a fusion of CRISPR RNA (crRNA) and trans-activating crRNA (tracrRNA). The crRNA region contains the spacer sequence used to guide the Cas9 nuclease to the BFP target gene. The BFP CRISPR spacer sequence is 5'GTCGTGCTGCTTCATGTGGT3' (SEQ ID NO:25). In this example the BFP CRISPR was used which targets the bfp gene. The GRONs contain the coding sequence of the bfp gene near the site of conversion. Table 8 gives a list of the GRONs used.

TABLE 8

List of GRONs used in these examples. (SEQ ID NOS 26, 27, and 22, respectively, in order of appearance).

| GRON Name | GRON Chemisty | GRON Sequence |
|---|---|---|
| BFP4/C 60-mer (1 wobble) | 3PS | 5' GTGACCACCTTCACCTACGGCGTGCAGTGCTTCAGCCGCTACCCAGACCACAT-GAAGCAG 3' |
| BFP4/C 101-mer (1 wobble) | 3PS | 5' CCACCGGCAAGCTGCCCGTGCCCTGGCCCACCCTCGTGACCACCTTCACCTACGGCGTGCAGTGCTTCAGCCGCTACCCAGACCACATGAAGCAGCACGAC 3' |
| BFP4/C 201-mer (1 wobble) | 3PS | 5' GGGCGAGGGCGATGCCACCTACGGCAAGCTGACCCTGAAGTTCATCTGCACCACCGGCAAGCTGCCCGTGCCCTGGCCCACCCTCGTGACCACCTTCACCTACGGCGTGCAGTGCTTCAGCCGCTACCCAGACCACATGAAGCAGCACGACTTCTTCAAGTCCGCCATGCCCGAAGGCTACGTCCAGGAGCGCACCATCTT 3' |

Methods

Figure 5:
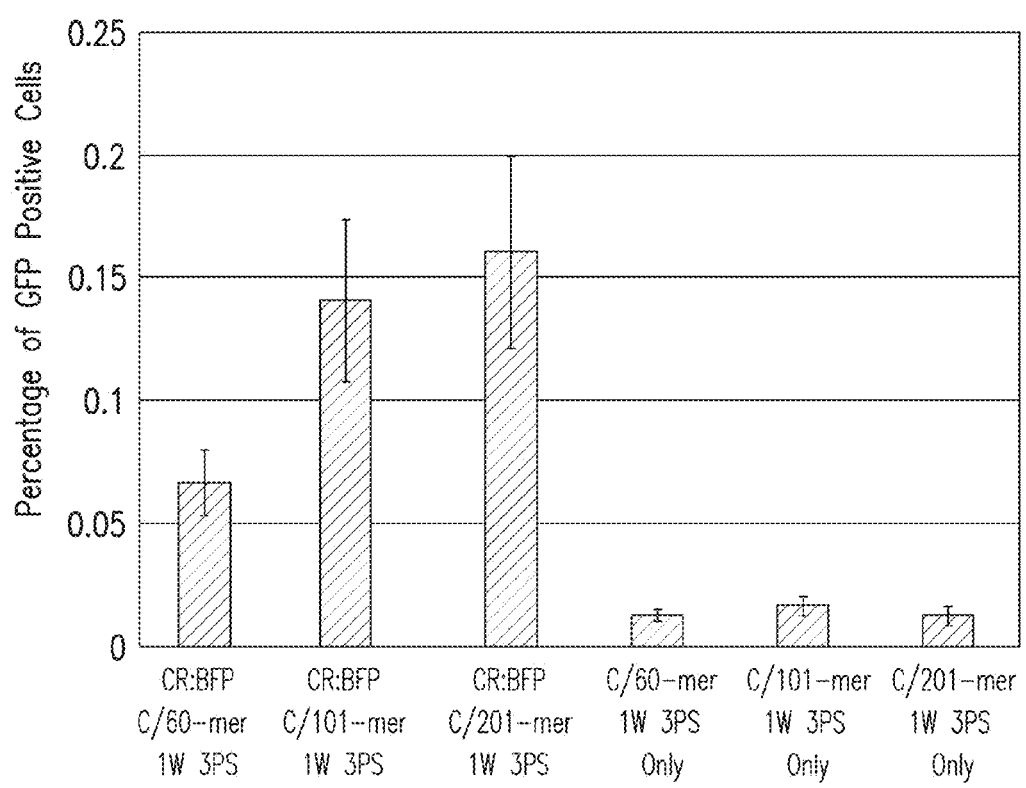
FIG. 5 shows the results of the effect of CRISPRs introduced with the 3P5 GRONs at various lengths, on the percentage of BFP to GFP conversion in a BFP transgenic *Arabidopsis thaliana* model system.

BFP transgenic *Arabidopsis thaliana* protoplasts derived from induced root tissue were seeded on a flat-bottom Results Using the BFP CRISPR, GRONs at lengths ≥101 nt are better at mediating BFP to GFP conversion when directly compared to the 60 nt long GRONs (FIG. 5). Overall, the samples containing the BFP CRISPR and GRON have higher levels of BFP to GFP conversion when compared to the GRON only samples (FIG. 5), demonstrating the positive impact CRISPRs have on increasing conversion rates. This data further demonstrates that the length of the GRON that is most efficacious in mediating BFP to GFP conversion, when used along with the CRISPR, needs to be ≥101 nt in length.

Example 9: CRISPR with 2'-O-Me GRONs

Figure 6A:
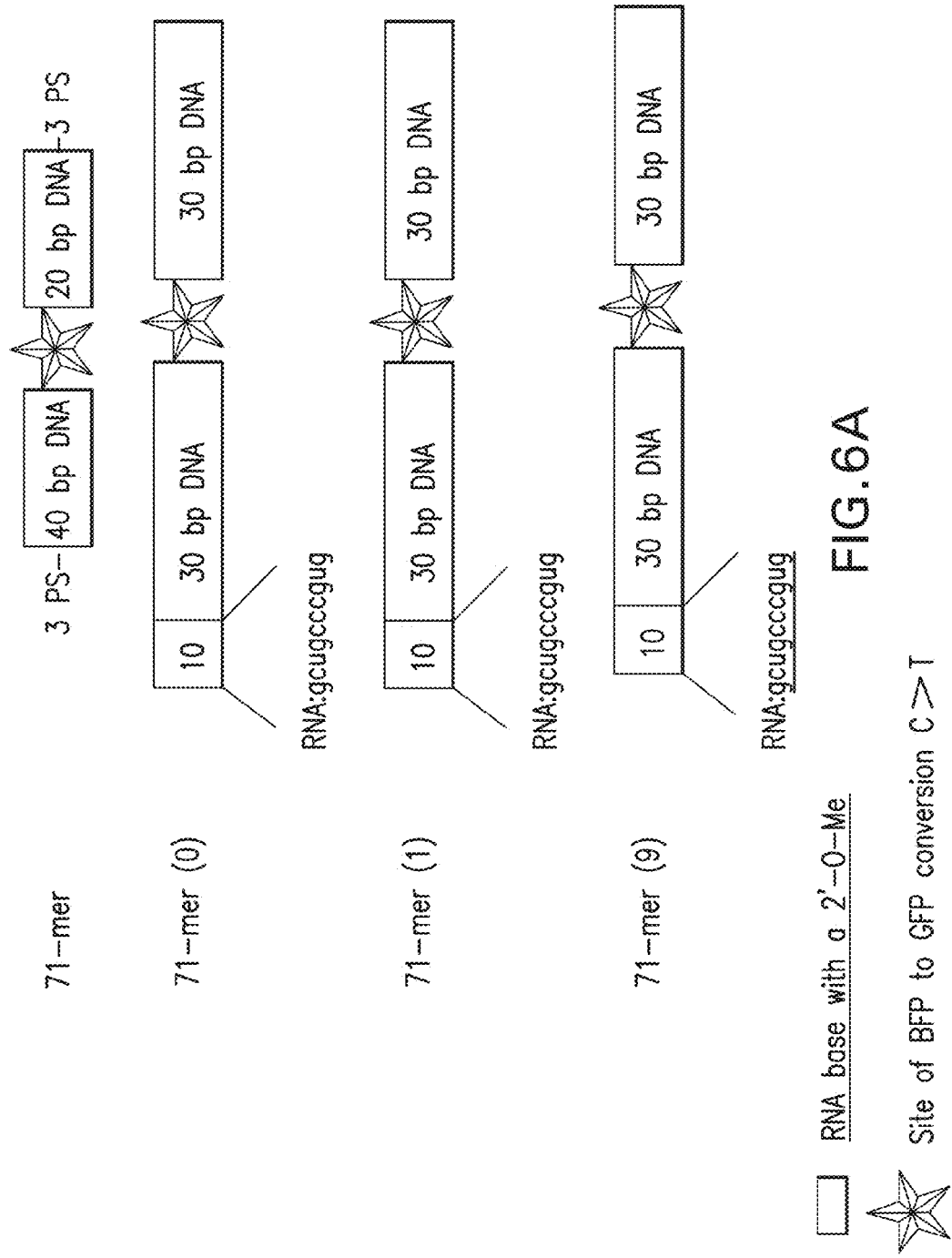
FIG. 6A discloses GRON "gcugcccgug" (SEQ ID NO: 233) used in Example 9.
Figure 6B:
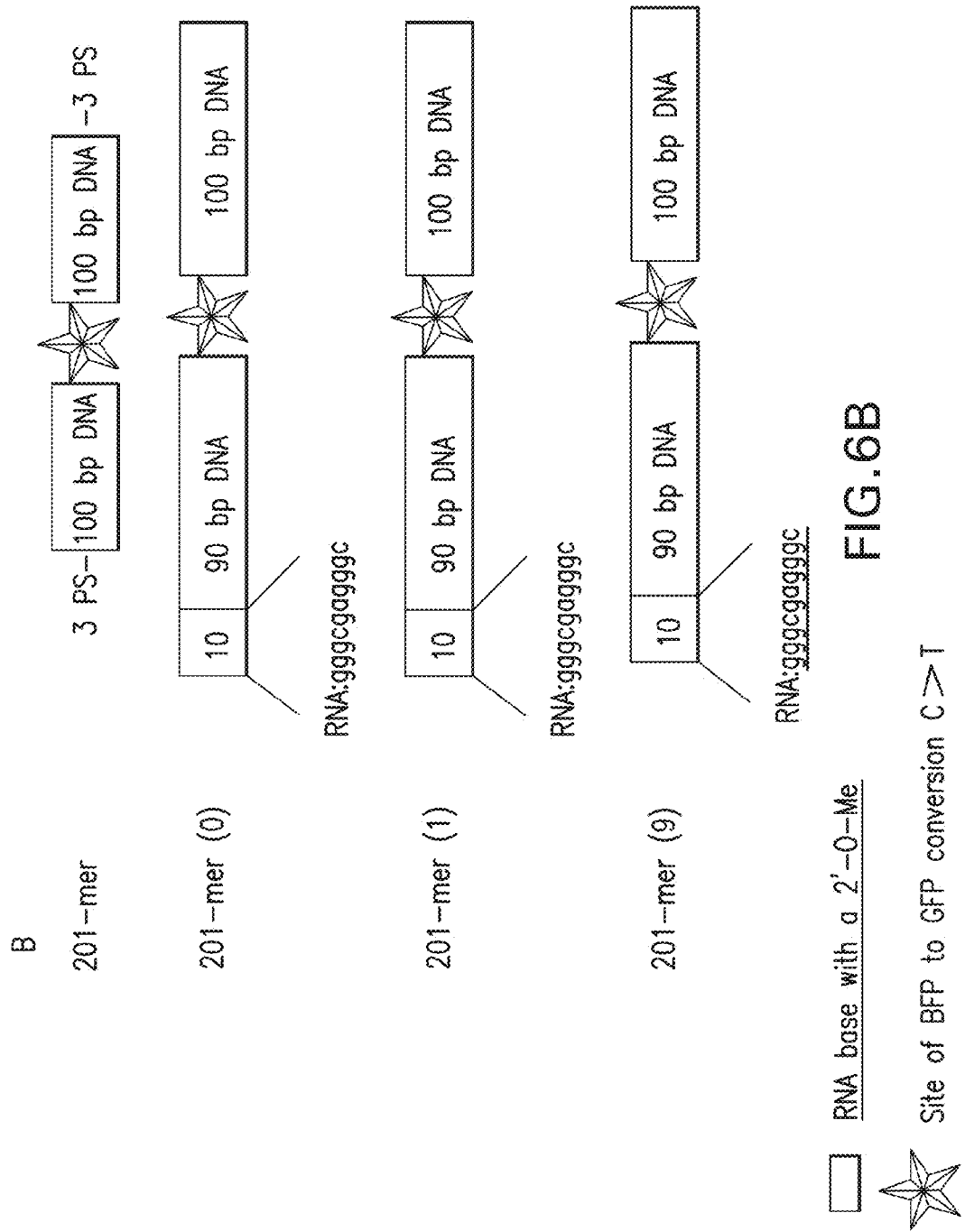
FIG. 6B discloses GRON "gggcgagggc" (SEQ ID NO: 234) used in Example 9.

The purpose of this examples is to demonstrate BFP to GFP conversion in our *Arabidopsis thaliana* BFP transgenic model system using CRISPRs to create targeted double-stranded breaks in the bfp gene and GRONs to mediate conversion. The BFP CRISPR used in this example targets the bfp gene and causes a double-stranded break in the DNA near the site of conversion. The GRONs used with the BFP CRISPR, contain either the coding or non-coding sequence of the bfp gene around the site of conversion with the first ten 5' bases of the GRON being RNA bases instead of DNA bases. These RNA bases are labeled with 2'-O-Me group(s) at either the first 5' RNA base or the first nine 5' RNA bases as depicted in FIG. 6. These GRONs are herein referred to as 2'-O-Me GRONs and are directly compared to the 3P5 GRONs of similar lengths that contain DNA bases with 3 phosphothioate linkages on both the 5' and 3' ends of the GRON. These GRONs are herein referred to as 3P5 GRONs. See Table 9 for the list of GRONs used in these examples.

Methods

BFP transgenic *Arabidopsis thaliana* protoplasts derived from induced root tissue were seeded on a flat-bottom 96-well plate, at 250,000 cells per well at a cell density of 1×107 cells/ml. The CRISPR encoded plasmids contain the MAS promoter driving the Cas9 coding sequence with a rbcSE9 terminator and the *Arabidopsis* U6 promoter driving the sgRNA with a poly-T10 terminator ("T10" disclosed as SEQ ID NO: 21). The sgRNA is a fusion of CRISPR RNA (crRNA) and trans-activating crRNA (tracrRNA). The CRISPR plasmids along with GRON were introduced into protoplasts by PEG mediated delivery at a final concentration of 0.05 µg/µl for the CRISPR, 0.5 µM for the 71-mer and 0.16 µM for the 201-mer GRONs. GRON treatments alone received a final GRON concentration after PEG delivery of 5.0 µM for the 71-mer and 2.5 µM for the 201-mer. Protoplasts were incubated in the dark at 23° C. for 72 hours, and then they were analyzed by flow cytometer in order to determine the percentage of GFP positive protoplasts within a given treatment.

The CRISPR consists of two components: the plant codon-optimized *Streptococcus pyogenes* Cas9 (SpCas9) and sgRNA both of which were expressed from the same plasmid. The sgRNA is a fusion of CRISPR RNA (crRNA) and trans-activating crRNA (tracrRNA). The crRNA region contains the spacer sequence used to guide the Cas9 nuclease to the BFP target gene. The BFP CRISPR spacer sequence is 5'CTCGTGACCACCTTCACCCA 3' (SEQ ID NO:28). In this example the BFP CRISPR was used which targets the bfp gene. The GRONs contain either the coding or non-coding sequence of the bfp gene near the site of conversion. Table 9 shows a list of the GRONs used.

TABLE 9

List of GRONs used in these examples (SEQ ID NOS 29, 30, 19, 17, 29, 31, 19, and 32, respectively, in order of appearance)

| GRON Name | GRON Chemistry | GRON Sequence |
|---|---|---|
| BFP4/C 71-mer | 3PS | 5' GCUGCCCGUGCCCTGGCCCACCCTCGTGACCACCTTCACCTACGGCGTGCAGTGCTTCAGCC GCTACCCCG 3' |
| BFP4/NC 71-mer | 3PS | 5' TTCATGTGGTCGGGGTAGCGGCTGAAGCACTGCACGCCGTAGGTGAAGGTGGTCACGAGGGT GGGCCAGGG 3' |
| BFP4/C 201-mer | 3PS | 5' GGGCGAGGGCGAT3CCACCTACGGCAAGCTGACCCTGAAGTTCATCTGCACCACCGGCAAGC TGCCCGTGCCCTGGCCCACCCTCGTGACCACCTTCACCTACGGCGTGCAGTGCTTCAGCCGCTA CCCCGACCACATGAAGCAGCACGACTTCTTCAAGTCCGCCATGCCCGAAGGCTACGTCCAGGAG CGCACCATCTT 3' |
| BFP4/NC 201-mer | 3P | 5' AAGATGGTGCGCTCCTGGACGTAGCCTTCGGGCATGGCGGACTTGAAGAAGTCGTGCTGCTT CATGTGGTCTGGGTAGCGGCTGAAGCACTGCACGCCGTAGGTGAAGGTGGTCACGAGGGTGGG CCAGGGCACGGGCACCTTGCCGGTGGTGCAGATGAACTTCAGGGTCAGCTTGCCGTAGGTGGC ATCGCCCTCGCCC 3' |
| BFP4/C 71-mer | 2'-O-Me | 5' gcugcccgugCCCTGGCCCACCCTCGTGACCACCTTCACCTACGGCGTGCAGTGCTTCA-GCCGC TACCCCG 3' |
| BFP4/NC 71-mer | | 5' uucaugugguCGGGGTAGCGGCTGAAGCACTGCACGCCGTAGGTGAAGGTGGTCACGAGGGT GGGCCAGGG 3' |
| BFP4/C 201-mer | 2'-O-Me | 5' gggcgagggcGATGCCACCTACGGCAAGCTGACCCTGAAGTTCATCTGCACCACCG-GCAAGCTG CCCGTGCCCTGGCCCACCCTCGTGACCACCTTCACCTACGGCGTGCAGTGCTTCAGCCGCTACC CCGACCACATGAAGCAGCACGACTTCTTCAAGTCCGCCATGCCCGAAGGCTACGTCCAGGAGCG CACCATCTT 3' |
| BFP4/NC 201-mer | 2'-O-Me | 5' aagauggugcGCTCCTGGACGTAGCCTTCGGGCATGGCGGACTTGAAGAAGTCGTGCT-GCTTCA TGTGGTCGGGGTAGCGGCTGAAGCACTGCACGCCGTAGGTGAAGGTGGTCACGAGGGTGGGC CAGGGCACGGGCAGCTTGCCGGTGGTGCAGATGAACTTCAGGGTCAGCTTGCCGTAGGTGGCA TCGCCCTCGCCC 3' |

Results

Figure 7:
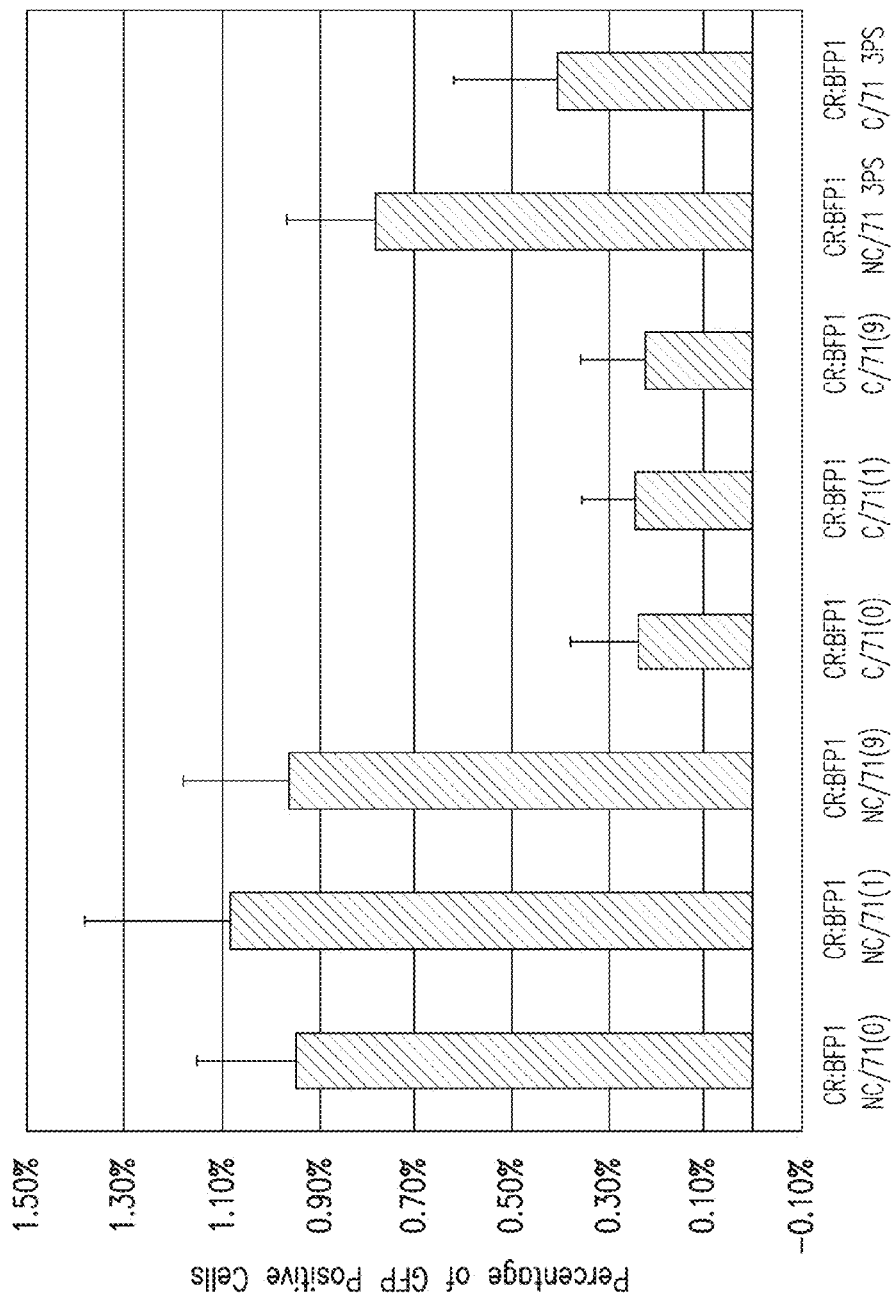
FIG. 7 shows the measurement of mean percentage GFP positive protoplasts from an *Arabidopsis thaliana* BFP transgenic model system as determined by flow cytometry from 71-mer GRONs.
Figure 8:
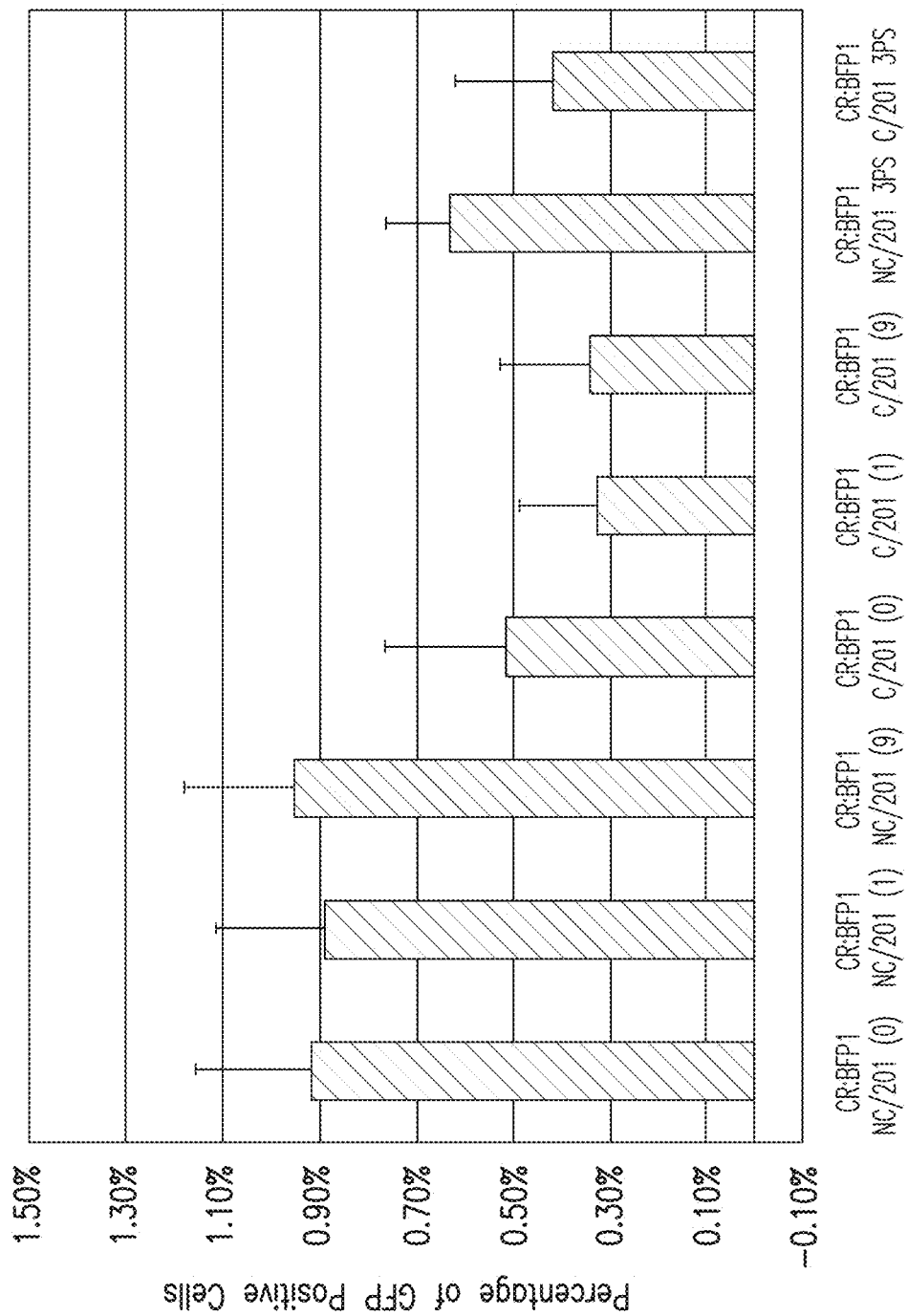
FIG. 8 shows the measurement of GFP positive protoplasts from *Arabidopsis thaliana* BFP transgenic model system as determined by flow cytometry from 201-mer GRONs.

The 71-mer and 201-mer 2'-O-Me GRONs had similar BFP to GFP conversion when compared to the various different types of GRON protections of (0), (1) or (9) using the BFP CRISPRs (FIGS. 7 and 8). The 2'-O-Me GRONs are more efficacious than their 3P5 GRON counterparts at mediating BFP to GFP conversion using the BFP CRISPRs (FIGS. 7 and 8).

Example 10: CRISPR Nickases with GRONs

Introduction

The purpose of this examples is to demonstrate BFP to GFP conversion in our *Arabidopsis thaliana* BFP transgenic model system using CRISPRs to create targeted single-stranded nicks in the bfp gene and GRONs to mediate conversion. The BFP1 CRISPR (CR:BFP1) used in this example targets the bfp gene and contains mutations in the catalytic residues (D10A in RuvC and H840A in HNH) that causes single-stranded nicks in the DNA of the bfp gene near the site of conversion on either the DNA strands complementary or non-complementary to the guide RNA respectively. These CRISPRs are herein referred to as BFP1 CRISPR nickase D10A and BFP1 CRISPR nickase H840A and are used either alone or with BFP5 sgRNA on a separate plasmid. When multiple CRISPR nickases are used together in this example, they can either nick the same DNA strand or opposite DNA strands. When both Cas9 proteins that contain the same mutations, either D10A or H840A, are used together, they nick the same strand of DNA. Conversely, when two Cas9 proteins are used together and one of them contains the D10A mutation and the other one contains the H840A mutation, they nick opposite strands of the DNA. The GRONs used with the nickase CRISPRs, contains either the coding or the non-coding sequence of the bfp gene around the site of conversion with one wobble base located in the PAM sequence of BFP5 CRISPR. These GRONs have 3 phosphothioate linkages on both the 5' and 3' ends and are herein referred to as 3P5 GRONs. See Table 10 for the list of GRONs used in these examples. The nickase CRISPRs are directly compared to their CRISPR counterparts that are able to cause targeted double-stranded breaks in the DNA of the bfp gene.

Methods

BFP transgenic *Arabidopsis thaliana* protoplasts derived from induced root tissue are seeded on a flat-bottom 96-well plate, at 250,000 cells per well at a cell density of 1×10⁷ cells/ml. The CRISPR encoded plasmids contain the MAS promoter driving the Cas9 coding sequence with an rbcSE9 terminator and the *Arabidopsis thaliana* U6 promoter driving the sgRNA with a poly-T10 terminator ("T10" disclosed as SEQ ID NO: 21). The sgRNA is a fusion of CRISPR RNA (crRNA) and trans-activating crRNA (tracrRNA). The Cas9 gene contains mutations in the catalytic residues, either D10A in RuvC or H840A in HNH. The CRISPR plasmids along with GRON are introduced into protoplasts by PEG mediated delivery at a final concentration of 0.05 µg/µl for the CRISPR and 0.16 µM for the 201-mer. GRON treatments alone received a final GRON concentration after PEG delivery of 2.5 µM for the 201-mer. Protoplasts were incubated in the dark at 23° C. for 72 hours, and then they were analyzed by flow cytometer in order to determine the percentage of GFP positive protoplasts within a given treatment.

The CRISPR consists of two components: the plant codon-optimized *Streptococcus pyogenes* Cas9 (SpCas9) and sgRNA both of which were expressed from the same plasmid. The sgRNA is a fusion of CRISPR RNA (crRNA) and trans-activating crRNA (tracrRNA). The crRNA region contains the spacer sequence used to guide the Cas9 nuclease to the BFP target gene. In this example the BFP1 and BFP5 sgRNA was used that targets different regions the bfp gene near the site of conversion. The BFP1 spacer (5'CTCGTGACCACCTTCACCCA 3'(SEQ ID NO:28)) targets the coding-strand while the BFP5 spacer (5'GTCGTGCTGCTTCATGTGGT3' (SEQ ID NO:25)) targets the non-coding strand of the bfp gene. The GRONs contain either the coding or non-coding sequence of the bfp gene near the site of conversion. Table 10 shows a list of the GRONs used.

TABLE 10

List of GRONs used in these examples (SEQ ID NOS 17 and 22, respectively, in order of appearance)

| GRON Name | GRON Chemistry | GRON Sequence | CRISPR |
|---|---|---|---|
| BFP4/NC 201-mer (1 wobble; BFP5) | 3PS | 5' AAGATGGTGCGCTCCTGGACGTAGCCTTCGGGCATGGCGGACTTGAAGAAGTCG TGCTGCTTCATGTGGTCTGGGTAGCGGCTGAAGCACTGCACGCCGTAGGTGAAGGT GGTCACGAGGGTGGGCCAGGGCACGGGCAGCTTGCCGGTGGTGCAGATGAACTTCA GGGTCAGCTTGCCGTAGGTGGCATCGCCCTCGCCC 3' | BFP1 and BFP5 |
| BFP4/C 201-mer (1 wobble; BFP5) | 3PS | 5' GGGCGAGGGCGATGCCACCTACGGCAAGCTGACCCTGAAGTTCATCTGCACCACC GGCAAGCTGCCCGTGCCCTGGCCCACCCTCGTGACCACCTTCACCTACGGCGTGCAGT GCTTCAGCCGCTACCCAGACCACATGAAGCAGCACGACUCUCAAGTCCGCCATGCCCG AAGGCTACGTCCAGGAGCGCACCATCTT 3' | BFR1 and BFP6 |

Results

Figure 9:
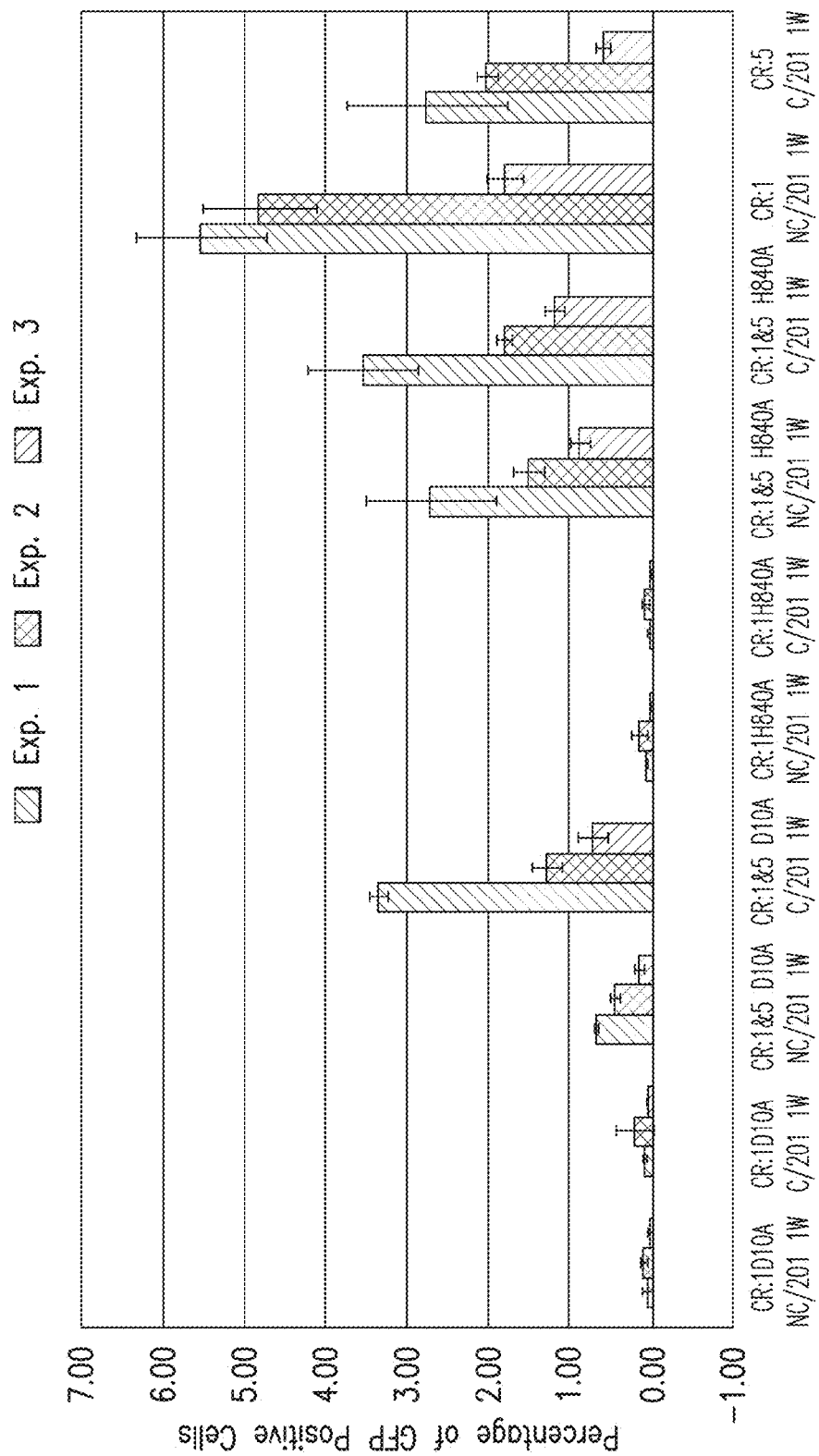
FIG. 9 shows the effect of CRISPRs introduced with coding and non-coding GRONs on the mean percentage of GFP positive cells in a BFP transgenic *Arabidopsis thaliana* model system.

Both of the CRISPR nickases (D10A and H840A) are more efficient at mediating BFP to GFP conversion when the BFP1 CRISPR and the BFP5 CRISPR were used together instead of separately (FIG. 9). In addition, when the BFP1 and BFP5 D10A CRISPR nickases are used together with the C/2011W GRON, the BFP to GFP conversion is significantly higher when compared to treatments where these CRISPR nickases are used with the NC/201 1W GRON (FIG. 9). When the BFP1 and BFP5 H840A CRISPR nickases are used together roughly the same level of BFP to GFP conversion is observed with either the C/201 or NC/201 1W GRONs (FIG. 9). These levels of BFP to GFP conversion are slightly higher than when the BFP5 CRISPR is used alone and slightly lower than when the BFP1 CRISPR is used alone (FIG. 9).

Example 11: Use of CRISPRs to Target Multiple Genes

The purpose of this example is to demonstrate conversion of multiple genes simultaneously in a given population of protoplasts derived from the *Arabidopsis thaliana* model system using CRISPRs to create double-stranded breaks in targeted genes and GRONs to mediate conversion. The CRISPRs used in this example target both the BFP and acetohydroxy acid synthase (AHAS) genes in the *Arabidopsis thaliana* genome by introducing into protoplasts plasmid (s) encoding the Cas9 gene and multiple sgRNA targeting these two different genes. The sgRNA is a fusion of CRISPR RNA (crRNA) and trans-activating crRNA (tracrRNA). This will allow Cas9 to cause double-stranded breaks in both the BFP and AHAS genes in the presence of GRONs that will mediate their conversion.

Methods

*Arabidopsis thaliana* protoplasts derived from induced root tissue are seeded on a flat-bottom 96-well plate, at 250,000 cells per well at a cell density of 1×107 cells/ml. The CRISPR encoded plasmids contain the MAS promoter driving the Cas9 coding sequence with a rbcSE9 terminator and *Arabidopsis thaliana* U6 promoter driving multiple different sgRNAs with a poly-T10 terminator ("T10" disclosed as SEQ ID NO: 21). The sgRNA is a fusion of CRISPR RNA (crRNA) and trans-activating crRNA (tracrRNA). The CRISPR plasmids along with GRON are introduced into protoplasts by PEG mediated delivery at a final concentration of 0.05 µg/µl for the CRISPR and 0.16 µM for the 201-mer. GRON treatments alone receive a final GRON concentration after PEG delivery of 2.5 µM for the 201-mer. Protoplasts will be incubated in the dark at 23° C. for 72 hours, and then they are analyzed by flow cytometer and an allele specific PCR assay in order to determine the percentage of both BFP to GFP and AHAS converted protoplasts respectively within a given treatment.

In the an allele specific PCR assay 10-16 replicates of 5,000 genome equivalents of genomic DNA were used in the primary PCR reactions.

The CRISPR consists of two components: the plant codon-optimized *Streptococcus pyogenes* Cas9 (SpCas9) and sgRNA both of which were expressed from the same or multiple plasmids. The sgRNA is a fusion of CRISPR RNA (crRNA) and trans-activating crRNA (tracrRNA). The crRNA region contains the spacer sequence used to guide the Cas9 nuclease to the targeted genes. In this example different sgRNAs and GRONs are used to target multiple genes near their sites of conversion; BFP spacer (5'CTCGTGACCACCTTCACCCA 3' (SEQ ID NO:28)) and AHAS spacer (5' TGGTTATGCAATTGGAAGATCGC 3'(SEQ ID NO:33). Table 11 describes the GRONs used.

TABLE 11

List of GRONs used in this example (SEQ ID NOS 19 and 34, respectively, in order of appearance)

| GRON Name | Target Gene | GRON Chemistry | GRON Sequence |
| --- | --- | --- | --- |
| BFP/C 201-mer | BFP | 3PS | 5' GGGCGAGGGCGATGCCACCTACGGCAAGCTGACCCTGAAG1TCATCTGCACCA CCGGCAAGCTGCCCGTGCCCTGGCCCACCCTCGTGACCACCTTCACCTACGGCGT GCAGTGCTTCAGCCGCTACCCCGACCACATGAAGCAGCACGACTTCTTCAAGTCC GCCATGCCCGAAGGCTACGTCCAGGAGCGCACCATCTT 3' |
| AHAS(W) 574/NC 201-mer | AHAS | 3PS | 5' AGCTGCTGCAAACAGCAACATGTTCGGGAATATCTCGTCCTCCTGAGCCG-GATC CCCGAGAAATGTGTGAGCTCGGTTAGCTTTGTAGAAGCGATCTTCCAATTGCATA ACCATGCCAAGATGCTGGTTGTTTAATAAAAGTACCTTCACTGGAAGATTCTCTAC ACGAATAGTGGCTAGCTCTTGCACATTCATTATAAA 3' |

Results

BFP to GFP and AHAS conversion was determined at 144 h post PEG delivery of the BFP and AHAS CRISPR plasmids and the BFP/C 201-mer and AHAS(W)574/NC 201-mer GRONs into the *Arabidopsis thaliana* BFP transgenic line. Flow cytometry data revealed that Treatment 1 resulted in 0.20% BFP to GFP conversion (Table 12). Allele specific PCR assay revealed that Treatment 1 resulted in 0.01% AHAS converted protoplasts (Table 12). GRON only treatments had minimal conversion using both assays (Table 12). This example demonstrates the successful simultaneous conversion of two independent target genes (BFP and AHAS) within a given population of protoplasts derived from the *Arabidopsis thaliana* BFP model system.

TABLE 12

Measurement of conversion of both the BFP and AHAS genes at 144 h post
PEG delivery of CRISPR plasmids and GRONs into a given population of protoplasts derived
from the *Arabidopsis thaliana* BFP model system either by: (1) flow cytometry which
determines the percentage of GFP positive protoplasts or (2) allele specific PCR which
determines the percentage of AHAS converted protoplasts.

| Treatment | CRISPR | GRONs | BFP to GFP conversion Flow Cytometry | AHAS-W574L Conversion Allele Specific PCR |
|---|---|---|---|---|
| 1 | CR-BFP and CR-AHAS | BFP/C 201-mer and AHAS(W)574/NC 201-mer | 0.20% | ~0.01% |
| 2 | None | BFP/C 201-mer and AHAS(W)574/NC 201-mer | 0.01% | ~0.001% |
| 3 | None | None | 0.01% | ~0.001% |

Example 12: Delivery of Cas9 mRNA into Plant Cells

This example makes use of direct delivery of recombinant Cas9 mRNA into plant cells as an alternative to delivery of CRISPR-Cas expression plasmids. This method includes (1) in vitro synthesis of modified mRNA and (2) Delivery of this modified mRNA into plant cells.

Methods

A Cas9 mRNA will be transcribed in vitro using an RNA polymerase such as T7, T3 or 5P6 from a linearized plasmid template including components of a 5'UTR, the coding sequence (CDS) for the protein and a 3'UTR. One RNA polymerase may incorporate a particular modified nucleoside better than another. The 5' UTR may contain elements that improve its stability such as the MiR-122 of hepatitis C virus (Shimakami et al., 2012). In vitro synthesis will incorporate nucleosides that are protective and ensure good translation in the target plant cells. Recombinant Cas9 mRNA will be capped and contain a polyA tail.

BFP transgenic *Arabidopsis thaliana* protoplasts derived from induced root tissue are seeded on a flat-bottom 96-well plate at 250,000 cells per well at a cell density of 1×107 cells/ml. Recombinant Cas9 mRNA will be delivered into plant cells in one of the following means (list not inclusive): cell penetrating peptides (CPP), transfection liposome reagents, poly(ethylene glycol) (PEG) either alone or in combination to allow for delivery of active recombinant Cas9 mRNA into cells.

Example 13: CRISPR-Cas for Tethering DNA, RNA or Proteins

Figure 10:
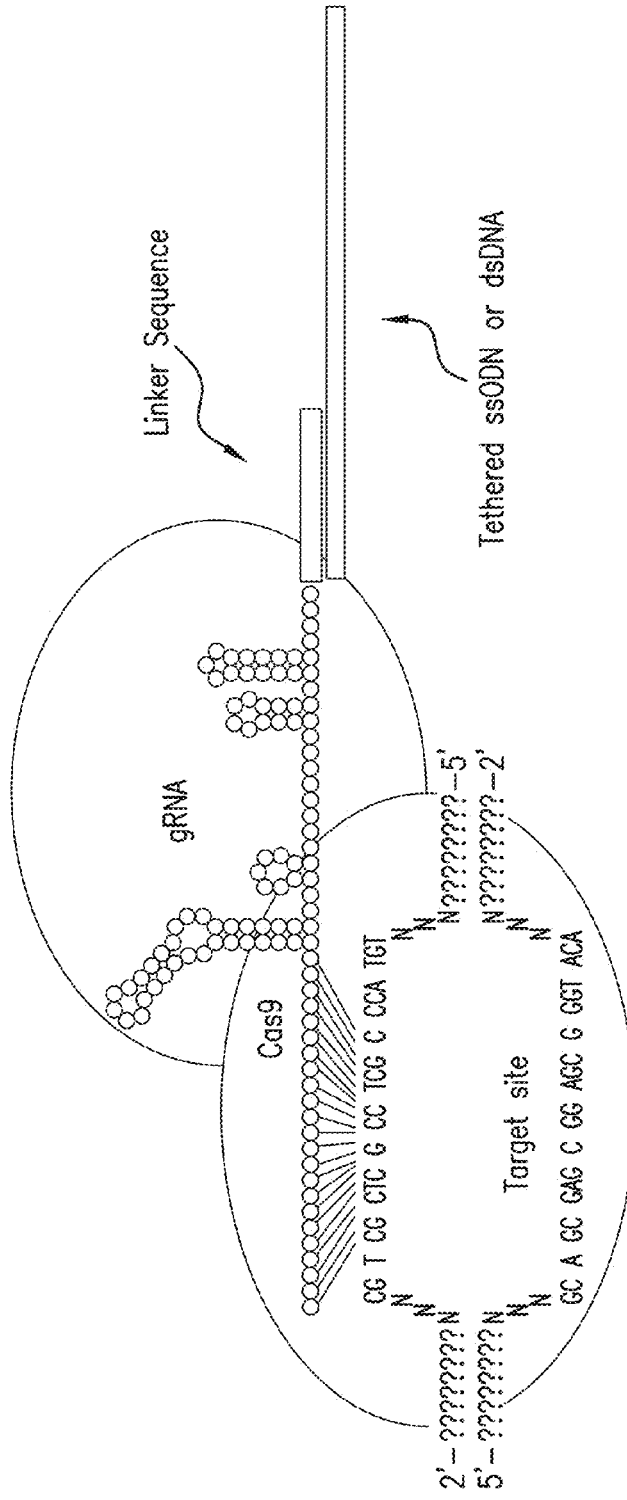
FIG. 10 is a schematic of tethering a single stranded GRON or double stranded DNA to the CRISPR/Cas complex. Figure discloses SEQ ID NOS 235-239, respectively, in order of appearance.

This example makes use of a modified single guide RNA (sgRNA) cassette wherein a linker sequence (may also be referred to as a tethering sequence) is included at the 3' end of the tracrRNA but 5' of the RNA polymerase III termination signal as shown in the example below (FIG. 10). The sgRNA is a fusion of CRISPR RNA (crRNA) and trans-activating crRNA (tracrRNA). Though preferred, the placement of the linker is not limited to the 3' end of the tracerRNA but will be investigated at several positions within the sgRNA cassette. The linker sequence may vary in nucleotide length or contain secondary structure that would improve tethering or increase the number of molecules tethered through triplex interactions.

The linker will allow for Watson-Crick base pairing with a DNA, RNA or proteins that contains the complementary sequence (FIG. 10). Additionally, linker sequence in sgRNA cassettes will be designed to contain advanced secondary and tertiary structure allowing for more complex multifaceted interaction regions that would tether multiple DNA, RNA or protein molecules.

The overall concept is that a CRISPR-Cas complex will tether biological molecules to the site of nuclease activity thereby increasing the likelihood of gene editing. These biological molecules include the GRON which will mediate conversion of targeted gene(s). Tethering linkers can be added to sgRNA by simply using, for example, Gene Strings or annealed oligos.

Methods

BFP transgenic *Arabidopsis thaliana* protoplasts derived from induced root tissue are seeded on a flat-bottom 96-well plate, at 250,000 cells per well at a cell density of 1×107 cells/ml. The CRISPR-Cas tethering plasmids contains the MAS promoter driving the Cas9 coding sequence with a rbcSE9 terminator and

*Arabidopsis thaliana* U6 promoter driving sgRNAs with a linker sequence that is complementary to a polynucleotide tract of 15-30 bp located on a 201-mer editing GRON targeting bfp (as shown in FIG. 10). The sgRNA tethering cassette is terminated by a poly-T10 terminator ("T10" disclosed as SEQ ID NO: 21). The CRISPR-Cas plasmids along with GRON are introduced into protoplasts by PEG mediated delivery at a final concentration of 0.05 µg/µl for the CRISPR and 0.16 µM of the 201-mer GRON. GRON treatments alone received a final GRON concentration after PEG delivery of 2.5 µM for the 201-mer. Protoplasts were incubated in the dark at 23° C. for 72 hours, and then they were analyzed by flow cytometer in order to determine the percentage of GFP positive protoplasts within a given treatment.

The CRISPR consists of two components: the plant codon-optimized *Streptococcus pyogenes* Cas9 (SpCas9) and sgRNA both of which are expressed from the same or different plasmids. The sgRNA is a fusion of CRISPR RNA (crRNA) and trans-activating crRNA (tracrRNA) and linker. The crRNA region contains the spacer sequence used to guide the Cas9 nuclease to the BFP target gene. In this example CRISPR is used which targets the bfp gene. The GRONs contain either the coding or non-coding sequence of the bfp gene near the site of conversion.

Example 14: CRISPRs with Truncated gRNA

The purpose of this example is to demonstrate conversion of BFP to GFP in protoplasts derived from the *Arabidopsis thaliana* BFP model system using CRISPRs to create double-stranded breaks in targeted genes and GRONs to mediate conversion. The CRISPRs used in this example targets the bfp gene in the *Arabidopsis thaliana* genome by introducing into protoplasts plasmid(s) encoding the Cas9 gene and one sgRNAs that is two different lengths. The sgRNA is a fusion of CRISPR RNA (crRNA) and trans-activating crRNA (tracrRNA). The crRNA which guides the Cas9 to the target genes is called the spacer and it is typically 20-nt in length (CR:BFP1 20-nt), however, in these examples we tested the effectiveness of using a smaller length spacer of 17-nt (CR:BFP1 17-nt) in mediating BFP to GFP conversion.

Methods

Arabidopsis thaliana protoplasts derived from induced root tissue are seeded on a flat-bottom 96-well plate, at 250,000 cells per well at a cell density of 1×107 cells/ml. The CRISPR encoded plasmids contain the MAS promoter driving the Cas9 coding sequence with a rbcSE9 terminator and Arabidopsis thaliana U6 promoter driving multiple different sgRNAs with a poly-T10 terminator ("T10" disclosed as SEQ ID NO: 21). The sgRNA is a fusion of CRISPR RNA (crRNA) and trans-activating crRNA (tracrRNA). The CRISPR plasmids along with GRON are introduced into protoplasts by PEG mediated delivery at a final concentration of 0.05 μg/μl for the CRISPR and 0.16 μM for the 201-mer. GRON treatments alone receive a final GRON concentration after PEG delivery of 2.5 μM for the 201-mer. Protoplasts will be incubated in the dark at 23° C. for 72 hours, and then they are analyzed by flow cytometer in order to determine the percentage of BFP to GFP within a given treatment.

The CRISPR consists of two components: the plant codon-optimized Streptococcus pyogenes Cas9 (SpCas9) and sgRNA both of which were expressed from the same or multiple plasmids. The sgRNA is a fusion of CRISPR RNA (crRNA) and trans-activating crRNA (tracrRNA). The crRNA region contains the spacer sequence used to guide the Cas9 nuclease to the targeted genes. In these examples, two different length BFP1 spacers of 20-nt (5'CTCGTGAC-CACCTTCACCCA 3' (SEQ ID NO:28)) vs. 17-nt (5'GT-GACCACCTTCACCCA 3'(SEQ ID NO:35)) were tested. Table 13 describes the GRON used mediate conversion. The CRISPRs used in this Example targets the bfp gene in the Arabidopsis thaliana genome by introducing into protoplasts plasmid(s) encoding the Cas9 gene and one sgRNAs that is either encoded on a plasmid or introduced into protoplasts as an amplicon. The sgRNA is a fusion of CRISPR RNA (crRNA) and trans-activating crRNA (tracrRNA). The crRNA guides the Cas9 to the target genes, where Cas9 creates a double-stranded break and the GRON is used as a template to convert BFP to GFP in a site-directed manner.

Methods

Arabidopsis thaliana protoplasts derived from induced root tissue are seeded on a flat-bottom 96-well plate, at 250,000 cells per well at a cell density of 1×10$^7$ cells/ml. The CRISPR encoded plasmids contain the MAS promoter driving the Cas9 coding sequence with a rbcSE9 terminator and Arabidopsis U6 promoter driving multiple different sgRNAs with a poly-T$_{10}$ terminator ("T10" disclosed as SEQ ID NO: 21). The sgRNA is a fusion of CRISPR RNA (crRNA) and trans-activating crRNA (tracrRNA). The CRISPR plasmids along with GRON are introduced into protoplasts by PEG mediated delivery at a final concentration of 0.05 μg/μl for the CRISPR and 0.16 μM for the 201-mer. GRON treatments alone receive a final GRON concentration after PEG delivery of 2.5 μM for the 201-mer. Protoplasts will be incubated in the dark at 23° C. for 72 hours, and then they are analyzed by flow cytometer in order to determine the percentage of BFP to GFP within a given treatment.

TABLE 13

List of GRON used in this example (SEQ ID NO: 36)

| GRON Name | GRON Chemistry | GRON Sequence |
|---|---|---|
| BFP4/NC 201-mer 3W | 3PS | 5' AAGATGGTGCGCTCCTGGACGTAGCCTTCGGGCATGGCGGACTTGAAGAAGTCG TGCTGCTTCATGTGGTCGGGGTAGCGGCTGAAGCACTGCACGCCGTACGTAAACGTGGTCACG AGGGTGGGCCAGGGCACGGGCAGCTTGCCGGTGGTGCAGATGAACTTCAGGGTCAGCTTGCCG TAGGTGGCATCGCCCTCGCCC 3' |

Results

Figure 11:
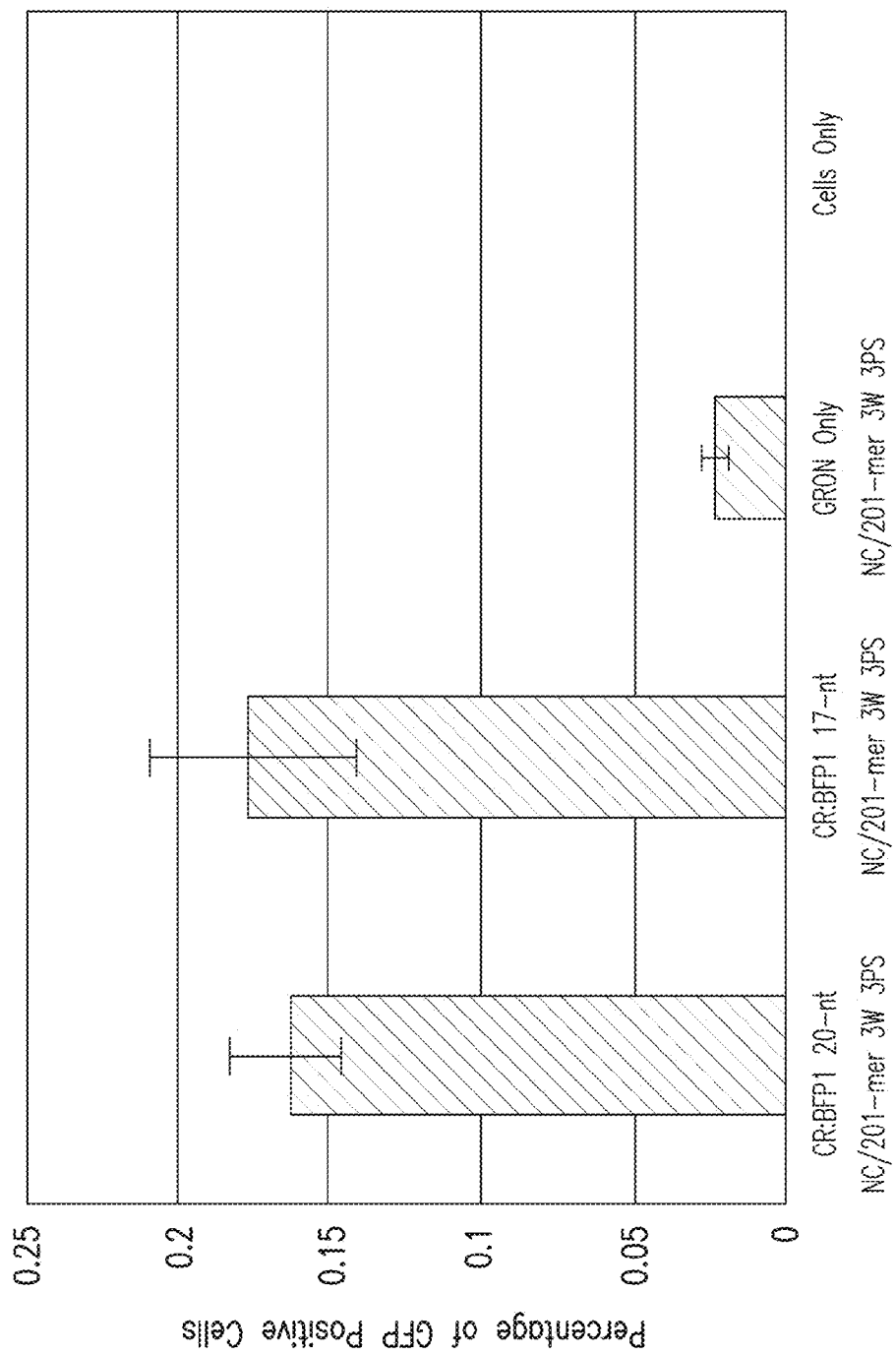
FIG. 11 shows the results of the effect of CRISPRs and GRONs in mediating BFP to GFP conversion in a BFP transgenic *Arabidopsis thaliana* model system of spacers of differing lengths.

Reducing the length of the BFP1 protospacer from 20 bp to 17 bp had similar levels of BFP to GFP conversion of 0.163% vs. 0.177% respectively at 72 h post PEG delivery of plasmids and GRONs into the Arabidopsis thaliana BFP model system (FIG. 11).

Example 15: CRISPRs with Amplicon gRNA

The purpose of this Example is to demonstrate conversion of BFP to GFP in protoplasts derived from the Arabidopsis thaliana BFP model system using CRISPRs to create double-stranded breaks in targeted genes and GRONs to The CRISPR consists of two components: the plant codon-optimized Streptococcus pyogenes Cas9 (SpCas9) and sgRNA both of which were expressed from the same or multiple plasmids. The sgRNA is a fusion of CRISPR RNA (crRNA) and trans-activating crRNA (tracrRNA). The crRNA region contains the spacer sequence used to guide the Cas9 nuclease to the targeted genes. In these examples, the same BFP6 gRNA (5'GGTGCCGCACGTCAC-GAAGTCGG 3' (SEQ ID NO:23)) was delivered into protoplasts either as an amplicon or encoded on a plasmid. Table 14 describes the GRONs used.

TABLE 14

List of GRONs used in this example (SEQ ID NOS 17 and 19, respectively, in order of appearance)

| GRON Name | GRON Chemistry | GRON Sequence |
|---|---|---|
| BFP4/NC201-mer | 3PS | 5' AAGATGGTGCGCTCCTGGACGTAGCCTTCGGGCATGGCGGACTTGAAGAAGTCGTGCTGCTT CATGTGGTCTGGGTAGCGGCTGAAGCACTGCACGCCGTAGGTGAAGGTGGTCACGAGGGTGGG CCAGGGCACGGGCAGCTTGCCGGTGGTGCAGATGAACTTCAGGGTCAGCTTGCCGTAGGTGGC ATCGCCCTCGCCC 3' |
| BFP4/C201-mer | 3PS | 5' GGGCGAGGGCGATGCCACCTACGGCAAGCTGACCCTGAAGTTCATCTGCACCACCGGCAAG TGCCCGTGCCCTGGCCCACCCTCGTGACCACCTTCACCTACGGCGTGCAGTGCTTCAGCCGCTA |

TABLE 14-continued

List of GRONs used in this example (SEQ ID NOS 17 and 19, respectively, in order of appearance)

| GRON Name | GRON Chemistry | GRON Sequence |
|---|---|---|
| | | CCCCGACCACATGAAGCAGCACGACTTCTTCAAGTCCGCCATGCCCGAAGGCTACGTCCAGGA GCGCACCATCTT 3' |

Results

Figure 12:
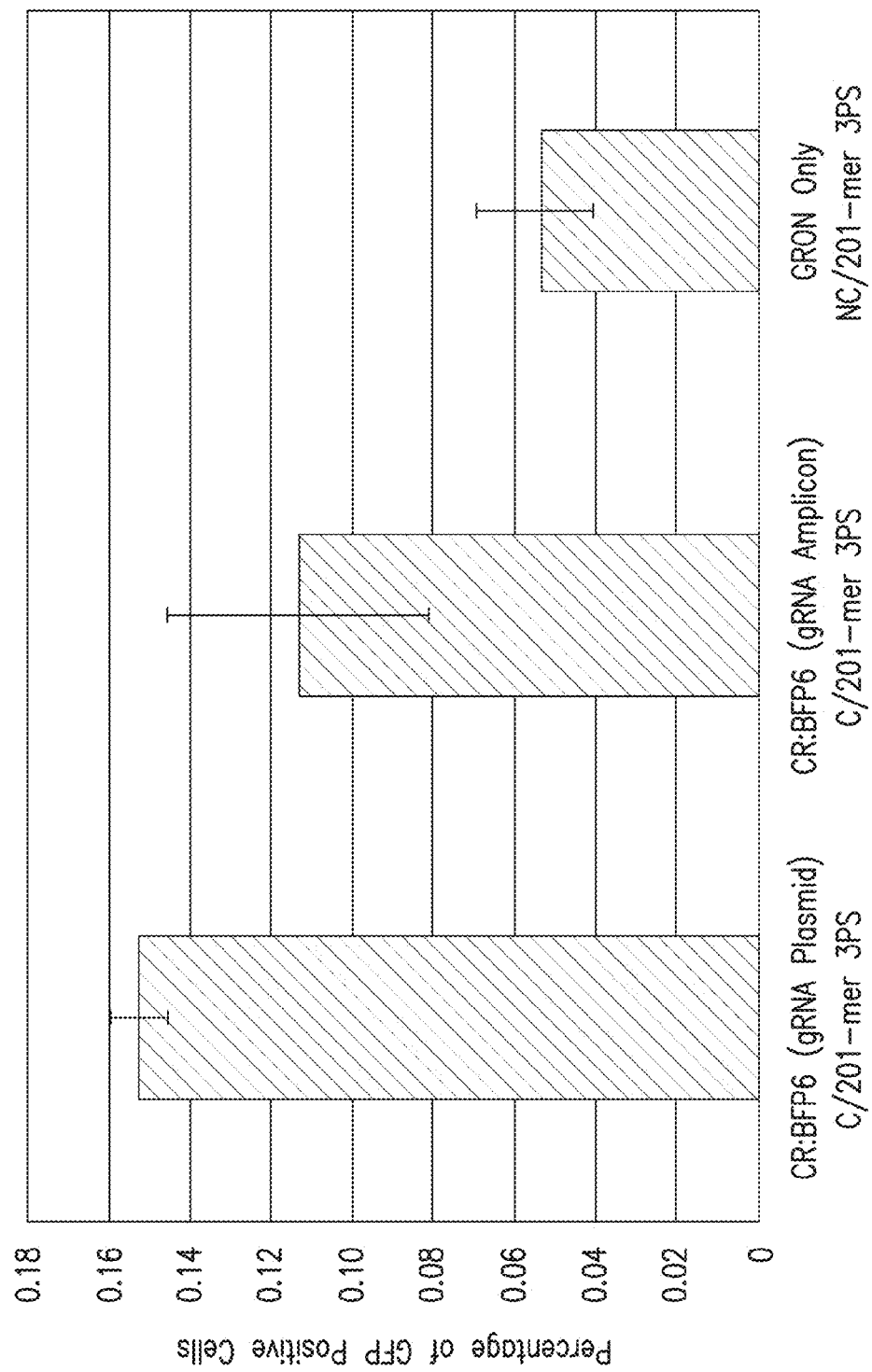
FIG. 12 shows the results of the effect of CRISPRs and GRONs in mediating BFP to GFP conversion in a BFP transgenic *Arabidopsis thaliana* model system of spacers were encoded on a plasmid (gRNA plasmid) or used as an amplicon (gRNA amplicon).

Delivery of the BFP6 gRNA as an amplicon (CR:BFP6 (gRNA amplicon)) along with a plasmid containing only Cas9 had similar rates of BFP to GFP conversion when compared to treatments with both the gRNA (gRNA plasmid) and Cas9 being encoded on separate plasmids at 72 h post PEG delivery of plasmids and GRONs into the *Arabidopsis thaliana* BFP model system (FIG. 12).

Example 16: CRISPRs with Unmodified GRONs

The purpose of this example is to demonstrate BFP to GFP conversion in our *Arabidopsis thaliana* BFP transgenic model system using CRISPRs to create targeted double-stranded breaks in the bfp gene and GRONs to mediate conversion. The BFP CRISPR used in this example targets the bfp gene and causes a double-stranded break in the DNA near the site of conversion. The 3P5 GRONs contain DNA bases with 3 phosphothioate linkages on both the 5' and 3' ends of the GRON and are herein referred to as 3P5 GRONs. The 3P5 GRONs were directly compared to their unmodified GRON counterparts in mediated BFP to GFP conversion using the BFP CRISPRs in our BFP transgenic *Arabidopsis thaliana* model system. See Table 15 for the list of GRONs used in these examples rbcSE9 terminator and the *Arabidopsis* U6 promoter driving the sgRNA with a poly-T10 terminator ("T10" disclosed as SEQ ID NO: 21). The sgRNA is a fusion of CRISPR RNA (crRNA) and trans-activating crRNA (tracrRNA). The CRISPR plasmids along with GRON were introduced into protoplasts by PEG mediated delivery at a final concentration of 0.05 µg/µl for the CRISPR, 0.16 µM for the 41-mer GRONs. GRON treatments alone received a final GRON concentration after PEG delivery of 0.8 µM for the 41-mer. Protoplasts were incubated in the dark at 23° C. for 72 hours, and then they were analyzed by flow cytometer in order to determine the percentage of GFP positive protoplasts within a given treatment.

The CRISPR consists of two components: the plant codon-optimized *Streptococcus* pyogenes Cas9 (SpCas9) and sgRNA both of which were expressed from the same plasmid. The sgRNA is a fusion of CRISPR RNA (crRNA) and trans-activating crRNA (tracrRNA). The crRNA region contains the spacer sequence used to guide the Cas9 nucle-

TABLE 15

List of GRONs used in this example (SEQ ID NOS 24 and 37, respectively, in order of appearance)

| GRON Name | GRON Chemistry | GRON Sequence |
|---|---|---|
| BFP4/C41-mer | 3PS | 5'CCCTCGTGACCACCTTCACCTACGGCGTGCAGTGCTTCAGC 3' |
| BFP4/NC41-mer | None | 5' GCTGAAGCACTGCACGCCGTAGGTGAAGGTGGTCAC-GAGGG 3' |

Methods

BFP transgenic *Arabidopsis thaliana* protoplasts derived from induced root tissue were seeded on a flat-bottom 96-well plate, at 250,000 cells per well at a cell density of 1×107 cells/ml. The CRISPR encoded plasmids contain the MAS promoter driving the Cas9 coding sequence with a ase to the BFP target gene. The BFP CRISPR spacer sequence is 5'CTCGTGACCACCTTCACCCA 3' (SEQ ID NO:28). In this example the BFP CRISPR was used which targets the bfp gene. The GRONs contain the non-coding sequence of the bfp gene near the site of conversion. Table 16 shows a list of the GRONs used

TABLE 16

List of GRONs used in this example. (SEQ ID NOS 24 and 37, respectively, in order of appearance).

| GRON Name | GRON Chemisty | GRON Sequence |
|---|---|---|
| BFP4/C 41-mer | 3PS | 5' CCCTCGTGACCACCTTCACCTACGGCGTGCAGTGCT-TCAGC 3' |
| BFP4/NC 41-mer | None | 5' GCTGAAGCACTGCACGCCGTAGGTGAAGGTGGTCAC-GAGGG 3' |

Results

Figure 13:
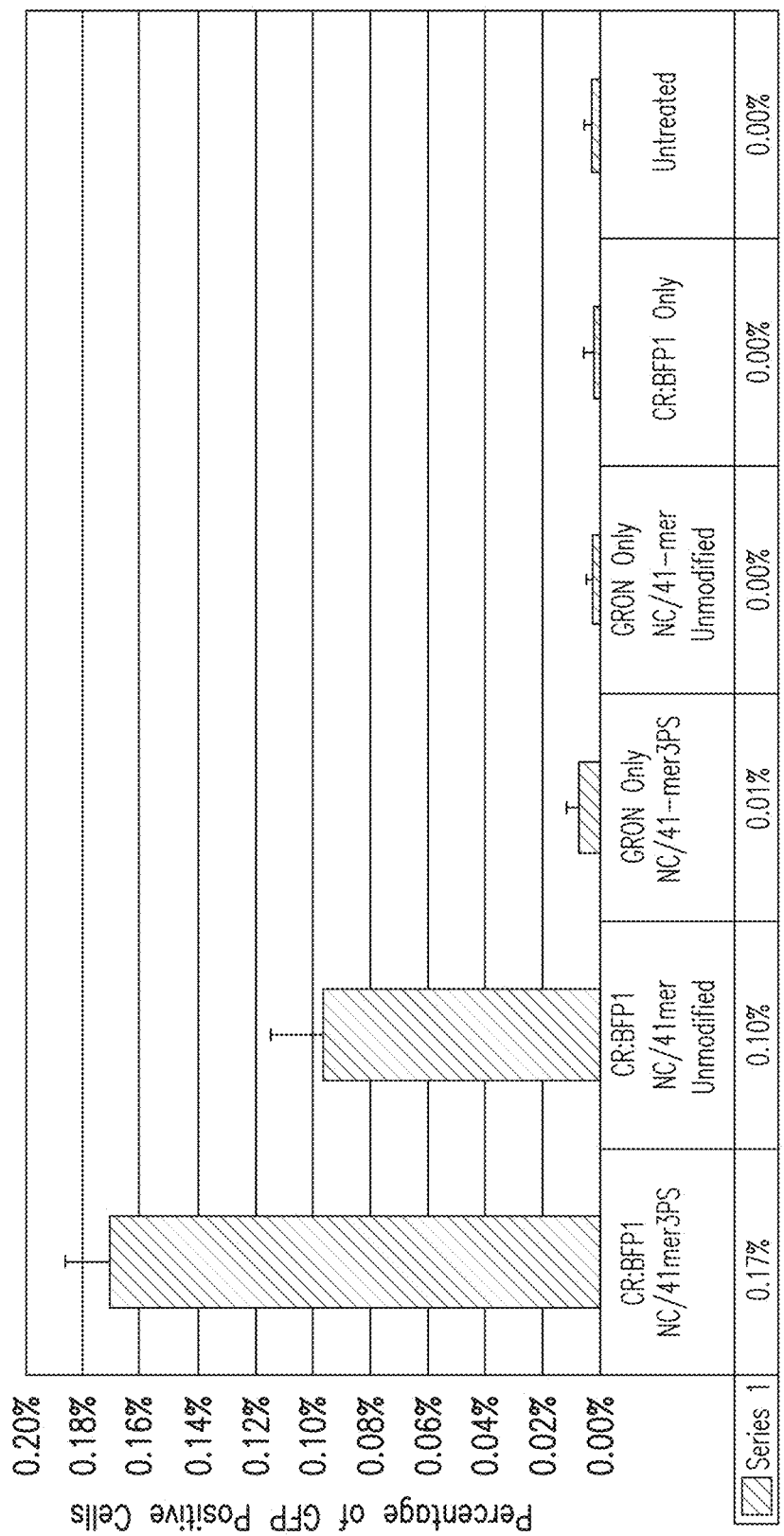
FIG. 13 shows the results of the effect of CRISPRs and GRONs in mediating BFP to GFP conversion in a BFP transgenic *Arabidopsis thaliana* model system of unmodified vs. 3P5 modified 41-mer GRONs.

The 41-mer 3P5 GRONs are more efficacious than their unmodified GRON counterparts at mediating BFP to GFP conversion using the BFP CRISPRs (FIG. 13).

Example 17: TALENs and GRONs in Flax

The purpose of this example is to demonstrate EPSPS conversion in flax at both 24 hours in protoplasts and 3-weeks in microcalli after delivery of TALEN plasmids and GRONs. The TALENs used in this example targets the epsps gene in the *Linum usitatissimum* genome by introducing into shoot tip derived protoplasts plasmid(s) encoding TALENs creates a double-stranded break and the GRON is used as a template to convert the epsps gene in a site-directed manner.

Methods

Flax protoplasts were isolated from shoot tips obtained from in vitro germinated seedlings. The TALEN plasmids along with GRONs were introduced into protoplasts by PEG mediated delivery at a final concentration of 0.05 µg/µl and 0.5 µM respectively. Protoplasts were incubated in the dark at 25° C. for up to 48 h in liquid medium, or embedded in alginate beads ($5\times10^5$ cells/ml), and cultured in liquid medium to induce cell division and the formation of microcalli. Protoplasts or microcalli samples obtained 24 h or 3 weeks after DNA delivery were analyzed by NGS to determine the percentage of cells (DNA reads) carrying out the target mutation within a given treatment. The percent of indels generated by imperfect NHEJ-mediated DNA repair was also estimated.

TALEN constructs include two arms (left and right), each consisting of a TAL effector-like DNA binding domain linked to a catalytic DNA cleavage domain of FokI. The TAL effector-like DNA binding domain guides the TALEN arms to specific sites of DNA which allows the FokI endonucleases of each arm to dimerize together and cleave double-stranded DNA. The TALEN encoded plasmids contains MasP::LuEPSPS (Left arm)-T2A-LuEPSPS_(right arm) with a rbcSE9 terminator. LuEPSPS_(left arm) sequence is 5'TGGAACAGCTATGCGTCCG 3' (SEQ ID NO:38) and the LuEPSPS_(right arm) sequence is 5'TGAGTTGCCTCCAGCGGCT 3' (SEQ ID NO:39). GRONs (144-mers) targeting LuEPSPS with or without wobble bases were used to determine their effect on rate of conversion.

Results 24 hour protoplasts and 3-week old microcalli have 0.067% and 0.051% EPSPS conversion respectively as determined by Next Generation Sequencing (FIG. 14). Additionally, these data show that the TALEN is active and able to cleave the epsps target gene in *Linum usitatissimum* and form indels of 2.60% and 1.84% respectively at 24 hours in protoplasts and up to 3-week in microcalli. Moreover, EPSPS conversion and indels are maintained up to 3 weeks after the TALEN plasmid and GRON are introduced.

Example 18: CRISPRs and GRONs in Flax

The purpose of this example is to demonstrate activity of Cas9 in flax microcalli three and six weeks after delivery of a Cas9 plasmid. The CRISPRs used in this example targets the epsps gene in the *Linum usitatissimum* genome by introducing into shoot tip derived protoplasts plasmid(s) encoding the Cas9 gene and a sgRNAs. The sgRNA is a fusion of CRISPR RNA (crRNA) and trans-activating crRNA (tracrRNA). The crRNA guides the Cas9 to the target genes, where Cas9 creates a double-stranded break in the epsps gene in a site-directed manner. The double-stranded breaks in the epsps gene when repaired by the ubiquitous NHEJ pathway will cause indels to form around the cleavage site.

Methods

Flax protoplasts were isolated from shoot tips obtained from in vitro germinated seedlings. The CRISPR encoded plasmids contains the MAS promoter driving the Cas9 coding sequence with an rbcSE9 terminator and the *Arabidopsis thaliana* U6 promoter driving the sgRNA with a poly-$T_{10}$ terminator ("T10" disclosed as SEQ ID NO: 21). The CRISPR plasmids were introduced into protoplasts by PEG mediated delivery at a final concentration of 0.05 µg/µl. Protoplasts were embedded in alginate beads ($5\times10^5$ cells/ml), cultured in liquid medium, and incubated in a rotatory shaker (30 rpm) in the dark at 25° C. Microcalli developed from individual cells were analyzed by NGS, 3 and 6 weeks after CRISPR plasmid delivery, to determine the percentage of cells (DNA reads) carrying out indels generated by the error-prone NHEJ-mediated DNA repair pathway.

The CRISPR consists of two components: the plant codon-optimized *Streptococcus pyogenes* Cas9 (SpCas9) and sgRNA both of which were expressed from the same plasmid. The sgRNA is a fusion of CRISPR RNA (crRNA) and trans-activating crRNA (tracrRNA). The crRNA region contains the spacer sequence used to guide the Cas9 nuclease to the target gene. In this example the CRISPR targets the epsps gene.

Results 3- and 6-week old microcalli have 46.5% and 54.7% indel formation respectively as determined by Next Generation Sequencing (FIG. 15). These data shows that Cas9 is active and able to cleave the EPSPS target gene in *Linum usitatissimum* and form indels. Moreover, these indels are maintained up to 6 weeks after the CRISPR plasmid was introduced.

Example 19: Construction of Engineered Nucleases

CRISPR-Cas

For construction of transient CRISPR-Cas9 expression plasmids, a higher plant codon-optimized SpCas9 gene containing a SV40 NLS at both the N- and C-terminal and a 2x FLAG tag on the N-terminal was synthesized as a series of GeneArt® Strings™ (Life Technology, Carlsbad, Calif.), then cloned downstream of the mannopine synthase (MAS) promoter and upstream of the pea ribulose bisphosphate carboxylase (rbcsE9) terminator by Gibson's method. Next, an sgRNA cassette consisting of a chimeric gRNA whose expression is driven by the *Arabidopsis* U6 promoter, was synthesized as GeneArt® Strings™, then shuttled into the Cas9 containing construct using Gibson's method forming pBCRISPR. To specify the chimeric gRNA for the respective target sequence, pairs of DNA oligonucleotides encoding the variable 20-nt sgRNA targeting sequences (Extended Data Table 2) were annealed to generate short double strand fragments with 4-bp overhangs. The fragments were ligated into BbsI digested pBCrispr to yield CRISPR-Cas constructs BC-1, BC-2 and BC-3.

TALEN

Design and construction of TALEN expression constructs BT-1 and LuET-1 was based on rules as described in Cermak et al., *Nucleic Acids Res.* 39, e82 (2011). The target sequence was selected based on the gene editing site and the repeat variable i-residue (RVD) following the rules that NG, HD, NI, and NN recognize T, C, A, and G, respectively. The assembly of TAL effector domain linked to the heterodimeric FokI domains was completed through a commercial service (GeneArt; Life Technologies). TALEN monomers were cloned downstream of the MAS promoter and upstream of the rbcE9 terminator using Gibson's method and expressed as a 2A coupled unit.

Cell Culture and Protoplast Isolation

Surface-sterilized *Arabidopsis* seeds were germinated on solid ½ MS medium (Minerals and vitamins according to XX$_{[48]}$; ½ concentrated; 87.7 mM sucrose) at 28° C. under a 12 h light/dark cycle. Root material from 2 to 3-week-old seedlings were collected and maintained in ½ MS liquid medium under low light conditions at 28° C. Root cultures were transferred and maintained in MSAR[0.22% ½ MS, 87.7 mM sucrose, 11.4 μM IAA, 2.3 μM 2,4-D, 1.5 μM 2iP, pH 5.8] three weeks prior to protoplast isolation. Roots were cut into approximately 6 mm segments and incubated in MSAP solution[0.22% ½ MS, 87.7 mM sucrose, 11.4 μM IAA, 2.3 μM 2,4-D, 1.5 μM 2iP, and 400 mM mannitol, pH 5.8] containing cell wall digesting enzymes [1.25% Cellulase RS, 0.25% Macerozyme R-10, 0.6 M mannitol, 5 mM MES, 0.1% BSA] for 3-4 h in the dark with gentle shaking. The released protoplasts were collected and passed through a sterile 100 μm filter and 35 μm filter. The protoplast filtrate was mixed with 0.8 times the volume of Optiprep™ Density Gradient Medium (Sigma) and mixed gently. A 60% W5 [154 mM NaCl, 5 mM KCl, 125 mM CaCl$_2$.2H$_2$O, 5 mM glucose, 10 mM MES, (pH 5.8)]/40% Optiprep solution followed by 90% W5/10% Optiprep solution were slowly layered onto the filtrate/Optiprep solution to make a gradient, which was centrifuged at 198 RCF for 10 min. The white protoplast layer was collected and mixed with 2 times the volume of W5. Protoplasts were centrifuged at 44 RCF for 10 min and re-suspended in TM solution [14.8 mM MgCl$_2$.6H$_2$O, 5 mM MES, 572 mM mannitol, (pH 5.8)] at a density of 1×10$^7$ cells/ml. For experiments with Zeocin™ (Life Technologies, Carlsbad, Calif.) and phleomycin (InvivoGen, San Diego, Calif.), protoplasts were kept in TM adjusted to pH 7.0 for 90 min on ice before transfection. For antibiotic concentrations see Extended Data FIG. 1.

Flax protoplasts were isolated from shoot tips obtained from 3-week-old seedlings germinated in vitro. Shoot tips were finely chopped with a scalpel, pre-plasmolyzed for 1 h at room temperature in B-medium [B5 salts and vitamins (Gamborg et al., 1968), 4 mM CaCl$_2$, 0.1 M glucose, 0.3 M mannitol, 0.1 M glycine, 250 mg/l casein hydrolysate, 10 mg/l L-cystein-HCL, 0.5% polyvinylpyrrolidone (MW 10,000), 0.1% BSA, 1 mg/l BAP, 0.2 mg/l NAA, and 0.5 mg/l 2,4-D], and incubated in a cell wall digesting enzyme solution containing B-medium supplemented with 0.66% Cellulase YC and 0.16% Macerozyme R-10 over a rotatory shaker (50 rpm) at 25° C. for 5 h. Released protoplasts were sieved and purified by density gradient centrifugation using Optiprep (Sigma) layers, counted with a hemocytometer, and kept stationary overnight in the dark at a density of 0.5×10$^6$ protoplasts/ml in B medium.

Protoplast Transfection

In a 96-well flat bottom plate, 2.5×10$^5$ cells per well were transfected with 10 pmol GRON, 10 pmol GRON plus 3.25 μg CRISPR-Cas or TALEN expression construct or mock using PEG [270 mM mannitol, 67.5 mM Ca(NO$_3$)$_2$, 38.4% PEG 1500, (pH 5.8)]. Cells and DNA were incubated with PEG on ice for 30 minutes followed by a wash with 200 μl of W5 solution. Finally, 85 μl of MSAP++ [MSAP containing 50 nM phytosulfokine-α and 20 μM n-propyl gallate] was added and the cells cultured in low light conditions at 28° C.

After about 18 h of culture, protoplasts were transfected with TALEN plasmid along with GRONs (20 μg plasmid and 0.2 nmol GRON/10$^6$ protoplasts) using PEG mediated delivery. Treated protoplasts were incubated in the dark at 25° C. for up to 48 h in B medium, or embedded in alginate beads 24 h after transfection, and cultured in V-KM liquid medium to induce cell division and the formation of microcalli. For the antibiotic experiments, 1.25×10$^5$ cells per well were transfected with 8 μM GRON CG13 using the PEG solution described above.

Cytometry

Seventy-two h after transfection, cells were analyzed by cytometry using the Attune® Acoustic Focusing cytometer (Applied Biosystems®) with excitation and detection of emission as appropriate for GFP. Background level was based on PEG-treated protoplasts without DNA delivery. For antibiotic experiments, protoplasts treated with Zeocin or phleomycin prior to transfection were analyzed by cytometry 48 h after transfection.

Sequencing Analysis

Genomic DNA was extracted from CRISPR-Cas or TALEN-treated protoplasts using the NucleoSpin® Plant II kit as per the manufacturer's recommendations (Machery-Nagel, Bethlehem, Pa.). Amplicons flanking the TALEN or CRISPR target region were generated using Phusion® polymerase with 100 ng of genomic DNA and primers BFPF-1 (5'-GGACGACGGCAACTACAAGACC-3' (SEQ ID NO:40))/BFPR-1 (5'-TAAACGGCCACAAGTTCAGC-3' (SEQ ID NO:41)) for *Arabidopsis* CRISPR and TALEN; or LuEPF-1 (5'-GCATAGCAGTGAGCAGAAGC-3' (SEQ ID NO:42))/LuEPR-1 5'-AGAAGCTGAAAGGCTGGAAG-3' (SEQ ID NO:43) for *L. usitatissimum* TALEN. The amplicons were purified and concentrated using Qiaquick MinElute columns (Qiagen, Valencia, Calif.). Deep sequencing of the amplicons was performed by GeneWiz (South Plainfield, N.J.) using a 2×250 bp MiSeq run (Illumina, San Diego, Calif.). For data analysis fastq files for read 1 and read 2 were imported into CLC Genomics Workbench 7.0.4 (CLCBio, Boston, Mass.). Paired reads were merged into a single sequence if their sequences overlapped. A sequence for an amplicon was identified if it or its reverse and complemented sequence contained both forward and reverse primer sequences. Occurrence of a unique sequence in a sample was recorded as its abundance. Percent indel or gene edit was calculated by dividing the number of reads with the edit or indel by the total number of sequenced reads, and then multiplying by 100.

| Sequence of CRISPR-Cas photospacers (SEQ ID NOS 28, 25, and 44, respectively, in order of appearance) | | |
|---|---|---|
| Name | Sequence (5' to 3') | Figure Reference |
| BC-1 | CTCGTGACCACCTTCACCCA | 1a; 1b; 2a; 2c |
| BC-2 | GTCGTGCTGCTTCATGTGGT | 2b |
| BC-3 | GGCTGAAGCACTGCACGCCG | 2d |

-continued

| TALEN binding domain sequences (SEQ ID NOS 45, 46, 38, and 39, respectively, in order of appearance) | | |
|---|---|---|
| Paper Name | Sequence (5' to 3') | Figure Reference |
| BT-1 | Left arm: TGGTCGGGGTAGCGGCTGA<br>Right arm: TCGTGACCACCTTCACCCA | 3a; 3b |
| LuET-1 | Left arm: TGGAACAGCTATGCGTCCG<br>Right arm: TGAGTTGCCTCCAGCGGCT | 3c; 3d |

| GRON sequences used (SEQ ID NOS 37, 37, 24, 47, 26, 48, 19, 22, 36, 32, 32, 49, 50, and 51, respectively, in order of appearance) | | | |
|---|---|---|---|
| Name | Sequence (5' to 3') | Chemistry | Figure Reference |
| CG1 | GCTGAAGCACTGCACGCCGTAGGTGAAGGTGGTCACGAGGG | unmodified | 2a |
| CG2 | G*C*T*GAAGCACTGCACGCGTAGGTGAAGGTGGTCACGA*G*G*G | (*) = 3PS | 2a |
| CG3 | C*C*C*TCGTGACCACCTTCACCTACGGCGTGCAGTGCTTC*A*G*C | (*) = 3PS | 2d; 3a |
| CG4 | VCCCTCGTGACCACCTTCACCTTCACCTACGGCGTGCAGTGCTTCAGCH | V= CY3;<br>H = 3'DMT dC CPG | 2d |
| CG5 | G*T*G*ACCACCTTCACCTACGGCGTGCAGTGCTTCAGCCGCTACCCAGACCACATGAAG*C*A*G | (*) = 3PS | 2b |
| CG6 | A*A*G*ATGGTGCGCTCCTGGACGTAGCCTTCGGGCATGGCGGACTTGAAGAAGTCGTGCTGCTTCATGTGGTCGGGGTAGCGGCTGAAGCACTGCACGCCGTAGGTGAAGGTGGTCACGAGGGTGGGCCAGGGCACGGGCAGCTTGCCGGTGGTGCAGATGAACTTCAGGGTCAGCTTGCCGTAGGTGGCATGCCCTCG*C*C*C | (*) = 3PS | 1b; 2c |
| CG7 | G*G*G*CGAGGGCGATGCCACCTACGGCAAGCTGACCCTGAAGTTCATCTGCACCACCGGCAAGCTGCCCGTGCCCTGGCCCACCCTCGTGACCACCTTCACCTACGGCGTGCAGTGCTTCAGCGCTACCCCGACCACATGAAGCAGCACGACTTCTTCAAGTCCGCCATGCCCGAAGGCTACGTCCAGGA GCGCACCAT*C*T*T | (*) = 3PS | 3b |
| CG8 | G*G*G*CGAGGGCGATGCCACCTACGGCAAGCTGACCCTGAAGTTCATCTGCACCACCGGCAAGCTGCCGTGCCCTGGCCCACCCTCGTGACCACCTTCACCTACGGCGTGCAGTGCTTCAGCCGCTACCCAGACCACATGAAGCAGCACGACTTCTTCAAGTCCGCCATGCCCGAAGGCTACGTCCAGGA GCGCACCAT*C*T*T | (*) = 3PS | 2b |
| CG9 | A*A*G*ATGGTGCGCTCCTGGACGTAGCCTTCGGGCATGGCGGACTTGAAGAAGTCGTGCTGCTTCATGTGGTCGGGGTAGCGGCTGAAGCACTGCACGCCGTACGTAAACGTGGTCACGAGGGTGGGCCAGGGCACGGGCAGCTTGCCGGTGGTGCAGATGAACTTCAGGGTCAGCTTGCCG TAGGTGGCATCGCCCTCG*C*C*C | (*) = 3PS | 1a |
| CG10 | (a)agauggugcGCTCCTGGACGTAGCCTTCGGGCATGGCGGACTTGAAGAAGTCGTGCTGCTTCATGTGGTCGGGGTAGCGGCTGAAGCACTGCACGCCGTAGGTGAAGGTGGTCACGAGGGTGGGCCAGGGCACGGGCAGCTTGCCGGTGGTGCAGATGAACTTCAGGGTCAGCTTGCCGTAGGTGGCATCGCCCTCGCCC | Lower Case = RNA bases:<br>(base) = 2'-O-Me; Upper Case = DNA bases | 2c |
| CG11 | (a)(a)(g)(a)(u)(g)(g)(u)(g)cGCTCCTGGACGTAGCCTTCGGGCATGGCGGACTTGAAGAAGTCGTGCTGCTTCATGTGGTCGGGGTAGCGGCTGAAGCACTGCACGCCGTAGGTGAAGGTGGTCACGAGGGTGGGCCAGGGCACGGGCAGCTTGCCGGTGGTGCAGATGAACTTCAGGGTCAGCTTGCCGTAGGTGGCATCGCCCTCGCCC | Lower Case = RNA bases:<br>(base) = 2'-O-Me; Upper Case = DNA bases | 2c |
| CG12 | VCGGTCGGATAAACTGGCGAAGAACGATATTGAACTTTTCCTTGAAATGCTGGAATAGCTATGCGTCGCTGACAGCTGCTGTAACAGCCGCTGGAGGCAACTCAAGGTCCCTTCCCTCAACTCCTTCCAGCCTTTCAGCTTCTTH<br>and<br>VCGGTCGGTAAACTGGCGAACGATATTGAACTTTTCCTTGGAAATGCTGGAATAGCTATGCGTGCGCTGACAGCTGCTGTAACAGCCGCTGGAGGCAACTCAAGGTTCCTTCCCTCAACTCCTTCCAGCCTTTCAGCTTCTTH | V= CY3;<br>H = 3'DMT dC CPG | 3c; 3d |
| CG13 | G*C*T*GAAGCACTGCACGCGTGGGTGAAGGTGGTCACGA*G*G*G | (*) = 3PS | Extended Data FIG. 1 |

Statistical Analysis

Statistical significance was determined using a Student's t-test with two-tailed distribution. P-values <0.05 were considered as significant. Data are shown as mean and SEM.

Results

CRISPR-Cas nuclease activity and gene editing in *A. thaliana* protoplasts.

Engineered nucleases such as TAL effector nucleases (TALENs) and clustered regularly interspaced short palindromic repeats (CRISPR)-associated endonuclease Cas9 (CRISPR-Cas9) can be programmed to target and cleave double-stranded DNA with high specificity. TALENs consist of two arms, both having a TAL effector-like DNA binding domain (TALE) linked to a catalytic DNA nuclease domain of FokI. The TALE domains guide the TALEN arms to specific sites of DNA allowing for dimerization of the FokI endonucleases and subsequent generation of a double strand break (DSB). The CRISPR-Cas9 system consists of a two components; a *Streptococcus pyogenes* Cas9 nuclease (Sp-Cas9) and a chimeric fusion of two RNAs (crRNA and tracrRNA) referred to as an engineered single guide (sgRNA). The sgRNA supports targeted nucleic acid specificity for Cas9 through base pairing of its first twenty 5' bases with the DNA target, subsequently resulting in a site-specific DSB.

In plants, DSB s are typically repaired by the error prone non-homologous end joining (NHEJ) DNA repair pathway resulting in random deletions and/or insertions (indels) at the site of repair. In contrast precision genome editing, relies on nuclease induced DSBs near the targeted change to be repaired by homology directed repair (HDR), a repair pathway that is more precise than NHEJ due to the requirement of a homologous template DNA—in most cases sister chromatid. By harnessing the HDR pathway, it is possible to use an engineered oligonucleotide as the repair template to edit DNA specifically, when cleaved by nucleases or non-specifically when used in combination with double strand break inducing antibiotics.

FIG. 16 depicts CRISPR-Cas9 nuclease activity in *Arabidopsis thaliana* protoplasts derived from the BFP transgenic model system in which a stably integrated BFP gene can be converted to GFP by editing the codon encoding H66 (CACTAC H66Y). When cells were treated with CRISPR-Cas9 (BC-1), NHEJ induced indels were produced at a frequency of 0.79% near the H66 locus of the BFP gene by deep sequencing (FIG. 16a). The majority of indels were single bp and none longer than 9 bp. Conversely, cells treated with GRON only or mock-treated did not exhibit indels (data not shown). These results show that CRISPR-Cas9 nuclease can actively target the BFP gene in this transgenic model system.

With regard to the effectiveness of CRISPR-Cas9 in combination with GRON to mediate BFP to GFP gene editing in protoplasts derived from our transgenic model system, a 7.4-fold improvement in BFP to GFP editing was observed when both CRISPR-Cas9 and phosphorothioate (PS) modified GRONs (CG6) are introduced concurrently when compared to GRON alone or CRISPR-Cas9 alone treatments (FIG. 16b). These results demonstrate that introducing CRISPR-Cas9 with PS modified GRONs into *Arabidopsis* protoplasts significantly increase the frequency of BFP to GFP gene editing.

Figure 17A:
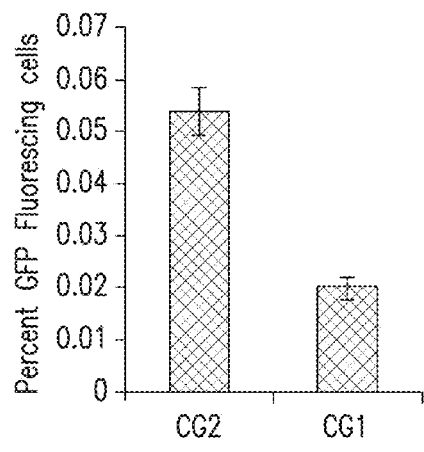
FIG. 17A shows a comparison of 3P5 and unmodified GRONs in BFP to GFP gene editing as measured by flow cytometry at 72 h after delivery of plasmid (BC-1) and GRONs (CG-1) or (CG-2).
Figure 17B:
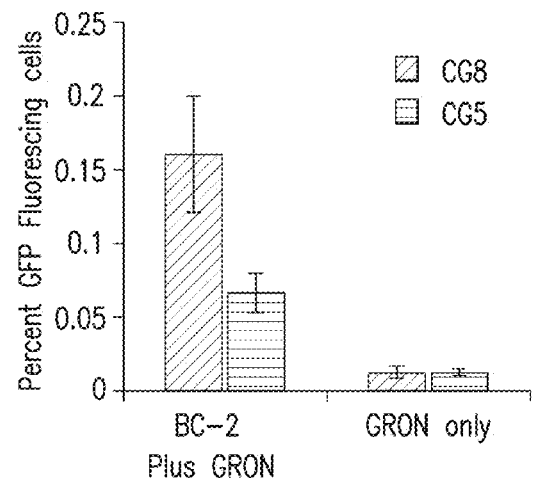
FIG. 17B shows a comparison of GRON lengths in BFP to GFP gene editing as measured by flow cytometry at 72 hours post delivery of plasmid (BC-2) and GRONs (CG-5) or (CG-8).

GRONs containing three adjacent PS modifications (herein refer to as 3P5) at both the 5' and 3' ends positively effect BFP to GFP editing when compared to an unmodified GRON. The 3P5 modified GRON (CG2), when combined with CRISPR-Cas9 (BC-1), is more efficacious at BFP to GFP editing when compared to an unmodified GRON template (CG1; FIG. 17a). In addition, a positive correlation between editing and GRON length (FIG. 17b) was observed. Taken together, these results show that both GRON modification and length can greatly improve the frequency of gene editing in plants such as *Arabidopsis* in the presence of CRISPR-Cas9.

Figure 17C:
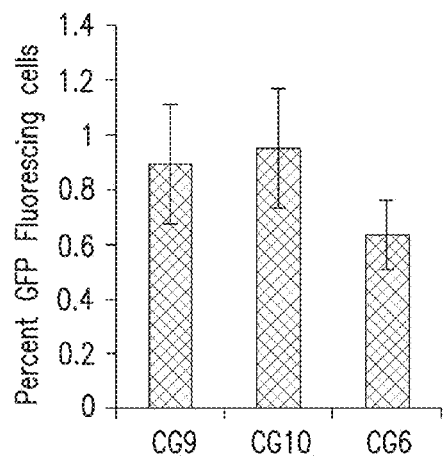
FIG. 17C shows a comparison of 3PS to 2'-O-Me GRONs for BFP to GFP gene editing as measured by flow cytometry at 72 h post delivery of plasmid (BC-1) and GRONs (CG-6), (CG-9) or (CG-10).
Figure 17D:
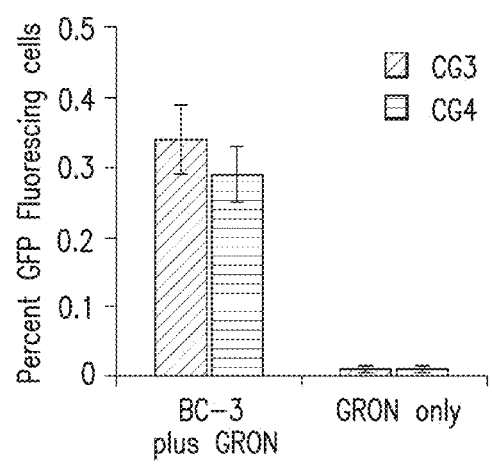
FIG. 17D shows a comparison of 3P5- to Cy3GRONs in BFP to GFP gene editing as measured by flow cytometry at 72 h post delivery of plasmid (BC-3) and GRONs (CG-3) or (CG-4). Error bars are s.e.m. (n=3). (CG-1): BFP antisense 41 nb unmodified; (CG-2): BFP antisense 41 nb 3P5 modified; (CG-3): BFP sense 41 nb 3P5 modified; (CG-4): BFP sense 41 nb Cy3 modified; (CG-5): BFP sense 60 nb 3P5 modified; (CG-6): BFP antisense 201 nb 3P5 modified; (CG-8): BFP sense 201 nb 3P5 modified; (CG-9): BFP antisense 201 nb 2'-O-Me modification on the first 5' RNA base; (CG-10): BFP antisense 201 nb 2'-O-Me modifications on the first nine 5' RNA bases.

When either the 201 nucleobase (nb) 3P5 modified GRON (CG6), or the 201 nb 2'-O-methyl modified GRONs (CG9) or (CG10), consisting of the first ten 5' bases as RNA with either the first RNA base or the first 9 RNA bases modified with 2'-O-methyl are introduced along with CRISPR-Cas9 (BC-1) into *Arabidopsis* protoplasts, no statistical difference in BFP to GFP editing between them was observed (FIG. 17c). Similarly, when either the 201 nb 3P5 modified GRON (CG3) or the 201 nb Cy3 modified GRON (CG4), comprising of a 5' Cy3 and an 3' idC reverse base, were introduced along with CRISPR-Cas9 (BC-3) into *Arabidopsis* protoplasts, no statistical difference in editing frequencies was observed (FIG. 17d). Overall, these data show that diverse GRON modifications can greatly improve the frequency of gene editing in *Arabidopsis* in the presence of CRISPR-Cas9.

Figure 18B:
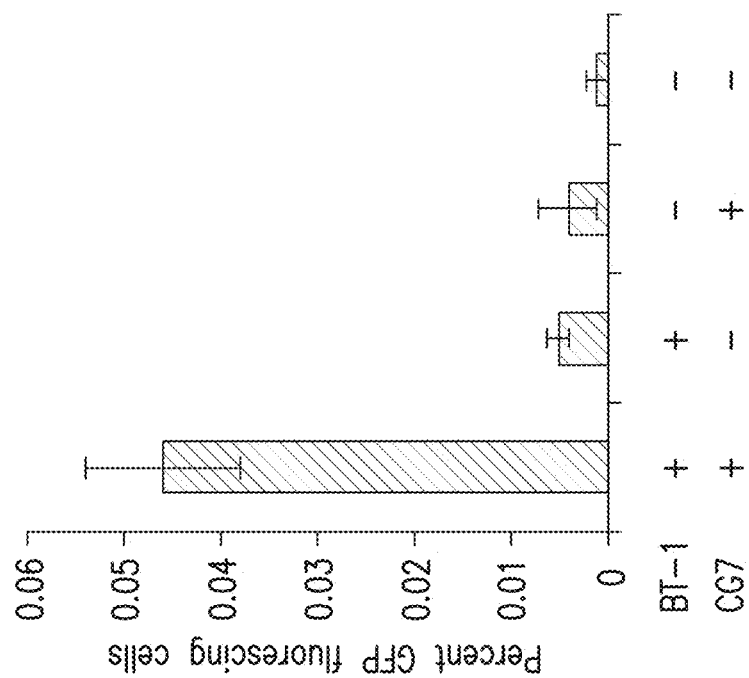
FIG. 18B shows BFP to GFP gene editing as measured by flow cytometry at 48 h post delivery of plasmid (BT-1) and GRON (CG-7).
Figure 18A:
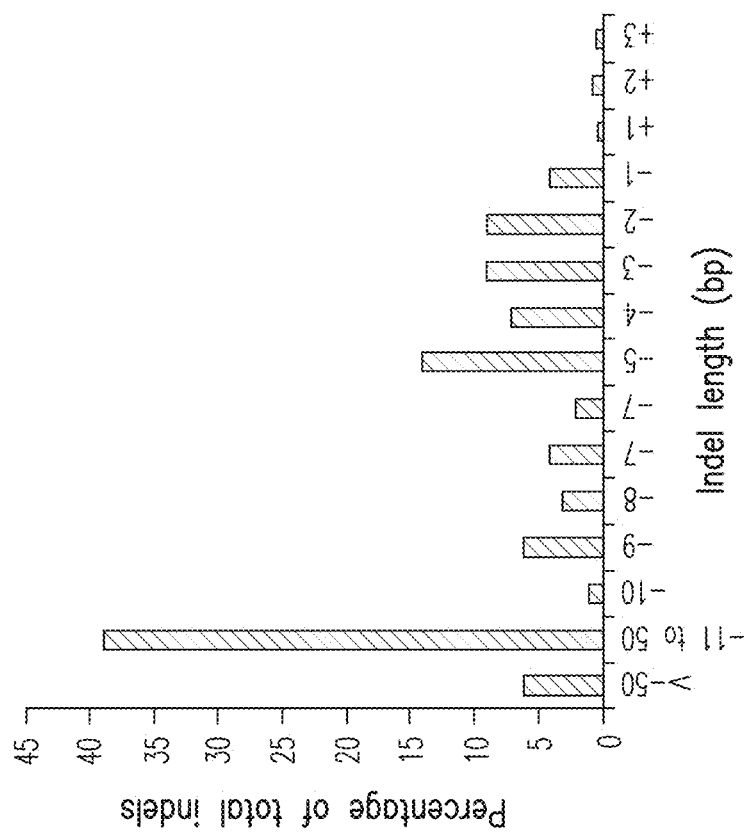
FIG. 18A shows a distribution of indels based on size as determined by deep sequencing in *Arabidopsis* protoplasts treated with TALEN plasmid (BT-1) at 72 h post delivery. Indels represented 0.51% of the total reads.

Based on these results with CRISPR-Cas9 and modified GRONs, it was determined if modified GRONs coupled with TALEN pairs targeting the BFP gene result in improved BFP to GFP gene editing as well. To first show effective nuclease activity at the BFP locus *Arabidopsis* protoplasts were treated with TALENs (BT-1) and found 0.51% indels at or near the expected cleavage site by deep sequencing—indicating that TALENs are as active as CRISPR-Cas9 in this model system (FIG. 18a). The majority of deletions were >10 bp but less than 50 bp, while insertions, significantly less abundant than deletions were three bp or less. Next we examined the effectiveness of TALENs coupled with modified GRON to edit BFP to GFP. A 9.2-fold improvement in the frequency of BFP to GFP editing was observed when both the BFP TALEN (BT-1) and 3P5 GRON (CG7) are introduced when compared to 3P5 GRON alone (FIG. 18b). Similar to the CRISPR-Cas experiments described above, these results demonstrate that introducing TALENs with 3P5 modified GRONs into *Arabidopsis* protoplasts also significantly increases the frequency of BFP to GFP gene editing.

The EPSPS (5'-enolpyruvylshikimate-3-phosphate synthase) loci in *Linum usitatissimum* (Common flax) was also used as a target in this system. The EPSPS genes encode an enzyme in the shikimate pathway that participates in the biosynthesis of the aromatic amino acids phenylalanine, tyrosine and tryptophan. In plants, EPSPS is a target for the herbicide, glyphosate, where it acts as a competitive inhibitor of the binding site for phosphoenolpyruvate.

Figure 18D:
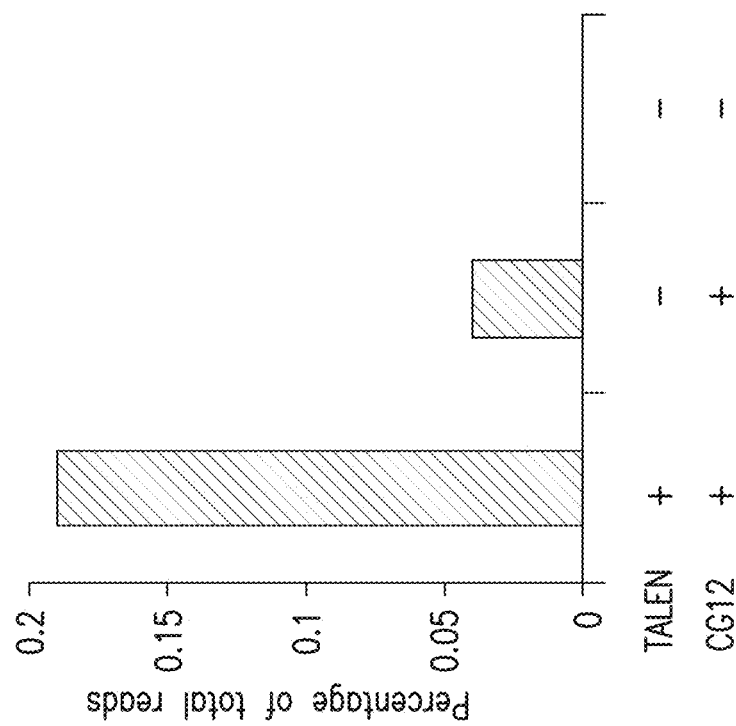
FIG. 18D shows *L. usitatissimum* EPSPS gene editing as measured by deep sequencing at 7 d post delivery of plasmid (LuET-1) and GRON (CG-11) into protoplasts. Percentage of total reads represents the number of reads containing both T97I and P101A edits as a percentage of the total reads. Error bars are s.e.m. (n=3). (CG-7): BFP sense 201 nb 3P5 modified; (CG-11): EPSPS sense 144 nb Cy3 modified.
Figure 18C:
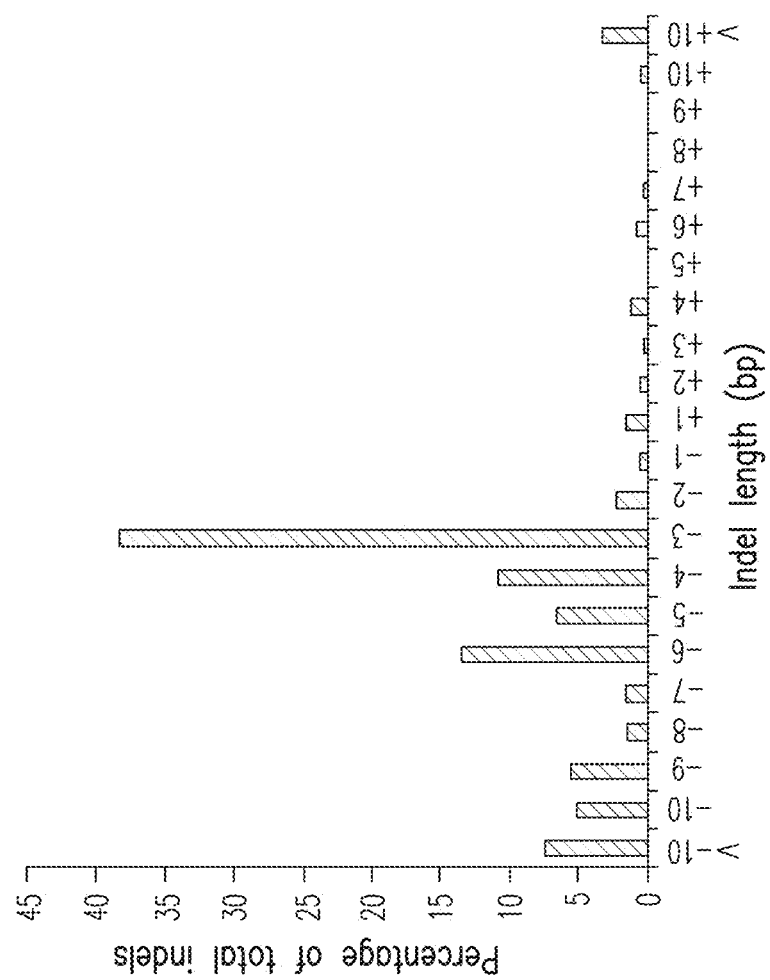
FIG. 18C shows a representative distribution of indels based on bp length in *L. usitatissimum* protoplasts treated with a TALEN (LuET-1) targeting the EPSPS genes 7 d after delivery. Total frequency of indels is 0.50%.

TALENs targeting a site near two loci (T97I and P101A) in *L. usitatissimum* that when edited will render EPSPS tolerant to glyphosate (Extended Data FIG. 18b) were selected. Delivering TALEN (LuET-1) together with a 144 nb 5' Cy3 modified GRON (CG11) containing the targeted changes at T97I and P101A into protoplasts, gene editing frequencies of 0.19% at both loci and indel frequency at 0.5% seven days after introduction were observed (FIG. 18c, 18d). The majority of indels were 10 bp or less (FIG. 18c). These results demonstrate that introducing TALENs with Cy3 modified GRONs into *L. usitatissimum* protoplasts significantly increase the frequency of EPSPS gene editing and further that multiple nucleotide edits can be realized with a single GRON.

Example 20: Effect of Two Members of the Bleomycin Family of Antibiotics on Conversion The purpose of this series of examples was to evaluate the effect of antibiotics on conversion efficiencies.

Methods

Protoplasts from an *Arabidopsis thaliana* line with multiple copies of a blue fluorescent protein gene were treated with GRON as described in Example 1, with the following modification: before the addition of GRON, the protoplasts were kept for 90 minutes on ice in a solution of TM (14.8 mM $MgCl_2 \times 6H_2O$, 5 mM 2-(N-morpholino)ethanesulfonic acid, 572 mM mannitol), supplemented with 0, 250, or 1000 µg/ml Zeocin™ or phleomycin. The pH of the solutions was adjusted to 7.0. The percentage of green-fluorescing cells resulting from BFP to GFP conversion was evaluated by flow cytometry as described in Example 1.

Results

Figure 19:
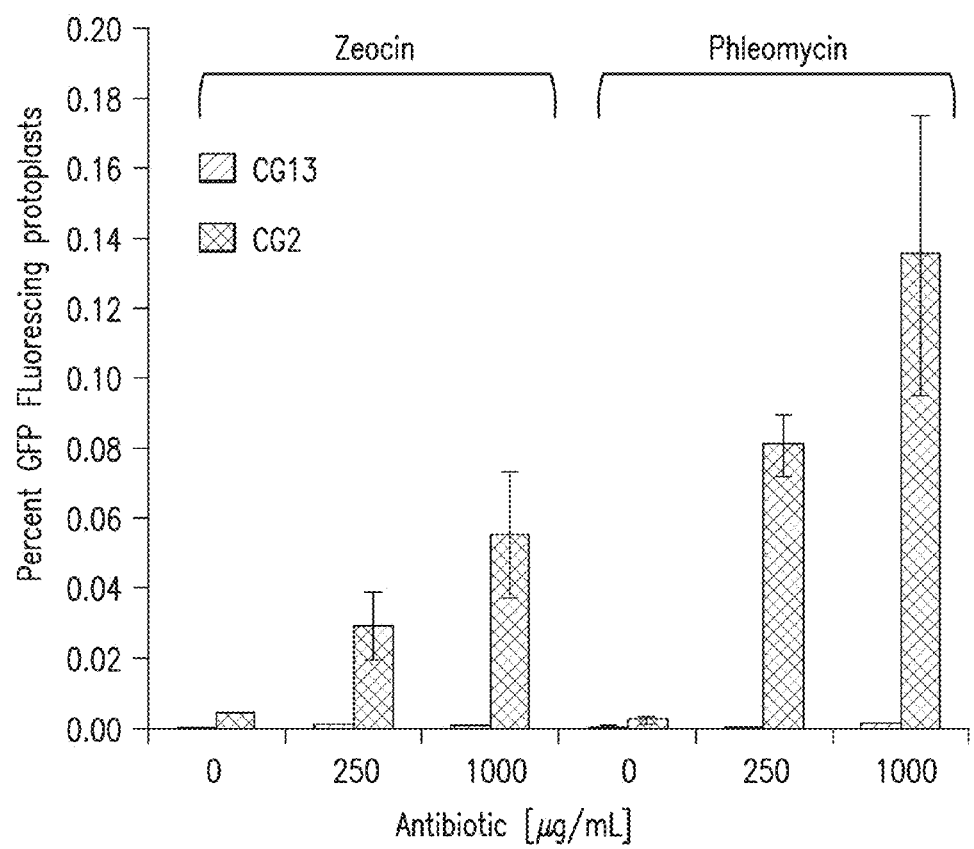
FIG. 19 shows effects of the double strand break inducing antibiotics zeocin and phleomycin on BFP to GFP editing in transgenic *A. thaliana* protoplasts. Protoplasts were treated with zeocin or phleomycin for 90 min before PEG introduction of GRON (CG2). Successful editing resulted in GFP fluorescence. Green fluorescing protoplasts were quantified using an Attune Acoustic Focusing Cytometer.
Figure 20:
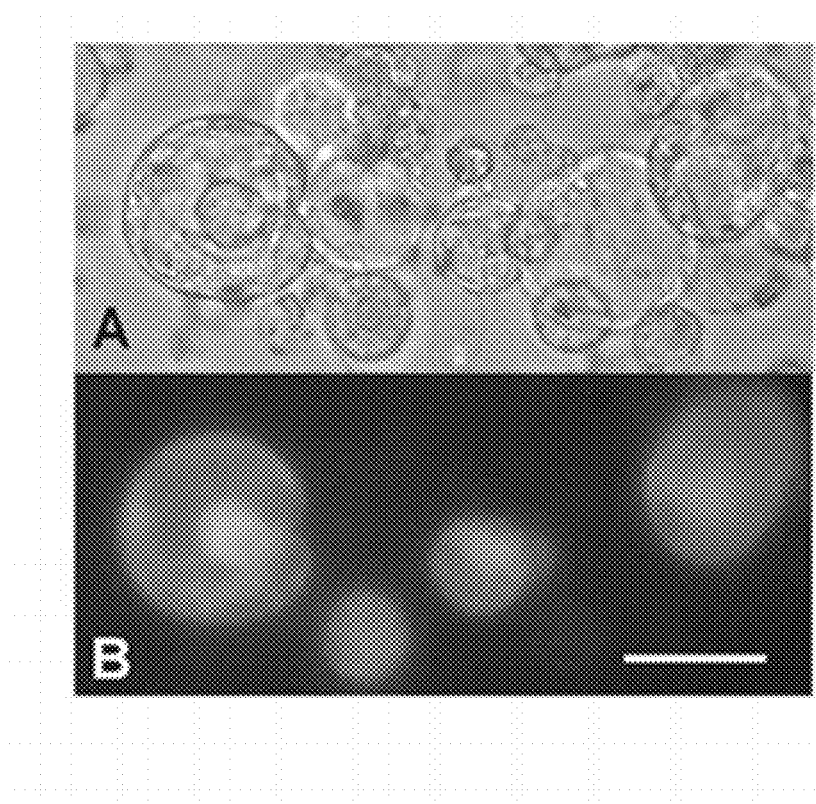
FIG. 20 shows converted BFP transgenic *A. thaliana* cells five days after GRON delivery into BFP transgenic protoplasts, targeting the conversion from BFP to GFP. Green fluorescence is indicative of BFP-GFP editing. A brightfield image; B, the same field of view in blue light. Error bars are s.e.m. (n=4); (CG2): BFP antisense 41 nb 3P5 modified; (CG12) BFP antisense 41 nb 3P5 modified non-targeting. Images were acquired with an ImageXpress Micro system (Molecular Devices, Sunnyvale, Calif., USA) Scale bar=20 μm
Figure 21A:
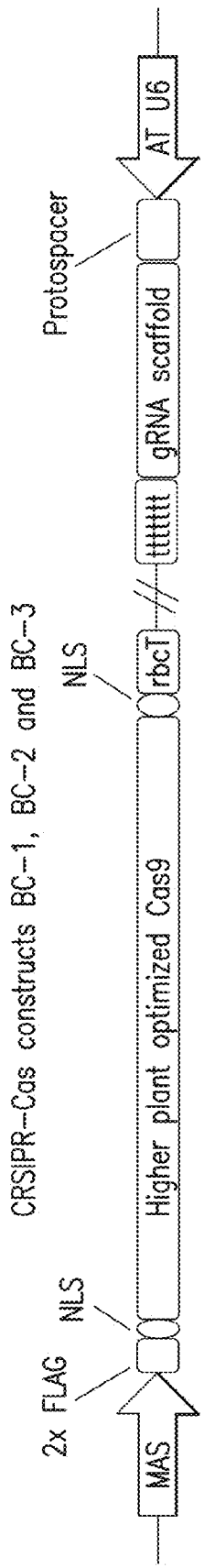
FIG. 21A shows a schematic of the CRISPR-Cas plasmid. The mannopine synthase (Mas) promoter is driving the transcription of the Cas9 gene that is codon optimized for higher plants. The Cas9 gene contains two SV40 nuclear localization signals (NLS) at either end of the gene and a 2× FLAG epitope tag. *A. thaliana* U6 promoter is driving the transcription of the gRNA scaffold and transcription is terminated using a poly(T) signal.
Figure 21B:
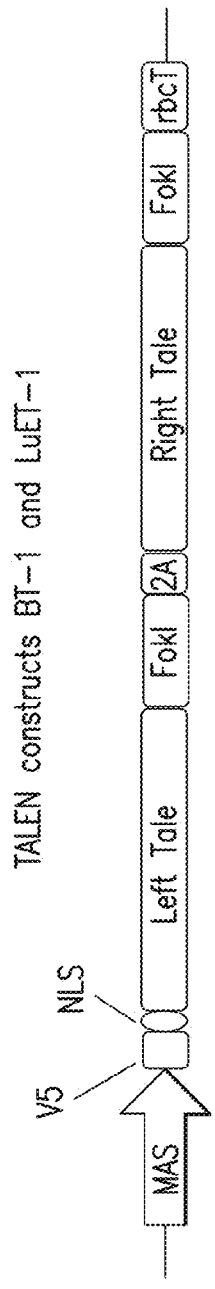
FIG. 21B shows a schematic of the TALEN plasmid. The Mas promoter is driving the transcription of the right and left tale arms linked together with a 2A ribosome skipping sequence. A Fok1 endonuclease is linked to the 3' end of each Tale arm. The 5' end of the left tale contains a nuclear localization signal (NLS) and a V5 epitope tag. rbcT is the *Pisum sativum* RBCSE9 gene terminator.
Figure 22A:
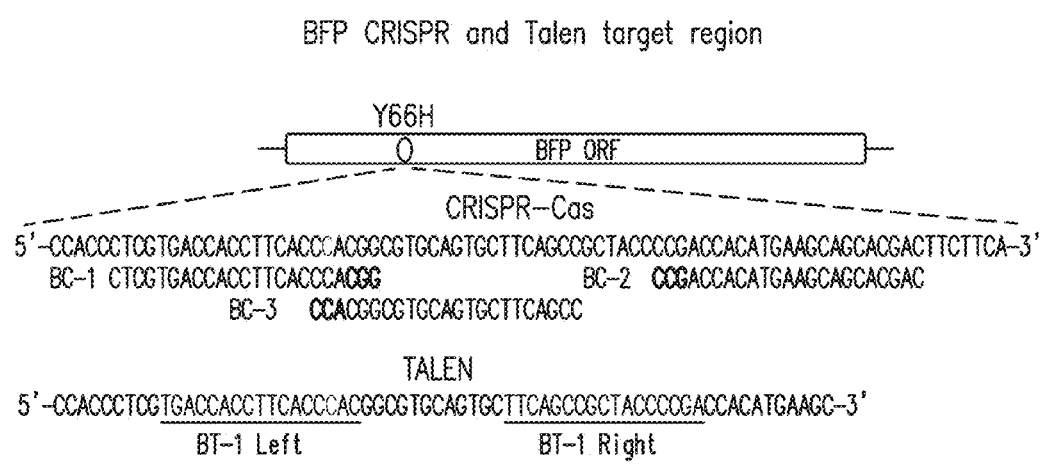
FIG. 22A shows a BFP gene target region for the CRISPR-Cas protospacers, BC-1, BC-2 and BC-3 and the TALEN BT-1, left and right tale arms. The PAM sequence is shown in red. TALEN binding sites are bold and underlined. The site of BFP to GFP editing CACTAC (H66Y) is in bold green.
Figure 22B:
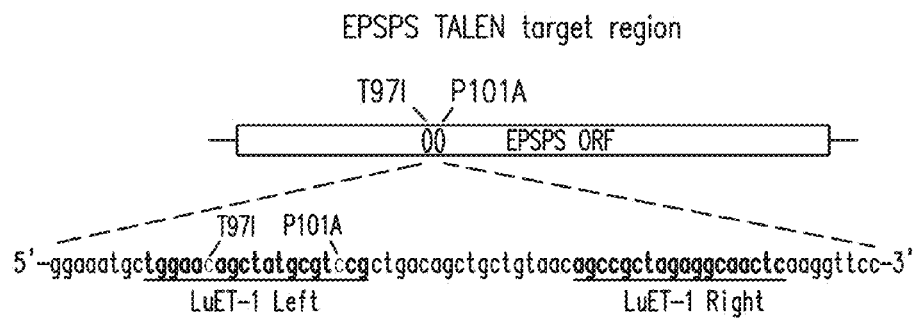
FIG. 22B shows an EPSPS gene target region for the TALEN, LuET-1, left and right tale arms. The site of EPSPS conversions ACA>ATA and CCG>GCG (T97I and P101A) are in green. Figure discloses SEQ ID NOS 240-245, respectively, in order of appearance.

Zeocin and phleomycin at both concentrations used (250 and 1000 µg/ml) resulted in an increase in BFP to GFP gene editing (see FIG. 19). Green-fluorescing cells resulting from BFP to GFP gene editing were observed five days after GRON delivery (FIG. 20).

References

1. LeCong et al 2013 Science: vol. 339 no. 6121 pp. 819-823.
2. Jinek et al 2012 Science. 337:816-21
3. Wang et al 2008 RNA 14: 903-9D
4. Zhang et al 2013. Plant Physiol. 161: 20-27

Example 21: CRISPRs and GRONs in Rice

The purpose of this experiment is to demonstrate ACCase conversion in *Oryza sativa* at 120 hours after PEG delivery of CRISPR-Cas plasmids and GRONs into protoplasts. The CRISPR-Cas used in this experiment targets the accase gene in the rice genome by introducing into protoplasts plasmid(s) encoding the Cas9 gene and a sgRNAs. The sgRNA is a fusion of CRISPR RNA (crRNA) and trans-activating crRNA (tracrRNA). The crRNA guides the Cas9 to the target genes, where Cas9 creates a double-stranded break in the accase gene and the GRON is used as a template to convert the accase gene in a site-directed manner.

Methods

Rice protoplasts were isolated from calli. The CRISPR-Cas encoded plasmids contains the corn ubiquitin promoter driving the Cas9 coding sequence with an rbcSE9 terminator and a rice U6 promoter promoter driving the sgRNA with a poly-$T_{10}$ terminator ("T10" disclosed as SEQ ID NO: 21). The CRISPR-Cas plasmids were introduced into protoplasts by PEG mediated delivery at a final concentration of 0.05 µg/µl. GRONs with the following sequence, 5' V C TGA CCT GAA CTT GAT CTC AAT TAA CCC TTG CGG TTC CAG AAC ATT GCC TTT TGC AGT CCT CTC AGC ATA GCA CTC AAT GCG GTC TGG GTT TAT CTT GCT TCC AAC GAC AAC CCA AGC CCC TCC TCG TAG CTC TGC AGC CAT GGG AAT GTA GAC AAA GGC AGG CTG ATT GTA TGT CCT AAG GTT CTC AAC AAT AGT CGA GCC H 3' (SEQ ID NO:52), were used at a final concentration of 0.8 µM. Protoplasts were embedded in agarose ($2.5 \times 10^6$ cells/ml), cultured in liquid medium, and incubated in a rotatory shaker (60 rpm) in the dark at 28° C. Individual samples were analyzed by NGS, 120 hours after CRISPR-Cas plasmid and/or GRON delivery, to determine the percentage of cells (DNA reads) carrying the ACCase conversion and having indels in the accase gene.

The CRISPR consists of two components: the plant codon-optimized *Streptococcus pyogenes* Cas9 (SpCas9) and sgRNA both of which were expressed from the same plasmid. The sgRNA is a fusion of CRISPR RNA (crRNA) and trans-activating crRNA (tracrRNA). The crRNA region contains the spacer sequence (5'-ACGAGGAGGGGCT-TGGGTTGTGG-3' (SEQ ID NO:53)) used to guide the Cas9 nuclease to the target gene. In this experiment the CRISPR targets the accase gene.

Results

At 120 h, rice protoplasts have 0.026% ACCase conversion as determined by Next Generation Sequencing. GRON only controls with no CRISPR-Cas showed minimal Accase conversion of 0.002% at 120 hours and the untreated controls showed no conversion. Additionally, these data show that the CRISPR-Cas is active and able to cleave the ACCase target gene and form indels of 8.0%.

References

5. LeCong et al 2013 Science: vol. 339 no. 6121 pp. 819-823.
6. Jinek et al 2012 Science. 337:816-21
7. Wang et al 2008 RNA 14: 903-913
8. Zhang et al 2013. Plant Physiol. 161: 20-27

Example 22: CRISPRs and GRONs in Rice

Summary:

Targeted ACCase mutations have been identified in nineteen week-old calli by PCR and DNA sequencing analyses.

Introduction

The purpose of this experiment is to demonstrate ACCase conversion in *Oryza sativa* calli after PEG delivery of CRISPR-Cas plasmids and GRONs into protoplasts. The CRISPR-Cas used in this experiment targets the ACCase gene in the rice genome by introducing into protoplasts plasmid(s) encoding the Cas9 gene and a sgRNAs. The sgRNA is a fusion of CRISPR RNA (crRNA) and trans-activating crRNA (tracrRNA). The crRNA guides the Cas9 to the target gene, where Cas9 creates a either a double-stranded break or a nick at a targeted location in the ACCase gene and the GRONs are used as a template to convert the ACCase gene in a site-directed manner.

Results

Targeted OsACCase mutations described in the tables below, have been identified in nineteen week-old calli by PCR and DNA sequencing analyses.

Methods

Rice protoplasts were isolated from suspension cultures initiated from mature seed-derived embryogenic calli. The CRISPR-Cas plasmids with GRONs at a final concentration of 0.05 µg/µl and 0.8 µM, respectively, were introduced into protoplasts by PEG mediated delivery method. An exemplary range for CRISPR-Cas plasmids at a final concentration include, but is not limited to 0.01 to 0.2 µg/µl. An exemplary range for GRON at a final concentration include, but is not limited to 0.01 to 4 µM. The CRISPR-Cas encoded plasmids contains the corn ubiquitin promoter driving the Cas9 coding sequence with an rbcSE9 terminator and a rice U6 promoter promoter driving the sgRNA with a poly-$T_{10}$ terminator ("T10" disclosed as SEQ ID NO: 21). Sequence information of the GRONs are described in Table 3. Following the PEG treatment, protoplasts were embedded in agarose ($1.25 \times 10^6$ cells/ml), cultured in liquid medium, and incubated in a rotatory shaker (60 rpm) in the dark at 28° C. An exemplary range for embedding protoplasts in agarose include, but is not limited to $0.625 \times 10^6$ to $2.5 \times 10^6$ cells/ml. Samples from each treatment were analyzed by Next Generation Sequencing after 4 weeks post CRISPR-Cas plasmid and/or GRON treatment to determine the proportion of cells (DNA reads) carrying the ACCase conversion. Microcalli from converted treatments were released onto solid selection medium containing clethodim (0.25-0.5 µM) or sethoxydim (2.5 µM). Individual callus lines growing on this selection medium after 19 weeks of culture were analyzed by in-house screening methods as well as DNA sequencing in order to identify individual calli containing the targeted ACCase conversions.

The CRISPR consists of two components: the Cas9, such as a plant codon-optimized *Streptococcus pyogenes* Cas9 (SpCas9) and sgRNA both of which were expressed from plasmid(s). Cas9 and sgRNA can also be delivered by mRNA/RNA or protein/RNA respectively. The sgRNA is a fusion of CRISPR RNA (crRNA) and trans-activating crRNA (tracrRNA). The crRNA region contains the spacer with sequences described in Table 2, which were used to guide the Cas9 nuclease to the target gene. In this experiment the CRISPR targets the rice ACCase gene.

List of conversions in OsACCase at two different locations within the gene, Site 1 and Site 2. For each site, all combinations of conversion events are possible.

| OsACCase | |
|---|---|
| Site1 | Site 2 |
| I1781A | D2078G |
| I1781L | D2078K |
| I1781M | D2078T |
| I1781N | S2079F |
| I1781S | K2080E |
| I1781T | C2088F |
| I1781V | C2088G |
| G1783C | C2088H |
| A1786P | C2088K |
|  | C2088L |
|  | C2088N |
|  | C2088P |
|  | C2088Q |
|  | C2088R |
|  | C2088S |
|  | C2088T |
|  | C2088V |
|  | C2088W |

List of CRISPR-Cas gRNA spacer sequences used in this experiment. Spacer length may vary up to ±20 bp. Mismatched within the spacer sequence can be tolerated up to 10 bp.

| | | OsACCase | | |
|---|---|---|---|---|
| Sample ID | Spacer RNA Sequence (5' to 3') | Site 1 | Site 2 | SEQ ID NO |
| 1 | CAUAAGAUGCAGCUAGACAG | X | | 54 |
| 2 | AGCUAGACAGUGGUGAAAUU | X | | 55 |
| 3 | UAGACAGUGGUGAAAUUAGG | X | | 56 |
| 4 | AGACAGUGGUGAAAUUAGGU | X | | 57 |
| 5 | GUGGGUUAUUGAUUCUGUUG | X | | 58 |
| 6 | UGGGUUAUUGAUUCUGUUGU | X | | 59 |
| 7 | UAUUGAUUCUGUUGUGGGCA | X | | 60 |
| 8 | UCUGUUGUGGGCAAGGAAGA | X | | 61 |
| 9 | GUGGGCAAGGAAGAUGGACU | X | | 62 |
| 10 | CAAGGAAGAUGGACUUGGUG | X | | 63 |
| 11 | CUUGGUGUGGAGAAUAUACA | X | | 64 |
| 12 | CUAUUGCCAGUGCUUAUUCU | X | | 65 |
| 13 | UGCUUAUUCUAGGGCAUAUA | X | | 66 |
| 14 | UUUACACUUACAUUUGUGAC | X | | 67 |
| 15 | UUUGUGACUGGAAGAACUGU | X | | 68 |
| 16 | ACUGGAAGAACUGUUGGAAU | X | | 69 |
| 17 | GGAGCUUAUCUUGCUCGACU | X | | 70 |
| 18 | AUAUGCCCUAGAAUAAGCAC | X | | 71 |
| 19 | GAUAAGAUGCAGCUAGACAG | X | | 72 |
| 20 | GGCUAGACAGUGGUGAAAUU | X | | 73 |
| 21 | GAGACAGUGGUGAAAUUAGG | X | | 74 |
| 22 | GGACAGUGGUGAAAUUAGGU | X | | 75 |
| 24 | GGGGUUAUUGAUUCUGUUGU | X | | 76 |
| 25 | GAUUGAUUCUGUUGUGGGCA | X | | 77 |
| 26 | GCUGUUGUGGGCAAGGAAGA | X | | 78 |
| 28 | GAAGGAAGAUGGACUUGGUG | X | | 79 |
| 29 | GUUGGUGUGGAGAAUAUACA | X | | 80 |
| 30 | GUAUUGCCAGUGCUUAUUCU | X | | 81 |
| 31 | GGCUUAUUCUAGGGCAUAUA | X | | 82 |
| 32 | GUUACACUUACAUUUGUGAC | X | | 83 |
| 33 | GUUGUGACUGGAAGAACUGU | X | | 84 |
| 34 | GCUGGAAGAACUGUUGGAAU | X | | 85 |
| 36 | GUAUGCCCUAGAAUAAGCAC | X | | 86 |
| 37 | CGACUAUUGUUGAGAACCUU | | X | 87 |
| 38 | UGCCUUUGUCUACAUUCCCA | | X | 88 |
| 39 | CCCAUGGCUGCAGAGCUACG | | X | 89 |
| 40 | AUGGCUGCAGAGCUACGAGG | | X | 90 |
| 41 | UGGCUGCAGAGCUACGAGGA | | X | 91 |
| 42 | GGCUGCAGAGCUACGAGGAG | | X | 92 |
| 43 | CAGAGCUACGAGGAGGGGCU | | X | 93 |
| 44 | AGAGCUACGAGGAGGGGCUU | | X | 94 |
| 45 | ACGAGGAGGGGCUUGGGUUG | | X | 95 |

OsACCase

| Sample ID | Spacer RNA Sequence (5' to 3') | Site 1 | Site 2 | SEQ ID NO |
|---|---|---|---|---|
| 46 | GCAUUGAGUGCUAUGCUGAG | | X | 96 |
| 47 | UAUGCUGAGAGGACUGCAAA | | X | 97 |
| 48 | GACUGCAAAAGGCAAUGUUC | | X | 98 |
| 49 | GGCAAUGUUCUGGAACCGCA | | X | 99 |
| 50 | GCAAUGUUCUGGAACCGCAA | | X | 100 |
| 51 | GGUUAAUUGAGAUCAAGUUC | | X | 101 |
| 52 | UGAGAUCAAGUUCAGGUCAG | | X | 102 |
| 53 | GUUCAGGUCAGAGGAACUCC | | X | 103 |
| 54 | AACUCCAGGAUUGCAUGAGU | | X | 104 |
| 55 | CAAGCCGACUCAUGCAAUCC | | X | 105 |
| 56 | UUGAUCUCAAUUAACCCUUG | | X | 106 |
| 57 | UCUCAGCAUAGCACUCAAUG | | X | 107 |
| 58 | GCAUAGCACUCAAUGCGGUC | | X | 108 |
| 59 | CAUAGCACUCAAUGCGGUCU | | X | 109 |
| 60 | UCCUCGUAGCUCUGCAGCCA | | X | 110 |
| 61 | AGCCAUGGGAAUGUAGACAA | | X | 111 |
| 62 | AUGGGAAUGUAGACAAAGGC | | X | 112 |
| 63 | CAGGCUGAUUGUAUGUCCUA | | X | 113 |
| 64 | GGACUAUUGUUGAGAACCUU | | X | 114 |
| 65 | GGCCUUUGUCUACAUUCCCA | | X | 115 |
| 66 | GCCAUGGCUGCAGAGCUACG | | X | 116 |
| 67 | GUGGCUGCAGAGCUACGAGG | | X | 117 |
| 68 | GGGCUGCAGAGCUACGAGGA | | X | 118 |
| 69 | GAGAGCUACGAGGAGGGGCU | | X | 119 |
| 70 | GGAGCUACGAGGAGGGGCUU | | X | 120 |
| 71 | GCGAGGAGGGGCUUGGGUUG | | X | 121 |
| 72 | GAUGCUGAGAGGACUGCAAA | | X | 122 |
| 73 | GGAGAUCAAGUUCAGGUCAG | | X | 123 |
| 74 | GACUCCAGGAUUGCAUGAGU | | X | 124 |
| 75 | GAAGCCGACUCAUGCAAUCC | | X | 125 |
| 76 | GUGAUCUCAAUUAACCCUUG | | X | 126 |
| 77 | GCUCAGCAUAGCACUCAAUG | | X | 127 |
| 78 | GAUAGCACUCAAUGCGGUCU | | X | 128 |
| 79 | GCCUCGUAGCUCUGCAGCCA | | X | 129 |
| 80 | GGCCAUGGGAAUGUAGACAA | | X | 130 |
| 81 | GUGGGAAUGUAGACAAAGGC | | X | 131 |
| 82 | GAGGCUGAUUGUAUGUCCUA | | X | 132 |

A list of GRON sequences suitable for use in this experiment are provided in the table below (V=CY3; H=3'DMT dC CPG).

1  VGTCATAGCACATAAGATGCAGCTAGACAGTGGTGAAATTAGGTGGG
TTATTGATTCTGTTGTGGGCAAGGAAGATGGACTTGGTGTGGAGAAT
GCTCATGGAAGTGCTGCTATTGCCAGTGCTTATTCAGGGCATATAA
GGAGACATTTACACTTACATTTGTGACTGGAAGAACTGTTGGAATAG
GAGCTTATCTTGCTCH (SEQ ID NO: 133)

2  VGAGCAAGATAAGCTCCTATTCCAACAGTTCTTCCAGTCACAAATGT
AAGTGTAAATGTCTCCTTATATGCCCTAGAATAAGCACTGGCAATAG
CAGCACTTCCCATGCAGATTCTCCACACCAAGTCCATCTTCCTTGCCC
ACAACAGAATCAATAACCCACCTAATTTCACCACTGTCTAGCTGCAT
CTTATGTGCTATGACH (SEQ ID NO: 134)

3  VGTCATAGCACATAAGATGCAGCTAGACAGTGGTGAAATTAGGTGGG
TTATTGATTCTGTTGTGGGCAAGGAAGATGGACTTGGTGTGGAGAAT
ATACATTGCAGTGCTGCTATTGCCAGTGCTTATTCAGGGCATATAA
GGAGACATTTACACTTACATTTGTGACTGGAAGAACTGTTGGAATAG
GAGCTTATCTTGCTCH (SEQ ID NO: 135)

4  VGAGCAAGATAAGCTCCTATTCCAACAGTTCTTCCAGTCACAAATGT
AAGTGTAAATGTCTCCTTATATGCCCTAGAATAAGCACTGGCAATAG
CAGCTGCAATGTATATTCTCCACACCAAGTCCATCTTCCTTGCCC
ACAACAGAATCAATAACCCACCTAATTTCACCACTGTCTAGCTGCAT
CTTATGTGCTATGACH (SEQ ID NO: 136)

5  VGTCATAGCACATAAGATGCAGCTAGACAGTGGTGAAATTAGGTGGG
TTATTGATTCTGTTGTGGGCAAGGAAGATGGACTTGGTGTGGAGAAT
ATACATGGAAGTGCTCCAATTGCCAGTGCTTATTCAGGGCATATAA
GGAGACATTTACACTTACATTTGTGACTGGAAGAACTGTTGGAATAG
GAGCTTATCTTGCTCH (SEQ ID NO: 137)

6  VGAGCAAGATAAGCTCCTATTCCAACAGTTCTTCCAGTCACAAATGT
AAGTGTAAATGTCTCCTTATATGCCCTAGAATAAGCACTGGCAATGG
TAGCACTTCCATGTATATTCTCCACACCAAGTCCATCTTCCTTGCCC
ACAACAGAATCAATAACCCACCTAATTTCACCACTGTCTAGCTGCAT
CTTATGTGCTATGACH (SEQ ID NO: 138)

7  VCTGACCTGAACTTGATCTCAATTAACCCTTGCGGTTCCAGAACATT
GCCTTTTGCAGTCCTCTCAGCATAGCACTCAATGCGGTCTGGGTTTA
TCTTGCTTCCAACGACAACCCAAGCCCCTCCTCGTAGCTCTGCAGCC
ATGGGAATGTAGACAAAGGCAGGCTGATTGTATGTCCTAAGGTTCTC
AACAATAGTCGAGCCH (SEQ ID NO: 52)

8  VGGCTCGACTATTGTTGAGAACCTTAGGACATACAATCAGCCTGCCT
TTGTCTACATTCCCATGGCTGCAGAGCTACGAGGAGGGGCTTGGGTT
GTGGTTGGTAGCAAGATAAACCCAGACCGCATTGAGTGCTATGCTGA
GAGGACTGCAAAAGGCAATGTTCTGGAACCGCAAGGGTTAATTGAGA
TCAAGTTCAGGTCAGH (SEQ ID NO: 139)

9  VCTGACCTGAACTTGATCTCAATTAACCCTTGCGGTTCCAGAACATT
GCCTTTTGCAGTCCTCTCAGCATAGCACTCAATGCGGTCTGGGTTTA
TCTTAAAATCAACGACAACCCAAGCCCCTCCTCGTAGCTCTGCAGCC
ATGGGAATGTAGACAAAGGCAGGCTGATTGTATGTCCTAAGGTTCTC
AACAATAGTCGAGCCH (SEQ ID NO: 140)

10  VGGCTCGACTATTGTTGAGAACCTTAGGACATACAATCAGCCTGCCT
TTGTCTACATTCCCATGGCTGCAGAGCTACGAGGAGGCGCTTGGGTT
GTGGTTGATAGCAAGATAAACCCAGACCGCATTGAGAGGTATGCTGA
GAGGACTGCAAAAGGCAATGTTCTGAACCGCAAGGGTTAATTGAGA
TCAAGTTCAGGTCAGH (SEQ ID NO: 141)

11  VGGCTCGACTATTGTTGAGAACCTTAGGACATACAATCAGCCTGCCT
TTGTCTACATTCCCATGGCTGCAGAGCTACGAGGAGGGGCTTGGGTT
GTGGTTGATAGCGAAATAAACCCAGACCGCATTGAGTGCTATGCTGA
GAGGACTGCAAAAGGCAATGTTCTGGAACCGCAAGGGTTAATTGAGA
TCAAGTTCAGGTCAGH (SEQ ID NO: 142)

12  VCTGACCTGAACTTGATCTCAATTAACCCTTGCGGTTCCAGAACATT
GCCTTTTGCAGTCCTCTCAGCATAGCACTCAATGCGGTCTGGGTTTA
TTTCGCTATCAACCACAACCCAAGCGCCTCCTCGTAGCTCTGCAGCC
ATGGGAATGTAGACAAAGGCAGGCTGATTGTATGTCCTAAGGTTCTC
AACAATAGTCGAGCCH (SEQ ID NO: 143)

13  VGGCTCGACTATTGTTGAGAACCTTAGGACATACAATCAGCCTGCCT
TTGTCTACATTCCCATGGCTGCAGAGCTACGAGGAGGGGCTTGGGTT
GTGGTTGATAGCAAGATAAACCCAGACCGCATTGAGCGTTATGCTGA

-continued

GAGGACTGCAAAAGGCAATGTTCTGGAACCGCAAGGGTTAATTGAGA
TCAAGTTCAGGTCAGH (SEQ ID NO: 144)

14  VCTGACCTGAACTTGATCTCAATTAACCCTTGCGGTTCCAGAACATT
    GCCTTTTGCAGTCCTCTCAGCATATTGCTCAATGCGGTCTGGGTTTA
    TCTTGCTATCAACGACAACCCAAGCCCCTCCTCGTAGCTCTGCAGCC
    ATGGGAATGTAGACAAAGGCAGGCTGATTGTATGTCCTAAGGTTCTC
    AACAATAGTCGAGCCH (SEQ ID NO: 145)

Example 23: CRISPRs and GRONs in Flax

Summary:

Targeted LuEPSPS mutations have been identified in four week-old calli by PCR and DNA sequencing analyses.

Introduction

The purpose of this experiment is to demonstrate conversion of the EPSPS genes in the *Linum usitatissimum* genome in shoot tip derived protoplasts by PEG mediated delivery of CRISPR-Cas plasmids and GRONs. The CRISPR-Cas and GRONs used in this experiment target the EPSPS genes in the flax genome. The CRISPR consists of two components: a Cas9, such as a plant codon-optimized *Streptococcus pyogenes* Cas9 (SpCas9) and sgRNA both of which are expressed from plasmid(s). Cas9 and sgRNA can also be delivered by mRNA/RNA or protein/RNA respectively. The sgRNA is a fusion of CRISPR RNA (crRNA) and trans-activating crRNA (tracrRNA). The crRNA guides the Cas9 to the targeted genes, where Cas9 creates a either a double-stranded break or nick in the EPSPS genes and the GRONs are used as a template to convert the EPSPS genes in a site-directed manner.

Results

Targeted LuEPSPS (T97I and/or the P101A, P101T or P101S and/or the G96A) mutations have been identified in four week-old calli by PCR and DNA sequencing analyses. Shoots have been regenerated from these converted calli.

Methods

Flax protoplasts were isolated from shoot tips obtained from in vitro germinated seedlings. The CRISPR-Cas encoded plasmids contain the MAS promoter driving the Cas9 coding sequence with an rbcSE9 terminator and the *Arabidopsis thaliana* U6 promoter driving the sgRNA with a poly-$T_{10}$ terminator ("T10" disclosed as SEQ ID NO: 21). The CRISPR-Cas plasmids were introduced into protoplasts by PEG mediated delivery at a final concentration of 0.05 μg/μl. GRONs targeting each of the two flax LuEPSPS genes (Table 2) were used at a final concentration of 4.0 μM. An exemplary range for CRISPR-Cas plasmids at a final concentration include, but is not limited to 0.01 to 0.2 μg/μl. An exemplary range for GRON at a final concentration include, but is not limited to 0.01 to 4 μM. Protoplasts were embedded in alginate beads ($5\times10^5$ cells/ml), cultured in liquid medium, and incubated in a rotatory shaker (30 rpm) in the dark at 25° C. An exemplary range for embedding protoplasts in alginate beads include, but is not limited to $3.0\times10^5$ to $7.5\times10^5$ cells/ml. Microcalli developed from individual cells were analyzed by Next Generation Sequencing, 3 and 7 weeks after CRISPR-Cas plasmid and GRON delivery, to determine the proportion of cells (DNA reads) carrying the targeted mutations in the LuEPSPS genes. Larger calli were grown from 8-week-old converted microcalli plated over solid regeneration medium, and shoots started differentiating from regenerated calli after about 4-8 weeks. Converted calli and shoots with the targeted EPSPS gene mutations were identified by PCR and DNA sequencing analyses.

The CRISPR consists of two components: the plant codon-optimized *Streptococcus pyogenes* Cas9 (SpCas9) and sgRNA both of which were expressed from plasmid(s). The sgRNA is a fusion of CRISPR RNA (crRNA) and trans-activating crRNA (tracrRNA). The crRNA region contains the spacer with sequences described in the table below, which were used to guide the Cas9 nuclease to the EPSPS targeted genes.

List of CRISPR-Cas gRNA spacer sequences used in this experiment. Spacer length may vary up to ±20 bp. Mismatched within the spacer sequence can be tolerated up to 10 bp.

| Sample ID | Spacer RNA Sequence (5' to 3') | LuEPSPS Site 1 | LuEPSPS Site 2 | SEQ ID NO: |
|---|---|---|---|---|
| 1 | CAGAAGCGCGCCAUUGUUGA | X | X | 146 |
| 2 | CGCGCCAUUGUUGAAGGUUG | X |  | 147 |
| 3 | CGCGCCAUUGUUGAAGGUCG |  | X | 148 |
| 4 | GCCAUUGUUGAAGGUUGUGG | X |  | 149 |
| 5 | GCCAUUGUUGAAGGUCGUGG |  | X | 150 |
| 6 | AGGUUGUGGUGGUGUGUUUC | X |  | 151 |
| 7 | AGGUCGUGGUGGUGUGUUUC |  | X | 152 |
| 8 | UGUGGUGGUGUGUUUCCGGU | X |  | 153 |
| 9 | CGUGGUGGUGUGUUUCCGGU |  | X | 154 |
| 10 | UGUGUUUCCGGUCGGUAAAC | X | X | 155 |
| 11 | UGUUUCCGGUCGGUAAACUG |  | X | 156 |
| 12 | AACGAUAUUGAACUUUUCCU | X |  | 157 |
| 13 | AACGAUAUCGAACUUUUCCU |  | X | 158 |
| 14 | GAACUUUUCCUUGGAAAUGC | X | X | 159 |
| 15 | ACAGCUGCUGUAACAGCCGC | X | X | 160 |
| 16 | GCUGCUGUAACAGCCGCUGG | X | X | 161 |
| 17 | AACUCAAGCUACAUACUCGA | X |  | 162 |
| 18 | AACUCAAGCUACAUACUCGA |  | X | 163 |
| 19 | CGAAUGAGAGAGAGACCAAU | X |  | 164 |
| 20 | CGAAUGAGAGAGAGACCGAU |  | X | 165 |
| 21 | AGAGAGACCAAUGGAGAUU | X |  | 166 |
| 22 | CCAAUUGGAGAUUUGGUUGU | X |  | 167 |
| 23 | CCGAUUGGAGAUUUAGUUGU |  | X | 168 |
| 24 | CCAACAACCAAAUCUCCAAU | X |  | 169 |
| 25 | CCAACAACUAAAUCUCCAAU |  | X | 170 |
| 26 | AUUGGUCUCUCUCUCAUUCG | X |  | 171 |
| 27 | AUCGGUCUCUCUCUCAUUCG |  | X | 172 |
| 28 | GUAGCUUGAGUUGCCUCCAG | X | X | 173 |
| 29 | GCUGUUACAGCAGCUGUCAG | X | X | 174 |
| 30 | UAGCUGUUCCAGCAUUUCCA | X | X | 175 |

-continued

| | | LuEPSPS | | |
|---|---|---|---|---|
| Sample ID | Spacer RNA Sequence (5' to 3') | Site 1 | Site 2 | SEQ ID NO: |
| 31 | UUCUUCGCCAGUUUACCGAC | X | | 176 |
| 32 | UUCUUCCCCAGUUUACCGAC | | X | 177 |
| 33 | ACCACCACAACCUUCAACAA | X | | 178 |
| 34 | ACCACCACGACCUUCAACAA | | X | 179 |
| 35 | GAGAAGCGCGCCAUUGUUGA | X | X | 180 |
| 36 | GGCGCCAUUGUUGAAGGUUG | X | | 181 |
| 37 | GGCGCCAUUGUUGAAGGUCG | | X | 182 |
| 38 | GGGUUGUGGUGGUGUGUUUC | X | | 183 |
| 39 | GGGUCGUGGUGGUGUGUUUC | | X | 184 |
| 40 | GGUGGUGGUGUGUUUCCGGU | X | | 185 |
| 41 | GGUGGUGGUGUGUUUCCGGU | | X | 186 |
| 42 | GGUGUUUCCGGUCGGUAAAC | X | X | 187 |
| 43 | GGUUUCCGGUCGGUAAACUG | | X | 188 |
| 44 | GACGAUAUUGAACUUUUCCU | X | | 189 |
| 45 | GACGAUAUCGAACUUUUCCU | | X | 190 |
| 46 | GCAGCUGCUGUAACAGCCGC | X | X | 191 |
| 47 | GACUCAAGCUACAUACUCGA | X | | 192 |
| 48 | GACUCAAGCUACAUACUCGA | | X | 193 |
| 49 | GGAAUGAGAGAGAGACCAAU | X | | 194 |
| 50 | GGAAUGAGAGAGAGACCGAU | | X | 195 |
| 51 | GGAGAGACCAAUUGGAGAUU | X | | 196 |
| 52 | GCAAUGGAGAUUUGGUUGU | X | | 197 |
| 53 | GCGAUUGGAGAUUUAGUUGU | | X | 198 |
| 54 | GCAACAACCAAAUCUCCAAU | X | | 199 |
| 55 | GCAACAACUAAAUCUCCAAU | | X | 200 |
| 56 | GUUGGUCUCUCUCUCAUUCG | X | | 201 |
| 57 | GUCGGUCUCUCUCUCAUUCG | | X | 202 |
| 58 | GAGCUGUUCCAGCAUUUCCA | X | X | 203 |
| 59 | GUCUUCGCCAGUUUACCGAC | X | | 204 |
| 60 | GUCUUCCCCAGUUUACCGAC | | X | 205 |
| 61 | GCCACCACAACCUUCAACAA | X | | 206 |
| 62 | GCCACCACGACCUUCAACAA | | X | 207 |

A list of GRON sequences suitable for use in this experiment are provided in the table below (V=CY3; H=3'DMT dC CPG).

1 VCGGTCGGTAAACTGGCGAAGAACGATATTGAACTTTTCCTTGGA
AATGCTGCTATAGCTATGCGTGCGCTGACAGCTGCTGTAACAGCC
GCTGGAGGCAACTCAAGGTCCCTTCCCTCAACTCCTTCCAGCCTT
TCAGCTTCTTH (SEQ ID NO: 208)

2 VAAGAAGCTGAAAGGCTGGAAGGAGTTGAGGGAAGGGACCTTGAG
TTGCCTCCAGCGGCTGTTACAGCAGCTGTCAGCGGACGCATAGCT
GTGGCAGCATTTCCAAGGAAAAGTTCAATATCGTTCTTCGCCAGT
TTACCGACCGH (SEQ ID NO: 209)

3 VCGGTCGGTAAACTGGCGAAGAACGATATTGAACTTTTCCTTGGA
AATGCTGGAATAGCTATGCGTGCGCTGACAGCTGCTGTAACAGCC
GCTGGAGGCAACTCAAGGTCCCTTCCCTCAACTCCTTCCAGCCTT
TCAGCTTCTTH (SEQ ID NO: 49)

4 VAAGAAGCTGAAAGGCTGGAAGGAGTTGAGGGAAGGGACCTTGAG
TTGCCTCCAGCGGCTGTTACAGCAGCTGTCAGCGCACGCATAGCT
ATTCCAGCATTTCCAAGGAAAAGTTCAATATCGTTCTTCGCCAGT
TTACCGACCGH (SEQ ID NO: 210)

5 VCGGTCGGTAAACTGGCGAAGAACGATATTGAACTTTTCCTTGGA
AATGCTGGAATTGCTATGCGTTCTCTGACAGCTGCTGTAACAGCC
GCTGGAGGCAACTCAAGGTCCCTTCCCTCAACTCCTTCCAGCCTT
TCAGCTTCTTH (SEQ ID NO: 211)

6 VAAGAAGCTGAAAGGCTGGAAGGAGTTGAGGGAAGGGACCTTGAG
TTGCCTCCAGCGGCTGTTACAGCAGCTGTCAGTGACGCATAGCA
ATTCCAGCATTTCCAAGGAAAAGTTCAATATCGTTCTTCGCCAGT
TTACCGACCGH (SEQ ID NO: 212)

7 VCGGTCGGTAAACTGGCGAAGAACGATATTGAACTTTTCCTTGGA
AATGCTGGAATCGCTATGCGTACTCTGACAGCTGCTGTAACAGCC
GCTGGAGGCAACTCAAGGTCCCTTCCCTCAACTCCTTCCAGCCTT
TCAGCTTCTTH (SEQ ID NO: 213)

8 VAAGAAGCTGAAAGGCTGGAAGGAGTTGAGGGAAGGGACCTTGAG
TTGCCTCCAGCGGCTGTTACAGCAGCTGTCAGTGTACGCATAGCA
ATTCCAGCATTTCCAAGGAAAAGTTCAATATCGTTCTTCGCCAGT
TTACCGACCGH (SEQ ID NO: 214)

9 VCGGTCGGTAAACTGGCGAAGAACGATATTGAACTTTTCCTTGGA
AATGCTGGAATTGCTATGCGTGCGCTGACAGCTGCTGTAACAGCC
GCTGGAGGCAACTCAAGGTCCCTTCCCTCAACTCCTTCCAGCCTT
TCAGCTTCTTH (SEQ ID NO: 215)

10 VAAGAAGCTGAAAGGCTGGAAGGAGTTGAGGGAAGGAACCTTGAG
TTGCCTCCAGCGGCTGTTACAGCAGCTGTCAGCGCACGCATAGCT
ATTCCAGCATTTCCAAGGAAAAGTTCGATATCGTTCTTCCCCAGT
TTACCGACCGH (SEQ ID NO: 216)

11 VCGGTCGGTAAACTGGCGAAGAACGATATTGAACTTTTCCTTGGA
AATGCTGGAATAGCTATGCGTGCTCTGACAGCTGCTGTAACAGCC
GCTGGAGGCAACTCAAGGTCCCTTCCCTCAACTCCTTCCAGCCTT
TCAGCTTCTTH (SEQ ID NO: 217)

12 VAAGAAGCTGAAAGGCTGGAAGGAGTTGAGGGAAGGGACCTTGAG
TTGCCTCCAGCGGCTGTTACAGCAGCTGTCAGCGCACGCATAGCT
GTTCCAGCATTTCCAAGGAAAAGTTCAATATCGTTCTTCGCCAGT
TTACCGACCGH (SEQ ID NO: 218)

13 VCGGTCGGTAAACTGGGGAAGAACGATATCGAACTTTTCCTTGGA
AATGCTGCTATAGCTATGCGTGCGCTGACAGCTGCTGTAACAGCC
GCTGGAGGCAACTCAAGGTCCTTCCCTCAACTCCTTCCAGCCTT
TCAGCTTCTTH (SEQ ID NO:219)

14 VAAGAAGCTGAAAGGCTGGAAGGAGTTGAGGGAAGGAACCTTGAG
TTGCCTCCAGCGGCTGTTACAGCAGCTGTCAGCGGACGCATAGCT
GTTGCAGCATTTCCAAGGAAAAGTTCGATATCGTTCTTCCCCAGT
TTACCGACCGH (SEQ ID NO: 220)

15 VCGGTCGGTAAACTGGGGAAGAACGATATCGAACTTTTCCTTGGA
AATGCTGGAATAGCTATGCGTGTGCTGACAGCTGCTGTAACAGCC
GCTGGAGGCAACTCAAGGTCCTTCCCTCAACTCCTTCCAGCCTT
TCAGCTTCTTH (SEQ ID NO: 221)

16 VAAGAAGCTGAAAGGCTGGAAGGAGTTGAGGGAAGGAACCTTGAG
TTGCCTCCAGCGGCTGTTACAGCAGCTGTCAGCGCACGCATAGCT
ATTCCAGCATTTCCAAGGAAAAGTTCGATATCGTTCTTCCCCAGT
TTACCGACCGH (SEQ ID NO: 222)

17 VCGGTCGGTAAACTGGGGAAGAACGATATCGAACTTTTCCTTGGA
AATGCTGGAATTGCTATGCGTTCTCTGACAGCTGCTGTAACAGCC
GCTGGAGGCAACTCAAGGTCCTTCCCTCAACTCCTTCCAGCCTT
TCAGCTTCTTH (SEQ ID NO: 223)

```
18    VAAGAAGCTGAAAGGCTGGAAGGAGTTGAGGGAAGGAACCTTGAG
      TTGCCTCCAGCGGCTGTTACAGCAGCTGTCAGTGAACGCATAGCG
      ATTCCAGCATTTCCAAGGAAAAGTTCGATATCGTTCTTCCCCAGT
      TTACCGACCGH (SEQ ID NO: 224)

19    VCGGTCGGTAAACTGGGGAAGAACGATATCGAACTTTTCCTTGGA
      AATGCTGGAATCGCTATGCGTACTCTGACAGCTGCTGTAACAGCC
      GCTGGAGGCAACTCAAGGTTCCTTCCCTCAACTCCTTCCAGCCTT
      TCAGCTTCTTH (SEQ ID NO: 225)

20    VAAGAAGCTGAAAGGCTGGAAGGAGTTGAGGGAAGGAACCTTGAG
      TTGCCTCCAGCGGCTGTTACAGCAGCTGTCAGTGTACGCATAGCT
      ATTCCAGCATTTCCAAGGAAAAGTTCGATATCGTTCTTCCCCAGT
      TTACCGACCGH (SEQ ID NO: 226)

21    VCGGTCGGTAAACTGGGGAAGAACGATATCGAACTTTTCCTTGGA
      AATGCTGGAATCGCTATGCGTGCGCTGACAGCTGCTGTAACAGCC
      GCTGGAGGCAACTCAAGGTTCCTTCCCTCAACTCCTTCCAGCCTT
      TCAGCTTCTTH (SEQ ID NO: 227)

22    VAAGAAGCTGAAAGGCTGGAAGGAGTTGAGGGAAGGAACCTTGAG
      TTGCCTCCAGCGGCTGTTACAGCAGCTGTCAGCGGACGCATAGCT
      ATTCCAGCATTTCCAAGGAAAAGTTCGATATCGTTCTTCCCCAGT
      TTACCGACCGH (SEQ ID NO: 228)

23    VCGGTCGGTAAACTGGGGAAGAACGATATCGAACTTTTCCTTGGA
      AATGCTGGAATAGCTATGCGTGCTCTGACAGCTGCTGTAACAGCC
      GCTGGAGGCAACTCAAGGTTCCTTCCCTCAACTCCTTCCAGCCTT
      TCAGCTTCTTH (SEQ ID NO: 229)

24    VAAGAAGCTGAAAGGCTGGAAGGAGTTGAGGGAAGGAACCTTGAG
      TTGCCTCCAGCGGCTGTTACAGCAGCTGTCAGGGAACGCATAGCT
      GTTCCAGCATTTCCAAGGAAAAGTTCGATATCGTTCTTCCCCAGT
      TTACCGACCGH (SEQ ID NO: 230)
```

One skilled in the art readily appreciates that the present disclosure is well adapted to carry out the objects and obtain the ends and advantages mentioned, as well as those inherent therein. The examples provided herein are representative of preferred embodiments, are exemplary, and are not intended as limitations on the scope of the disclosure.

It will be readily apparent to a person skilled in the art that varying substitutions and modifications may be made to the disclosure disclosed herein without departing from the scope and spirit of the disclosure.

The disclosure illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

Thus, it should be understood that although the present disclosure has been specifically disclosed by preferred embodiments and optional features, modification, improvement, and variation of the disclosures disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method of causing a targeted genetic change within a plant cell, comprising:
   contacting the plant cell with (i) a gene repair oligonucleobase (GRON) configured to mediate introduction of the targeted genetic change within the gene, and (ii) a Clustered Regularly Interspaced Short Palindromic Repeat complex configured to introduce single strand or double strand breaks within the gene (a CRISPR), under conditions in which the targeted genetic change is introduced within the plant cell,
   wherein the GRON configured to mediate introduction of the targeted genetic change within the gene comprises one or more alterations from conventional nucleic acids selected from the group consisting of one or more 2'O-methyl nucleotides at the 5' end thereof, one or more 2'O-methyl nucleotides at the 3' end thereof, a terminus cap at the 5' end thereof, a fluorescent dye conjugated at the 5' end thereof, a fluorescent dye conjugated to the 3' end thereof, one or more phosphothioate residues at the 5' end thereof, one or more phosphothioate residues at the 3' end thereof, and a reverse base at the 3' end thereof, and, wherein the targeted genetic change is introduced without the insertion of the GRON configured to mediate introduction of the targeted change within the gene.

2. A method according to claim 1, wherein the targeted genetic change is introduced by DNA repair systems present within the plant cell.

3. A method according to claim 1, wherein the GRON configured to mediate introduction of the targeted genetic change within the gene comprises one or more contiguous 2'0-methyl RNA nucleotides at the 5' end thereof.

4. A method according to claim 1, wherein the GRON configured to mediate introduction of the targeted genetic change within the gene comprises from 2-10 contiguous 2'0-methyl RNA nucleotides at the 5' end thereof.

5. A method according to claim 1, wherein the GRON configured to mediate introduction of the targeted genetic change within the gene comprises one or more contiguous phosphothioate residues at the 5' end thereof.

6. A method according to claim 1, wherein the GRON configured to mediate introduction of the targeted genetic change within the gene comprises three contiguous phosphothioate residues at the 5' end thereof.

7. A method according to claim 1, wherein the GRON configured to mediate introduction of the targeted genetic change within the gene comprises a fluorescent dye at the 5' end thereof.

8. A method according to claim 1, wherein the GRON configured to mediate introduction of the targeted genetic change within the gene comprises a fluorescent dye at the 3' end thereof.

9. A method according to claim 1, wherein the GRON configured to mediate introduction of the targeted genetic change within the gene comprises one or more contiguous phosphothioate residues at the 3' end thereof.

10. A method according to claim 1, wherein the GRON configured to mediate introduction of the targeted genetic change within the gene comprises three contiguous phosphothioate residues at the 3' end thereof.

11. A method according to claim 1, wherein the GRON configured to mediate introduction of the targeted genetic change within the gene comprises one or more contiguous 2'0-methyl nucleotides at the 3' end thereof.

12. A method according to claim 1, wherein the targeted genetic change is a single base change in the gene.

13. A method according to claim 1, wherein the GRON configured to mediate introduction of the targeted genetic change within the gene is greater than 55 bases in length.

14. A method according to claim 1, wherein the GRON configured to mediate introduction of the targeted genetic change within the gene is single stranded.

15. A method according to claim 1, wherein the CRISPR is configured to introduce a double strand break.

16. A method according to claim 1, wherein the one or more alterations from conventional nucleic acids comprise:
   a first alteration selected from the group consisting of one or more 2'O-methyl nucleotides at the 5' end thereof, a terminus cap at the 5' end thereof, a fluorescent dye conjugated at the 5' end thereof, and one or more phosphothioate residues at the 5' end thereof, and
   one or more second alterations selected from the group consisting of one or more 2'O-methyl nucleotides at the 3' end thereof, a fluorescent dye conjugated at the 3' end thereof, one or more phosphothioate residues at the 3' end thereof, and a reverse base at the 3' end thereof.

17. A method according to claim 16, wherein the one or more alterations from conventional nucleic acids comprise from 2-10 contiguous 2'O-methyl RNA nucleotides at the 5' end thereof.

* * * * *